(12) United States Patent
Hinkle

(10) Patent No.: US 10,597,661 B2
(45) Date of Patent: Mar. 24, 2020

(54) POLYNUCLEOTIDE AGENTS TARGETING PATATIN-LIKE PHOSPHOLIPASE DOMAIN CONTAINING 3 (PNPLA3) AND METHODS OF USE THEREOF

(71) Applicant: Alnylam Pharmaceuticals, Inc., Cambridge, MA (US)

(72) Inventor: Gregory Hinkle, Plymouth, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 15/917,990

(22) Filed: Mar. 12, 2018

(65) Prior Publication Data
US 2018/0201936 A1 Jul. 19, 2018

Related U.S. Application Data

(63) Continuation of application No. PCT/US2016/051252, filed on Sep. 12, 2016.

(60) Provisional application No. 62/218,100, filed on Sep. 14, 2015.

(51) Int. Cl.
| | | |
|---|---|---|
| *A61K 48/00* | (2006.01) | |
| *C07H 21/04* | (2006.01) | |
| *C12N 15/113* | (2010.01) | |
| *A61K 31/7125* | (2006.01) | |
| *A61K 47/54* | (2017.01) | |
| *A61K 31/7008* | (2006.01) | |
| *A61K 31/712* | (2006.01) | |

(52) U.S. Cl.
CPC ...... *C12N 15/1137* (2013.01); *A61K 31/7008* (2013.01); *A61K 31/712* (2013.01); *A61K 31/7125* (2013.01); *A61K 47/546* (2017.08); *A61K 47/549* (2017.08); *C12N 15/113* (2013.01); *C12N 2310/111* (2013.01); *C12N 2310/321* (2013.01); *C12N 2310/3231* (2013.01); *C12N 2310/3341* (2013.01); *C12N 2310/341* (2013.01); *C12N 2310/351* (2013.01)

(58) Field of Classification Search
CPC .... C12N 15/113; C12N 15/111; A61K 31/713
See application file for complete search history.

(56) References Cited

U.S. PATENT DOCUMENTS

| | | | | |
|---|---|---|---|---|
| 5,801,154 A | * | 9/1998 | Baracchini | C07H 21/00 435/325 |
| 2012/0016009 A1 | * | 1/2012 | Fitzgerald | C12N 15/1137 514/44 A |
| 2017/0340661 A1 | | 11/2017 | Fitzgerald et al. | |
| 2018/0201931 A1 | * | 7/2018 | Collard | A61K 31/7088 |

FOREIGN PATENT DOCUMENTS

JP 2011061161 * 5/2011 ........... C12N 15/111

OTHER PUBLICATIONS

U.S. Appl. No. 15/670,132, filed Aug. 7, 2017, US 20170340661, Published.
Kumashiro et al. "Role of patatin-like phospholipase domain-containing 3 on lipid-induced hepatic steatosis and insulin resistance in rats," Hepatology, vol. 57, No. 5, 2013.
Hao et al., "Shifts in dietary carbohydrate-lipid exposure regulate expression of the non-alcoholic fatty liver disease-associated gene PNPLA3/adiponutrin in mouse liver and HepG2 human liver cells," Metabolism—Clinical and Experimental (2014), vol. 63, Issue 10, 1352-1362.
"GalNAc-siRNA with Enchanced stabilization chemistry: ESC-GalNAc-siRNA," Retrieved from the Internet: hhttp://www.alnylam.com/web/ . . . /ALNY-ESC-GalNAc-siRNA-TIDES-May2014-Capella.pdf.
International Search Report and Written Opinion from PCT/US2016/017550 dated Aug. 5, 2016.
International Search Report and Written Opinion from PCT/US2016/051252 dated Feb. 6, 2017.
Database EMBL [Online] Sep. 12, 2011, "JP 2006507841-A/567366: Functional and Hyperfunctional siRNA.", retrieved from EBI accession No. EM_PAT:GB004957.

* cited by examiner

*Primary Examiner* — Amy H Bowman
(74) *Attorney, Agent, or Firm* — McCarter & English, LLP; Maria Laccotripe Zacharakis; Deborah L. Nagle

(57) ABSTRACT

The invention relates to polynucleotide agents targeting a Patatin-Like Phospholipase Domain Containing 3 (PNPLA3) gene, and methods of using such polynucleotide agents to inhibit expression of a PNPLA3 gene and methods of treating subjects having Nonalcoholic Fatty Liver Disease (NAFLD) and/or a PNPLA3-associated disorder.

24 Claims, No Drawings
Specification includes a Sequence Listing.

SEQUENCE LISTING

<160> NUMBER OF SEQ ID NOS: 522

<210> SEQ ID NO 1
<211> LENGTH: 2805
<212> TYPE: DNA
<213> ORGANISM: Homo sapiens

<400> SEQUENCE: 1

```
atggtccgag gggggcgggg ctgacgtcgc gctgggaatg ccctggccga gacactgagg    60
cagggtagag agcgcttgcg ggcgccgggc ggagctgctg cggatcagga cccgagccga   120
ttcccgatcc cgacccagat cctaacccgc gccccgccc gccgccgcc gccatgtacg   180 acgcagagcg cggctggagc ttgtccttcg cgggctgcgg cttcctgggc ttctaccacg   240
```

```
tcggggcgac ccgctgcctg agcgagcacg ccccgcacct cctccgcgac gcgcgcatgt    300
tgttcggcgc ttcggccggg gcgttgcact gcgtcggcgt cctctccggt atcccgctgg    360
agcagactct gcaggtcctc tcagatcttg tgcggaaggc caggagtcgg aacattggca    420
tcttccatcc atccttcaac ttaagcaagt cctccgaca gggtctctgc aaatgcctcc     480
cggccaatgt ccaccagctc atctccggca aataggcat ctctcttacc agagtgtctg     540
atggggaaaa cgttctggtg tctgactttc ggtccaaaga cgaagtcgtg gatgccttgg    600
tatgttcctg cttcatcccc ttctacagtg gccttatccc tccttccttc agaggcgtgc    660
gatatgtgga tggaggagtg agtgacaacg tacccttcat tgatgccaaa caaccatca     720
ccgtgtcccc cttctatggg gagtacgaca tctgccctaa agtcaagtcc acgaactttc    780
ttcatgtgga catcaccaag ctcagtctac gcctctgcac agggaacctc taccttctct    840
cgagagcttt tgtcccccg atctcaagg tgctgggaga gatatgcctt cgaggatatt      900
tggatgcatt caggttcttg gaagagaagg gcatctgcaa caggcccag ccaggcctga     960
agtcatcctc agaagggatg gatcctgagg tcgccatgcc cagctgggca aacatgagtc    1020
tggattcttc cccggagtcg gctgccttgg ctgtgaggct ggagggagat gagctgctag    1080
accacctgcg tctcagcatc ctgccctggg atgagagcat cctggacacc ctctcgccca    1140
ggctcgctac agcactgagt gaagaaatga aagacaaagg tggatacatg agcaagattt    1200
gcaacttgct acccattagg ataatgtctt atgtaatgct gccctgtacc ctgcctgtgg    1260
aatctgccat tgcgattgtc cagagactgg tgacatggct tccagatatg cccgacgatg    1320
tcctgtggtt gcagtgggtg acctcacagg tgttcactcg agtgctgatg tgtctgctcc    1380
ccgcctccag gtcccaaatg ccagtgagca gccaacaggc ctccccatgc acacctgagc    1440
aggactggcc ctgctggact ccctgctccc caagggctg tccagcagag accaaagcag     1500
aggccacccc gcggtccatc ctcaggtcca gcctgaactt cttcttgggc aataaagtac    1560
ctgctggtgc tgaggggctc tccaccttc ccagttttc actagagaag agtctgtgag      1620
tcacttgagg aggcgagtct agcagattct ttcagaggtg ctaaagtttc ccatctttgt    1680
gcagctacct ccgcattgct gtgtagtgac ccctgcctgt gacgtggagg atcccagcct    1740
ctgagctgag ttggttttat gaaaagctag gaagcaacct ttcgcctgtg cagcggtcca    1800
gcacttaact ctaatacatc agcatgcgtt aattcagctg gttgggaaat gacaccagga    1860
agcccagtgc agagggtccc ttactgactg tttcgtggcc ctattaatgg tcagactgtt    1920
ccagcatgag gttcttagaa tgacaggtgt ttggatgggt ggggccttg tgatgggggg     1980
taggctggcc catgtgtgat cttgtggggt ggagggaaga gaatagcatg atcccacttc    2040
cccatgctgt gggaaggggt gcagttcgtc cccaagaacg acactgcctg tcaggtggtc    2100
tgcaaagatg ataaccttga ctactaaaaa cgtctccatg gcggggtaa caagatgata    2160
atctacttaa ttttagaaca ccttttcac ctaactaaaa taatgtttaa agagttttgt     2220
ataaaaatgt aaggaagcgt tgttacctgt tgaatttgt attatgtgaa tcagtgagat     2280
gttagtagaa taagccttaa aaaaaaaaa atcggttggg tgcagtggca cacggctgta    2340
atcccagcac tttgggaggc caaggttggc agatcacctg aggtcaggag ttcaagacca    2400
gtctggccaa catagcaaaa ccctgtctct actaaaaata caaaaattat ctgggcatgg    2460
tggtgcatgc ctgtaatccc agctattcgg aaggctgagg caggagaatc acttgaaccc    2520
aggaggcgga ggttgcggtg agctgagatt gcaccatttc attccagcct gggcaacatg    2580
agtgaaagtc tgactcaaaa aaaaaaatt taaaaaacaa aataatctag tgtgcagggc    2640
```

-continued

| | |
|---|---|
| attcacctca gcccccagg caggagccaa gcacagcagg agcttccgcc tcctctccac | 2700 |
| tggagcacac aacttgaacc tggcttattt tctgcaggga ccagccccac atggtcagtg | 2760 |
| agtttctccc catgtgtggc gatgagagag tgtagaaata aagac | 2805 |

<210> SEQ ID NO 2
<211> LENGTH: 2805
<212> TYPE: DNA
<213> ORGANISM: Homo sapiens

<400> SEQUENCE: 2

| | |
|---|---|
| gtctttatttt ctacactctc tcatcgccac acatggggag aaactcactg accatgtggg | 60 |
| gctggtccct gcagaaaata agccaggttc aagttgtgtg ctccagtgga gaggaggcgg | 120 |
| aagctcctgc tgtgcttggc tcctgcctgg ggggctgagg tgaatgccct gcacactaga | 180 |
| ttattttgtt ttttaaattt ttttttttg agtcagactt tcactcatgt tgcccaggct | 240 |
| ggaatgaaat ggtgcaatct cagctcaccg caacctccgc ctcctgggtt caagtgattc | 300 |
| tcctgcctca gccttccgaa tagctgggat tacaggcatg caccaccatg cccagataat | 360 |
| ttttgtattt ttagtagaga cagggttttg ctatgttggc cagactggtc ttgaactcct | 420 |
| gacctcaggt gatctgccaa ccttggcctc ccaaagtgct gggattacag ccgtgtgcca | 480 |
| ctgcacccaa ccgattttt ttttttaag gcttattcta ctaacatctc actgattcac | 540 |
| ataatacaaa attcaacagg taacaacgct tccttacatt tttatacaaa actctttaaa | 600 |
| cattattta gttaggtgaa aaaggtgttc taaaattaag tagattatca tcttgttacc | 660 |
| cccgccatgg agacgttttt agtagtcaag gttatcatct ttgcagacca cctgacaggc | 720 |
| agtgtcgttc ttggggacga actgcacccc ttcccacagc atggggaagt gggatcatgc | 780 |
| tattctcttc cctccacccc acaagatcac acatgggcca gcctaccccc catcacaagg | 840 |
| cccccaccca tccaaacacc tgtcattcta agaacctcat gctggaacag tctgaccatt | 900 |
| aatagggcca cgaaacagtc agtaagggac cctctgcact gggcttcctg gtgtcatttc | 960 |
| ccaaccagct gaattaacgc atgctgatgt attagagtta agtgctggac cgctgcacag | 1020 |
| gcgaaaggtt gcttcctagc ttttcataaa accaactcag ctcagaggct gggatcctcc | 1080 |
| acgtcacagg caggggtcac tacacagcaa tgcggaggta gctgcacaaa gatgggaaac | 1140 |
| tttagcaccct ctgaaagaat ctgctagact cgcctcctca agtgactcac agactcttct | 1200 |
| ctagtgaaaa actgggaaag gtggagagcc cctcagcacc agcaggtact ttattgccca | 1260 |
| agaagaagtt caggctggac ctgaggatgg accgcgggt ggcctctgct ttggtctctg | 1320 |
| ctggacagcc cttggggag cagggagtcc agcagggcca gtcctgctca ggtgtgcatg | 1380 |
| gggaggcctg ttggctgctc actggcattt gggacctgga ggcggggagc agacacatca | 1440 |
| gcactcgagt gaacacctgt gaggtcaccc actgcaacca caggacatcg tcgggcatat | 1500 |
| ctggaagcca tgtcaccagt ctctggacaa tcgcaatggc agattccaca ggcagggtac | 1560 |
| agggcagcat tacataagac attatcctaa tgggtagcaa gttgcaaatc ttgctcatgt | 1620 |
| atccaccttt gtcttttcatt tcttcactca gtgctgtagc gagcctgggc gagagggtgt | 1680 |
| ccaggatgct ctcatcccag gcaggatgc tgagacgcag gtggtctagc agctcatctc | 1740 |
| cctccagcct cacagccaag gcagccgact ccggggaaga atccagactc atgtttgccc | 1800 |
| agctgggcat ggcgacctca ggatccatcc cttctgagga tgacttcagg cctggctggg | 1860 |
| gcctgttgca gatgcccttc tcttccaaga acctgaatgc atccaaatat cctcgaaggc | 1920 |

| | |
|---|---:|
| atatctctcc cagcaccttg agatccgggg ggacaaaagc tctcgagaga aggtagaggt | 1980 |
| tccctgtgca gaggcgtaga ctgagcttgg tgatgtccac atgaagaaag ttcgtggact | 2040 |
| tgactttagg gcagatgtcg tactccccat agaaggggga cacggtgatg gttgttttgg | 2100 |
| catcaatgaa gggtacgttg tcactcactc ctccatccac atatcgcacg cctctgaagg | 2160 |
| aaggagggat aaggccactg tagaagggga tgaagcagga acataccaag gcatccacga | 2220 |
| cttcgtcttt ggaccgaaag tcagacacca gaacgttttc cccatcagac actctggtaa | 2280 |
| gagagatgcc tattttgccg gagatgagct ggtggacatt ggccgggagg catttgcaga | 2340 |
| gaccctgtcg gaggaacttg cttaagttga aggatggatg gaagatgcca atgttccgac | 2400 |
| tcctggcctt ccgcacaaga tctgagagga cctgcagagt ctgctccagc gggataccgg | 2460 |
| agaggacgcc gacgcagtgc aacgccccgg ccgaagcgcc gaacaacatg cgcgcgtcgc | 2520 |
| ggaggaggtg cggggcgtgc tcgctcaggc agcgggtcgc cccgacgtgg tagaagccca | 2580 |
| ggaagccgca gcccgcgaag acaagctcc agccgcgctc tgcgtcgtac atggcggcgg | 2640 |
| cggcggggcg gggcgcgggg ttaggatctg ggtcgggatc gggaatcggc tcgggtcctg | 2700 |
| atccgcagca gctccgcccg gcgccgcaa gcgctctcta ccctgcctca gtgtctcggc | 2760 |
| cagggcattc ccagcgcgac gtcagccccg ccccctcgg accat | 2805 |

<210> SEQ ID NO 3
<211> LENGTH: 4649
<212> TYPE: DNA
<213> ORGANISM: Mus musculus

<400> SEQUENCE: 3

| | |
|---|---:|
| agagcagcaa caccgggagc agagctgaac tgcagcgccg cccggagctt caagcaccat | 60 |
| gtatgaccca gagcgccgct ggagcctgtc gtttgcaggc tgcggcttcc tgggcttcta | 120 |
| ccacgtcggg gctacgctat gtctgagcga gcgcgccccg cacctcctcc gcgatgcgcg | 180 |
| cactttcttt ggctgctcgg ccggtgcact gcacgcggtc accttcgtgt gcagtctccc | 240 |
| tctcggccgt ataatggaga tcctcatgga cctcgtgcgg aaagccagga gccgcaacat | 300 |
| cggcaccctc cacccgttct tcaacattaa caagtgcatc agagacgggc tccaggagag | 360 |
| cctcccagac aatgtccacc aggtcatttc tggcaaggtt cacatctcac tcaccagggt | 420 |
| gtcggatggg gagaacgtgc tggtgtctga gttccattcc aaagacgaag tcgtggatgc | 480 |
| cctggtgtgt tcctgcttca ttcccctctt ctctggccta atccctcctt ccttccgagg | 540 |
| cgagcggtac gtggacggag gagtgagcga caacgtccct gtgctggatg ccaaaaccac | 600 |
| catcacggtg tcacctttct acggtgagca tgacatctgc cccaaagtca agtccaccaa | 660 |
| cttcttccac gtgaatatca ccaacctcag cctccgcctc tgcactggga acctccaact | 720 |
| tctgaccaga gcgctcttcc cgtctgatgt gaaggtgatg ggagagctgt gctatcaagg | 780 |
| gtacctggac gccttccggt tcctggagga aatggcatc tgtaacgggc acagcgcag | 840 |
| cctgagtctg tccttggtgg cgccagaagc ctgcttggaa aatggcaaac ttgtgggaga | 900 |
| caaggtgcca gtcagcctat gctttacaga tgagaacatc tgggagacac tgtcccccga | 960 |
| gctcagcaca gctctgagtg aagcgattaa ggacagggag ggctacctga gcaaagtctg | 1020 |
| caacctcctg cccgtcagga tcctgtccta catcatgctg ccctgcagtc tgcccgtgga | 1080 |
| gtcggctatc gctgcagtcc acaggctggt gacatggctc cctgatatcc aggatgatat | 1140 |
| ccagtggcta caatgggcga catcccaggt ttgtgcccga atgacgatgt gcctgctccc | 1200 |
| ctctaccagg taaatacttg ggcccagggt gtgtgggcca gataggcatc cctcccggtt | 1260 |

```
gttcccagag ctcttagggt cagagcttgg gtggtgacag ccttaacaag ccaggctcag    1320
ccgcctgtcc ccagcatgcc attaaagaaa ccggtagcag agaaagcagg tttattcgaa    1380
tataaaaagg ttcaagcccc cacccggtta atctttaaga taccaacagg aggcttaagt    1440
ttaaacagag ttacacataa acagtctgaa tcagggcgtg gtcctgccca ccattgtctg    1500
ggcttcaagg ttccttcttt ctctccctag catgagattc ctgggacaat cccaattcct    1560
tggcctccat tgtatcaaag ggctgaaaac caaaggaag gcacagctgt ctcttcagca    1620
tgcctcttct gccagaacca ctgcaaggtt tggtgctcag gctgtgcaaa cattctagca    1680
atgtttgact cagtgtcaag caggtgacaa ggaacatggt gctgtgtggg gggaacccat    1740
ggcccaggtg agggcttatt ggtgggtgaa gctgtgggtg ttcaggtggt ggagaaggcc    1800
ttaagggatg ggactgacac ctcagcactg aaggcaggag gaagctgtgg ctctgggttg    1860 caccctgcc tggctccacc ctctctggca tctgtagaag ttacagctgg ttcttcctct    1920
cagccccatg ctcccagaaa taagactcag acccaaatta tagttacaaa taccttggcc    1980
atatagctag gctcttctca gactagctca taacttaact cattaatttt aacctccatc    2040
ctgccacatg gctggtggcc tgtgctcagg taccatgagt ccagctcttc acatctttcc    2100
ggatgaatct tccataattc tttctgcctc ctggatgttc caccttctat tccacctttt    2160
cctataggcc atggttttgt ttttgttttt tttttccaaa tttaatttaa ttaattaatt    2220
tatttatttt tggttttttcg agacagggtt tctctgtatc gccctggctg tcctggaact    2280
cactatgtaa gccaggctgg cctcaaactc agaaatccgc ctgcctctgc ctcctgagtg    2340
ctgggattaa aggcgtgcgc aaccatgccc ggtgtggttt tttttttttt ttaattgaca    2400
ggtggatgca tctatataat ccataacata ttctctctac aggtatctat taggttttgg    2460
gtgaggtgtg gagttctagg gaactctgag agaaattcct ggggagtaag tggtttatca    2520
agttgattgg aggagttttt aatgctatgg acagacagac agaaggacaa cagcatagtc    2580
ggggctacca gggagttcag gccccggcat cggagataga agcaggatgg ggtctttgaa    2640
gagattctga gcccacacag cagaggaggg actctctctt tagagctttt gaggatgagg    2700
gaggttgact gcaagagcct acagccaggc tcgaggcagg caggggggtgg ggagcaggat    2760 gtaaacccct tcgatgctga cagactcact tctggggtaa aatattatga gatgcctgtc    2820
agtgtctgtg aagagacctg agcagagtct ggattctgac atcaatcatg ttcttacaat    2880
actgaagacc tgagagcctg caatcttggt ttgtaaattg ctggtctccg tgcttccagt    2940
gaacttggac attcttctca tggttggtcc aggagaggcc aaagctgagg gcaccctgcc    3000
ttccaccccc agtccagctt gacctttat ctggagcaac agtgtctaga tgatgggtgg    3060
gtgaggggtc ctatactgtc tgtccctctg ggaagggttc tgttacttt ggaggcagct    3120 aggaagtttc tctgtgcagc tgcccctgg tgctgtgtgg tgacctcatt gcctgtgacc    3180
ccaggatcac aggatctggg ctaaagtggt agtccataga aaccaaagac aatgatttgg    3240
tgtttagaaa gctactcttg gtctgggtga agtctggtgc ttaagggcta tcacaaagag    3300
cgtgtcaaac catctctcag cctgtgagtc agtggggagc ccaagggcat cagtgtttgg    3360
aaactggaat ccaaaccggg caatctcgga aggaaactgt ttaggaattg tgatgggacg    3420
ggccgtggct gtctctgaaa agggcctgcc agataactta ttacttttaa ggacaccttt    3480
ggctcttact aatttataaa gcattttata taaacacacc agggagtgca tggtgaacta    3540
cacgtatgat cagttaagtg gggctagaat taggtaggga gagcatcgga cctctgcctc    3600
```

```
ctcaacctca acttgcttgc tttctccact ggctccaaat ctttgtatag tcatcagcca    3660
tgaccacctc tctccctccc catctactac cagcagcgtt aatgggaata agtacccact    3720
tctctcaggt gtactataca gctgtgggtg tggtgtgtgt ttcctgtaat tcacacttta    3780
gaaaggaaac aagcaaacaa agaaaccag gtgctgccca tactcctaag tgtagacagt    3840
gaaggtgtgt gtctcccatg cctgagtctc ctggaggcct agtgagctcc aggttcatgc    3900
aagcacatca ggaggaatca tataatctca gcacggttga tccagatggg ataagaaagg    3960
actctgggag agagaatgtg gttctagaga caaagtgtct aggctacaca aagataaga    4020
ctgtcccaag gaaagaaaag aaaccaggaa ctagggtgca gctcagttgt cagaggactt    4080
ctctaggctt gaagcccaga gtccaatctc agcaccttat aaactgtgga gtgacaggca    4140
gtgacatcgg cctgtaatcc caacactcaa gcagtagagg caagaggatc ataagttcaa    4200
ggtcttcctt ggctatttag ggagttggag gttagctctg gctacatgag accctgtctc    4260
aaaaaaaaaa aaaaaaaaaa gtagaaactt ctgccttgct ttgagctgcc cctttctgga    4320
cgtttctcat cagtagagaa tattcctgcc accctatcag acaaaactcc cactgggttg    4380
gagtctctcc attctcagga cacctcagg agtcagacag tgagcagcag ggagcaatgt    4440
cttgacttgt aagcccctta gcaaggctgg ttcatttgtt tattaaaagc aggtgtgggt    4500
gaatttatgc aaatgagtat gcaaactagt ggaacagcag aaggattgaa tggatacacc    4560
aaaaataacc acaactgttt aagggaaaag ggtccataat aaatgtgggg aacaaaaaac    4620
aaataaatgt gattttttt agaaaaatg                                       4649
```

<210> SEQ ID NO 4
<211> LENGTH: 4649
<212> TYPE: DNA
<213> ORGANISM: Mus musculus

<400> SEQUENCE: 4

```
cattttcta aaaaaatca catttatttg ttttttgttc cccacattta ttatggaccc       60
ttttccctta aacagttgtg gttattttg gtgtatccat tcaatccttc tgctgttcca      120
ctagtttgca tactcatttg cataaattca cccacacctg cttttaataa acaaatgaac     180
cagccttgct aaggggctta caagtcaaga cattgctccc tgctgctcac tgtctgactc     240
ctgaggtgtt cctgagaatg gagagactcc aaaccagtgg gagttttgtc tgatagggtg     300
gcaggaatat tctctactga tgagaaacgt ccagaaaggg gcagctcaaa gcaaggcaga     360
agtttctact tttttttttt ttttttttg agacagggtc tcatgtagcc agagctaacc     420
tccaactccc taaatagcca aggaagacct tgaacttatg atcctcttgc ctctactgct     480
tgagtgttgg gattacaggc cgatgtcact gcctgtcact ccacagttta taaggtgctg     540
agattggact ctgggcttca agcctagaga agtcctctga caactgagct gcaccctagt     600
tcctggtttc ttttctttcc ttgggacagt cttatcttct gtgtagccta gacactttgt     660
ctctagaacc acattctctc tcccagagtc ctttcttatc ccatctggat caaccgtgct     720
gagattatat gattcctcct gatgtgcttg catgaacctg gagctcacta ggcctccagg     780
agactcaggc atgggagaca cacccttca ctgtctacac ttaggagtat gggcagcacc     840
tggtttcttt tgtttgcttg tttccttct aaagtgtgaa ttacaggaaa cacacaccac     900
acccacagct gtatagtaca cctgagaaa gtgggtactt attcccatta acgctgctgg     960
tagtagatgg ggagggagag aggtggtcat ggctgatgac tatacaaaga tttgagcca    1020
gtggagaaag caagcaagtt gaggttgagg aggcagaggt ccgatgctct ccctacctaa   1080
```

```
ttctagcccc acttaactga tcatacgtgt agttcaccat gcactccctg gtgtgtttat   1140
ataaaatgct ttataaatta gtaagagcca aaggtgtcct taaaagtaat aagttatctg   1200
gcaggcccct tcagagaca gccacggccc gtcccatcac aattcctaaa cagtttcctt    1260
ccgagattgc ccggtttgga ttccagtttc caaacactga tgcccttggg ctccccactg   1320
actcacaggc tgagagatgg tttgacacgc tctttgtgat agcccttaag caccagactt   1380
cacccagacc aagagtagct ttctaaacac caaatcattg tctttggttt ctatggacta   1440
ccactttagc ccagatcctg tgatcctggg gtcacaggca atgaggtcac cacacagcac   1500 caggggggcag ctgcacagag aaacttccta gctgcctcca aaagtaacag aacccttccc  1560
agagggacag acagtatagc accccctcacc cacccatcat ctagacactg ttgctccaga  1620
taaaaggtca agctggactg ggggtggaag gcagggtgcc ctcagctttg gcctctcctg   1680
gaccaaccat gagaagaatg tccaagttca ctggaagcac ggagaccagc aatttacaaa   1740
ccaagattgc aggctctcag gtcttcagta ttgtaagaac atgattgatg tcagaatcca   1800
gactctgctc aggtctcttc acagacactg acaggcatct cataatattt taccccagaa   1860
gtgagtctgt cagcatcgaa gggggtttaca tcctgctccc cacccctgc ctgcctcgag    1920 cctggctgta ggctcttgca gtcaacctcc ctcatcctca aaagctctaa agagagagtc   1980
cctcctctgc tgtgtgggct cagaatctct tcaaagaccc catcctgctt ctatctccga   2040
tgccggggcc tgaactccct ggtagccccg actatgctgt tgtccttctg tctgtctgtc   2100
catagcatta aaaactcctc caatcaactt gataaaccac ttactcccca ggaatttctc   2160
tcagagttcc ctagaactcc acacctcacc caaaacctaa tagatacctg tagagagaat   2220
atgttatgga ttatatagat gcatccacct gtcaattaaa aaaaaaaaaa aaccacaccg   2280
ggcatggttg cgcacgcctt taatcccagc actcaggagg cagaggcagg cggatttctg   2340
agtttgaggc cagcctggct tacatagtga gttccaggac agccagggcg atacagagaa   2400
accctgtctc gaaaaaccaa aaataaataa attaattaat taaattaaat ttggaaaaaa   2460
aaaacaaaaa caaaaccatg gcctatagga aaaggtggaa tagaaggtgg aacatccagg   2520
aggcagaaag aattatggaa gattcatccg gaaagatgtg aagagctgga ctcatggtac   2580
ctgagcacag gccaccagcc atgtggcagg atggaggtta aaattaatga gttaagttat   2640
gagctagtct gagaagagcc tagctatatg gccaaggtat ttgtaactat aatttgggtc   2700
tgagtcttat ttctgggagc atggggctga gaggaagaac cagctgtaac ttctacagat   2760
gccagagagg gtgagccag gcaggggtgc aacccagagc cacagcttcc tcctgccttc   2820
agtgctgagg tgtcagtccc atcccttaag gccttctcca ccacctgaac acccacagct   2880
tcacccacca ataagccctc acctgggcca tgggttcccc ccacacagca ccatgttcct   2940
tgtcacctgc ttgacactga gtcaaacatt gctagaatgt tgcacagcc tgagcaccaa    3000 accttgcagt ggttctggca gaagaggcat gctgaagaga cagctgtgcc ttcccttttgg  3060 ttttcagccc tttgatacaa tggaggccaa ggaattggga ttgtcccagg aatctcatgc   3120
tagggagaga aagaaggaac cttgaagccc agacaatggt gggcaggacc acgccctgat   3180
tcagactgtt tatgtgtaac tctgtttaaa cttaagcctc ctgttggtat cttaaagatt   3240
aaccgggtgg gggcttgaac cttttttatat tcgaataaac ctgctttctc tgctaccggt   3300
ttctttaatg gcatgctggg gacaggcggc tgagcctggc ttgttaaggc tgtcaccacc   3360
caagctctga ccctaagagc tctgggaaca accgggaggg atgcctatct ggcccacaca   3420
```

| | |
|---|---|
| ccctgggccc aagtatttac ctggtagagg ggagcaggca catcgtcatt cgggcacaaa | 3480 |
| cctgggatgt cgcccattgt agccactgga tatcatcctg gatatcaggg agccatgtca | 3540 |
| ccagcctgtg gactgcagcg atagccgact ccacgggcag actgcagggc agcatgatgt | 3600 |
| aggacaggat cctgacgggc aggaggttgc agactttgct caggtagccc tccctgtcct | 3660 |
| taatcgcttc actcagagct gtgctgagct cgggggacag tgtctcccag atgttctcat | 3720 |
| ctgtaaagca taggctgact ggcaccttgt ctcccacaag tttgccattt tccaagcagg | 3780 |
| cttctggcgc caccaaggac agactcaggc tgcgctgtgg cccgttacag atgccattct | 3840 |
| cctccaggaa ccggaaggcg tccaggtacc cttgatagca cagctctccc atcaccttca | 3900 |
| catcagacgg gaagagcgct ctggtcagaa gttggaggtt cccagtgcag aggcggaggc | 3960 |
| tgaggttggt gatattcacg tggaagaagt tggtggactt gactttgggg cagatgtcat | 4020 |
| gctcaccgta gaaaggtgac accgtgatgg tggttttggc atccagcaca gggacgttgt | 4080 |
| cgctcactcc tccgtccacg taccgctcgc ctcggaagga aggagggatt aggccagaga | 4140 |
| agagggaat gaagcaggaa cacaccaggg catccacgac ttcgtctttg aatggaact | 4200 |
| cagacaccag cacgttctcc ccatccgaca ccctggtgag tgagatgtga accttgccag | 4260 |
| aaaatgacctg gtggacattg tctgggaggc tctcctggaa cccgtctctg atgcacttgt | 4320 |
| taatgttgaa gaacgggtgg agggtgccga tgttgcggct cctggctttc cgcacgaggt | 4380 |
| ccatgaggat ctccattata cggccgagag ggagactgca cacgaaggtg accgcgtgca | 4440 |
| gtgcaccggc cgagcagcca agaaagtgc gcgcatcgcg gaggaggtgc ggggcgcgct | 4500 |
| cgctcagaca tagcgtagcc ccgacgtggt agaagcccag gaagccgcag cctgcaaacg | 4560 |
| acaggctcca gcggcgctct gggtcataca tggtgcttga agctccgggc ggcgctgcag | 4620 |
| ttcagctctg ctcccggtgt tgctgctct | 4649 |

<210> SEQ ID NO 5
<211> LENGTH: 2759
<212> TYPE: DNA
<213> ORGANISM: Rattus norvegicus

<400> SEQUENCE: 5

| | |
|---|---|
| cccggagcag aattgagctg catcgccttc cggagcctcc agcgccatgt acgacccaga | 60 |
| gcgccgctgg agcctgtcgt tcgcaggctg cggcttccta ggcttctacc acatcggggc | 120 |
| tacgctatgt ctgagcgagc gcgctccgca catcctccgc gaagcgcgca ctttcttcgg | 180 |
| ctgctcggcc ggtgcactgc acgcggtcac cttcgtgtgc agtctccctc tcgatcacat | 240 |
| catggagatc ctcatggacc tcgtgcggaa agccaggagc cgcaacatcg gcaccctcca | 300 |
| cccgttcttc aacattaaca agtgcgtcag agacggcctt caggagaccc tcccagacaa | 360 |
| cgtccaccag atcatttctg gcaaggttta catctcactc accagagtgt ccgatgggga | 420 |
| gaacgtgctg gtgtctgagt tccattccaa agacgaagtg gtggatgccc tggtgtgctc | 480 |
| ctgcttcatt cctctcttct ctggcctaat ccctccttcc ttccgaggtg agcggtacgt | 540 |
| ggatggagga gtgagtgaca acgtccctgt gctggacgcc aaaaccacca tcacggtgtc | 600 |
| ccctttctat ggtgagcatg acatctgtcc caaagtgaag tccaccaact tcctccaggt | 660 |
| gaatatcacc aacctcagtc ttcgtctctg cactgggaac cttcatcttc tgaccagagc | 720 |
| actcttccca tctgatgtga aggtgatggg agagctgtgc tttcaagggt acctggacgc | 780 |
| cttccggttc ctggaagaga acggcatctg taatgggcca cagcgcagcc tgagtctgtc | 840 |
| cttggagaag gaaatggcgc cagaaaccat gataccctgc ttggaaaatg gccaccttgt | 900 |

```
agcagggaac aaggtgccag taagctgtgt atgccttaca gctgtgccgt cggatgagag      960
catctgggag atgctgtccc ccaagctcag cacagctctg actgaagcga ttaaagacag     1020
gggggggctac ctgaacaaag tctgcaacct cctgcccatt aggatcctgt cctacatctt    1080
gctgccctgc actctgcccg tggagtcggc catcgctgca gtccacaggc tggtgatgtg     1140
gctccctgat atccatgaag atatccagtg gctacagtgg gcaacatccc aggtgtgtgc     1200
ccgaatgacc atgtgcctgc tcccctctac cagatccaga gcatccaagg ataaccatca     1260
aacactcaag catggatatc acccatctct ccacaaaccc caaggcagct ctgccggttt     1320
gtaaattgct ggtctccgtg cttccgatga acttgggcat tctccctgtg atggttcca     1380
ggagaggcca tagctgaagg cactctgcct tccaccccaa gtccagtttg acctttatct     1440
agagcaacag tgtctagatg ataggtgggt gggggtgct gtctctctgt ttccctctgg     1500
gaagggttct gttaactttt ggaggcagct aggaaatttc tctccaggag ctgagcctgt     1560
gcagctgccc ccttggtgct gtgtggtaac ctcattgcct gtgaccctag gatcatagga     1620
tctgggctaa ataggtagtt catagaaacc aaagacaata atttggtgtt tagaaaacta     1680
cttttggtct gggtgaagtc tggtgcttga gagttagtgc agagagaacg gtcaaaccgt     1740
ctctcagcct gtggatctat ggggattcca agggcttcag tgtttggaaa cggcaatcca     1800
aacgggcaat cttgtgcaat cttggaagga gaactgttca ggaagtgtga tgggatgagc     1860
tgtggctgtc tctgaaaagg gcctaccata taacttatta ctttcaagga taccttggc     1920
tcttactaaa atagtttata aagcatttta tagaaacaca ccagggaatg cgtggtgaac     1980
tacatgtatg atcagtgaac tgtgactaga attaaccta aaatctcttg tatgtggggc     2040
cagagcaaca caggtgggaa acgcagcgga cctctgcctc ctcggcctca acatgaactt     2100
ggcttgcttt ctccaccgtc tccaaatctt tgtatagtca tcgaccatta ccacctctcc     2160
tttcccatct actacagcag ccttaatggg gataagtacc ccttttctc aggtgtccga     2220
ataagctgtg ggtgtggcct gtgtttcctg taattctgag gttagattgg aacataagca     2280
agcagacaaa caagcagaca aacaaacaag gttctactca tattcctaag cagtgacagt     2340
gaaggcatgt gtctcccatg cctgagtctc ctagggtcct agtgagctct gggttcatgc     2400
aagcacttcc ggaggaattg caccctccat ggaacacata atctccactg gttgatcct     2460
gattggataa gaaaggatct cggggagaga atgtggttcc agaggcaaag tgtctaggct     2520
acacagaaaa ggtaagactg tccccaaggg aagaaaacaa actgggagct ggggtccagc     2580
tcaattgtta agagtgcttc tctagtatgc gtgaagccca gagtccaatc tcagtaccag     2640
atacacggta caggcagtga catatgcctg taatcccaac cctcaagcag tagaggcaag     2700
aggatcagaa gttcatggtc atccttgact acttatactt agggagttgg aggtcagcc     2759
```

<210> SEQ ID NO 6
<211> LENGTH: 2759
<212> TYPE: DNA
<213> ORGANISM: Rattus norvegicus

<400> SEQUENCE: 6

```
ggctgacctc caactcccta agtataagta gtcaaggatg accatgaact tctgatcctc       60
ttgcctctac tgcttgaggg ttgggattac aggcatatgt cactgcctgt accgtgtatc     120
tggtactgag attggactct gggcttcacg catactagaa aagcactctt aacaattgag     180
ctggacccca gctcccagtt tgttttcttc ccttggggac agtcttacct tttctgtgta    240
```

```
gcctagacac tttgcctctg gaaccacatt ctctccccga gatcctttct tatccaatca      300
ggatcaaccc agtggagatt atgtgttcca tggagggtgc aattcctccg gaagtgcttg      360
catgaaccca gagctcacta ggaccctagg agactcaggc atgggagaca catgccttca      420
ctgtcactgc ttaggaatat gagtagaacc ttgtttgttt gtctgcttgt ttgtctgctt      480
gcttatgttc caatctaacc tcagaattac aggaaacaca ggccacaccc acagcttatt      540
cggacacctg agaaaagggg gtacttatcc ccattaaggc tgctgtagta gatgggaaag      600
gagaggtggt aatggtcgat gactatacaa agatttggag acggtggaga aagcaagcca      660
agttcatgtt gaggccgagg aggcagaggt ccgctgcgtt cccacctgt gttgctctgg       720 ccccacatac aagagatttt aaggttaatt ctagtcacag ttcactgatc atacatgtag      780
ttcaccacgc attccctggt gtgtttctat aaaatgcttt ataaactatt ttagtaagag      840
ccaaaggtat ccttgaaagt aataagttat atggtaggcc cttttcagag acagccacag      900
ctcatcccat cacacttcct gaacagttct ccttccaaga ttgcacaaga ttgcccgttt      960
ggattgccgt ttcaaacac tgaagccctt ggaatcccca tagatccaca ggctgagaga      1020
cggtttgacc gttctctctg cactaactct caagcaccag acttcaccca gaccaaaagt      1080
agttttctaa acaccaaatt attgtctttg gtttctatga actacctatt tagcccagat      1140
cctatgatcc tagggtcaca ggcaatgagg ttaccacaca gcaccaaggg ggcagctgca      1200
caggctcagc tcctggagag aaatttccta gctgcctcca aaagttaaca gaaccccttcc    1260 cagagggaaa cagagagaca gcaccccca cccacctatc atctagacac tgttgctcta      1320
gataaaggtc aaactggact tgggggtggaa ggcagagtgc cttcagctat ggcctctcct    1380
ggaaccatcc acagggagaa tgcccaagtt catcggaagc acggagacca gcaatttaca     1440
aaccggcaga gctgccttgg ggtttgtgga gagatgggtg atatccatgc ttgagtgttt     1500
gatggttatc cttggatgct ctggatctgg tagaggggag caggcacatg gtcattcggg     1560
cacacacctg ggatgttgcc cactgtagcc actggatatc ttcatggata tcagggagcc     1620
acatcaccag cctgtggact gcagcgatgg ccgactccac gggcagagtg cagggcagca    1680
agatgtagga caggatccta atgggcagga ggttgcagac tttgttcagg tagcccccccc     1740 tgtctttaat cgcttcagtc agagctgtgc tgagcttggg ggacagcatc tcccagatgc     1800
tctcatccga cggcacagct gtaaggcata cacagcttac tggcaccttg ttccctgcta     1860
caaggtggcc attttccaag cagggtatca tggtttctgg cgccatttcc ttctccaagg     1920
acagactcag gctgcgctgt ggcccattac agatgccgtt ctcttccagg aaccggaagg     1980
cgtccaggta cccttgaaag cacagctctc ccatcaccct cacatcagat gggaagagtg     2040
ctctggtcag aagatgaagg ttcccagtgc agagacgaag actgaggttg gtgatattca     2100
cctggaggaa gttggtggac ttcactttgg gacagatgtc atgctcacca tagaaagggg    2160
acaccgtgat ggtggttttg gcgtccagca cagggacgtt gtcactcact cctccatcca     2220
cgtaccgctc acctcggaag gaaggaggga ttaggccaga gaagagagga atgaagcagg    2280
agcacaccag ggcatccacc acttcgtctt tggaatggaa ctcagacacc agcacgttct     2340
ccccatcgga cactctggtg agtgagatgt aaaccttgcc agaaatgatc tggtggacgt     2400
tgtctgggag ggtctcctga aggccgtctc tgacgcactt gttaatgttg aagaacgggt    2460
ggagggtgcc gatgttgcgg ctcctggctt tccgcacgag gtccatgagg atctccatga    2520
tgtgatcgag agggagactg cacacgaagg tgaccgcgtg cagtgcaccg gccgagcagc     2580
cgaagaaagt gcgcgcttcg cggaggatgt gcggagcgcg ctcgctcaga catagcgtag     2640
```

```
cccgatgtg gtagaagcct aggaagccgc agcctgcgaa cgacaggctc cagcggcgct    2700
ctgggtcgta catggcgctg gaggctccgg aaggcgatgc agctcaattc tgctccggg    2759

<210> SEQ ID NO 7
<211> LENGTH: 2281
<212> TYPE: DNA
<213> ORGANISM: Macaca fascicularis

<400> SEQUENCE: 7
tgctgcggat caggacccga gccgatcccc gatcccgact ccgatccgga tccgcgcccc      60
cgcccccgcc ccgccatgta cgacgccgag cgcggctgga gcttgtcctt cgcgggctgc     120
ggcttcctgg gcttctacca cgtcggggcg acccggtgcc tgagcgagca cgccccgcac     180
ctcctccgcg acgcgcgcat gttgttcggc gcctcggccg gggcgttgca ctgcgtcggc     240
gtcctctccg ggatcccgct ggagcagact ctgcaggtcc tctcagatct tgtccggaag     300
gccaggagtc ggaacattgg tatcttccat ccatccttca acataggcaa gttcctccga     360
caggatctct acaaatacct cccggccaat gtccaccagc tcatctctgg caaaatatgc     420
gtctcactca ccagagtgtc tgatgggaaa acgttctgg tgtctgactt tcagtccaaa      480
gacgaagtcg tggatgcctt gatttgttcc tgcttcatcc ctttctacag tggccttatc     540
cctccttcct tcagaggcgt gcgatatgtg gatggaggag cgagtgacaa cgtacccttc     600
attgatgcca agacaaccat caccgtgtcg cccttctatg gggagtacga catctgccct     660
aaagtcaagt ccaccaactt tcttcatgtg gacatcacca agctcagcct acgcctctgc     720
acagggaacc tctaccttct ctcaagagcg tttgtccccc cggatctcaa ggtgctggga     780
gagatatgcc ttcgaggata tttgacgcg ttcaggttct tggaagagaa gggcatctgc      840
aacaagcccc agcggggtct gaagtcatcc tcagaaggga tggattctga ggtcactgcg     900
cccggctggg aaaacacaag tctggattct tccccggagc cggctgcctt ggctatgagg     960
ctggatggag atgagctgct agaccacctg cgtctcagca tcctgccctg ggatgagagc    1020
atcctggaca ccctgtcgcc cgagctcgct acagcagtga gtgaagcaat gaaagacaaa    1080
ggtggataca tgagcaagat ttgcaacttg ctacccatta ggataatatc ttatgtgatg    1140
ctgccctgta ccctgcctgt ggagtctgcc attgcgattg ccagagact ggtgacatgg     1200 cttccagata tgcccgacga tgtgcagtgg ctgcagtggg tgacctcaca ggtcttcact    1260
cgagcgctga tgtgtctgct tcccgcctcc aggtcccaaa tgccagtgag cagcgaacag    1320
gcctccccat gcaaaccgga gcaggactgg cactgctgga ctccctgctc ccccgaggac    1380
tgtcctgcag aggccaaagc agaggctacc ccacggtcca tcctcaggtc cagcctgaac    1440
ttcttctggg gcaataaagt acctgctggt gctgaggggc tctccacctt tcccagtttt    1500
tcactggaga agaatttgtg agtcatttga ggaggcgagt ctaggagatt ctttcagagg    1560
tgctaaagct tccatctttt gtgcagctac ctccgcattg ccgtgtagtg acccctgcct    1620
gtgacgtgga ggatcccagc ctctgagctg agttggtttt atgaaaagct aggaagcaat    1680
gtttggtctg tgcagcagtc cagcacttaa gtctaatacg tcagcatgcg ttagttcagc    1740
tggttgggaa atgacaccgg gaagcctagc gcagagggtc ccttactgac tatttcatgg    1800
tcctattaat ggtcagactg ttccagtgtg aggttcttag aatgactagt gtttggatgg    1860
gtgggggcct tgtggtgggg ggtgggctgg cctatgtgtg atcttgtggg gtggaaggaa    1920
gagagtagca caatcccacc tccccatgcc gtgggaaggg gtgcacttgg ttcccaagaa    1980
```

```
ggacactgcc tgtcaggtgg cctgcaaata taataacctt gacaactaaa aacctctcca    2040
tgggggtggg aggtaccaag ataataaccg atttacattt tagagcacct ttttcaccta    2100
actaaaataa tgtttaaaga gttttatata aaaatgtaag gaagagttgt tatctgttga    2160
attttgtatt atatgaatca gtgagatgtt aatagaataa gcctttaaaa agaaaaaaag    2220
ttcagccagg cgctgtggca cacgcctgta atcccagcac tttggaaggc cgaggtgggc    2280
a                                                                   2281

<210> SEQ ID NO 8
<211> LENGTH: 2281
<212> TYPE: DNA
<213> ORGANISM: Macaca fascicularis

<400> SEQUENCE: 8
tgcccacctc ggccttccaa agtgctggga ttacaggcgt gtgccacagc gcctggctga      60 acttttttc tttttaaagg cttattctat taacatctca ctgattcata taatacaaaa     120
ttcaacagat aacaactctt ccttacattt ttatataaaa ctctttaaac attattttag    180
ttaggtgaaa aagtgctct aaaatgtaaa tcggttatta tcttggtacc tcccacccc     240 atggagaggt tttagttgt caaggttatt atatttgcag gccacctgac aggcagtgtc     300
cttcttggga accaagtgca ccccttccca cggcatgggg aggtgggatt gtgctactct    360
cttccttcca ccccacaaga tcacacatag gccagcccac cccccaccac aaggccccca    420
cccatccaaa cactagtcat tctaagaacc tcacactgga acagtctgac cattaatagg    480
accatgaaat agtcagtaag ggaccctctg cgctaggctt cccggtgtca tttcccaacc    540
agctgaacta acgcatgctg acgtattaga cttaagtgct ggactgctgc acagaccaaa    600
cattgcttcc tagcttttca taaaaccaac tcagctcaga ggctgggatc ctccacgtca    660
caggcagggg tcactacacg gcaatgcgga ggtagctgca caaagatggg aagctttagc    720
acctctgaaa gaatctccta gactcgcctc ctcaaatgac tcacaaattc ttctccagtg    780
aaaaactggg aaaggtggag agcccctcag caccagcagg tactttattg ccccagaaga    840
agttcaggct ggacctgagg atggaccgtg gggtagcctc tgctttggcc tctgcaggac    900
agtcctcggg ggagcaggga gtccagcagt gccagtcctg ctccggtttg catggggagg    960
cctgttcgct gctcactggc atttgggacc tggaggcggg aagcagacac atcagcgctc   1020
gagtgaagac ctgtgaggtc acccactgca gccactgcac atcgtcgggc atatctggaa   1080
gccatgtcac cagtctctgg acaatcgcaa tggcagactc cacaggcagg gtacagggca   1140
gcatcacata agatattatc ctaatgggta gcaagttgca aatcttgctc atgtatccac   1200 cttttgtcttt cattgcttca ctcactgctg tagcgagctc gggcgacagg gtgtccagga   1260
tgctctcatc ccagggcagg atgctgagac gcaggtggtc tagcagctca tctccatcca   1320
gcctcatagc caaggcagcc ggctccgggg aagaatccag acttgtgttt tcccagccgg   1380
gcgcagtgac ctcagaatcc atcccttctg aggatgactt cagaccccgc tggggcttgt   1440
tgcagatgcc cttctcttcc aagaacctga cgcgtccaa atatcctcga aggcatatct    1500
ctcccagcac cttgagatcc ggggggacaa acgctcttga gagaaggtag aggttccctg   1560
tgcagaggcg taggctgagc ttggtgatgt ccacatgaag aaagttggtg gacttgactt   1620
tagggcagat gtcgtactcc ccatagaagg gcgacacggt gatggttgtc ttggcatcaa   1680
tgaagggtac gttgtcactc gctcctccat ccacatatcg cacgcctctg aaggaaggag   1740
ggataaggcc actgtagaaa gggatgaagc aggaacaaat caaggcatcc acgacttcgt   1800
```

```
ctttggactg aaagtcagac accagaacgt tttccccatc agacactctg gtgagtgaga    1860
cgcatatttt gccagagatg agctggtgga cattggccgg gaggtatttg tagagatcct    1920
gtcggaggaa cttgcctatg ttgaaggatg gatggaagat accaatgttc gactcctgg     1980 ccttccggac aagatctgag aggacctgca gagtctgctc cagcgggatc ccggagagga    2040
cgccgacgca gtgcaacgcc ccggccgagg cgccgaacaa catgcgcgcg tcgcggagga    2100
ggtgcggggc gtgctcgctc aggcaccggg tcgccccgac gtggtagaag cccaggaagc    2160
cgcagcccgc gaaggacaag ctccagccgc gctcggcgtc gtacatggcg ggcgggggc     2220 gggggcgcgg atccggatcg gagtcgggat cggggatcgg ctcgggtcct gatccgcagc    2280
a                                                                    2281

<210> SEQ ID NO 9
<211> LENGTH: 1544
<212> TYPE: DNA
<213> ORGANISM: Macaca mulatta

<400> SEQUENCE: 9
cgcttgcggg cgcccggcgg agctgctgcg gatcaggacc cgagccgatc cccgatcccg      60
actccgatcc ggatccgcgc cccgccccc gccccgccat gtacgacgcc gagcgcggct     120
ggagcttgtc cttcgcggc tgcggcttcc tgggcttcta ccacgtcggg gcgacccgct     180
gcctgagcga gcacgccccg cacctcctcc gcgacgcgcg catgttgttc ggcgcctcgg    240
ccggggcgtt gcactgcgtc ggcgtcctct ccgggatccc gctggagcag actctgcagg    300
tcctctcaga tcttgtccgg aaggccagga gtcggaacat tggtatcttc catccatcct    360
tcaacatagg caagttcctc cgacaggatc tctacaaata cctcccggcc aatgtccacc    420
agctcatctc tggcaaaata tgcgtctcac tcaccagagt gtctgatggg gaaaacgttc    480
tggtgtctga ctttcagtcc aaagacgaag tcgtggatgc cttgatttgt tcctgcttca    540
tcccttctca cagtggcctt atccctcctt ccttcagagg cgtgcgatat gtggatggag    600
gagcgagtga caacgtaccc ttcattgatg ccaagacaac catcaccgtg tcgcccttct    660
atggggagta cgacatctgc cctaaagtca agtccaccaa ctttcttcat gtggacatca    720
ccaagctcag cctacgcctc tgcacaggga acctctacct tctctcaaga gcgtttgtcc    780
ccccggatct caaggtgctg ggagagatat gccttgaggg atatttggac gcgttcaggt    840
tcttggaaga aagggcatc tgcaacaagc cccagcgggg tctgaagtca tcctcagaag    900
ggatggattc tgaggtcact gcgcccggct gggaaaacac aagtctggat tcttccccgg    960
agccggctgc cttggctatg aggctggatg gagatgagct gctagaccac ctgcgtctca    1020
gcatcctgcc ctgggatgag agcatcctgg acaccctgtc gcccgagctc gctacagcag    1080
tgagtgaagc aatgaaagac aaaggtggat acatgagcaa gatttgcaac ttgctaccca    1140
ttaggataat gtcttatgtg atgctgccct gtacccgcc tgtggagtct gccattgcga    1200
ttgtccagag actggtgaca tggcttccgg atatgcccga cgatgtgcag tggctgcagt    1260
gggtgacctc acaggtcttc actcgagcgc tgatgtgtct gcttcccgcc tccaggtccc    1320
aaatgccagt gagcggcgaa caggcctccc catgcaaacc ggagcaggac tggcactgct    1380
ggactccctg ctcccccgag gactgtcctg cagaggccaa agcagaggct accccacggt    1440
ccatcctcag gtccagcctg aacttcttct ggggcaataa agtacctgct ggtgctgagg    1500
ggctctccac ctttcccagt ttttcactgg agaagaattt gtga                    1544
```

<210> SEQ ID NO 10
<211> LENGTH: 1544
<212> TYPE: DNA
<213> ORGANISM: Macaca mulatta

<400> SEQUENCE: 10

| | | | | | |
|---|---|---|---|---|---|
| tcacaaattc | ttctccagtg | aaaaactggg | aaggtggag | agccctcag | caccagcagg | 60 |
| tactttattg | ccccagaaga | agttcaggct | ggacctgagg | atggaccgtg | gggtagcctc | 120 |
| tgctttggcc | tctgcaggac | agtcctcggg | ggagcaggga | gtccagcagt | gccagtcctg | 180 |
| ctccggtttg | catggggagg | cctgttcgcc | gctcactggc | atttgggacc | tggaggcggg | 240 |
| aagcagacac | atcagcgctc | gagtgaagac | ctgtgaggtc | acccactgca | gccactgcac | 300 |
| atcgtcgggc | atatccggaa | gccatgtcac | cagtctctgg | acaatcgcaa | tggcagactc | 360 |
| cacaggcagg | gtacagggca | gcatcacata | agacattatc | ctaatgggta | gcaagttgca | 420 |
| aatcttgctc | atgtatccac | ctttgtcttt | cattgcttca | ctcactgctg | tagcgagctc | 480 |
| gggcgacagg | gtgtccagga | tgctctcatc | ccagggcagg | atgctgagac | gcaggtggtc | 540 |
| tagcagctca | tctccatcca | gcctcatagc | caaggcagcc | ggctccgggg | aagaatccag | 600 |
| acttgtgttt | tccagccgg | gcgcagtgac | ctcagaatcc | atcccttctg | aggatgactt | 660 |
| cagaccccgc | tggggcttgt | tgcagatgcc | cttctcttcc | aagaacctga | acgcgtccaa | 720 |
| atatcctcga | aggcatatct | ctcccagcac | cttgagatcc | gggggacaa | acgctcttga | 780 |
| gagaaggtag | aggttccctg | tgcagaggcg | taggctgagc | ttggtgatgt | ccacatgaag | 840 |
| aaagttggtg | gacttgactt | tagggcagat | gtcgtactcc | ccatagaagg | gcgacacggt | 900 |
| gatggttgtc | ttggcatcaa | tgaagggtac | gttgtcactc | gctcctccat | ccacatatcg | 960 |
| cacgcctctg | aaggaaggag | ggataaggcc | actgtagaaa | gggatgaagc | aggaacaaat | 1020 |
| caaggcatcc | acgacttcgt | ctttggactg | aaagtcagac | accagaacgt | tttccccatc | 1080 |
| agacactctg | tgagtgaga | cgcatatttt | gccagagatg | agctggtgga | cattggccgg | 1140 |
| gaggtatttg | tagagatcct | gtcggaggaa | cttgcctatg | ttgaaggatg | gatggaagat | 1200 |
| accaatgttc | cgactcctgg | ccttccggac | aagatctgag | aggacctgca | gagtctgctc | 1260 |
| cagcgggatc | ccggagagga | cgccgacgca | gtgcaacgcc | ccggccgagg | cgccgaacaa | 1320 |
| catgcgcgcg | tcgcgagga | ggtgcggggc | gtgctcgctc | aggcagcggg | tcgcccgac | 1380 |
| gtggtagaag | cccaggaagc | cgcagcccgc | gaaggacaag | ctccagccgc | gctcggcgtc | 1440 |
| gtacatggcg | gggcggggc | gggggcgcgg | atccggatcg | gagtcgggat | cggggatcgg | 1500 |
| ctcgggtcct | gatccgcagc | agctccgccg | ggcgcccgca | agcg | | 1544 |

<210> SEQ ID NO 11
<211> LENGTH: 1495
<212> TYPE: DNA
<213> ORGANISM: Macaca fascicularis

<400> SEQUENCE: 11

| | | | | | |
|---|---|---|---|---|---|
| gctgctgcgg | atcaggaccc | gagccgatcc | ccgatcccga | ctccgatccg | gatccgcgcc | 60 |
| cccgccccg | ccccgccatg | tacgacgccg | agcgcggctg | gagcttgtcc | ttcgcgggct | 120 |
| gcggcttcct | gggcttctac | cacgtcgggg | cgacccggtg | cctgagcgag | cacgccccgc | 180 |
| acctcctccg | cgacgcgcgc | atgttgttcg | gcgcctcggc | cggggcgttg | cactgcgtcg | 240 |
| gcgtcctctc | cgggatcccg | ctggagcaga | ctctgcaggt | cctctcagat | cttgtccgga | 300 |
| aggccaggag | tcggaacatt | ggtatcttcc | atccatcctt | caacataggc | aagttcctcc | 360 |

```
gacaggatct ctacaaatac ctcccggcca atgtccacca gctcatctct ggcaaaatat      420
gcgtctcact caccagagtg tctgatgggg aaaacgttct ggtgtctgac tttcagtcca      480
aagacgaagt cgtggatgcc ttgatttgtt cctgcttcat ccctttctac agtggcctta      540
tccctccttc cttcagaggc gtgcgatatg tggatggagg agcgagtgac aacgtaccct      600
tcattgatgc caagacaacc atcaccgtgt cgcccttcta ggggagtac gacatctgcc       660 ctaaagtcaa gtccaccaac tttcttcatg tggacatcac caagctcagc ctacgcctct      720
gcacagggaa cctctacctt ctctcaagag cgtttgtccc cccggatctc aaggtgctgg      780
gagagatatg ccttcgagga tatttggacg cgttcaggtt cttggaagag aagggcatct      840
gcaacaagcc ccagcggggt ctgaagtcat cctcagaagg gatggattct gaggtcactg      900
cgcccggctg ggaaaacaca agtctggatt cttccccgga gccggctgcc ttggctatga      960
ggctggatgg agatgagctg ctagaccacc tgcgtctcag catcctgccc tgggatgaga    1020
gcatcctgga caccctgtcg cccgagctcg ctacagcagt gagtgaagca atgaaagaca    1080
aaggtggata catgagcaag atttgcaact tgctacccat taggataata tcttatgtga    1140
tgctgccctg taccctgcct gtggagtctg ccattgcgat tgtccagagt gtaagtcctt    1200
tgagctttct tgaaccagaa gtggcctcat tttgctttag agatttcaga tgggctcatc    1260
cttgtcctgt catcccagat ccacctgctg ggaagtcatc agattggaga tgatgttggc    1320
ggcttttgta acaaagggt ggtgttgtaa gctgttgtgt ctgcctgtgt gtgtgtttgt      1380
gtacttggtc ttatctctgc agactggtga catggcttcc agatatgccc gacgatgtgc    1440
agtggctgca gtgggtgacc tcacaggtct tcactcgagc gctgatgtgt ctgct         1495

<210> SEQ ID NO 12
<211> LENGTH: 1495
<212> TYPE: DNA
<213> ORGANISM: Macaca fascicularis

<400> SEQUENCE: 12
agcagacaca tcagcgctcg agtgaagacc tgtgaggtca cccactgcag ccactgcaca       60
tcgtcgggca tatctggaag ccatgtcacc agtctgcaga gataagacca agtacacaaa      120
cacacacaca ggcagacaca acagcttaca acaccaccct ttgtttacaa agccgccaa       180 catcatctcc aatctgatga cttcccagca ggtggatctg ggatgacagg acaaggatga      240
gcccatctga aatctctaaa gcaaaatgag gccacttctg gttcaagaaa gctcaaagga      300
cttacactct ggacaatcgc aatggcagac tccacaggca gggtacaggg cagcatcaca      360
taagatatta tcctaatggg tagcaagttg caaatcttgc tcatgtatcc acctttgtct      420
ttcattgctt cactcactgc tgtagcgagc tcgggcgaca gggtgtccag gatgctctca      480
tcccagggca ggatgctgag acgcaggtgg tctagcagct catctccatc agcctcata      540 gccaaggcag ccggctccgg ggaagaatcc agacttgtgt tttcccagcc gggcgcagtg      600
acctcagaat ccatcccttc tgaggatgac ttcagacccc gctgggcctt gttgcagatg      660
cccttctctt ccaagaacct gaacgcgtcc aaatatcctc gaaggcatat ctctcccagc      720
accttgagat ccgggggggac aaacgctctt gagagaaggt agaggttccc tgtgcagagg     780
cgtaggctga gcttggtgat gtccacatga agaaagttgg tggacttgac tttagggcag      840
atgtcgtact cccatagaa gggcgacacg gtgatggttg tcttggcatc aatgaagggt        900
acgttgtcac tcgctcctcc atccacatat cgcacgcctc tgaaggaagg agggataagg     960
```

```
ccactgtaga aagggatgaa gcaggaacaa atcaaggcat ccacgacttc gtctttggac    1020
tgaaagtcag acaccagaac gttttcccca tcagacactc tggtgagtga gacgcatatt    1080
ttgccagaga tgagctggtg gacattggcc gggaggtatt tgtagagatc ctgtcggagg    1140
aacttgccta tgttgaagga tggatggaag ataccaatgt tccgactcct ggccttccgg    1200
acaagatctg agaggacctg cagagtctgc tccagcggga tcccggagag gacgccgacg    1260
cagtgcaacg ccccggccga ggcgccgaac aacatgcgcg cgtcgcggag gaggtgcggg    1320
gcgtgctcgc tcaggcaccg ggtcgccccg acgtggtaga agcccaggaa gccgcagccc    1380
gcgaaggaca agctccagcc gcgctcggcg tcgtacatgg cggggcgggg gcggggcgc    1440 ggatccggat cggagtcggg atcggggatc ggctcgggtc ctgatccgca gcagc          1495
```

<210> SEQ ID NO 13
<211> LENGTH: 16
<212> TYPE: PRT
<213> ORGANISM: Unknown
<220> FEATURE:
<221> NAME/KEY: source
<223> OTHER INFORMATION: /note="Description of Unknown:
      hydrophobic MTS-containing sequence"

<400> SEQUENCE: 13

Ala Ala Val Ala Leu Leu Pro Ala Val Leu Leu Ala Leu Leu Ala Pro
1               5                   10                  15

<210> SEQ ID NO 14
<211> LENGTH: 11
<212> TYPE: PRT
<213> ORGANISM: Unknown
<220> FEATURE:
<221> NAME/KEY: source
<223> OTHER INFORMATION: /note="Description of Unknown:
      RFGF analogue sequence"

<400> SEQUENCE: 14

Ala Ala Leu Leu Pro Val Leu Leu Ala Ala Pro
1               5                   10

<210> SEQ ID NO 15
<211> LENGTH: 13
<212> TYPE: PRT
<213> ORGANISM: Human immunodeficiency virus

<400> SEQUENCE: 15

Gly Arg Lys Lys Arg Arg Gln Arg Arg Arg Pro Pro Gln
1               5                   10

<210> SEQ ID NO 16
<211> LENGTH: 16
<212> TYPE: PRT
<213> ORGANISM: Drosophila sp.

<400> SEQUENCE: 16

Arg Gln Ile Lys Ile Trp Phe Gln Asn Arg Arg Met Lys Trp Lys Lys
1               5                   10                  15

<210> SEQ ID NO 17
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17
cgacgucagc cccgccccc                                                    20

<210> SEQ ID NO 18
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 18
ggcauuccca gcgcgacguc                                                   20

<210> SEQ ID NO 19
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 19
gucucggcca gggcauuccc                                                   20

<210> SEQ ID NO 20
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 20
ugccucagug ucucggccag                                                   20

<210> SEQ ID NO 21
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 21
cgcucucuac ccugccucag                                                   20

<210> SEQ ID NO 22
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 22
gcgcccgcaa gcgcucucua                                                   20

<210> SEQ ID NO 23
<211> LENGTH: 20
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 23
cagcuccgcc cggcgcccgc                                               20

<210> SEQ ID NO 24
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 24
ugauccgcag cagcuccgcc                                               20

<210> SEQ ID NO 25
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25
gcucgggucc ugauccgcag                                               20

<210> SEQ ID NO 26
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 26
aucgggaauc ggcucggguc                                               20

<210> SEQ ID NO 27
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27 ucuggucgg gaucgggaau                                                20

<210> SEQ ID NO 28
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 28
cgcggguuag gaucuggguc                                               20
```

```
<210> SEQ ID NO 29
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 29
ggggcggggg cgcggguuag                                              20

<210> SEQ ID NO 30
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 30
ggcggcggcg gcggggcggg                                              20

<210> SEQ ID NO 31
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 31
ugcgucguac auggcggcgg                                              20

<210> SEQ ID NO 32
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 32
agccgcgcuc ugcgucguac                                              20

<210> SEQ ID NO 33
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 33
aggacaagcu ccagccgcgc                                              20

<210> SEQ ID NO 34
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 34
agcccgcgaa ggacaagcuc                                         20

<210> SEQ ID NO 35
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 35
caggaagccg cagcccgcga                                         20

<210> SEQ ID NO 36
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 36
cgugguagaa gcccaggaag                                         20

<210> SEQ ID NO 37
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 37
ucgccccgac gugguagaag                                         20

<210> SEQ ID NO 38
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 38
caggcagcgg gucgccccga                                         20

<210> SEQ ID NO 39
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 39
gggcgugcuc gcucaggcag                                         20

<210> SEQ ID NO 40
<211> LENGTH: 20

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 40
aggaggugcg gggcgugcuc                                              20

<210> SEQ ID NO 41
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 41
cgcgcgucgc ggaggaggug                                              20

<210> SEQ ID NO 42
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 42
aacaacaugc gcgcgucgcg                                              20

<210> SEQ ID NO 43
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 43
gccgaagcgc cgaacaacau                                              20

<210> SEQ ID NO 44
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 44
ugcaacgccc cggccgaagc                                              20

<210> SEQ ID NO 45
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 45
```
gccgacgcag ugcaacgccc                                              20

<210> SEQ ID NO 46
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 46
cggagaggac gccgacgcag                                              20

<210> SEQ ID NO 47
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 47
uccagcggga uaccggagag                                              20

<210> SEQ ID NO 48
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 48
agagucugcu ccagcgggau                                              20

<210> SEQ ID NO 49
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 49
agaggaccug cagagucugc                                              20

<210> SEQ ID NO 50
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 50
cgcacaagau cugagaggac                                              20

<210> SEQ ID NO 51
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 51
ccuggccuuc cgcacaagau                                                    20

<210> SEQ ID NO 52
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 52
uguuccgacu ccuggccuuc                                                    20

<210> SEQ ID NO 53
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 53
ggaagaugcc aauguuccga                                                    20

<210> SEQ ID NO 54
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 54
aaggauggau ggaagaugcc                                                    20

<210> SEQ ID NO 55
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 55
ugcuuaaguu gaaggaugga                                                    20

<210> SEQ ID NO 56
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 56
gucggaggaa cuugcuuaag                                                    20

<210> SEQ ID NO 57

```
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 57
gcagagaccc ugucggagga                                              20

<210> SEQ ID NO 58
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 58
cgggaggcau uugcagagac                                              20

<210> SEQ ID NO 59
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 59
ggacauuggc cgggaggcau                                              20

<210> SEQ ID NO 60
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 60
agaugagcug guggacauug                                              20

<210> SEQ ID NO 61
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 61
auuuugccgg agaugagcug                                              20

<210> SEQ ID NO 62
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 62
```
agagaugccu auuuugccgg                                              20

<210> SEQ ID NO 63
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 63
acacucuggu aagagagaug                                              20

<210> SEQ ID NO 64
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 64
ccccaucaga cacucuggua                                              20

<210> SEQ ID NO 65
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 65
accagaacgu uuuccccauc                                              20

<210> SEQ ID NO 66
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 66
aagucagaca ccagaacguu                                              20

<210> SEQ ID NO 67
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 67
cuuuggaccg aaagucagac                                              20

<210> SEQ ID NO 68
<211> LENGTH: 20
<212> TYPE: RNA
<213> ORGANISM: Artificial Sequence
<220> FEATURE:

-continued

```
<221> NAME/KEY: source
<223> OTHER INFORMATION: /note="Description of Artificial Sequence:
      Synthetic oligonucleotide"

<400> SEQUENCE: 68
ccacgacuuc gucuuuggac                                                  20

<210> SEQ ID NO 69
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 69
accaaggcau ccacgacuuc                                                  20

<210> SEQ ID NO 70
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 70
aagcaggaac auaccaaggc                                                  20

<210> SEQ ID NO 71
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 71
agaaggggau gaagcaggaa                                                  20

<210> SEQ ID NO 72
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 72
aggccacugu agaaggggau                                                  20

<210> SEQ ID NO 73
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 73
aaggagggau aaggccacug                                                  20
```

```
<210> SEQ ID NO 74
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 74
cgccucugaa ggaaggaggg                                              20

<210> SEQ ID NO 75
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 75
acauaucgca cgccucugaa                                              20

<210> SEQ ID NO 76
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 76
acuccuccau ccacauaucg                                              20

<210> SEQ ID NO 77
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 77
acguugucac ucacuccucc                                              20

<210> SEQ ID NO 78
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 78
aaugaagggu acguugucac                                              20

<210> SEQ ID NO 79
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 79
guuuuggcau caaugaaggg                                              20

<210> SEQ ID NO 80
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 80
ggugaugguu guuuuggcau                                              20

<210> SEQ ID NO 81
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 81
agaaggggga cacggugaug                                              20

<210> SEQ ID NO 82
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 82
acuccccaua gaaggggac                                               20

<210> SEQ ID NO 83
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 83
gcagaugucg uacuccccau                                              20

<210> SEQ ID NO 84
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 84
acuugacuuu agggcagaug                                              20

<210> SEQ ID NO 85
<211> LENGTH: 20
<212> TYPE: RNA
<213> ORGANISM: Artificial Sequence
```

-continued

```
<220> FEATURE:
<221> NAME/KEY: source
<223> OTHER INFORMATION: /note="Description of Artificial Sequence:
      Synthetic oligonucleotide"

<400> SEQUENCE: 85
aaaguucgug gacuugacuu                                               20

<210> SEQ ID NO 86
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 86
ccacaugaag aaaguucgug                                               20

<210> SEQ ID NO 87
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 87
uuggugaugu ccacaugaag                                               20

<210> SEQ ID NO 88
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 88
cguagacuga gcuuggugau                                               20

<210> SEQ ID NO 89
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 89
cugugcagag gcguagacug                                               20

<210> SEQ ID NO 90
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 90
guagagguuc ccugugcaga                                               20
```

```
<210> SEQ ID NO 91
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 91
ucgagagaag guagagguuc                                          20

<210> SEQ ID NO 92
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 92
gggacaaaag cucucgagag                                          20

<210> SEQ ID NO 93
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 93
ugagauccgg ggggacaaaa                                          20

<210> SEQ ID NO 94
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 94
ccagcaccuu gagauccggg                                          20

<210> SEQ ID NO 95
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 95
aggcauaucu cucccagcac                                          20

<210> SEQ ID NO 96
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

<400> SEQUENCE: 96
uauccucgaa ggcauaucuc                                                    20

<210> SEQ ID NO 97
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 97
gaaugcaucc aaauauccuc                                                    20

<210> SEQ ID NO 98
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 98
uccaagaacc ugaaugcauc                                                    20

<210> SEQ ID NO 99
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 99
ugcccuucuc uuccaagaac                                                    20

<210> SEQ ID NO 100
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 100
uguugcagau gcccuucucu                                                    20

<210> SEQ ID NO 101
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 101
cuggcugggg ccuguugcag                                                    20

<210> SEQ ID NO 102
<211> LENGTH: 20
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 102
augacuucag gccuggcugg                                               20

<210> SEQ ID NO 103
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 103
cccuucugag gaugacuuca                                               20

<210> SEQ ID NO 104
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 104
caggauccau cccuucugag                                               20

<210> SEQ ID NO 105
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 105
auggcgaccu caggauccau                                               20

<210> SEQ ID NO 106
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 106
ugcccagcug ggcauggcga                                               20

<210> SEQ ID NO 107
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 107
acucauguuu gcccagcugg                                               20
```

<210> SEQ ID NO 108
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 108
ggaagaaucc agacucaugu                                                    20

<210> SEQ ID NO 109
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 109
agccgacucc ggggaagaau                                                    20

<210> SEQ ID NO 110
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 110
acagccaagg cagccgacuc                                                    20

<210> SEQ ID NO 111
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 111
ccuccagccu cacagccaag                                                    20

<210> SEQ ID NO 112
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 112
gcucaucucc cuccagccuc                                                    20

<210> SEQ ID NO 113
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:

```
        Synthetic oligonucleotide"

<400> SEQUENCE: 113
agguggucua gcagcucauc                                                    20

<210> SEQ ID NO 114
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 114
cugagacgca gguggucuag                                                    20

<210> SEQ ID NO 115
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 115
agggcaggau gcugagacgc                                                    20

<210> SEQ ID NO 116
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 116
gcucucaucc cagggcagga                                                    20

<210> SEQ ID NO 117
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 117
guguccagga ugcucucauc                                                    20

<210> SEQ ID NO 118
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 118
cugggcgaga ggguguccag                                                    20

<210> SEQ ID NO 119
<211> LENGTH: 20
```

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 119
cuguagcgag ccugggcgag                                              20

<210> SEQ ID NO 120
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 120
ucacucagug cuguagcgag                                              20

<210> SEQ ID NO 121
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 121
cuuucauuuc uucacucagu                                              20

<210> SEQ ID NO 122
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 122
auccaccuuu gucuuucauu                                              20

<210> SEQ ID NO 123
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 123
uugcucaugu auccaccuuu                                              20

<210> SEQ ID NO 124
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 124
```
aguugcaaau cuugcucaug                                              20

<210> SEQ ID NO 125
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 125
aauggguagc aaguugcaaa                                              20

<210> SEQ ID NO 126
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 126
agacauuauc cuaaugggua                                              20

<210> SEQ ID NO 127
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 127
agcauuacau aagacauuau                                              20

<210> SEQ ID NO 128
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 128
aggguacagg gcagcauuac                                              20

<210> SEQ ID NO 129
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 129
auuccacagg caggguacag                                              20

<210> SEQ ID NO 130
<211> LENGTH: 20
<212> TYPE: RNA
<213> ORGANISM: Artificial Sequence
<220> FEATURE:
<221> NAME/KEY: source -continued
<223> OTHER INFORMATION: /note="Description of Artificial Sequence:
      Synthetic oligonucleotide"

<400> SEQUENCE: 130
cgcaauggca gauuccacag                                              20

<210> SEQ ID NO 131
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 131
cuggacaauc gcaauggcag                                              20

<210> SEQ ID NO 132
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 132
gucaccaguc ucuggacaau                                              20

<210> SEQ ID NO 133
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 133
aucuggaagc caugucacca                                              20

<210> SEQ ID NO 134
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 134
ucgucgggca uaucuggaag                                              20

<210> SEQ ID NO 135
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 135
cacaggacau cgucgggcau                                              20

<210> SEQ ID NO 136

```
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 136
acccacugca accacaggac                                                    20

<210> SEQ ID NO 137
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 137
accugugagg ucacccacug                                                    20

<210> SEQ ID NO 138
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 138
cucgagugaa caccugugag                                                    20

<210> SEQ ID NO 139
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 139
acaucagcac ucgagugaac                                                    20

<210> SEQ ID NO 140
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 140
gcggggagca gacacaucag                                                    20

<210> SEQ ID NO 141
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 141
```

```
gaccuggagg cggggagcag                                              20

<210> SEQ ID NO 142
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 142
acuggcauuu gggaccugga                                              20

<210> SEQ ID NO 143
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 143
uuggcugcuc acuggcauuu                                              20

<210> SEQ ID NO 144
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 144
auggggaggc cuguuggcug                                              20

<210> SEQ ID NO 145
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 145
ucaggugugc auggggaggc                                              20

<210> SEQ ID NO 146
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 146
ggccaguccu gcucaggugu                                              20

<210> SEQ ID NO 147
<211> LENGTH: 20
<212> TYPE: RNA
<213> ORGANISM: Artificial Sequence
<220> FEATURE:
```

<221> NAME/KEY: source
<223> OTHER INFORMATION: /note="Description of Artificial Sequence:
      Synthetic oligonucleotide"

<400> SEQUENCE: 147
guguccagca gggccagucc                                                   20

<210> SEQ ID NO 148
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 148
gggagcaggg aguccagcag                                                   20

<210> SEQ ID NO 149
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 149
acagcccuug ggggagcagg                                                   20

<210> SEQ ID NO 150
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 150
gucucugcug gacagcccuu                                                   20

<210> SEQ ID NO 151
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 151
gccucugcuu uggucucugc                                                   20

<210> SEQ ID NO 152
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 152
ccgcggggug gccucugcuu                                                   20

```
<210> SEQ ID NO 153
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 153
accugaggau ggaccgcggg                                                    20

<210> SEQ ID NO 154
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 154
guucaggcug gaccugagga                                                    20

<210> SEQ ID NO 155
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 155
ccaagaagaa guucaggcug                                                    20

<210> SEQ ID NO 156
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 156
guacuuuauu gcccaagaag                                                    20

<210> SEQ ID NO 157
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 157
agcaccagca gguacuuuau                                                    20

<210> SEQ ID NO 158
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 158
gagagccccu cagcaccagc                                               20

<210> SEQ ID NO 159
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 159
ggaaaggugg agagccccuc                                               20

<210> SEQ ID NO 160
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 160
agugaaaaac ugggaaaggu                                               20

<210> SEQ ID NO 161
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 161
acucuucucu agugaaaaac                                               20

<210> SEQ ID NO 162
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 162
aagugacuca cagacucuuc                                               20

<210> SEQ ID NO 163
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 163
cucgccuccu caagugacuc                                               20

<210> SEQ ID NO 164
<211> LENGTH: 20
<212> TYPE: RNA
<213> ORGANISM: Artificial Sequence
```

-continued

```
<220> FEATURE:
<221> NAME/KEY: source
<223> OTHER INFORMATION: /note="Description of Artificial Sequence:
      Synthetic oligonucleotide"

<400> SEQUENCE: 164
ucugcuagac ucgccuccuc                                                    20

<210> SEQ ID NO 165
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 165
accucugaaa gaaucugcua                                                    20

<210> SEQ ID NO 166
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 166
aaacuuuagc accucugaaa                                                    20

<210> SEQ ID NO 167
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 167
acaaagaugg gaaacuuuag                                                    20

<210> SEQ ID NO 168
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 168
ggagguagcu gcacaaagau                                                    20

<210> SEQ ID NO 169
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 169
cagcaaugcg gagguagcug                                                    20
```

```
<210> SEQ ID NO 170
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 170
aggggucacu acacagcaau                                                  20

<210> SEQ ID NO 171
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 171
acgucacagg cagggggucac                                                 20

<210> SEQ ID NO 172
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 172
ugggauccuc cacgucacag                                                  20

<210> SEQ ID NO 173
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 173
gcucagaggc ugggauccuc                                                  20

<210> SEQ ID NO 174
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 174
aaaccaacuc agcucagagg                                                  20

<210> SEQ ID NO 175
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 175
uagcuuuuca uaaaaccaac                                          20

<210> SEQ ID NO 176
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 176
agguugcuuc cuagcuuuuc                                          20

<210> SEQ ID NO 177
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 177
acaggcgaaa gguugcuucc                                          20

<210> SEQ ID NO 178
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 178
uggaccgcug cacaggcgaa                                          20

<210> SEQ ID NO 179
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 179
agaguuaagu gcuggaccgc                                          20

<210> SEQ ID NO 180
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 180
gcugauguau uagaguuaag                                          20

<210> SEQ ID NO 181
<211> LENGTH: 20
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 181
auuaacgcau gcugauguau                                                    20

<210> SEQ ID NO 182
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 182
ccaaccagcu gaauuaacgc                                                    20

<210> SEQ ID NO 183
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 183
ggugucauuu cccaaccagc                                                    20

<210> SEQ ID NO 184
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 184
ugggcuuccu ggugucauuu                                                    20

<210> SEQ ID NO 185
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 185
gacccucugc acugggcuuc                                                    20

<210> SEQ ID NO 186
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 186
agucaguaag ggacccucug                                                    20
```

-continued

<210> SEQ ID NO 187
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 187
gccacgaaac agucaguaag                                                    20

<210> SEQ ID NO 188
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 188
ccauuaauag ggccacgaaa                                                    20

<210> SEQ ID NO 189
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 189
ggaacagucu gaccauuaau                                                    20

<210> SEQ ID NO 190
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 190
accucaugcu ggaacagucu                                                    20

<210> SEQ ID NO 191
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 191
ugucauucua agaaccucau                                                    20

<210> SEQ ID NO 192
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 192
ccaaacaccu gucauucuaa                                              20

<210> SEQ ID NO 193
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 193
gcccccaccc auccaaacac                                              20

<210> SEQ ID NO 194
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 194
ccccaucaca aggcccccac                                              20

<210> SEQ ID NO 195
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 195
cagccuaccc cccaucacaa                                              20

<210> SEQ ID NO 196
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 196
ucacacaugg gccagccuac                                              20

<210> SEQ ID NO 197
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 197
caccccacaa gaucacacau                                              20

<210> SEQ ID NO 198
<211> LENGTH: 20

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 198
ucuucccucc accccacaag                                                     20

<210> SEQ ID NO 199
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 199
ucaugcuauu cucuucccuc                                                     20

<210> SEQ ID NO 200
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 200
gggaaguggg aucaugcuau                                                     20

<210> SEQ ID NO 201
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 201
ucccacagca ugggaagug                                                      20

<210> SEQ ID NO 202
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 202
acugcacccc uucccacagc                                                     20

<210> SEQ ID NO 203
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 203
```

-continued ucuuggggac gaacugcacc                               20

<210> SEQ ID NO 204
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 204
gcagugucgu ucuuggggac                               20

<210> SEQ ID NO 205
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 205
accaccugac aggcaguguc                               20

<210> SEQ ID NO 206
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 206
aucuuugcag accaccugac                               20

<210> SEQ ID NO 207
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 207
caagguuauc aucuuugcag                               20

<210> SEQ ID NO 208
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 208
guuuuuagua gucaagguua                               20

<210> SEQ ID NO 209
<211> LENGTH: 20
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 209
cgccauggag acguuuuag                                                    20

<210> SEQ ID NO 210
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 210
cuuguuaccc ccgccaugga                                                   20

<210> SEQ ID NO 211
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 211
agauuaucau cuuguuaccc                                                   20

<210> SEQ ID NO 212
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 212
aaaauuaagu agauuaucau                                                   20

<210> SEQ ID NO 213
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 213
aaagguguuc uaaaauuaag                                                   20

<210> SEQ ID NO 214
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 214
aguuagguga aaaagguguu                                                   20

<210> SEQ ID NO 215
```

```
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 215
aaacauuauu uuaguuaggu                                              20

<210> SEQ ID NO 216
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 216
aaaacucuuu aaacauuauu                                              20

<210> SEQ ID NO 217
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 217
acauuuuuau acaaaacucu                                              20

<210> SEQ ID NO 218
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 218
aacgcuuccu uacauuuuua                                              20

<210> SEQ ID NO 219
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 219
aacagguaac aacgcuuccu                                              20

<210> SEQ ID NO 220
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 220
```

```
auacaaaauu caacagguaa                                          20

<210> SEQ ID NO 221
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 221
acugauucac auaauacaaa                                          20

<210> SEQ ID NO 222
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 222
acuaacaucu cacugauuca                                          20

<210> SEQ ID NO 223
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 223
aggcuuauuc uacuaacauc                                          20

<210> SEQ ID NO 224
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 224
uuuuuuuuuu aaggcuuauu                                          20

<210> SEQ ID NO 225
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 225
aaccgauuuu uuuuuuuuua                                          20

<210> SEQ ID NO 226
<211> LENGTH: 20
<212> TYPE: RNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 226
ccacugcacc caaccgauuu                                                20

<210> SEQ ID NO 227
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 227
acagccgugu gccacugcac                                                20

<210> SEQ ID NO 228
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 228
aagugcuggg auuacagccg                                                20

<210> SEQ ID NO 229
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 229
uuggccuccc aaagugcugg                                                20

<210> SEQ ID NO 230
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 230
aucugccaac cuuggccucc                                                20

<210> SEQ ID NO 231
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 231
accucaggug aucugccaac                                                20
```

```
<210> SEQ ID NO 232
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 232
cuugaacucc ugaccucagg                                              20

<210> SEQ ID NO 233
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 233
ccagacuggu cuugaacucc                                              20

<210> SEQ ID NO 234
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 234
ugcuauguug gccagacugg                                              20

<210> SEQ ID NO 235
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 235
gacaggguuu ugcuauguug                                              20

<210> SEQ ID NO 236
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 236
auuuuuagua gagacagggu                                              20

<210> SEQ ID NO 237
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 237
auaauuuuug uauuuuuagu                                               20

<210> SEQ ID NO 238
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 238
accaugccca gauaauuuuu                                               20

<210> SEQ ID NO 239
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 239
aggcaugcac caccaugccc                                               20

<210> SEQ ID NO 240
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 240
agcugggauu acaggcaugc                                               20

<210> SEQ ID NO 241
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 241
cuuccgaaua gcugggauua                                               20

<210> SEQ ID NO 242
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 242
ccugccucag ccuuccgaau                                               20

<210> SEQ ID NO 243
<211> LENGTH: 20
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 243
ucaagugauu cuccugccuc                                               20

<210> SEQ ID NO 244
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 244
ccuccugggu ucaagugauu                                               20

<210> SEQ ID NO 245
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 245
ccgcaaccuc cgccuccugg                                               20

<210> SEQ ID NO 246
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 246
aaucucagcu caccgcaacc                                               20

<210> SEQ ID NO 247
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 247
ugaaauggug caaucucagc                                               20

<210> SEQ ID NO 248
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 248
aggcuggaau gaaauggugc                                               20
```

<210> SEQ ID NO 249
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 249
acucauguug cccaggcugg                                               20

<210> SEQ ID NO 250
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 250
ucagacuuuc acucauguug                                               20

<210> SEQ ID NO 251
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 251
uuuuuuuuug agucagacuu                                               20

<210> SEQ ID NO 252
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 252
uuuuaaauuu uuuuuuuuug                                               20

<210> SEQ ID NO 253
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 253
gauuauuuug uuuuuuaaau                                               20

<210> SEQ ID NO 254
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 254
cugcacacua gauuauuuug                                           20

<210> SEQ ID NO 255
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 255
aggugaaugc ccugcacacu                                           20

<210> SEQ ID NO 256
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 256
uggggggcug aggugaaugc                                           20

<210> SEQ ID NO 257
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 257
cuuggcuccu gccuggggg                                            20

<210> SEQ ID NO 258
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 258
ccugcugugc uuggcuccug                                           20

<210> SEQ ID NO 259
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 259
aggcggaagc uccugcugug                                           20

<210> SEQ ID NO 260
<211> LENGTH: 20
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 260
caguggagag gaggcggaag                                                    20

<210> SEQ ID NO 261
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 261
aguugugugc uccaguggag                                                    20

<210> SEQ ID NO 262
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 262
agccagguuc aaguugugug                                                    20

<210> SEQ ID NO 263
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 263
gcagaaaaua agccagguuc                                                    20

<210> SEQ ID NO 264
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 264
ggggcugguc ccugcagaaa                                                    20

<210> SEQ ID NO 265
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 265
acugaccaug ugggcuggu                                                     20
```

<210> SEQ ID NO 266
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 266
ggagaaacuc acugaccaug                                                   20

<210> SEQ ID NO 267
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 267
cgccacacau ggggagaaac                                                   20

<210> SEQ ID NO 268
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 268
acucucucau cgccacacau                                                   20

<210> SEQ ID NO 269
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 269
cuuuauuucu acacucucuc                                                   20

<210> SEQ ID NO 270
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 270
cgacgtcagc cccgcccccc                                                   20

<210> SEQ ID NO 271
<211> LENGTH: 20
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 271
ggcautccca gcgcgacguc                                              20

<210> SEQ ID NO 272
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 272
gucucggcca gggcauuccc                                              20

<210> SEQ ID NO 273
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 273
ugccucagtg tctcggccag                                              20

<210> SEQ ID NO 274
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 274
cgcuctctac cctgccucag                                              20

<210> SEQ ID NO 275
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
```

```
<223> OTHER INFORMATION: /note="Description of Combined DNA/RNA
      Molecule: Synthetic oligonucleotide"

<400> SEQUENCE: 275
gcgcccgcaa gcgctcucua                                                    20

<210> SEQ ID NO 276
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 276
cagcuccgcc cggcgcccgc                                                    20

<210> SEQ ID NO 277
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 277
ugauccgcag cagctccgcc                                                    20

<210> SEQ ID NO 278
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 278
gcucgggtcc tgatccgcag                                                    20

<210> SEQ ID NO 279
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 279
aucgggaatc ggctcggguc                                                    20
```

```
<210> SEQ ID NO 280
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 280
ucugggtcgg gatcgggaau                                              20

<210> SEQ ID NO 281
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 281
cgcgggttag gatctggguc                                              20

<210> SEQ ID NO 282
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 282
ggggcggggg cgcggguuag                                              20

<210> SEQ ID NO 283
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 283
ggcggcggcg gcggggcggg                                              20

<210> SEQ ID NO 284
<211> LENGTH: 20
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 284
ugcgucgtac atggcggcgg                                                    20

<210> SEQ ID NO 285
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 285
agccgcgctc tgcgtcguac                                                    20

<210> SEQ ID NO 286
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 286
aggacaagct ccagccgcgc                                                    20

<210> SEQ ID NO 287
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 287
agcccgcgaa ggacaagcuc                                                    20

<210> SEQ ID NO 288
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

```
<400> SEQUENCE: 288
caggaagccg cagcccgcga                                              20

<210> SEQ ID NO 289
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 289
cguggtagaa gcccaggaag                                              20

<210> SEQ ID NO 290
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 290
ucgccccgac gtggtagaag                                              20

<210> SEQ ID NO 291
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 291
caggcagcgg gtcgccccga                                              20

<210> SEQ ID NO 292
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 292
gggcgtgctc gctcaggcag                                              20

<210> SEQ ID NO 293
<211> LENGTH: 20
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 293
aggaggtgcg gggcgugcuc                                              20

<210> SEQ ID NO 294
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 294
cgcgcgtcgc ggaggaggug                                              20

<210> SEQ ID NO 295
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 295
aacaacatgc gcgcgucgcg                                              20

<210> SEQ ID NO 296
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 296
gccgaagcgc cgaacaacau                                              20

<210> SEQ ID NO 297
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

-continued

```
<221> NAME/KEY: source
<223> OTHER INFORMATION: /note="Description of Combined DNA/RNA
      Molecule: Synthetic oligonucleotide"

<400> SEQUENCE: 297
ugcaacgccc cggccgaagc                                                    20

<210> SEQ ID NO 298
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 298
gccgacgcag tgcaacgccc                                                    20

<210> SEQ ID NO 299
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 299
cggagaggac gccgacgcag                                                    20

<210> SEQ ID NO 300
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 300
uccagcggga taccggagag                                                    20

<210> SEQ ID NO 301
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 301
agaguctgct ccagcgggau                                                    20
```

<210> SEQ ID NO 302
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 302
agaggacctg cagagucugc                                         20

<210> SEQ ID NO 303
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 303
cgcacaagat ctgagaggac                                         20

<210> SEQ ID NO 304
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 304
ccuggccttc cgcacaagau                                         20

<210> SEQ ID NO 305
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 305
uguuccgact cctggccuuc                                         20

<210> SEQ ID NO 306
<211> LENGTH: 20
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 306
ggaagatgcc aatgtuccga                                           20

<210> SEQ ID NO 307
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 307
aaggatggat ggaagaugcc                                           20

<210> SEQ ID NO 308
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 308
ugcuuaagtt gaaggaugga                                           20

<210> SEQ ID NO 309
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 309
gucggaggaa cttgcuuaag                                           20

<210> SEQ ID NO 310
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

<400> SEQUENCE: 310
gcagagaccc tgtcggagga                                          20

<210> SEQ ID NO 311
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 311
cgggaggcat ttgcagagac                                          20

<210> SEQ ID NO 312
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 312
ggacattggc cgggaggcau                                          20

<210> SEQ ID NO 313
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 313
agaugagctg gtggacauug                                          20

<210> SEQ ID NO 314
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 314
auuuugccgg agatgagcug                                          20

<210> SEQ ID NO 315

-continued

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 315
agagatgcct attttgccgg                                             20

<210> SEQ ID NO 316
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 316
acacuctggt aagagagaug                                             20

<210> SEQ ID NO 317
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 317
ccccatcaga cactcuggua                                             20

<210> SEQ ID NO 318
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 318
accagaacgt tttccccauc                                             20

<210> SEQ ID NO 319
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<220> FEATURE:
<221> NAME/KEY: source
<223> OTHER INFORMATION: /note="Description of Combined DNA/RNA
      Molecule: Synthetic oligonucleotide"

<400> SEQUENCE: 319
aagucagaca ccagaacguu                                              20

<210> SEQ ID NO 320
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 320
cuuuggaccg aaagtcagac                                              20

<210> SEQ ID NO 321
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 321
ccacgacttc gtcttuggac                                              20

<210> SEQ ID NO 322
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 322
accaaggcat ccacgacuuc                                              20

<210> SEQ ID NO 323
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 323
```

-continued aagcaggaac ataccaaggc                                             20

<210> SEQ ID NO 324
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 324 agaagggat gaagcaggaa                                              20

<210> SEQ ID NO 325
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 325
aggccactgt agaaggggau                                             20

<210> SEQ ID NO 326
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 326
aaggagggat aaggccacug                                             20

<210> SEQ ID NO 327
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 327
cgccuctgaa ggaaggaggg                                             20

<210> SEQ ID NO 328
<211> LENGTH: 20
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 328
acauatcgca cgcctcugaa                                               20

<210> SEQ ID NO 329
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 329
acucctccat ccacauaucg                                               20

<210> SEQ ID NO 330
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 330
acguugtcac tcactccucc                                               20

<210> SEQ ID NO 331
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 331
aaugaagggt acgttgucac                                               20

<210> SEQ ID NO 332
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
```

Molecule: Synthetic oligonucleotide"

<400> SEQUENCE: 332
guuuuggcat caatgaaggg                                                     20

<210> SEQ ID NO 333
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 333
ggugatggtt gttttggcau                                                     20

<210> SEQ ID NO 334
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 334
agaaggggga cacggugaug                                                     20

<210> SEQ ID NO 335
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 335
acuccccata gaaggggggac                                                    20

<210> SEQ ID NO 336
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 336
gcagatgtcg tactccccau                                                     20

```
<210> SEQ ID NO 337
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 337
acuugacttt agggcagaug                                               20

<210> SEQ ID NO 338
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 338
aaagutcgtg gacttgacuu                                               20

<210> SEQ ID NO 339
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 339
ccacatgaag aaagtucgug                                               20

<210> SEQ ID NO 340
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 340
uuggugatgt ccacaugaag                                               20

<210> SEQ ID NO 341
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 341
cguagactga gcttggugau                                                    20

<210> SEQ ID NO 342
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 342
cugugcagag gcgtagacug                                                    20

<210> SEQ ID NO 343
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 343
guagaggttc cctgtgcaga                                                    20

<210> SEQ ID NO 344
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 344
ucgagagaag gtagagguuc                                                    20

<210> SEQ ID NO 345
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 345
gggacaaaag ctctcgagag                                      20

<210> SEQ ID NO 346
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 346
ugagatccgg ggggacaaaa                                      20

<210> SEQ ID NO 347
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 347
ccagcacctt gagatccggg                                      20

<210> SEQ ID NO 348
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 348
aggcatatct ctcccagcac                                      20

<210> SEQ ID NO 349
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 349
uaucctcgaa ggcataucuc                                      20

<210> SEQ ID NO 350
<211> LENGTH: 20
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 350
gaaugcaucc aaauauccuc                                              20

<210> SEQ ID NO 351
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 351
uccaagaacc tgaatgcauc                                              20

<210> SEQ ID NO 352
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 352
ugcccttctc ttccaagaac                                              20

<210> SEQ ID NO 353
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 353
uguugcagat gccctucucu                                              20

<210> SEQ ID NO 354
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
```

```
<223> OTHER INFORMATION: /note="Description of Combined DNA/RNA
      Molecule: Synthetic oligonucleotide"

<400> SEQUENCE: 354
cuggctgggg cctgtugcag                                                      20

<210> SEQ ID NO 355
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 355
augacttcag gcctggcugg                                                      20

<210> SEQ ID NO 356
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 356
cccuuctgag gatgacuuca                                                      20

<210> SEQ ID NO 357
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 357
caggatccat cccttcugag                                                      20

<210> SEQ ID NO 358
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 358
auggcgacct caggauccau                                                      20
```

```
<210> SEQ ID NO 359
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 359
ugcccagctg ggcatggcga                                         20

<210> SEQ ID NO 360
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 360
acucatgttt gcccagcugg                                         20

<210> SEQ ID NO 361
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 361
ggaagaatcc agactcaugu                                         20

<210> SEQ ID NO 362
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 362
agccgactcc ggggaagaau                                         20

<210> SEQ ID NO 363
<211> LENGTH: 20
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 363
acagccaagg cagccgacuc                                                  20

<210> SEQ ID NO 364
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 364
ccuccagcct cacagccaag                                                  20

<210> SEQ ID NO 365
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 365
gcucatctcc ctccagccuc                                                  20

<210> SEQ ID NO 366
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 366
agguggtcta gcagcucauc                                                  20

<210> SEQ ID NO 367
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

<400> SEQUENCE: 367
cugagacgca ggtggucuag                                           20

<210> SEQ ID NO 368
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 368
agggcaggat gctgagacgc                                           20

<210> SEQ ID NO 369
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 369
gcucucatcc cagggcagga                                           20

<210> SEQ ID NO 370
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 370
guguccagga tgctcucauc                                           20

<210> SEQ ID NO 371
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 371
cugggcgaga gggtguccag                                           20

<210> SEQ ID NO 372
<211> LENGTH: 20

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 372
cuguagcgag cctgggcgag                                               20

<210> SEQ ID NO 373
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 373
ucacucagtg ctgtagcgag                                               20

<210> SEQ ID NO 374
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 374
cuuucatttc ttcacucagu                                               20

<210> SEQ ID NO 375
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 375
auccaccttt gtcttucauu                                               20

<210> SEQ ID NO 376
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

```
<221> NAME/KEY: source
<223> OTHER INFORMATION: /note="Description of Combined DNA/RNA
      Molecule: Synthetic oligonucleotide"

<400> SEQUENCE: 376
uugcucatgt atccaccuuu                                              20

<210> SEQ ID NO 377
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 377
aguugcaaat cttgcucaug                                              20

<210> SEQ ID NO 378
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 378
aaugggtagc aagttgcaaa                                              20

<210> SEQ ID NO 379
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 379
agacattatc ctaatgggua                                              20

<210> SEQ ID NO 380
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 380
agcautacat aagacauuau                                              20
```

```
<210> SEQ ID NO 381
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 381
aggguacagg gcagcauuac                                               20

<210> SEQ ID NO 382
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 382
auuccacagg caggguacag                                               20

<210> SEQ ID NO 383
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 383
cgcaatggca gattccacag                                               20

<210> SEQ ID NO 384
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 384
cuggacaatc gcaatggcag                                               20

<210> SEQ ID NO 385
<211> LENGTH: 20
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 385
gucaccagtc tctggacaau                                               20

<210> SEQ ID NO 386
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 386
aucuggaagc catgtcacca                                               20

<210> SEQ ID NO 387
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 387
ucgucgggca tatctggaag                                               20

<210> SEQ ID NO 388
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 388
cacaggacat cgtcgggcau                                               20

<210> SEQ ID NO 389
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

-continued

<400> SEQUENCE: 389
acccactgca accacaggac                                              20

<210> SEQ ID NO 390
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 390
accugtgagg tcacccacug                                              20

<210> SEQ ID NO 391
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 391
cucgagtgaa cacctgugag                                              20

<210> SEQ ID NO 392
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 392
acaucagcac tcgagugaac                                              20

<210> SEQ ID NO 393
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 393
gcggggagca gacacaucag                                              20

<210> SEQ ID NO 394

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 394
gaccuggagg cggggagcag                                              20

<210> SEQ ID NO 395
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 395
acuggcattt gggaccugga                                              20

<210> SEQ ID NO 396
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 396
uuggctgctc actggcauuu                                              20

<210> SEQ ID NO 397
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 397 augggggaggc ctgttggcug                                             20

<210> SEQ ID NO 398
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

```
<220> FEATURE:
<221> NAME/KEY: source
<223> OTHER INFORMATION: /note="Description of Combined DNA/RNA
      Molecule: Synthetic oligonucleotide"

<400> SEQUENCE: 398
ucaggtgtgc atggggaggc                                              20

<210> SEQ ID NO 399
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 399
ggccagtcct gctcaggugu                                              20

<210> SEQ ID NO 400
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 400
gaguccagca gggccagucc                                              20

<210> SEQ ID NO 401
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 401
gggagcaggg agtccagcag                                              20

<210> SEQ ID NO 402
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 402
```
acagcccttg ggggagcagg         20

<210> SEQ ID NO 403
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 403
gucuctgctg gacagcccuu         20

<210> SEQ ID NO 404
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 404
gccuctgctt tggtcucugc         20

<210> SEQ ID NO 405
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 405
ccgcggggtg gcctcugcuu         20

<210> SEQ ID NO 406
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 406
accugaggat ggaccgcggg         20

<210> SEQ ID NO 407
<211> LENGTH: 20
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 407
guucaggcug gaccugagga                                              20

<210> SEQ ID NO 408
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 408
ccaagaagaa guucaggcug                                              20

<210> SEQ ID NO 409
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 409
guacuuuauu gcccaagaag                                              20

<210> SEQ ID NO 410
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 410
agcaccagca ggtacuuuau                                              20

<210> SEQ ID NO 411
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
```

Molecule: Synthetic oligonucleotide"

<400> SEQUENCE: 411
gagagcccct cagcaccagc                                             20

<210> SEQ ID NO 412
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 412
ggaaaggtgg agagccccuc                                             20

<210> SEQ ID NO 413
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 413
agugaaaaac tgggaaaggu                                             20

<210> SEQ ID NO 414
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 414
acucutctct agtgaaaaac                                             20

<210> SEQ ID NO 415
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 415
aagugactca cagacucuuc                                             20

```
<210> SEQ ID NO 416
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 416
cucgcctcct caagtgacuc                                                20

<210> SEQ ID NO 417
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 417
ucugctagac tcgccuccuc                                                20

<210> SEQ ID NO 418
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 418
accuctgaaa gaatcugcua                                                20

<210> SEQ ID NO 419
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 419
aaacuttagc acctcugaaa                                                20

<210> SEQ ID NO 420
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

```
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 420
acaaagatgg gaaacuuuag                                                     20

<210> SEQ ID NO 421
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 421
ggaggtagct gcacaaagau                                                     20

<210> SEQ ID NO 422
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 422
cagcaatgcg gaggtagcug                                                     20

<210> SEQ ID NO 423
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 423
aggggtcact acacagcaau                                                     20

<210> SEQ ID NO 424
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 424
```

-continued acgucacagg cagggggucac 20

<210> SEQ ID NO 425
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 425
ugggauccuc cacgucacag 20

<210> SEQ ID NO 426
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 426
gcucagaggc ugggauccuc 20

<210> SEQ ID NO 427
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 427
aaaccaacuc agcucagagg 20

<210> SEQ ID NO 428
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 428
uagcuuuuca uaaaccaac 20

<210> SEQ ID NO 429
<211> LENGTH: 20
<212> TYPE: DNA

-continued

<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 429
agguugcuuc ctagcuuuuc                                                    20

<210> SEQ ID NO 430
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 430
acaggcgaaa ggttgcuucc                                                    20

<210> SEQ ID NO 431
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 431
uggaccgctg cacaggcgaa                                                    20

<210> SEQ ID NO 432
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 432
agagutaagt gctggaccgc                                                    20

<210> SEQ ID NO 433
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source

```
<223> OTHER INFORMATION: /note="Description of Combined DNA/RNA
      Molecule: Synthetic oligonucleotide"

<400> SEQUENCE: 433
gcugatgtat tagaguuaag                                                       20

<210> SEQ ID NO 434
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 434
auuaacgcat gctgauguau                                                       20

<210> SEQ ID NO 435
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 435
ccaaccagct gaattaacgc                                                       20

<210> SEQ ID NO 436
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 436
ggugucattt cccaaccagc                                                       20

<210> SEQ ID NO 437
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 437
ugggcttcct ggtgtcauuu                                                       20
```

```
<210> SEQ ID NO 438
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 438
gaccctctgc actgggcuuc                                              20

<210> SEQ ID NO 439
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 439
agucagtaag ggacccucug                                              20

<210> SEQ ID NO 440
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 440
gccacgaaac agtcaguaag                                              20

<210> SEQ ID NO 441
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 441
ccauuaatag ggccacgaaa                                              20

<210> SEQ ID NO 442
<211> LENGTH: 20
<212> TYPE: DNA
<213> ORGANISM: Artificial Sequence
<220> FEATURE:
<221> NAME/KEY: source
```

<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 442
ggaacagtct gaccauuaau                                                   20

<210> SEQ ID NO 443
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 443
accucatgct ggaacagucu                                                   20

<210> SEQ ID NO 444
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 444
ugucattcta agaaccucau                                                   20

<210> SEQ ID NO 445
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 445
ccaaacacct gtcatucuaa                                                   20

<210> SEQ ID NO 446
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

-continued

<400> SEQUENCE: 446
gcccccaccc atccaaacac                                                    20

<210> SEQ ID NO 447
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 447
ccccatcaca aggcccccac                                                    20

<210> SEQ ID NO 448
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 448
cagcctaccc cccatcacaa                                                    20

<210> SEQ ID NO 449
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 449
ucacacatgg gccagccuac                                                    20

<210> SEQ ID NO 450
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 450
caccccacaa gatcacacau                                                    20

<210> SEQ ID NO 451
<211> LENGTH: 20

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 451
ucuuccctcc accccacaag                                                  20

<210> SEQ ID NO 452
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 452
ucaugctatt ctcttcccuc                                                  20

<210> SEQ ID NO 453
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 453
gggaagtggg atcatgcuau                                                  20

<210> SEQ ID NO 454
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 454
ucccacagca tggggaagug                                                  20

<210> SEQ ID NO 455
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

```
<221> NAME/KEY: source
<223> OTHER INFORMATION: /note="Description of Combined DNA/RNA
      Molecule: Synthetic oligonucleotide"

<400> SEQUENCE: 455
acugcacccc ttcccacagc                                                    20

<210> SEQ ID NO 456
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 456 ucuugggac gaactgcacc                                                     20

<210> SEQ ID NO 457
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 457
gcagugtcgt tcttggggac                                                    20

<210> SEQ ID NO 458
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 458
accacctgac aggcaguguc                                                    20

<210> SEQ ID NO 459
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 459
aucuutgcag accaccugac                                                    20
```

-continued

```
<210> SEQ ID NO 460
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 460
caaggttatc atcttugcag                                                  20

<210> SEQ ID NO 461
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 461
guuuutagta gtcaagguua                                                  20

<210> SEQ ID NO 462
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 462
cgccatggag acgttuuuag                                                  20

<210> SEQ ID NO 463
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 463
cuugutaccc ccgccaugga                                                  20

<210> SEQ ID NO 464
<211> LENGTH: 20
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 464
agauuatcat cttgtuaccc                                          20

<210> SEQ ID NO 465
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 465
aaaautaagt agattaucau                                          20

<210> SEQ ID NO 466
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 466
aaaggtgttc taaaauuaag                                          20

<210> SEQ ID NO 467
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 467
aguuaggtga aaaagguguu                                          20

<210> SEQ ID NO 468
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

```
<400> SEQUENCE: 468
aaacattatt ttagtuaggu                                              20

<210> SEQ ID NO 469
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 469
aaaactcttt aaacauuauu                                              20

<210> SEQ ID NO 470
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 470
acauutttat acaaaacucu                                              20

<210> SEQ ID NO 471
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 471
aacgcttcct tacatuuuua                                              20

<210> SEQ ID NO 472
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 472
aacaggtaac aacgcuuccu                                              20

<210> SEQ ID NO 473
```

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 473
auacaaaatt caacagguaa                                                    20

<210> SEQ ID NO 474
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 474
acugattcac ataatacaaa                                                    20

<210> SEQ ID NO 475
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 475
acuaacatct cactgauuca                                                    20

<210> SEQ ID NO 476
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 476
aggcutattc tactaacauc                                                    20

<210> SEQ ID NO 477
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<220> FEATURE:
<221> NAME/KEY: source
<223> OTHER INFORMATION: /note="Description of Combined DNA/RNA
      Molecule: Synthetic oligonucleotide"

<400> SEQUENCE: 477
uuuuuttttt aaggcuuauu                                               20

<210> SEQ ID NO 478
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 478
aaccgatttt tttttuuuua                                               20

<210> SEQ ID NO 479
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 479
ccacugcacc caaccgauuu                                               20

<210> SEQ ID NO 480
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 480
acagccgtgt gccacugcac                                               20

<210> SEQ ID NO 481
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 481
aagugcuggg attacagccg                                               20

<210> SEQ ID NO 482
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 482
uuggccucuc aaagtgcugg                                               20

<210> SEQ ID NO 483
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 483
aucugccaac cttggccucc                                               20

<210> SEQ ID NO 484
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 484
accucaggtg atctgccaac                                               20

<210> SEQ ID NO 485
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 485
cuugaacucc tgaccucagg                                               20

<210> SEQ ID NO 486
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 486
ccagactggt cttgaacucc                                               20

<210> SEQ ID NO 487
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 487
ugcuatgttg gccagacugg                                               20

<210> SEQ ID NO 488
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 488
gacagggttt tgctauguug                                               20

<210> SEQ ID NO 489
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 489
auuuutagta gagacagggu                                               20

<210> SEQ ID NO 490
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA -continued Molecule: Synthetic oligonucleotide"

<400> SEQUENCE: 490
auaauttttg tatttuuagu                                           20

<210> SEQ ID NO 491
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 491
accaugccca gataauuuuu                                           20

<210> SEQ ID NO 492
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 492
aggcatgcac caccaugccc                                           20

<210> SEQ ID NO 493
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 493
agcugggatt acaggcaugc                                           20

<210> SEQ ID NO 494
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 494
cuuccgaata gctgggauua                                           20

```
<210> SEQ ID NO 495
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 495
ccugcctcag ccttccgaau                                          20

<210> SEQ ID NO 496
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 496
ucaagtgatt ctcctgccuc                                          20

<210> SEQ ID NO 497
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 497
ccucctgggt tcaagugauu                                          20

<210> SEQ ID NO 498
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 498
ccgcaacctc cgcctccugg                                          20

<210> SEQ ID NO 499
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 499
aaucucagct caccgcaacc                                                    20

<210> SEQ ID NO 500
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 500
ugaaatggtg caatcucagc                                                    20

<210> SEQ ID NO 501
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 501
aggcuggaat gaaatggugc                                                    20

<210> SEQ ID NO 502
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 502
acucatgttg cccaggcugg                                                    20

<210> SEQ ID NO 503
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 503
ucagactttc actcauguug                                              20

<210> SEQ ID NO 504
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 504
uuuuuttttg agtcagacuu                                              20

<210> SEQ ID NO 505
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 505
uuuuaaattt tttttuuuug                                              20

<210> SEQ ID NO 506
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 506
gauuattttg tttttuaaau                                              20

<210> SEQ ID NO 507
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 507
cugcacacta gattauuuug                                              20

<210> SEQ ID NO 508
<211> LENGTH: 20
<212> TYPE: DNA

<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 508
aggugaatgc cctgcacacu                                             20

<210> SEQ ID NO 509
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 509 ugggggctg aggtgaaugc                                              20

<210> SEQ ID NO 510
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 510
cuuggctcct gcctgggggg                                             20

<210> SEQ ID NO 511
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 511
ccugctgtgc ttggcuccug                                             20

<210> SEQ ID NO 512
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source

```
<223> OTHER INFORMATION: /note="Description of Combined DNA/RNA
      Molecule: Synthetic oligonucleotide"

<400> SEQUENCE: 512
aggcggaagc tcctgcugug                                              20

<210> SEQ ID NO 513
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 513
caguggagag gaggcggaag                                              20

<210> SEQ ID NO 514
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 514
aguugtgtgc tccaguggag                                              20

<210> SEQ ID NO 515
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 515
agccaggttc aagttgugug                                              20

<210> SEQ ID NO 516
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 516
gcagaaaata agccagguuc                                              20
```

```
<210> SEQ ID NO 517
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 517
ggggctggtc cctgcagaaa                                                  20

<210> SEQ ID NO 518
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 518
acugaccatg tggggcuggu                                                  20

<210> SEQ ID NO 519
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 519
ggagaaactc actgaccaug                                                  20

<210> SEQ ID NO 520
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 520
cgccacacat ggggagaaac                                                  20

<210> SEQ ID NO 521
<211> LENGTH: 20
<212> TYPE: DNA
<213> ORGANISM: Artificial Sequence
```

-continued

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 521
acucuctcat cgccacacau                                            20

<210> SEQ ID NO 522
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 522
cuuuatttct acactcucuc                                            20
```

POLYNUCLEOTIDE AGENTS TARGETING PATATIN-LIKE PHOSPHOLIPASE DOMAIN CONTAINING 3 (PNPLA3) AND METHODS OF USE THEREOF

RELATED APPLICATIONS

This application is a 35 § U.S.C. 111(a) continuation application which claims the benefit of priority to PCT/US2016/051252, filed on Sep. 12, 2016 which, in turn, claims the benefit of priority to U.S. Provisional Patent Application No. 62/218,100, filed on Sep. 14, 2015. The entire contents of each of the foregoing applications are hereby incorporated herein by reference.

SEQUENCE LISTING

The instant application contains a Sequence Listing which has been submitted electronically in ASCII format and is hereby incorporated by reference in its entirety. Said ASCII copy, created on Mar. 5, 2018, is named 121301-04302_SL.txt and is 202,353 bytes in size.

BACKGROUND OF THE INVENTION

The accumulation of excess triglyceride in the liver is known as hepatic steatosis (or fatty liver), and is associated with adverse metabolic consequences, including insulin resistance and dyslipidemia. Fatty liver is frequently found in people who intake excessive alcohols and who have obesity, diabetes, or hyperlipidemia. Nonalcoholic fatty liver disease (NAFLD) refers to a wide spectrum of liver disease ranging from simple fatty liver (steatosis), to nonalcoholic steatohepatitis (NASH), to cirrhosis (irreversible, advanced scarring of the liver). All of the stages of NAFLD have in common the accumulation of fat (fatty infiltration) in the liver cells (hepatocytes), and NAFLD is now the leading cause of chronic liver disease in the United States.

The NAFLD spectrum is thought to begin with and progress from its simplest stage, called simple fatty liver (steatosis). Simple fatty liver involves the accumulation of fat (triglyceride) in the liver cells with no inflammation (hepatitis) or scarring (fibrosis). The next stage and degree of severity in the NAFLD spectrum is NASH, which involves the accumulation of fat in the liver cells, as well as inflammation of the liver. The inflammatory cells can destroy liver cells (hepatocellular necrosis), and NASH can ultimately lead to scarring of the liver (fibrosis), followed by irreversible, advanced scarring (cirrhosis). Cirrhosis that is caused by NASH is the last and most severe stage in the NAFLD spectrum.

In 2008, a genomewide association study of individuals with proton magnetic resonance spectroscopy of the liver to evaluate hepatic fat content, a significant association was identified between hepatic fat content and the Patatin-like Phospholipase Domain Containing 3 (PNPLA3) gene (see, for example, Romeo et al. (2008) Nat. Genet., 40(12):1461-1465). Studies with knock-in mice have demonstrated that expression of a sequence polymorphism (rs738409, I148M) in PNPLA3 causes NAFLD, and that the accumulation of catalytically inactive PNPLA3 on the surfaces of lipid droplets is associated with the accumulation of triglycerides in the liver (Smagris et al. (2015) Hepatology, 61:108-118). Specifically, the PNPLA3 I148M variant may promote the development of fibrogenesis by activating the hedgehog (Hh) signaling pathway, leading to the activation and proflieration of hepatic stellate cells and excessive generation and deposition of extracellular matrix (Chen et al. (2015) World J. Gastroenterol., 21(3):794-802).

Currently, treatments for NAFLD are directed towards weight loss and treatment of any secondary conditions, such as insulin resistance or dyslipidemia. To date, no pharmacologic treatments for NAFLD have been approved. Therefore, there is a need for therapies for subjects suffering from NAFLD.

SUMMARY OF THE INVENTION

The present invention provides polynucleotide agents, e.g., antisense polynucleotide agents, and compositions comprising such agents which target nucleic acids encoding a Patatin-Like Phospholipase Domain Containing 3 (PNPLA3) gene and interfere with the normal function of the targeted nucleic acid. The PNPLA3 nucleic acid may be within a cell, e.g., a cell within a subject, such as a human. The present invention also provides methods and combination therapies for treating a subject having a disorder that would benefit from inhibiting or reducing the expression of a PNPLA3 mRNA, e.g., a PNPLA3-associated disease, such as such as Nonalcoholic Fatty Liver Disease (NAFLD), using the polynucleotide agents and compositions of the invention, e.g., antisense polynucleotide agents and compositions of the invention.

Accordingly, in one aspect, the present invention provides antisense polynucleotide agents for inhibiting expression of a Patatin-Like Phospholipase Domain Containing 3 (PNPLA3) gene. The agents include about 4 to about 50 contiguous nucleotides, wherein at least one of the contiguous nucleotides is a modified nucleotide, and wherein the nucleotide sequence of the agent is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% complementary over its entire length to the equivalent region of the nucleotide sequence of any one of SEQ ID NOs:1-4.

In another aspect, the present invention provides antisense polynucleotide agents for inhibiting expression of a Patatin-Like Phospholipase Domain Containing 3 (PNPLA3) gene. The agents include at least 8 contiguous nucleotides differing by no more than 3 nucleotides from any one of the target nucleotide sequences of SEQ ID NO:1 provided in Tables 3 and 4 and are about 8 to about 50 nucleotides in length.

In some embodiments, substantially all of the nucleotides of the antisense polynucleotide agents of the invention are modified nucleotides. In other embodiments, all of the nucleotides of the antisense polynucleotide agent are modified nucleotides.

The antisense polynucleotide agent may be 10 to 40 nucleotides in length; 10 to 30 nucleotides in length; 18 to 30 nucleotides in length; 10 to 24 nucleotides in length; 18 to 24 nucleotides in length; or 20 nucleotides in length.

In one embodiment, the modified nucleotide comprises a modified sugar moiety selected from the group consisting of a 2'-O-methoxyethyl modified sugar moiety, a 2'-methoxy modified sugar moiety, a 2'-O-alkyl modified sugar moiety, and a bicyclic sugar moiety.

In one embodiment, the bicyclic sugar moiety has a (—CRH—)n group forming a bridge between the 2' oxygen and the 4' carbon atoms of the sugar ring, wherein n is 1 or 2 and wherein R is H, $CH_3$ or $CH_3OCH_3$.

In a further embodiment, n is 1 and R is CH₃.

In another embodiment, the modified nucleotide is a 5-methylcytosine.

In one embodiment, the modified nucleotide comprises a modified internucleoside linkage, such as a phosphorothioate internucleoside linkage.

In one embodiment, an agent of the invention comprises one 2'-deoxynucleotide. In another embodiment, an agent of the invention comprises one 2'-deoxynucleotide flanked on each side by at least one nucleotide having a modified sugar moiety.

In one embodiment, an agent of the invention comprises a plurality, e.g., more than 1, e.g., 2, 3, 4, 5, 6, or 7, 2'-deoxynucleotides. In one embodiment, an agent of the invention comprises a plurality, e.g., more than 1, e.g., 2, 3, 4, 5, 6, or 7, 2'-deoxynucleotides flanked on each side by at least one nucleotide having a modified sugar moiety.

In one embodiment, the agent is a gapmer comprising a gap segment comprised of linked 2'-deoxynucleotides positioned between a 5' and a 3' wing segment.

In one embodiment, the modified sugar moiety is selected from the group consisting of a 2'-O-methoxyethyl modified sugar moiety, a 2'-methoxy modified sugar moiety, a 2'-O-alkyl modified sugar moiety, and a bicyclic sugar moiety.

In one embodiment, the 5'-wing segment is 1 to 6 nucleotides in length, e.g., 2, 3, 4, or 5 nucleotides in length.

In one embodiment, the 3'-wing segment is 1 to 6 nucleotides in length, e.g., 2, 3, 4, or 5 nucleotides in length.

In one embodiment, the gap segment is 5 to 14 nucleotides in length, e.g., 6, 7, 8, 9, 10, 11, 12, or 13 nucleotides in length. In one embodiment, the gap segment is 10 nucleotides in length.

In one aspect, the present invention provides antisense polynucleotide agents for inhibiting expression of a Patatin-Like Phospholipase Domain Containing 3 (PNPLA3) gene. The agents include a gap segment consisting of linked deoxynucleotides; a 5'-wing segment consisting of linked nucleotides; a 3'-wing segment consisting of linked nucleotides; wherein the gap segment is positioned between the 5'-wing segment and the 3'-wing segment and wherein each nucleotide of each wing segment comprises a modified sugar moiety.

In one embodiment, the gap segment is ten 2'-deoxynucleotides in length and each of the wing segments is five nucleotides in length.

In another embodiment, the gap segment is ten 2'-deoxynucleotides in length and each of the wing segments is four nucleotides in length.

In yet another embodiment, the gap segment is ten 2'-deoxynucleotides in length and each of the wing segments is three nucleotides in length.

In another embodiment, the gap segment is ten 2'-deoxynucleotides in length and each of the wing segments is two nucleotides in length.

In one embodiment, the modified sugar moiety is selected from the group consisting of a 2'-O-methoxyethyl modified sugar moiety, a 2'-methoxy modified sugar moiety, a 2'-O-alkyl modified sugar moiety, and a bicyclic sugar moiety.

In some embodiments, the agents of the invention further comprise a ligand.

In one embodiment, the agent is conjugated to the ligand at the 3'-terminus.

In one embodiment, the ligand is an N-acetylgalactosamine (GalNAc) derivative.

In one embodiment, the ligand is

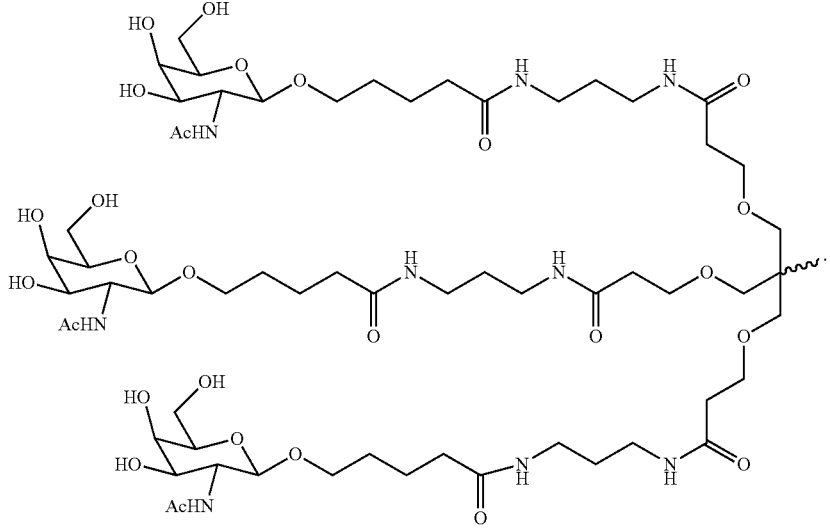 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In one aspect, the present invention provides pharmaceutical compositions for inhibiting expression of a Patatin-Like Phospholipase Domain Containing 3 (PNPLA3) gene comprising an agent of the invention.

In one embodiment, the agent is present in an unbuffered solution, such as saline or water.

In another embodiment, the agent is present in a buffer solution, such as a buffer comprising acetate, citrate, prolamine, carbonate, or phosphate or any combination thereof.

In one embodiment, the buffer solution is phosphate buffered saline (PBS).

In another aspect, the present invention provides pharmaceutical composition comprising an agent of the invention and a lipid formulation, such as a lipid formulation comprising an LNP or a MC3.

In one aspect, the present invention provides methods of inhibiting expression of a Patatin-Like Phospholipase Domain Containing 3 (PNPLA3) gene in a cell. The methods include contacting the cell with an agent of the invention or a pharmaceutical composition of the invention; and maintaining the cell for a time sufficient to obtain antisense inhibition of a PNPLA3 gene, thereby inhibiting expression of the PNPLA3 gene in the cell.

In one embodiment, the cell is within a subject.

In one embodiment, the subject is a human. In one embodiment, the subject is a female human. In another embodiment, the subject is a male human.

In one embodiment, the PNPLA3 expression is inhibited by at least about 30%, about 40%, about 50%, about 60%, about 70%, about 80%, about 90%, about 95%, about 98% or about 100%.

In another aspect, the present invention provides methods of treating a subject having a disease or disorder that would benefit from reduction in expression of a Patatin-Like Phospholipase Domain Containing 3 (PNPLA3) gene. The methods include administering to the subject a therapeutically effective amount of an agent of the invention or a pharmaceutical composition of the invention, thereby treating the subject.

In yet another aspect, the present invention provides methods of preventing at least one symptom in a subject having a disease or disorder that would benefit from reduction in expression of a Patatin-Like Phospholipase Domain Containing 3 (PNPLA3) gene. The methods include administering to the subject a prophylactically effective amount of an agent of the invention or a pharmaceutical composition of the invention, thereby preventing at least one symptom in the subject having a disorder that would benefit from reduction in expression of a PNPLA3 gene.

In one embodiment, the administration of the agent to the subject causes a decrease in the hedgehog signaling pathway and/or a decrease in PNPLA3 protein levels in the subject.

In one embodiment, the disorder is a PNPLA3-associated disease.

In one embodiment, the PNPLA3-associated disease is a PNPLA3-associated disease. In another embodiment, the PNPLA3-associated disease is nonalcoholic fatty liver disease (NAFLD). In another embodiment, the PNPLA3-associated disease is fatty liver (steatosis). In another embodiment, the PNPLA3-associated disease is nonalcoholic steatohepatitis (NASH). In another embodiment, the PNPLA3-associated disease is obesity. In one embodiment, the subject is human. In another embodiment, the subject is a female human. In another embodiment, the subject is a male human. In one embodiment, the subject has a PNPLA3 I148M mutation. In one embodiment, the mutation is heterozygous. In another embodiment, the mutation is homozygous.

In certain embodiments, the methods further comprise administering to the subject an additional therapeutic agent suitable for treatment of a PNPLA3-associated disease. In some embodiments, the additional therapeutic agent is an anti-PNPLA3 antibody, or antigen-binding fragment thereof.

In certain embodiments, the agent is administered at a dose of about 0.01 mg/kg to about 10 mg/kg or about 0.5 mg/kg to about 50 mg/kg.

In certain embodiments, the agent is administered at a dose of about 10 mg/kg to about 30 mg/kg.

In certain embodiments, the agent is administered to the subject once a week.

In alternative embodiments, the agent is administered to the subject twice a week.

In yet other embodiments, the agent is administered to the subject twice a month.

In certain embodiments, the agent is administered to the subject subcutaneously.

In another embodiment, the methods of the invention further comprise measuring hedgehog signaling pathway levels in the subject. In one embodiment, a decrease in the levels of expression or activity of the hedgehog (Hh) signaling pathway indicate that the PNPLA3-associated disease is being treated or prevented.

DETAILED DESCRIPTION OF THE INVENTION

The present invention provides polynucleotide agents, e.g., antisense polynucleotide agents, and compositions comprising such agents which target nucleic acids encoding Patatin-Like Phospholipase Domain Containing 3 (PNPLA3) (e.g., mRNA encoding PNPLA3 as provided in, for example, any one of SEQ ID NOs:1, 3, 5, 7, 9, and/or 11). The antisense polynucleotide agents bind to nucleic acids encoding PNPLA3 via, e.g., Watson-Crick base pairing, and interfere with the normal function of the targeted nucleic acid.

The polynucleotide agents, e.g., antisense polynucleotide agents, of the invention include a nucleotide sequence which is about 4 to about 50 nucleotides or less in length and which is about 80% complementary to at least part of an mRNA transcript of a PNPLA3 gene. The use of these antisense polynucleotide agents enables the targeted inhibition of RNA expression and/or activity of a PNPLA3 gene in mammals.

The present inventors have demonstrated that antisense polynucleotide agents targeting PNPLA3 can mediate antisense inhibition in vitro resulting in significant inhibition of expression of a PNPLA3 gene. Thus, methods and compositions including these antisense polynucleotide agents are useful for treating a subject who would benefit by a reduction in the levels and/or activity of an PNPLA3 protein, such as a subject having a PNPLA3-associated disease, such as Nonalcoholic Fatty Liver Disease (NAFLD).

The present invention also provides methods and combination therapies for treating a subject having a disorder that would benefit from inhibiting or reducing the expression of an PNPLA3 gene, e.g., an PNPLA3-associated disease, such as Nonalcoholic Fatty Liver Disease (NAFLD), using the antisense polynucleotide agents and compositions of the invention.

The present invention also provides methods for preventing at least one symptom, e.g., the presence of increased protein activity in the hedgehog (Hh) signaling pathway, fatty liver (steatosis), nonalcoholic steatohepatitis (NASH), cirrhosis of the liver, accumulation of fat in the liver, inflammation of the liver, hepatocellular necrosis, liver fibrosis, obesity, or nonalcoholic fatty liver disease (NAFLD), in a subject having a disorder that would benefit from inhibiting or reducing the expression of a PNPLA3 gene, e.g., a subject having a PNPLA3-associated disorder, e.g., nonalcoholic fatty liver disease (NAFLD). The present invention further provides compositions comprising antisense polynucleotide agents which effect antisense inhibition of a PNPLA3 gene. The PNPLA3 gene may be within a cell, e.g., a cell within a subject, such as a human.

The combination therapies of the present invention include administering to a subject having a PNPLA3-associated disease, an antisense polynucleotide agent of the invention and an additional therapeutic, such as an anti-PNPLA3 antibody, or antigen-binding fragment thereof. The combination therapies of the invention reduce PNPLA3 levels in the subject (e.g., by about 30%, 35%, 40%, 45%, 50%, 55%, 60%, 65%, 70%, 75%, 80%, 85%, 90%, 95%, or about 99%) by targeting PNPLA3 mRNA with an antisense polynucleotide agent of the invention and, accordingly, allow the therapeutically (or prophylactically) effective amount of the additional therapeutic agent(s) required to treat the subject to be reduced, thereby decreasing the costs of treatment and permitting easier and more convenient ways of administering certain agents, or decreasing side effects of certain agents.

The following detailed description discloses how to make and use antisense polynucleotide agents to inhibit the mRNA and/or protein expression of a PNPLA3 gene, as well as compositions, uses, and methods for treating subjects having diseases and disorders that would benefit from inhibition and/or reduction of the expression of this gene.

I. Definitions

In order that the present invention may be more readily understood, certain terms are first defined. In addition, it should be noted that whenever a value or range of values of a parameter are recited, it is intended that values and ranges intermediate to the recited values are also intended to be part of this invention.

The articles "a" and "an" are used herein to refer to one or to more than one (i.e., to at least one) of the grammatical object of the article. By way of example, "an element" means one element or more than one element, e.g., a plurality of elements.

The term "including" is used herein to mean, and is used interchangeably with, the phrase "including but not limited to".

The term "or" is used herein to mean, and is used interchangeably with, the term "and/or," unless context clearly indicates otherwise.

The term "about" is used herein to mean within the typical ranges of tolerances in the art.

As used herein, "Patatin-Like Phospholipase Domain Containing 3," used interchangeably with the term "PNPLA3," refers to the naturally occurring gene that encodes a triacylglycerol lipase that mediates triacyl glycerol hydrolysis in adipocytes. The amino acid and complete coding sequences of the reference sequence of the human PNPLA3 gene may be found in, for example, GenBank Accession No. GI:17196625 (RefSeq Accession No. NM_025225.2; SEQ ID NO:1; SEQ ID NO:2). Mammalian orthologs of the human PNPLA3 gene may be found in, for example, GenBank Accession Nos. GI: 544461323 (RefSeq Accession No. XM_055567051.1, cynomolgus monkey; SEQ ID NO:7 and SEQ ID NO:8); GI: 544461325 (RefSeq Accession No. XM_055567052.1, cynomolgus monkey; SEQ ID NO:11 and SEQ ID NO:12); GI:297261270 (RefSeq Accession No. XM_001109144.2, rhesus monkey, SEQ ID NO:9 and SEQ ID NO:10); GI:144226244 (RefSeq Accession No. NM_054088.3, mouse; SEQ ID NO:3 and SEQ ID NO:4); GI:537361027 (RefSeq Accession No. NM_001282324.1, rat; SEQ ID NO:5 and SEQ ID NO:6).

Additional examples of PNPLA3 mRNA sequences are readily available using publicly available databases, e.g., GenBank, UniProt, OMIM, and the *Macaca* genome project web site.

The term"PNPLA3," as used herein, also refers to naturally occurring DNA sequence variations of a PNPLA3 gene, such as a single nucleotide polymorphism (SNP) in a PNPLA3 gene. Exemplary SNPs may be found in the dbSNP database available at www.ncbi.nlm nih.gov/projects/SNP/.

As used herein, "target sequence" refers to a contiguous portion of the nucleotide sequence of an mRNA molecule formed during the transcription of a PNPLA3 gene, including mRNA that is a product of RNA processing of a primary transcription product.

As used herein, "target nucleic acid" refers to a nucleic acid molecule to which an antisense polynucleotide agent of the invention specifically hybridizes.

The terms "antisense polynucleotide agent" "antisense compound", and "agent" as used interchangeably herein, refer to an agent comprising a single-stranded oligonucleotide that contains RNA as that term is defined herein, and which targets nucleic acid molecules encoding PNPLA3 (e.g., mRNA encoding PNPLA3 as provided in, for example, any one of SEQ ID NOs:1, 3, 5, 7, 9, and/or 11). The antisense polynucleotide agents specifically bind to the target nucleic acid molecules via hydrogen bonding (e.g., Watson-Crick, Hoogsteen or reversed Hoogsteen hydrogen bonding) and interfere with the normal function of the targeted nucleic acid (e.g., by an antisense mechanism of action). This interference with or modulation of the function of a target nucleic acid by the polynucleotide agents of the present invention is referred to as "antisense inhibition."

The functions of the target nucleic acid molecule to be interfered with may include functions such as, for example, translocation of the RNA to the site of protein translation, translation of protein from the RNA, splicing of the RNA to yield one or more mRNA species, and catalytic activity which may be engaged in or facilitated by the RNA.

In some embodiments, antisense inhibition refers to "inhibiting the expression" of target nucleic acid levels and/or target protein levels in a cell, e.g., a cell within a subject, such as a mammalian subject, in the presence of the antisense polynucleotide agent complementary to a target nucleic acid as compared to target nucleic acid levels and/or target protein levels in the absence of the antisense polynucleotide agent. For example, the antisense polynucleotide agents of the invention can inhibit translation in a stoichiometric manner by base pairing to the mRNA and physically obstructing the translation machinery, see Dias, N. et al., (2002) *Mol Cancer Ther* 1:347-355.

As used herein, the term "specifically hybridizes" refers to an antisense polynucleotide agent having a sufficient degree of complementarity between the antisense polynucleotide agent and a target nucleic acid to induce a desired effect, while exhibiting minimal or no effects on non-target nucleic acids under conditions in which specific binding is desired, e.g., under physiological conditions in the case of in vivo assays and therapeutic treatments.

A target sequence may be from about 4-50 nucleotides in length, e.g., 8-45, 10-45, 10-40, 10-35, 10-30, 10-20, 11-45, 11-40, 11-35, 11-30, 11-20, 12-45, 12-40, 12-35, 12-30, 12-25, 12-20, 13-45, 13-40, 13-35, 13-30, 13-25, 13-20, 14-45, 14-40, 14-35, 14-30, 14-25, 14-20, 15-45, 15-40, 15-35, 15-30, 15-25, 15-20, 16-45, 16-40, 16-35, 16-30, 16-25, 16-20, 17-45, 17-40, 17-35, 17-30, 17-25, 17-20, 18-45, 18-40, 18-35, 18-30, 18-25, 18-20, 19-45, 19-40, 19-35, 19-30, 19-25, 19-20, e.g., 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 contiguous nucleotides of the nucleotide sequence of an mRNA molecule formed during the transcription of a PNPLA3 gene. Ranges and lengths intermediate to the above recited ranges and lengths are also contemplated to be part of the invention.

The terms "complementary," "fully complementary" and "substantially complementary" are used herein with respect to the base matching between an antisense polynucleotide agent and a target sequence. The term "complementarity" refers to the capacity for pairing between nucleobases of a first nucleic acid and a second nucleic acid.

As used herein, an antisense polynucleotide agent that is "substantially complementary to at least part of" a messenger RNA (mRNA) refers to an antisense polynucleotide agent that is substantially complementary to a contiguous portion of the mRNA of interest (e.g., an mRNA encoding a PNPLA3 gene). For example, a polynucleotide is complementary to at least a part of a PNPLA3 mRNA if the sequence is substantially complementary to a non-interrupted portion of an mRNA encoding PNPLA3.

As used herein, the term "region of complementarity" refers to the region of the antisense polynucleotide agent that is substantially complementary to a sequence, for example a target sequence, e.g., a PNPLA3 nucleotide sequence, as defined herein. Where the region of complementarity is not fully complementary to the target sequence, the mismatches can be in the internal or terminal regions of the molecule. Generally, the most tolerated mismatches are in the terminal regions, e.g., within 5, 4, 3, or 2 nucleotides of the 5'- and/or 3'-terminus of the antisense polynucleotide.

As used herein, and unless otherwise indicated, the term "complementary," when used to describe a first nucleotide sequence in relation to a second nucleotide sequence, refers to the ability of a polynucleotide comprising the first nucleotide sequence to hybridize and form a duplex structure under certain conditions with the second nucleotide sequence, as will be understood by the skilled person. Such conditions can, for example, be stringent conditions, where stringent conditions can include: 400 mM NaCl, 40 mM PIPES pH 6.4, 1 mM EDTA, 50° C. or 70° C. for 12-16 hours followed by washing (see, e.g., "Molecular Cloning: A Laboratory Manual, Sambrook, et al. (1989) Cold Spring Harbor Laboratory Press). Other conditions, such as physiologically relevant conditions as can be encountered inside an organism, can apply. The skilled person will be able to determine the set of conditions most appropriate for a test of complementarity of two sequences in accordance with the ultimate application of the nucleotides.

Complementary sequences include those nucleotide sequences of an antisense polynucleotide agent of the invention that base-pair to a second nucleotide sequence over the entire length of one or both nucleotide sequences. Such sequences can be referred to as "fully complementary" with respect to each other herein. However, where a first sequence is referred to as "substantially complementary" with respect to a second sequence herein, the two sequences can be fully complementary, or they can form one or more, but generally not more than 5, 4, 3 or 2 mismatched base pairs upon hybridization for a duplex up to 30 base pairs, while retaining the ability to hybridize under the conditions most relevant to their ultimate application, e.g., antisense inhibition of target gene expression.

"Complementary" sequences, as used herein, can also include, or be formed entirely from, non-Watson-Crick base pairs and/or base pairs formed from non-natural and modified nucleotides, in so far as the above requirements with respect to their ability to hybridize are fulfilled. Such non-Watson-Crick base pairs include, but are not limited to, G:U Wobble or Hoogstein base pairing.

As used herein, the term "strand comprising a sequence" refers to an oligonucleotide comprising a chain of nucleotides that is described by the sequence referred to using the standard nucleotide nomenclature.

"G," "C," "A," "T" and "U" each generally stand for a nucleotide that contains guanine, cytosine, adenine, thymidine and uracil as a base, respectively. However, it will be understood that the terms "deoxyribonucleotide", "ribonucleotide" and "nucleotide" can also refer to a modified nucleotide, as further detailed below, or a surrogate replacement moiety (see, e.g., Table 2). The skilled person is well aware that guanine, cytosine, adenine, and uracil can be replaced by other moieties without substantially altering the base pairing properties of an oligonucleotide comprising a nucleotide bearing such replacement moiety. For example, without limitation, a nucleotide comprising inosine as its base can base pair with nucleotides containing adenine, cytosine, or uracil. Hence, nucleotides containing uracil, guanine, or adenine can be replaced in the nucleotide sequences of the agents featured in the invention by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods featured in the invention.

A "nucleoside" is a base-sugar combination. The "nucleobase" (also known as "base") portion of the nucleoside is normally a heterocyclic base moiety. "Nucleotides" are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. "Polynucleotides," also referred to as "oligonucleotides," are formed through the covalent linkage of adjacent nucleosides to one another, to form a linear polymeric oligonucleotide. Within the polynucleotide structure, the phosphate groups are commonly referred to as forming the internucleoside linkages of the polynucleotide.

In general, the majority of nucleotides of the antisense polynucleotide agents are ribonucleotides, but as described in detail herein, the agents may also include one or more non-ribonucleotides, e.g., a deoxyribonucleotide. In addition, as used in this specification, an "antisense polynucleotide agent" may include nucleotides (e.g., ribonucleotides or deoxyribonucleotides) with chemical modifications; an antisense polynucleotide agent may include substantial modifications at multiple nucleotides.

As used herein, the term "modified nucleotide" refers to a nucleotide having, independently, a modified sugar moiety, a modified internucleotide linkage, and/or modified nucleobase. Thus, the term modified nucleotide encompasses substitutions, additions or removal of, e.g., a functional group or atom, to internucleoside linkages, sugar moieties, or nucleobases. The modifications suitable for use in the antisense polynucleotide agents of the invention include all types of modifications disclosed herein or known in the art. Any such modifications, as used in nucleotides, are encompassed by "antisense polynucleotide agent" for the purposes of this specification and claims.

As used herein, a "subject" is an animal, such as a mammal, including a primate (such as a human, a non-human primate, e.g., a monkey, and a chimpanzee), a non-primate (such as a cow, a pig, a camel, a llama, a horse, a goat, a rabbit, a sheep, a hamster, a guinea pig, a cat, a dog, a rat, a mouse, a horse, and a whale), or a bird (e.g., a duck or a goose). In an embodiment, the subject is a human, such as a human being treated or assessed for a disease, disorder or condition that would benefit from reduction in PNPLA3 gene expression and/or replication; a human at risk for a disease, disorder or condition that would benefit from reduction in PNPLA3 gene expression; a human having a disease, disorder or condition that would benefit from reduction in PNPLA3 gene expression; and/or human being treated for a disease, disorder or condition that would benefit from reduction in PNPLA3 gene expression, as described herein. In one embodiment, the subject is a female human. In another embodiment, the subject is a male human.

As used herein, the terms "treating" or "treatment" refer to a beneficial or desired result including, but not limited to, alleviation or amelioration of one or more symptoms associated with PNPLA3 gene expression and/or PNPLA3 protein production, e.g., the presence of increased protein activity in the hedgehog (Hh) signaling pathway, fatty liver (steatosis), nonalcoholic steatohepatitis (NASH), cirrhosis of the liver, accumulation of fat in the liver, inflammation of the liver, hepatocellular necrosis, liver fibrosis, obesity, or nonalcoholic fatty liver disease (NAFLD). "Treatment" can also mean prolonging survival as compared to expected survival in the absence of treatment.

The term "lower" in the context of the level of PNPLA3 in a subject or a disease marker or symptom refers to a statistically significant decrease in such level. The decrease can be, for example, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or more. In certain embodiments, a decrease is at least 20%. "Lower" in the context of the level of PNPLA3 in a subject is preferably down to a level accepted as within the range of normal for an individual without such disorder.

As used herein, "prevention" or "preventing," when used in reference to a disease, disorder or condition thereof, that would benefit from a reduction in expression of an PNPLA3 gene and/or production of PNPLA3 protein, refers to a reduction in the likelihood that a subject will develop a symptom associated with such a disease, disorder, or condition, e.g., a symptom of PNPLA3 gene expression, such as the presence of elevated levels of proteins in the hedgehog signaling pathway, fatty liver (steatosis), nonalcoholic steatohepatitis (NASH), cirrhosis of the liver, accumulation of fat in the liver, inflammation of the liver, hepatocellular necrosis, liver fibrosis, obesity, or nonalcoholic fatty liver disease (NAFLD). The failure to develop a disease, disorder or condition, or the reduction in the development of a symptom associated with such a disease, disorder or condition (e.g., by at least about 10% on a clinically accepted scale for that disease or disorder), or the exhibition of delayed symptoms delayed (e.g., by days, weeks, months or years) is considered effective prevention.

As used herein, the term "Patatin-Like Phospholipase Domain Containing 3-associated disease" or "PNPLA3-associated disease," is a disease or disorder that is caused by, or associated with PNPLA3 gene expression or PNPLA3 protein production. The term "PNPLA3-associated disease" includes a disease, disorder or condition that would benefit from a decrease in PNPLA3 gene expression, replication, or protein activity. Non-limiting examples of PNPLA3-associated diseases include, for example, fatty liver (steatosis), nonalcoholic steatohepatitis (NASH), cirrhosis of the liver, accumulation of fat in the liver, inflammation of the liver, hepatocellular necrosis, liver fibrosis, obesity, or nonalcoholic fatty liver disease (NAFLD). In another embodiment, the PNPLA3-associated disease is nonalcoholic fatty liver disease (NAFLD). In another embodiment, the PNPLA3-associated disease is nonalcoholic steatohepatitis (NASH). In another embodiment, the PNPLA3-associated disease is liver cirrhosis. In another embodiment, the PNPLA3-associated disease is insulin resistance. In another embodiment, the PNPLA3-associated disease is not insulin resistance. In one embodiment, the PNPLA3-associated disease is obesity.

In one embodiment, an PNPLA3-associated disease is nonalcoholic fatty liver disease (NAFLD). As used herein, "nonalcoholic fatty liver disease," used interchangeably with the term "NAFLD," refers to a disease defined by the presence of macrovascular steatosis in the presence of less than 20 gm of alcohol ingestion per day. NAFLD is the most common liver disease in the United States, and is commonly associated with insulin resistance/type 2 diabetes mellitus and obesity. NAFLD is manifested by steatosis, steatohepatitis, cirrhosis, and sometimes hepatocellaular carcinoma. For a review of NAFLD, see Tolman and Dalpiaz (2007) Ther. Clin. Risk. Manag., 3(6):1153-1163 the entire contents of which are incorporated herein by reference.

The term "sample," as used herein, includes a collection of similar fluids, cells, or tissues isolated from a subject, as well as fluids, cells, or tissues present within a subject. Examples of biological fluids include blood, serum and serosal fluids, plasma, cerebrospinal fluid, ocular fluids, lymph, urine, saliva, and the like. Tissue samples may include samples from tissues, organs or localized regions. For example, samples may be derived from particular organs, parts of organs, or fluids or cells within those organs. In certain embodiments, samples may be derived from the liver (e.g., whole liver or certain segments of liver or certain types of cells in the liver, such as, e.g., hepatocytes), the retina or parts of the retina (e.g., retinal pigment epithelium), the central nervous system or parts of the central nervous system (e.g., ventricles or choroid plexus), or the pancreas or certain cells or parts of the pancreas. In some embodiments, a "sample derived from a subject" refers to cerebrospinal fluid obtained from the subject. In preferred embodiments, a "sample derived from a subject" refers to blood or plasma drawn from the subject. In further embodiments, a "sample derived from a subject" refers to liver tissue (or subcomponents thereof) or retinal tissue (or subcomponents thereof) derived from the subject.

II. Polynucleotide Agents of the Invention

The present invention provides polynucleotide agents, e.g., antisense polynucleotide agents, and compositions comprising such agents, which target a PNPLA3 gene and inhibit the expression of the PNPLA3 gene. In one embodiment, the antisense polynucleotide agents inhibit the expression of a PNPLA3 gene in a cell, such as a cell within a subject, e.g., a mammal, such as a human having a PNPLA3-associated disease, e.g., nonalcoholic fatty liver disease (NAFLD).

The antisense polynucleotide agents of the invention include a region of complementarity which is complementary to at least a part of an mRNA formed in the expression of a PNPLA3 gene. The region of complementarity may be about 50 nucleotides or less in length (e.g., about 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, or 4 nucleotides or less in length). Upon contact with a cell expressing the PNPLA3 gene, the antisense polynucleotide agent inhibits the expression of the PNPLA3 gene (e.g., a human, a primate, a non-primate, or a bird PNPLA3 gene) by at least about 10% as assayed by, for example, a PCR or branched DNA (bDNA)-based method, or by a protein-based method, such as by immunofluorescence analysis, using, for example, western Blotting or flow cytometric techniques.

The region of complementarity between an antisense polynucleotide agent and a target sequence may be substantially complementary (e.g., there is a sufficient degree of complementarity between the antisense polynucleotide agent and a target nucleic acid to so that they specifically hybridize and induce a desired effect), but is generally fully complementary to the target sequence. The target sequence can be derived from the sequence of an mRNA formed during the expression of a PNPLA3 gene.

Accordingly, in one aspect, an antisense polynucleotide agent of the invention specifically hybridizes to a target nucleic acid molecule, such as the mRNA encoding PNPLA3, and comprises a contiguous nucleotide sequence which corresponds to the reverse complement of a nucleotide sequence of any one of SEQ ID NOs:1, 3, 5, 7, 9, and 11, or a fragment of any one of SEQ ID NOs:1, 3, 5, 7, 9, and 11.

In some embodiments, the antisense polynucleotide agents of the invention may be substantially complementary to the target sequence. For example, an antisense polynucleotide agent that is substantially complementary to the target sequence may include a contiguous nucleotide sequence comprising no more than 5 mismatches (e.g., no more than 1, no more than 2, no more than 3, no more than 4, or no more than 5 mismatches) when hybridizing to a target sequence, such as to the corresponding region of a nucleic acid which encodes a mammalian PNPLA3 mRNA. In some embodiments, the contiguous nucleotide sequence comprises no more than a single mismatch when hybridizing to the target sequence, such as the corresponding region of a nucleic acid which encodes a mammalian PNPLA3.

In some embodiments, the antisense polynucleotide agents of the invention that are substantially complementary to the target sequence comprise a contiguous nucleotide sequence which is at least about 80% complementary over its entire length to the equivalent region of the nucleotide sequence of any one of SEQ ID NOs:1, 3, 5, 7, 9, and 11, or a fragment of any one of SEQ ID NOs:1, 3, 5, 7, 9, and 11, such as about 85%, about 86%, about 87%, about 88%, about 89%, about 90%, about % 91%, about 92%, about 93%, about 94%, about 95%, about 96%, about 97%, about 98%, or about 99% complementary.

In some embodiments, an antisense polynucleotide agent comprises a contiguous nucleotide sequence which is fully complementary over its entire length to the equivalent region of the nucleotide sequence of any one of SEQ ID NOs:1, 3, 5, 7, 9, and 11 (or a fragment of any one of SEQ ID NOs:1-4).

An antisense polynucleotide agent may comprise a contiguous nucleotide sequence of about 4 to about 50 nucleotides in length, e.g., 8-49, 8-48, 8-47, 8-46, 8-45, 8-44, 8-43, 8-42, 8-41, 8-40, 8-39, 8-38, 8-37, 8-36, 8-35, 8-34, 8-33, 8-32, 8-31, 8-30, 8-29, 8-28, 8-27, 8-26, 8-25, 8-24, 8-23, 8-22, 8-21, 8-20, 8-19, 8-18, 8-17, 8-16, 8-15, 8-14, 8-13, 8-12, 8-11, 8-10, 8-9, 10-49, 10-48, 10-47, 10-46, 10-45, 10-44, 10-43, 10-42, 10-41, 10-40, 10-39, 10-38, 10-37, 10-36, 10-35, 10-34, 10-33, 10-32, 10-31, 10-30, 10-29, 10-28, 10-27, 10-26, 10-25, 10-24, 10-23, 10-22, 10-21, 10-20, 10-19, 10-18, 10-17, 10-16, 10-15, 10-14, 10-13, 10-12, 10-11, 11-49, 11-48, 11-47, 11-46, 11-45, 11-44, 11-43, 11-42, 11-41, 11-40, 11-39, 11-38, 11-37, 11-36, 11-35, 11-34, 11-33, 11-32, 11-31, 11-30, 11-29, 11-28, 11-27, 11-26, 11-25, 11-24, 11-23, 11-22, 11-21, 11-20, 11-19, 11-18, 11-17, 11-16, 11-15, 11-14, 11-13, 11-12, 12-49, 12-48, 12-47, 12-46, 12-45, 12-44, 12-43, 12-42, 12-41, 12-40, 12-39, 12-38, 12-37, 12-36, 12-35, 12-34, 12-33, 12-32, 12-31, 12-30, 12-29, 12-28, 12-27, 12-26, 12-25, 12-24, 12-23, 12-22, 12-21, 12-20, 12-19, 12-18, 12-17, 12-16, 12-15, 12-14, 12-13, 13-49, 13-48, 13-47, 13-46, 13-45, 13-44, 13-43, 13-42, 13-41, 13-40, 13-39, 13-38, 13-37, 13-36, 13-35, 13-34, 13-33, 13-32, 13-31, 13-30, 13-29, 13-28, 13-27, 13-26, 13-25, 13-24, 13-23, 13-22, 13-21, 13-20, 13-19, 13-18, 13-17, 13-16, 13-15, 13-14, 14-49, 14-48, 14-47, 14-46, 14-45, 14-44, 14-43, 14-42, 14-41, 14-40, 14-39, 14-38, 14-37, 14-36, 14-35, 14-34, 14-33, 14-32, 14-31, 14-30, 14-29, 14-28, 14-27, 14-26, 14-25, 14-24, 14-23, 14-22, 14-21, 14-20, 14-19, 14-18, 14-17, 14-16, 14-15, 15-49, 15-48, 15-47, 15-46, 15-45, 15-44, 15-43, 15-42, 15-41, 15-40, 15-39, 15-38, 15-37, 15-36, 15-35, 15-34, 15-33, 15-32, 15-31, 15-30, 15-29, 15-28, 15-27, 15-26, 15-25, 15-24, 15-23, 15-22, 15-21, 15-20, 15-19, 15-18, 15-17, 15-16, 16-49, 16-48, 16-47, 16-46, 16-45, 16-44, 16-43, 16-42, 16-41, 16-40, 16-39, 16-38, 16-37, 16-36, 16-35, 16-34, 16-33, 16-32, 16-31, 16-30, 16-29, 16-28, 16-27, 16-26, 16-25, 16-24, 16-23, 16-22, 16-21, 16-20, 16-19, 16-18, 16-17, 17-49, 17-48, 17-47, 17-46, 17-45, 17-44, 17-43, 17-42, 17-41, 17-40, 17-39, 17-38, 17-37, 17-36, 17-35, 17-34, 17-33, 17-32, 17-31, 17-30, 17-29, 17-28, 17-27, 17-26, 17-25, 17-24, 17-23, 17-22, 17-21, 17-20, 17-19, 17-18, 18-49, 18-48, 18-47, 18-46, 18-45, 18-44, 18-43, 18-42, 18-41, 18-40, 18-39, 18-38, 18-37, 18-36, 18-35, 18-34, 18-33, 18-32, 18-31, 18-30, 18-29, 18-28, 18-27, 18-26, 18-25, 18-24, 18-23, 18-22, 18-21, 18-20, 19-49, 19-48, 19-47, 19-46, 19-45, 19-44, 19-43, 19-42, 19-41, 19-40, 19-39, 19-38, 19-37, 19-36, 19-35, 19-34, 19-33, 19-32, 19-31, 19-30, 19-29, 19-28, 19-27, 19-26, 19-25, 19-24, 19-23, 19-22, 19-21, 19-20, 20-49, 20-48, 20-47, 20-46, 20-45, 20-44, 20-43, 20-42, 20-41, 20-40, 20-39, 20-38, 20-37, 20-36, 20-35, 20-34, 20-33, 20-32, 20-31, 20-30, 20-29, 20-28, 20-27, 20-26, 20-25, 20-24, 20-23, 20-22, 20-21, 21-49, 21-48, 21-47, 21-46, 21-45, 21-44, 21-43, 21-42, 21-41, 21-40, 21-39, 21-38, 21-37, 21-36, 21-35, 21-34, 21-33, 21-32, 21-31, 21-30, 21-29, 21-28, 21-27, 21-26, 21-25, 21-24, 21-23, 21-22, 22-49, 22-48, 22-47, 22-46, 22-45, 22-44, 22-43, 22-42, 22-41, 22-40, 22-39, 22-38, 22-37, 22-36, 22-35, 22-34, 22-33, 22-32, 22-31, 22-30, 22-29, 22-28, 22-27, 22-26, 22-25, 22-24, 22-23, 23-49, 23-48, 23-47, 23-46, 23-45, 23-44, 23-43, 23-42, 23-41, 23-40, 23-39, 23-38, 23-37, 23-36, 23-35, 23-34, 23-33, 23-32, 23-31, 23-30, 23-29, 23-28, 23-27, 23-26, 23-25, 23-24, 24-49, 24-48, 24-47, 24-46, 24-45, 24-44, 24-43, 24-42, 24-41, 24-40, 24-39, 24-38, 24-37, 24-36, 24-35, 24-34, 24-33, 24-32, 24-31, 24-30, 24-29, 24-28, 24-27, 24-26, 24-25, 25-49, 25-48, 25-47, 25-46, 25-45, 25-44, 25-43, 25-42, 25-41, 25-40, 25-39, 25-38, 25-37, 25-36, 25-35, 25-34, 25-33, 25-32, 25-31, 25-30, 25-29, 25-28, 25-27, 25-26, 26-49, 26-48, 26-47, 26-46, 26-45, 26-44, 26-43, 26-42, 26-41, 26-40, 26-39, 26-38, 26-37, 26-36, 26-35, 26-34, 26-33, 26-32, 26-31, 26-30, 26-29, 26-28, 26-27, 27-49, 27-48, 27-47, 27-46, 27-45, 27-44, 27-43, 27-42, 27-41, 27-40, 27-39, 27-38, 27-37, 27-36, 27-35, 27-34, 27-33, 27-32, 27-31, 27-30, 27-29, 27-28, 28-49, 28-48, 28-47, 28-46, 28-45, 28-44, 28-43, 28-42, 28-41, 28-40, 28-39, 28-38, 28-37, 28-36, 28-35, 28-34, 28-33, 28-32, 28-31, 28-30, 28-29, 29-49, 29-48, 29-47, 29-46, 29-45, 29-44, 29-43, 29-42, 29-41, 29-40, 29-39, 29-38, 29-37, 29-36, 29-35, 29-34, 29-33, 29-32, 29-31, 29-30, 30-49, 30-48, 30-47, 30-46, 30-45, 30-44, 30-43, 30-42, 30-41, 30-40, 30-39, 30-38, 30-37, 30-36, 30-35, 30-34, 30-33, 30-32, or 30-31 nucleotides in length, e.g., 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length.

In some embodiments, an antisense polynucleotide agent may comprise a contiguous nucleotide sequence of no more than 22 nucleotides, such as no more than 21 nucleotides, 20 nucleotides, 19 nucleotides, or no more than 18 nucleotides. In some embodiments the antisense polynucleotide agents of the invention comprises less than 20 nucleotides. In other embodiments, the antisense polynucleotide agents of the invention comprise 20 nucleotides.

In certain aspects, an antisense polynucleotide agent of the invention includes a sequence selected from the group of sequences provided in Tables 3 and 4. It will be understood that, although some of the sequences in Table 4 are described as modified and/or conjugated sequences, an antisense polynucleotide agent of the invention, may also comprise any one of the sequences set forth in Table 4 that is un-modified, un-conjugated, and/or modified and/or conjugated differently than described therein.

By virtue of the nature of the nucleotide sequences provided in Tables 3 and 4, antisense polynucleotide agents of the invention may include one of the sequences of Tables 3 and 4 minus only a few nucleotides on one or both ends and yet remain similarly effective as compared to the antisense polynucleotide agents described above. Hence, antisense polynucleotide agents having a sequence of at least 4, 5, 6, 7, 8, 9, 10, 11, 12, 13, 14, 15, 16, 17, 18, 19, 20, or more contiguous nucleotides derived from one of the sequences of Tables 3 and 4 and differing in their ability to inhibit the expression of a PNPLA3 gene by not more than about 5, 10, 15, 20, 25, or 30% inhibition from an antisense polynucleotide agent comprising the full sequence, are contemplated to be within the scope of the present invention.

In addition, the antisense polynucleotide agents provided in Tables 3 and 4 identify a region(s) in a PNPLA3 transcript that is susceptible to antisense inhibition (e.g., the regions in SEQ ID NO:1 which the antisense polynucleotide agents may target). As such, the present invention further features antisense polynucleotide agents that target within one of these sites.

As used herein, an antisense polynucleotide agent is said to target within a particular site of an RNA transcript if the antisense polynucleotide agent promotes antisense inhibition of the target at that site. Such an antisense polynucleotide agent will generally include at least about 15 contiguous nucleotides from one of the sequences provided in Tables 3 and 4 coupled to additional nucleotide sequences taken from the region contiguous to the selected sequence in a PNPLA3 gene.

While a target sequence is generally about 4-50 nucleotides in length, there is wide variation in the suitability of particular sequences in this range for directing antisense inhibition of any given target RNA. Various software packages and the guidelines set out herein provide guidance for the identification of optimal target sequences for any given gene target, but an empirical approach can also be taken in which a "window" or "mask" of a given size (as a non-limiting example, 20 nucleotides) is literally or figuratively (including, e.g., in silico) placed on the target RNA sequence to identify sequences in the size range that can serve as target sequences. By moving the sequence "window" progressively one nucleotide upstream or downstream of an initial target sequence location, the next potential target sequence can be identified, until the complete set of possible sequences is identified for any given target size selected. This process, coupled with systematic synthesis and testing of the identified sequences (using assays as described herein or as known in the art) to identify those sequences that perform optimally can identify those RNA sequences that, when targeted with an antisense polynucleotide agent, mediate the best inhibition of target gene expression. Thus, while the sequences identified, for example, in Tables 3 and 4, represent effective target sequences, it is contemplated that further optimization of antisense inhibition efficiency can be achieved by progressively "walking the window" one nucleotide upstream or downstream of the given sequences to identify sequences with equal or better inhibition characteristics.

Further, it is contemplated that for any sequence identified, e.g., in Tables 3 and 4, further optimization could be achieved by systematically either adding or removing nucleotides to generate longer or shorter sequences and testing those sequences generated by walking a window of the longer or shorter size up or down the target RNA from that point. Again, coupling this approach to generating new candidate targets with testing for effectiveness of antisense polynucleotide agents based on those target sequences in an inhibition assay as known in the art and/or as described herein can lead to further improvements in the efficiency of inhibition. Further still, such optimized sequences can be adjusted by, e.g., the introduction of modified nucleotides as described herein or as known in the art, addition or changes in length, or other modifications as known in the art and/or discussed herein to further optimize the molecule (e.g., increasing serum stability or circulating half-life, increasing thermal stability, enhancing transmembrane delivery, targeting to a particular location or cell type, increasing interaction with silencing pathway enzymes, increasing release from endosomes) as an expression inhibitor.

III. Modified Antisense Polynucleotide Agents of the Invention

In one embodiment, the nucleotides of an antisense polynucleotide agent of the invention are un-modified, and do not comprise, e.g., chemical modifications and/or conjugations known in the art and described herein. In another embodiment, at least one of the nucleotides of an antisense polynucleotide agent of the invention is chemically modified to enhance stability or other beneficial characteristics. In certain embodiments of the invention, substantially all of the nucleotides of an antisense polynucleotide agent of the invention are modified. In other embodiments of the invention, all of the nucleotides of an antisense polynucleotide agent of the invention are modified. Antisense polynucleotide agents of the invention in which "substantially all of the nucleotides are modified" are largely but not wholly modified and can include not more than 5, 4, 3, 2, or 1 unmodified nucleotides.

The nucleic acids featured in the invention can be synthesized and/or modified by standard methods known in the art as further discussed below, e.g., solution-phase or solid-phase organic synthesis or both, e.g., by use of an automated DNA synthesizer, such as are commercially available from, for example, Biosearch, Applied Biosystems®, Inc. Well-established methods for the synthesis and/or modification of the nucleic acids featured in the invention are described in, for example, "Current protocols in nucleic acid chemistry," Beaucage, S. L. et al. (Edrs.), John Wiley & Sons, Inc., New York, N.Y., USA, which is hereby incorporated herein by reference. Modifications include, for example, end modifications, e.g., 5'-end modifications (phosphorylation, conjugation, inverted linkages) or 3'-end modifications (conjugation, DNA nucleotides, inverted linkages, etc.); base modifications, e.g., replacement with stabilizing bases, destabilizing bases, or bases that base pair with an expanded repertoire of partners, removal of bases (abasic nucleotides), or conjugated bases; sugar modifications (e.g., at the 2'-position or 4'-position) or replacement of the sugar; and/or backbone modifications, including modification or replacement of the phosphodiester linkages.

Specific examples of modified nucleotides useful in the embodiments described herein include, but are not limited to nucleotides containing modified backbones or no natural internucleoside linkages. Nucleotides having modified backbones include, among others, those that do not have a phosphorus atom in the backbone. For the purposes of this specification, and as sometimes referenced in the art, modified nucleotides that do not have a phosphorus atom in their internucleoside backbone can also be considered to be oligonucleosides. In some embodiments, a modified antisense polynucleotide agent will have a phosphorus atom in its internucleoside backbone.

Modified nucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5'-linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. No. RE39464, the entire contents of each of which are hereby incorporated herein by reference.

Modified nucleotide backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, the entire contents of each of which are hereby incorporated herein by reference.

In other embodiments, suitable nucleotide mimetics are contemplated for use in antisense polynucleotide agents, in which both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, the entire contents of each of which are hereby incorporated herein by reference. Additional PNA compounds suitable for use in the antisense polynucleotide agents of the invention are described in, for example, in Nielsen et al., *Science,* 1991, 254, 1497-1500.

Some embodiments featured in the invention include polynucleotides with phosphorothioate backbones and oligonucleosides with heteroatom backbones, and in particular —$CH_2$—NH—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —N($CH_3$)—$CH_2$—$CH_2$—[wherein the native phosphodiester backbone is represented as —O—P—O—$CH_2$—] of the above-referenced U.S. Pat. No. 5,489,677, and the amide backbones of the above-referenced U.S. Pat. No. 5,602,240. In some embodiments, the antisense polynucleotide agents featured herein have morpholino backbone structures of the above-referenced U.S. Pat. No. 5,034,506.

Modified nucleotides can also contain one or more modified or substituted sugar moieties. The antisense polynucleotide agents featured herein can include one of the following at the 2'-position: OH; F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. Exemplary suitable modifications include O[($CH_2$)$_n$O]$_m$ $CH_3$, O($CH_2$)$_n$O$CH_3$, O($CH_2$)$_n$NH$_2$, O($CH_2$)$_n$$CH_3$, O($CH_2$)$_n$ONH$_2$, and O($CH_2$)$_n$ON[($CH_2$)$_n$$CH_3$)]$_2$, where n and m are from 1 to about 10.

In other embodiments, antisense polynucleotide agents include one of the following at the 2' position: $C_1$ to $C_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an antisense polynucleotide, or a group for improving the pharmacodynamic properties of an antisense polynucleotide agent, and other substituents having similar properties. In some embodiments, the modification includes a 2'-methoxyethoxy (2'-O—$CH_2CH_2OCH_3$, also known as 2'-O-(2-methoxyethyl) or 2'-MOE) (Martin et al., *Helv. Chim. Acta,* 1995, 78:486-504) i.e., an alkoxyalkoxy group. Another exemplary modification is 2'-dimethylaminooxyethoxy, i.e., a O($CH_2$)$_2$ON($CH_3$)$_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—CH$_2$—O—CH$_2$—N(CH$_2$)$_2$.

Other modifications include 2'-methoxy (2'-O—CH$_3$) also referred to as 2'-OMe, 2'-aminopropoxy (2'-OCH$_2$CH$_2$CH$_2$NH$_2$) and 2'-fluoro (2'-F) Similar modifications can also be made at other positions on a nucleotide of an antisense polynucleotide agent, particularly the 3' position of the sugar on the 3' terminal nucleotide. Antisense polynucleotide agents can also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application. The entire contents of each of the foregoing are hereby incorporated herein by reference.

Additional nucleotides having modified or substituted sugar moieties for use in the polynucleotide agents of the invention include nucleotides comprising a bicyclic sugar. A "bicyclic sugar" is a furanosyl ring modified by the bridging of two atoms. A "bicyclic nucleoside" ("BNA") is a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring. Thus, in some embodiments an antisense polynucleotide agent may include one or more locked nucleic acids. A "locked nucleic acid" ("LNA") is a nucleotide having a modified ribose moiety in which the ribose moiety comprises an extra bridge connecting the 2' and 4' carbons. In other words, an LNA is a nucleotide comprising a bicyclic sugar moiety comprising a 4'-CH$_2$—O-2' bridge. This structure effectively "locks" the ribose in the 3'-endo structural conformation. The addition of locked nucleic acids to santisense polynucleotide agents has been shown to increase santisense polynucleotide agent stability in serum, and to reduce off-target effects (Elmen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12):3185-3193).

Examples of bicyclic nucleosides for use in the polynucleotides of the invention include without limitation nucleosides comprising a bridge between the 4' and the 2' ribosyl ring atoms. In certain embodiments, the antisense polynucleotide agents of the invention include one or more bicyclic nucleosides comprising a 4' to 2' bridge. Examples of such 4' to 2' bridged bicyclic nucleosides, include but are not limited to 4'-(CH2)-O-2' (LNA); 4'-(CH2)-S-2'; 4'-(CH2)2-O-2' (ENA); 4'-CH(CH3)-O-2' (also referred to as "constrained ethyl" or "cEt") and 4'-CH(CH2OCH3)-O-2' (and analogs thereof; see, e.g., U.S. Pat. No. 7,399,845); 4'-C(CH3)(CH3)-O-2' (and analogs thereof; see e.g., U.S. Pat. No. 8,278,283); 4'-CH2-N(OCH3)-2' (and analogs thereof; see e.g., U.S. Pat. No. 8,278,425); 4'-CH2-O—N(CH3)-2' (see, e.g., U.S. Patent Publication No. 2004/0171570); 4'-CH2-N(R)—O-2', wherein R is H, C1-C12 alkyl, or a protecting group (see, e.g., U.S. Pat. No. 7,427,672); 4'-CH2-C(H)(CH3)-2' (see, e.g., Chattopadhyaya et al., *J. Org. Chem.*, 2009, 74, 118-134); and 4'-CH2-C(=CH2)-2' (and analogs thereof; see, e.g., U.S. Pat. No. 8,278,426). The entire contents of each of the foregoing are hereby incorporated herein by reference.

Additional representative U.S. patents and US patent Publications that teach the preparation of locked nucleic acid nucleotides include, but are not limited to, the following: U.S. Pat. Nos. 6,268,490; 6,525,191; 6,670,461; 6,770,748; 6,794,499; 6,998,484; 7,053,207; 7,034,133; 7,084,125; 7,399,845; 7,427,672; 7,569,686; 7,741,457; 8,022,193; 8,030,467; 8,278,425; 8,278,426; 8,278,283; US 2008/0039618; and US 2009/0012281, the entire contents of each of which are hereby incorporated herein by reference.

Any of the foregoing bicyclic nucleosides can be prepared having one or more stereochemical sugar configurations including for example α-L-ribofuranose and β-D-ribofuranose (see WO 99/14226).

In one particular embodiment of the invention, an antisense polynucleotide agent can include one or more constrained ethyl nucleotides. As used herein, a "constrained ethyl nucleotide" or "cEt" is a locked nucleic acid comprising a bicyclic sugar moiety comprising a 4'-CH(CH$_3$)—O-2' bridge. In one embodiment, a constrained ethyl nucleotide is in an S conformation and is referred to as an "S-constrained ethyl nucleotide" or "S-cEt."

Modified nucleotides included in the antisense polynucleotide agents of the invention can also contain one or more sugar mimetics. For example, the antisense polynucleotide agent may include a "modified tetrahydropyran nucleotide" or "modified THP nucleotide." A "modified tetrahydropyran nucleotide" has a six-membered tetrahydropyran "sugar" substituted in for the pentofuranosyl residue in normal nucleotides (a sugar surrogate). Modified THP nucleotides include, but are not limited to, what is referred to in the art as hexitol nucleic acid (HNA), anitol nucleic acid (ANA), manitol nucleic acid (MNA) (see, e.g., Leumann, *Bioorg. Med. Chem.*, 2002, 10, 841-854), or fluoro HNA (F-HNA).

In some embodiments of the invention, sugar surrogates comprise rings having more than 5 atoms and more than one heteroatom. For example nucleotides comprising morpholino sugar moieties and their use in oligomeric compounds has been reported (see for example: Braasch et al., *Biochemistry*, 2002, 41, 4503-4510; and U.S. Pat. Nos. 5,698,685; 5,166,315; 5,185,444; and 5,034,506). Morpholinos may be modified, for example by adding or altering various substituent groups from the above morpholino structure. Such sugar surrogates are referred to herein as "modified morpholinos."

Combinations of modifications are also provided without limitation, such as 2'-F-5'-methyl substituted nucleosides (see PCT International Application WO 2008/101157 published on Aug. 21, 2008 for other disclosed 5', 2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-CH2-O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., J. Am. Chem. Soc. 2007, 129(26), 8362-8379).

In certain embodiments, antisense compounds comprise one or more modified cyclohexenyl nucleosides, which is a nucleoside having a six-membered cyclohexenyl in place of the pentofuranosyl residue in naturally occurring nucleosides. Modified cyclohexenyl nucleosides include, but are not limited to those described in the art (see for example commonly owned, published PCT Application WO 2010/

036696, published on Apr. 10, 2010, Robeyns et al., J. Am. Chem. Soc., 2008, 130(6), 1979-1984; Horvath et al., Tetrahedron Letters, 2007, 48, 3621-3623; Nauwelaerts et al., J. Am. Chem. Soc., 2007, 129(30), 9340-9348; Gu et al., Nucleosides, Nucleotides & Nucleic Acids, 2005, 24(5-7), 993-998; Nauwelaerts et al., Nucleic Acids Research, 2005, 33(8), 2452-2463; Robeyns et al., Acta Crystallographica, Section F: Structural Biology and Crystallization Communications, 2005, F61(6), 585-586; Gu et al., Tetrahedron, 2004, 60(9), 2111-2123; Gu et al., Oligonucleotides, 2003, 13(6), 479-489; Wang et al., J. Org. Chem., 2003, 68, 4499-4505; Verbeure et al., Nucleic Acids Research, 2001, 29(24), 4941-4947; Wang et al., J. Org. Chem., 2001, 66, 8478-82; Wang et al., Nucleosides, Nucleotides & Nucleic Acids, 2001, 20(4-7), 785-788; Wang et al., J. Am. Chem., 2000, 122, 8595-8602; Published PCT application, WO 06/047842; and Published PCT Application WO 01/049687; the text of each is incorporated by reference herein, in their entirety).

An antisense polynucleotide agent can also include nucleobase modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as deoxy-thymine (dT), 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in "Modified Nucleosides in Biochemistry," *Biotechnology and Medicine*, Herdewijn, P. ed. Wiley-VCH, 2008; those disclosed in *The Concise Encyclopedia Of Polymer Science And Engineering*, pages 858-859, Kroschwitz, J. L, ed. John Wiley & Sons, 1990, these disclosed by Englisch et al., *Angewandte Chemie, International Edition*, 1991, 30, 613, and those disclosed by Sanghvi, Y S., Chapter 15, *antisense polynucleotide agent Research and Applications*, pages 289-302, Crooke, S. T. and Lebleu, B., Ed., CRC Press, 1993. Certain of these nucleobases are particularly useful for increasing the binding affinity of the agents featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., *antisense polynucleotide agent Research and Applications*, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. Nos. 3,687,808, 4,845,205; 5,130, 30; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, the entire contents of each of which are hereby incorporated herein by reference.

One or more of the nucleotides of an antisense polynucleotide agent of the invention may also include a hydroxymethyl substituted nucleotide. A "hydroxymethyl substituted nucleotide" is an acyclic 2'-3'-seco-nucleotide, also referred to as an "unlocked nucleic acid" ("UNA") modification. Representative U.S. publications that teach the preparation of UNA include, but are not limited to, U.S. Pat. No. 8,314,227; and US Patent Publication Nos. 2013/0096289; 2013/0011922; and 2011/0313020, the entire contents of each of which are hereby incorporated herein by reference.

Additional modifications which may potentially stabilize the ends of antisense polynucleotide agents can include N-(acetylaminocaproyl)-4-hydroxyprolinol (Hyp-C6-NHAc), N-(caproyl-4-hydroxyprolinol (Hyp-C6), N-(acetyl-4-hydroxyprolinol (Hyp-NHAc), thymidine-2'-0-deoxythymidine (ether), N-(aminocaproyl)-4-hydroxyprolinol (Hyp-C6-amino), 2-docosanoyl-uridine-3'-phosphate, inverted base dT(idT) and others. Disclosure of this modification can be found in US Patent Publication No. 2012/0142101.

Any of the antisense polynucleotide agents of the invention may be optionally conjugated with a GalNAc derivative ligand, as described in Section IV, below.

As described in more detail below, an agent that contains conjugations of one or more carbohydrate moieties to an antisense polynucleotide agent can optimize one or more properties of the agent. In many cases, the carbohydrate moiety will be attached to a modified subunit of the antisense polynucleotide agent. For example, the ribose sugar of one or more ribonucleotide subunits of an agent can be replaced with another moiety, e.g., a non-carbohydrate (preferably cyclic) carrier to which is attached a carbohydrate ligand. A ribonucleotide subunit in which the ribose sugar of the subunit has been so replaced is referred to herein as a ribose replacement modification subunit (RRMS). A cyclic carrier may be a carbocyclic ring system, i.e., all ring atoms are carbon atoms, or a heterocyclic ring system, i.e., one or more ring atoms may be a heteroatom, e.g., nitrogen, oxygen, sulfur. The cyclic carrier may be a monocyclic ring system, or may contain two or more rings, e.g. fused rings. The cyclic carrier may be a fully saturated ring system, or it may contain one or more double bonds.

The ligand may be attached to the polynucleotide via a carrier. The carriers include (i) at least one "backbone attachment point," preferably two "backbone attachment points" and (ii) at least one "tethering attachment point." A "backbone attachment point" as used herein refers to a functional group, e.g. a hydroxyl group, or generally, a bond available for, and that is suitable for incorporation of the carrier into the backbone, e.g., the phosphate, or modified phosphate, e.g., sulfur containing, backbone, of a ribonucleic acid. A "tethering attachment point" (TAP) in some embodiments refers to a constituent ring atom of the cyclic carrier, e.g., a carbon atom or a heteroatom (distinct from an atom which provides a backbone attachment point), that connects a selected moiety. The moiety can be, e.g., a carbohydrate, e.g. monosaccharide, disaccharide, trisaccharide, tetrasaccharide, oligosaccharide and polysaccharide. Optionally, the selected moiety is connected by an intervening tether to the cyclic carrier. Thus, the cyclic carrier will often include a functional group, e.g., an amino group, or generally, provide a bond, that is suitable for incorporation or tethering of another chemical entity, e.g., a ligand to the constituent ring.

The antisense polynucleotide agents may be conjugated to a ligand via a carrier, wherein the carrier can be cyclic group or acyclic group; preferably, the cyclic group is selected from pyrrolidinyl, pyrazolinyl, pyrazolidinyl, imidazolinyl, imidazolidinyl, piperidinyl, piperazinyl, [1,3]dioxolane, oxazolidinyl, isoxazolidinyl, morpholinyl, thiazolidinyl, isothiazolidinyl, quinoxalinyl, pyridazinonyl, tetrahydrofuryl and and decalin; preferably, the acyclic group is selected from serinol backbone or diethanolamine backbone.

In certain specific embodiments, the antisense polynucleotide agent for use in the methods of the invention is an agent selected from the group of agents listed in Tables 3 and 4. These agents may further comprise a ligand, as described in Section IV, below.

A. Antisense Polynucleotide Agents Comprising Motifs

In certain embodiments of the invention, at least one of the contiguous nucleotides of the antisense polynucleotide agents of the invention may be a modified nucleotide. In one embodiment, the modified nucleotide comprises one or more modified sugars. In other embodiments, the modified nucleotide comprises one or more modified nucleobases. In yet other embodiments, the modified nucleotide comprises one or more modified internucleoside linkages. In some embodiments, the modifications (sugar modifications, nucleobase modifications, and/or linkage modifications) define a pattern or motif. In one embodiment, the patterns of modifications of sugar moieties, internucleoside linkages, and nucleobases are each independent of one another.

Antisense polynucleotide agents having modified oligonucleotides arranged in patterns, or motifs may, for example, confer to the agents properties such as enhanced inhibitory activity, increased binding affinity for a target nucleic acid, or resistance to degradation by in vivo nucleases. For example, such agents may contain at least one region modified so as to confer increased resistance to nuclease degradation, increased cellular uptake, increased binding affinity for the target nucleic acid, and/or increased inhibitory activity. A second region of such agents may optionally serve as a substrate for the cellular endonuclease RNase H, which cleaves the RNA strand of an RNA:DNA duplex.

An exemplary antisense polynucleotide agent having modified oligonucleotides arranged in patterns, or motifs is a gapmer. In a "gapmer", an internal region or "gap" having a plurality of linked nucleotides that supports RNaseH cleavage is positioned between two external flanking regions or "wings" having a plurality of linked nucleotides that are chemically distinct from the linked nucleotides of the internal region. The gap segment generally serves as the substrate for endonuclease cleavage, while the wing segments comprise modified nucleotides.

The three regions of a gapmer motif (the 5'-wing, the gap, and the 3'-wing) form a contiguous sequence of nucleotides and may be described as "X—Y—Z", wherein "X" represents the length of the 5-wing, "Y" represents the length of the gap, and "Z" represents the length of the 3'-wing. In one embodiment, a gapmer described as "X—Y—Z" has a configuration such that the gap segment is positioned immediately adjacent to each of the 5' wing segment and the 3' wing segment. Thus, no intervening nucleotides exist between the 5' wing segment and gap segment, or the gap segment and the 3' wing segment. Any of the antisense compounds described herein can have a gapmer motif. In some embodiments, X and Z are the same, in other embodiments they are different.

In certain embodiments, the regions of a gapmer are differentiated by the types of modified nucleotides in the region. The types of modified nucleotides that may be used to differentiate the regions of a gapmer, in some embodiments, include β-D-ribonucleotides, β-D-deoxyribonucleotides, 2'-modified nucleotides, e.g., 2'-modified nucleotides (e.g., 2'-MOE, and 2'-O—CH3), and bicyclic sugar modified nucleotides (e.g., those having a 4'-(CH2)n-O-2' bridge, where n=1 or n=2).

In one embodiment, at least some of the modified nucleotides of each of the wings may differ from at least some of the modified nucleotides of the gap. For example, at least some of the modified nucleotides of each wing that are closest to the gap (the 3'-most nucleotide of the 5'-wing and the 5'-most nucleotide of the 3-wing) differ from the modified nucleotides of the neighboring gap nucleotides, thus defining the boundary between the wings and the gap. In certain embodiments, the modified nucleotides within the gap are the same as one another. In certain embodiments, the gap includes one or more modified nucleotides that differ from the modified nucleotides of one or more other nucleotides of the gap.

The length of the 5'-wing (X) of a gapmer may be 1 to 6 nucleotides in length, e.g., 2 to 6, 2 to 5, 3 to 6, 3 to 5, 1 to 5, 1 to 4, 1 to 3, 2 to 4 nucleotides in length, e.g., 1, 2, 3, 4, 5, or 6 nucleotides in length.

The length of the 3'-wing (Z) of a gapmer may be 1 to 6 nucleotides in length, e.g., 2 to 6, 2-5, 3 to 6, 3 to 5, 1 to 5, 1 to 4, 1 to 3, 2 to 4 nucleotides in length, e.g., 1, 2, 3, 4, 5, or 6 nucleotides in length.

The length of the gap (Y) of a gapmer may be 5 to 14 nucleotides in length, e.g., 5 to 13, 5 to 12, 5 to 11, 5 to 10, 5 to 9, 5 to 8, 5 to 7, 5 to 6, 6 to 14, 6 to 13, 6 to 12, 6 to 11, 6 to 10, 6 to 9, 6 to 8, 6 to 7, 7 to 14, 7 to 13, 7 to 12, 7 to 11, 7 to 10, 7 to 9, 7 to 8, 8 to 14, 8 to 13, 8 to 12, 8 to 11, 8 to 10, 8 to 9, 9 to 14, 9 to 13, 9 to 12, 9 to 11, 9 to 10, 10 to 14, 10 to 13, 10 to 12, 10 to 11, 11 to 14, 11 to 13, 11 to 12, 12 to 14, 12 to 13, or 13 to 14 nucleotides in length, e.g., 5, 6, 7, 8, 9, 10, 11, 12, 13, or 14 nucleotides in length.

In some embodiments of the invention X consists of 2, 3, 4, 5 or 6 nucleotides, Y consists of 7, 8, 9, 10, 11, or 12 nucleotides, and Z consists of 2, 3, 4, 5 or 6 nucleotides. Such gapmers include (X-Y-Z) 2-7-2, 2-7-3, 2-7-4, 2-7-5, 2-7-6, 3-7-2, 3-7-3, 3-7-4, 3-7-5, 3-7-6, 4-7-3, 4-7-4, 4-7-5, 4-7-6, 5-7-3, 5-7-4, 5-7-5, 5-7-6, 6-7-3, 6-7-4, 6-7-5, 6-7-6, 3-7-3, 3-7-4, 3-7-5, 3-7-6, 4-7-3, 4-7-4, 4-7-5, 4-7-6, 5-7-3, 5-7-4, 5-7-5, 5-7-6, 6-7-3, 6-7-4, 6-7-5, 6-7-6, 2-8-2, 2-8-3, 2-8-4, 2-8-5, 2-8-6, 3-8-2, 3-8-3, 3-8-4, 3-8-5, 3-8-6, 4-8-3, 4-8-4, 4-8-5, 4-8-6, 5-8-3, 5-8-4, 5-8-5, 5-8-6, 6-8-3, 6-8-4, 6-8-5, 6-8-6, 2-9-2, 2-9-3, 2-9-4, 2-9-5, 2-9-6, 3-9-2, 3-9-3, 3-9-4, 3-9-5, 3-9-6, 4-9-3, 4-9-4, 4-9-5, 4-9-6, 5-9-3, 5-9-4, 5-9-5, 5-9-6, 6-9-3, 6-9-4, 6-9-5, 6-9-6, 2-10-2, 2-10-3, 2-10-4, 2-10-5, 2-10-6, 3-10-2, 3-10-3, 3-10-4, 3-10-5, 3-10-6, 4-10-3, 4-10-4, 4-10-5, 4-10-6, 5-10-3, 5-10-4, 5-10-5, 5-10-6, 6-10-3, 6-10-4, 6-10-5, 6-10-6, 2-11-2, 2-11-3, 2-11-4, 2-11-5, 2-11-6, 3-11-2, 3-11-3, 3-11-4, 3-11-5, 3-11-6, 4-11-3, 4-11-4, 4-11-5, 4-11-6, 5-11-3, 5-11-4, 5-11-5, 5-11-6, 6-11-3, 6-11-4, 6-11-5, 6-11-6, 2-12-2, 2-12-3, 2-12-4, 2-12-5, 2-12-6, 3-12-2, 3-12-3, 3-12-4, 3-12-5, 3-12-6, 4-12-3, 4-12-4, 4-12-5, 4-12-6, 5-12-3, 5-12-4, 5-12-5, 5-12-6, 6-12-3, 6-12-4, 6-12-5, or 6-12-6.

In some embodiments of the invention, antisense polynucleotide agents targeting PNPLA3 include a 5-10-5 gapmer motif. In other embodiments of the invention, antisense polynucleotide agents targeting PNPLA3 include a 4-10-4 gapmer motif. In another embodiment of the invention, antisense polynucleotide agents targeting PNPLA3 include a 3-10-3 gapmer motif. In yet other embodiments of the invention, antisense polynucleotide agents targeting PNPLA3 include a 2-10-2 gapmer motif.

The 5'-wing and/or 3'-wing of a gapmer may independently include 1-6 modified nucleotides, e.g., 1, 2, 3, 4, 5, or 6 modified nucleotides.

In some embodiment, the 5'-wing of a gapmer includes at least one modified nucleotide. In one embodiment, the 5'-wing of a gapmer comprises at least two modified nucleotides. In another embodiment, the 5'-wing of a gapmer comprises at least three modified nucleotides. In yet another embodiment, the 5'-wing of a gapmer comprises at least four modified nucleotides. In another embodiment, the 5'-wing of a gapmer comprises at least five modified nucleotides. In certain embodiments, each nucleotide of the 5'-wing of a gapmer is a modified nucleotide.

In some embodiments, the 3'-wing of a gapmer includes at least one modified nucleotide. In one embodiment, the 3'-wing of a gapmer comprises at least two modified nucleotides. In another embodiment, the 3'-wing of a gapmer comprises at least three modified nucleotides. In yet another embodiment, the 3'-wing of a gapmer comprises at least four modified nucleotides. In another embodiment, the 3'-wing of a gapmer comprises at least five modified nucleotides. In certain embodiments, each nucleotide of the 3'-wing of a gapmer is a modified nucleotide.

In certain embodiments, the regions of a gapmer are differentiated by the types of sugar moieties of the nucleotides. In one embodiment, the nucleotides of each distinct region comprise uniform sugar moieties. In other embodiments, the nucleotides of each distinct region comprise different sugar moieties. In certain embodiments, the sugar nucleotide modification motifs of the two wings are the same as one another. In certain embodiments, the sugar nucleotide modification motifs of the 5'-wing differs from the sugar nucleotide modification motif of the 3'-wing.

The 5'-wing of a gapmer may include 1-6 modified nucleotides, e.g., 1, 2, 3, 4, 5, or 6 modified nucleotides.

In one embodiment, at least one modified nucleotide of the 5'-wing of a gapmer is a bicyclic nucleotide, such as a constrained ethyl nucleotide, or an LNA. In another embodiment, the 5'-wing of a gapmer includes 2, 3, 4, or 5 bicyclic nucleotides. In some embodiments, each nucleotide of the 5'-wing of a gapmer is a bicyclic nucleotide.

In one embodiment, the 5'-wing of a gapmer includes at least 1, 2, 3, 4, or 5 constrained ethyl nucleotides. In some embodiments, each nucleotide of the 5'-wing of a gapmer is a constrained ethyl nucleotide.

In one embodiment, the 5'-wing of a gapmer comprises at least one LNA nucleotide. In another embodiment, the 5'-wing of a gapmer includes 2, 3, 4, or 5 LNA nucleotides. In other embodiments, each nucleotide of the 5'-wing of a gapmer is an LNA nucleotide.

In certain embodiments, at least one modified nucleotide of the 5'-wing of a gapmer is a non-bicyclic modified nucleotide, e.g., a 2'-substituted nucleotide. A "2'-substituted nucleotide" is a nucleotide comprising a modification at the 2'-position which is other than H or OH, such as a 2'-OMe nucleotide, or a 2'-MOE nucleotide. In one embodiment, the 5'-wing of a gapmer comprises 2, 3, 4, or 5 2'-substituted nucleotides. In one embodiment, each nucleotide of the 5'-wing of a gapmer is a 2'-substituted nucleotide.

In one embodiment, the 5'-wing of a gapmer comprises at least one 2'-OMe nucleotide. In one embodiment, the 5'-wing of a gapmer comprises at least 2, 3, 4, or 5 2'-OMe nucleotides. In one embodiment, each of the nucleotides of the 5'-wing of a gapmer comprises a 2'-OMe nucleotide.

In one embodiment, the 5'-wing of a gapmer comprises at least one 2'-MOE nucleotide. In one embodiment, the 5'-wing of a gapmer comprises at least 2, 3, 4, or 5 2'-MOE nucleotides. In one embodiment, each of the nucleotides of the 5'-wing of a gapmer comprises a 2'-MOE nucleotide.

In certain embodiments, the 5'-wing of a gapmer comprises at least one 2'-deoxynucleotide. In certain embodiments, each nucleotide of the 5'-wing of a gapmer is a 2'-deoxynucleotide. In a certain embodiments, the 5'-wing of a gapmer comprises at least one ribonucleotide. In certain embodiments, each nucleotide of the 5'-wing of a gapmer is a ribonucleotide.

The 3'-wing of a gapmer may include 1-6 modified nucleotides, e.g., 1, 2, 3, 4, 5, or 6 modified nucleotides.

In one embodiment, at least one modified nucleotide of the 3'-wing of a gapmer is a bicyclic nucleotide, such as a constrained ethyl nucleotide, or an LNA. In another embodiment, the 3'-wing of a gapmer includes 2, 3, 4, or 5 bicyclic nucleotides. In some embodiments, each nucleotide of the 3'-wing of a gapmer is a bicyclic nucleotide.

In one embodiment, the 3'-wing of a gapmer includes at least one constrained ethyl nucleotide. In another embodiment, the 3'-wing of a gapmer includes 2, 3, 4, or 5 constrained ethyl nucleotides. In some embodiments, each nucleotide of the 3'-wing of a gapmer is a constrained ethyl nucleotide.

In one embodiment, the 3'-wing of a gapmer comprises at least one LNA nucleotide. In another embodiment, the 3'-wing of a gapmer includes 2, 3, 4, or 5 LNA nucleotides. In other embodiments, each nucleotide of the 3'-wing of a gapmer is an LNA nucleotide.

In certain embodiments, at least one modified nucleotide of the 3'-wing of a gapmer is a non-bicyclic modified nucleotide, e.g., a 2'-substituted nucleotide. In one embodiment, the 3'-wing of a gapmer comprises 2, 3, 4, or 5 2'-substituted nucleotides. In one embodiment, each nucleotide of the 3'-wing of a gapmer is a 2'-substituted nucleotide.

In one embodiment, the 3'-wing of a gapmer comprises at least one 2'-OMe nucleotide. In one embodiment, the 3'-wing of a gapmer comprises at least 2, 3, 4, or 5 2'-OMe nucleotides. In one embodiment, each of the nucleotides of the 3'-wing of a gapmer comprises a 2'-OMe nucleotide.

In one embodiment, the 3'-wing of a gapmer comprises at least one 2'-MOE nucleotide. In one embodiment, the 3'-wing of a gapmer comprises at least 2, 3, 4, or 5 2'-MOE nucleotides. In one embodiment, each of the nucleotides of the 3'-wing of a gapmer comprises a 2'-MOE nucleotide.

In certain embodiments, the 3'-wing of a gapmer comprises at least one 2'-deoxynucleotide. In certain embodiments, each nucleotide of the 3'-wing of a gapmer is a 2'-deoxynucleotide. In a certain embodiments, the 3'-wing of a gapmer comprises at least one ribonucleotide. In certain embodiments, each nucleotide of the 3'-wing of a gapmer is a ribonucleotide.

The gap of a gapmer may include 5-14 modified nucleotides, e.g., 5, 6, 7, 8, 9, 10, 11, 12, 13, or 14 modified nucleotides.

In one embodiment, the gap of a gapmer comprises at least one 5-methylcytosine. In one embodiment, the gap of a gapmer comprises at least 2, 3, 4, 5, 6, 7, 8, 9, 10, 11, 12, or 13 5-methylcytosines. In one embodiment, all of the nucleotides of the gap of a gapmer are 5-methylcytosines.

In one embodiment, the gap of a gapmer comprises at least one 2'-deoxynucleotide. In one embodiment, the gap of a gapmer comprises at least 2, 3, 4, 5, 6, 7, 8, 9, 10, 11, 12, or 13 2'-deoxynucleotides. In one embodiment, all of the nucleotides of the gap of a gapmer are 2'-deoxynucleotides.

A gapmer may include one or more modified internucleotide linkages. In some embodiments, a gapmer includes one or more phosphodiester internucleotide linkages. In other embodiments, a gapmer includes one or more phosphorothioate internucleotide linkages.

In one embodiment, each nucleotide of a 5'-wing of a gapmer are linked via a phosphorothioate internucleotide linkage. In another embodiment, each nucleotide of a 3'-wing of a gapmer are linked via a phosphorothioate internucleotide linkage. In yet another embodiment, each nucleotide of a gap segment of a gapmer is linked via a phosphorothioate internucleotide linkage. In one embodiment, all of the nucleotides in a gapmer are linked via phosphorothioate internucleotide linkages.

In one embodiment, an antisense polynucleotide agent targeting a PNPLA3 gene comprises a gap segment of ten 2'-deoxyribonucleotides positioned immediately adjacent to and between a 5'-wing segment comprising five nucleotides and a 3'-wing segment comprising 5 nucleotides.

In another embodiment, an antisense polynucleotide agent targeting a PNPLA3 gene comprises a gap segment of ten 2'-deoxyribonucleotides positioned immediately adjacent to and between a 5'-wing segment comprising four nucleotides and a 3'-wing segment comprising four nucleotides.

In another embodiment, an antisense polynucleotide agent targeting a PNPLA3 gene comprises a gap segment of ten 2'-deoxyribonucleotides positioned immediately adjacent to and between a 5'-wing segment comprising three nucleotides and a 3'-wing segment comprising three nucleotides.

In another embodiment, an antisense polynucleotide agent targeting a PNPLA3 gene comprises a gap segment of ten 2'-deoxyribonucleotides positioned immediately adjacent to and between a 5'-wing segment comprising two nucleotides and a 3'-wing segment comprising two nucleotides.

In one embodiment, each nucleotide of a 5-wing flanking a gap segment of 10 2'-deoxyribonucleotides comprises a modified nucleotide. In another embodiment, each nucleotide of a 3-wing flanking a gap segment of 10 2'-deoxyribonucleotides comprises a modified nucleotide. In one embodiment, each of the modified 5'-wing nucleotides and each of the modified 3'-wing nucleotides comprise a 2'-sugar modification. In one embodiment, the 2'-sugar modification is a 2'-OMe modification. In another embodiment, the 2'-sugar modification is a 2'-MOE modification. In one embodiment, each of the modified 5'-wing nucleotides and each of the modified 3'-wing nucleotides comprise a bicyclic nucleotide. In one embodiment, the bicyclic nucleotide is a constrained ethyl nucleotide. In another embodiment, the bicyclic nucleotide is an LNA nucleotide. In one embodiment, each cytosine in an antisense polynucleotide agent targeting a PNPLA3 gene is a 5-methylcytosine.

In one embodiment, an antisense polynucleotide agent targeting a PNPLA3 gene comprises a gap segment of ten 2'-deoxyribonucleotides positioned immediately adjacent to and between a 5'-wing segment comprising five nucleotides comprising a 2'OMe modification and a 3'-wing segment comprising five nucleotides comprising a 2'OMe modification, wherein each internucleotide linkage of the agent is a phosphorothioate linkage. In one embodiment, each cytosine of the agent is a 5-methylcytosine. In one embodiment, the agent further comprises a ligand.

In one embodiment, an antisense polynucleotide agent targeting a PNPLA3 gene comprises a gap segment of ten 2'-deoxyribonucleotides positioned immediately adjacent to and between a 5'-wing segment comprising five nucleotides comprising a 2'MOE modification and a 3'-wing segment comprising five nucleotides comprising a 2'MOE modification, wherein each internucleotide linkage of the agent is a phosphorothioate linkage. In one embodiment, each cytosine of the agent is a 5-methylcytosine. In one embodiment, the agent further comprises a ligand.

In one embodiment, an antisense polynucleotide agent targeting PNPLA3 gene comprises a gap segment of ten 2'-deoxyribonucleotides positioned immediately adjacent to and between a 5'-wing segment comprising five constrained ethyl nucleotides and a 3'-wing segment comprising five constrained ethyl nucleotides, wherein each internucleotide linkage of the agent is a phosphorothioate linkage. In one embodiment, each cytosine of the agent is a 5-methylcytosine.

In one embodiment, an antisense polynucleotide agent targeting a PNPLA3 gene comprises a gap segment of ten 2'-deoxyribonucleotides positioned immediately adjacent to and between a 5'-wing segment comprising five LNA nucleotides and a 3'-wing segment comprising five LNA nucleotides, wherein each internucleotide linkage of the agent is a phosphorothioate linkage. In one embodiment, each cytosine of the agent is a 5-methylcytosine.

In one embodiment, an antisense polynucleotide agent targeting a PNPLA3 gene comprises a gap segment of ten 2'-deoxyribonucleotides positioned immediately adjacent to and between a 5'-wing segment comprising four nucleotides comprising a 2'OMe modification and a 3'-wing segment comprising four nucleotides comprising a 2'OMe modification, wherein each internucleotide linkage of the agent is a phosphorothioate linkage. In one embodiment, each cytosine of the agent is a 5-methylcytosine.

In one embodiment, an antisense polynucleotide agent targeting a PNPLA3 gene comprises a gap segment of ten 2'-deoxyribonucleotides positioned immediately adjacent to and between a 5'-wing segment comprising four nucleotides comprising a 2'MOE modification and a 3'-wing segment comprising four nucleotides comprising a 2'MOE modification, wherein each internucleotide linkage of the agent is a phosphorothioate linkage. In one embodiment, each cytosine of the agent is a 5-methylcytosine.

In one embodiment, an antisense polynucleotide agent targeting a PNPLA3 gene comprises a gap segment of ten 2'-deoxyribonucleotides positioned immediately adjacent to and between a 5'-wing segment comprising four constrained ethyl nucleotides and a 3'-wing segment comprising four constrained ethyl nucleotides, wherein each internucleotide linkage of the agent is a phosphorothioate linkage. In one embodiment, each cytosine of the agent is a 5-methylcytosine.

In one embodiment, an antisense polynucleotide agent targeting PNPLA3 gene comprises a gap segment of ten 2'-deoxyribonucleotides positioned immediately adjacent to and between a 5'-wing segment comprising four LNA nucleotides and a 3'-wing segment comprising four LNA nucleotides, wherein each internucleotide linkage of the agent is a phosphorothioate linkage. In one embodiment, each cytosine of the agent is a 5-methylcytosine.

In one embodiment, an antisense polynucleotide agent targeting PNPLA3 gene comprises a gap segment of ten 2'-deoxyribonucleotides positioned immediately adjacent to and between a 5'-wing segment comprising three nucleotides comprising a 2'OMe modification and a 3'-wing segment comprising three nucleotides comprising a 2'OMe modification, wherein each internucleotide linkage of the agent is a phosphorothioate linkage. In one embodiment, each cytosine of the agent is a 5-methylcytosine.

In one embodiment, an antisense polynucleotide agent targeting a PNPLA3 gene comprises a gap segment of ten 2'-deoxyribonucleotides positioned immediately adjacent to and between a 5'-wing segment comprising three nucleotides comprising a 2'MOE modification and a 3'-wing segment comprising three nucleotides comprising a 2'MOE modification, wherein each internucleotide linkage of the agent is a phosphorothioate linkage. In one embodiment, each cytosine of the agent is a 5-methylcytosine.

In one embodiment, an antisense polynucleotide agent targeting a PNPLA3 gene comprises a gap segment of ten 2'-deoxyribonucleotides positioned immediately adjacent to and between a 5'-wing segment comprising three constrained ethyl nucleotides and a 3'-wing segment comprising three constrained ethyl nucleotides, wherein each internucleoitde linkage of the agent is a phosphorothioate linkage. In one embodiment, each cytosine of the agent is a 5-methylcytosine.

In one embodiment, an antisense polynucleotide agent targeting PNPLA3 gene comprises a gap segment of ten 2'-deoxyribonucleotides positioned immediately adjacent to and between a 5'-wing segment comprising three LNA nucleotides and a 3'-wing segment comprising three LNA nucleotides, wherein each internucleotide linkage of the agent is a phosphorothioate linkage. In one embodiment, each cytosine of the agent is a 5-methylcytosine.

In one embodiment, an antisense polynucleotide agent targeting a PNPLA3 gene comprises a gap segment of ten 2'-deoxyribonucleotides positioned immediately adjacent to and between a 5'-wing segment comprising two nucleotides comprising a 2'OMe modification and a 3'-wing segment comprising two nucleotides comprising a 2'OMe modification, wherein each internucleotide linkage of the agent is a phosphorothioate linkage. In one embodiment, each cytosine of the agent is a 5-methylcytosine.

In one embodiment, an antisense polynucleotide agent targeting a PNPLA3 gene comprises a gap segment of ten 2'-deoxyribonucleotides positioned immediately adjacent to and between a 5'-wing segment comprising two nucleotides comprising a 2'MOE modification and a 3'-wing segment comprising two nucleotides comprising a 2'MOE modification, wherein each internucleotide linkage of the agent is a phosphorothioate linkage. In one embodiment, each cytosine of the agent is a 5-methylcytosine.

In one embodiment, an antisense polynucleotide agent targeting a PNPLA3 gene comprises a gap segment of ten 2'-deoxyribonucleotides positioned immediately adjacent to and between a 5'-wing segment comprising two constrained ethyl nucleotides and a 3'-wing segment comprising two constrained ethyl nucleotides, wherein each internucleotide linkage of the agent is a phosphorothioate linkage. In one embodiment, each cytosine of the agent is a 5-methylcytosine.

In one embodiment, an antisense polynucleotide agent targeting a PNPLA3 gene comprises a gap segment of ten 2'-deoxyribonucleotides positioned immediately adjacent to and between a 5'-wing segment comprising two LNA nucleotides and a 3'-wing segment comprising two LNA nucleotides, wherein each internucleotide linkage of the agent is a phosphorothioate linkage. In one embodiment, each cytosine of the agent is a 5-methylcytosine.

Further gapmer designs suitable for use in the agents, compositions, and methods of the invention are disclosed in, for example, U.S. Pat. Nos. 7,687,617 and 8,580,756; U.S. Patent Publication Nos. 20060128646, 20090209748, 20140128586, 20140128591, 20100210712, and 20080015162A1; and International Publication No. WO 2013/159108, the entire content of each of which are incorporated herein by reference.

IV. Antisense Polynucleotide Agents Conjugated to Ligands

Another modification of the polynucleotide agents of the invention involves chemically linking to the agent one or more ligands, moieties or conjugates that enhance the activity, cellular distribution or cellular uptake of the antisense polynucleotide agent. Such moieties include but are not limited to lipid moieties such as a cholesterol moiety (Letsinger et al., *Proc. Natl. Acid. Sci. USA*, 1989, 86: 6553-6556), cholic acid (Manoharan et al., *Biorg. Med. Chem. Let.*, 1994, 4:1053-1060), a thioether, e.g., beryl-S-tritylthiol (Manoharan et al., *Ann. N.Y. Acad. Sci.*, 1992, 660:306-309; Manoharan et al., *Biorg. Med. Chem. Let.*, 1993, 3:2765-2770), a thiocholesterol (Oberhauser et al., *NucL Acids Res.*, 1992, 20:533-538), an aliphatic chain, e.g., dodecandiol or undecyl residues (Saison-Behmoaras et al., *EMBO J*, 1991, 10:1111-1118; Kabanov et al., *FEBS Lett.*, 1990, 259:327-330; Svinarchuk et al., *Biochimie*, 1993, 75:49-54), a phospholipid, e.g., di-hexadecyl-rac-glycerol or triethylammonium 1,2-di-O-hexadecyl-rac-glycero-3-phosphonate (Manoharan et al., *Tetrahedron Lett.*, 1995, 36:3651-3654; Shea et al., *Nucl. Acids Res.*, 1990, 18:3777-3783), a polyamine or a polyethylene glycol chain (Manoharan et al., *Nucleosides & Nucleotides*, 1995, 14:969-973), or adamantane acetic acid (Manoharan et al., *Tetrahedron Lett.*, 1995, 36:3651-3654), a palmityl moiety (Mishra et al., *Biochim. Biophys. Acta*, 1995, 1264:229-237), or an octadecylamine or hexylamino-carbonyloxycholesterol moiety (Crooke et al., *J. Pharmacol. Exp. Ther.*, 1996, 277:923-937).

In one embodiment, a ligand alters the distribution, targeting or lifetime of an antisense polynucleotide agent into which it is incorporated. In preferred embodiments a ligand provides an enhanced affinity for a selected target, e.g., molecule, cell or cell type, compartment, e.g., a cellular or organ compartment, tissue, organ or region of the body, as, e.g., compared to a species absent such a ligand. Preferred ligands will not take part in hybridization of an antisense polynucleotide agent to the targeted mRNA.

Ligands can include a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin, N-acetylgalactosamine, or hyaluronic acid); or a lipid. The ligand can also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucoseamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, vitamin A, biotin, or an RGD peptide or RGD peptide mimetic.

Other examples of ligands include dyes, intercalating agents (e.g. acridines), cross-linkers (e.g. psoralen, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g., cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a hepatic cell. Ligands can also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the antisense polynucleotide agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

In some embodiments, a ligand attached to an antisense polynucleotide agent as described herein acts as a pharmacokinetic modulator (PK modulator). PK modulators include lipophiles, bile acids, steroids, phospholipid analogues, peptides, protein binding agents, PEG, vitamins etc. Exemplary PK modulators include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g., oligonucleotides of about 5 bases, 10 bases, 15 bases or 20 bases, comprising multiple of phosphorothioate linkages in the backbone are also amenable to the present invention as ligands (e.g. as PK modulating ligands). In addition, aptamers that bind serum components (e.g. serum proteins) are also suitable for use as PK modulating ligands in the embodiments described herein.

Ligand-conjugated polynucleotides of the invention may be synthesized by the use of a polynucleotide that bears a pendant reactive functionality, such as that derived from the attachment of a linking molecule onto the oligonucleotide (described below). This reactive polynucleotide may be reacted directly with commercially-available ligands, ligands that are synthesized bearing any of a variety of protecting groups, or ligands that have a linking moiety attached thereto.

The polynucleotides used in the conjugates of the present invention may be conveniently and routinely made through the well-known technique of solid-phase synthesis. Equipment for such synthesis is sold by several vendors including, for example, Applied Biosystems® (Foster City, Calif.). Any other means for such synthesis known in the art may additionally or alternatively be employed. It is also known to use similar techniques to prepare other polynucleotides, such as the phosphorothioates and alkylated derivatives.

In the ligand-conjugated polynucleotides and ligand-molecule bearing sequence-specific linked nucleosides of the present invention, the polynucleotides and polynucleosides may be assembled on a suitable DNA synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using nucleotide-conjugate precursors that already bear a linking moiety, the synthesis of the sequence-specific linked nucleosides is typically completed, and the ligand molecule is then reacted with the linking moiety to form the ligand-conjugated oligonucleotide. In some embodiments, the polynucleotides or linked nucleosides of the present invention are synthesized by an automated synthesizer using phosphoramidites derived from ligand-nucleoside conjugates in addition to the standard phosphoramidites and non-standard phosphoramidites that are commercially available and routinely used in oligonucleotide synthesis.

A. Lipid Conjugates

In one embodiment, the ligand or conjugate is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, naproxen or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to inhibit, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by target cells such as liver cells. Also included are HSA and low density lipoprotein (LDL).

B. Cell Permeation Agents

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to antisense polynucleotide agents can affect pharmacokinetic distribution of the agent, such as by enhancing cellular recognition and absorption. The peptide or peptidomimetic moiety can be about 5-50 amino acids long, e.g., about 5, 10, 15, 20, 25, 30, 35, 40, 45, or 50 amino acids long.

A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO: 13). An RFGF analogue (e.g., amino acid sequence AALLPVLLAAP (SEQ ID NO: 14) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO: 15) and the Drosophila Antennapedia protein (RQIKIWFQNRRMK-WKK (SEQ ID NO: 16) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Examples of a peptide or peptidomimetic tethered to an antisens epolynucleotide agent via an incorporated monomer unit for cell targeting purposes is an arginine-glycine-aspartic acid (RGD)-peptide, or RGD mimic A peptide moiety can range in length from about 5 amino acids to about 40 amino acids. The peptide moieties can have a structural modification, such as to increase stability or direct conformational properties. Any of the structural modifications described below can be utilized.

An RGD peptide for use in the compositions and methods of the invention may be linear or cyclic, and may be modified, e.g., glycosylated or methylated, to facilitate targeting to a specific tissue(s). RGD-containing peptides and peptidiomimemtics may include D-amino acids, as well as synthetic RGD mimics. In addition to RGD, one can use other moieties that target the integrin ligand. Preferred conjugates of this ligand target PECAM-1 or VEGF.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

C. Carbohydrate Conjugates

In some embodiments of the compositions and methods of the invention, an antisense polynucleotide agent further comprises a carbohydrate. The carbohydrate conjugated agents are advantageous for the in vivo delivery of nucleic acids, as well as compositions suitable for in vivo therapeutic use, as described herein (see, e.g., Prakash, et al. (2014) Nuc Acid Res doi 10.1093/nar/gku531). As used herein, "carbohydrate" refers to a compound which is either a carbohydrate per se made up of one or more monosaccharide units having at least 6 carbon atoms (which can be linear, branched or cyclic) with an oxygen, nitrogen or sulfur atom bonded to each carbon atom; or a compound having as a part thereof a carbohydrate moiety made up of one or more monosaccharide units each having at least six carbon atoms (which can be linear, branched or cyclic), with an oxygen, nitrogen or sulfur atom bonded to each carbon atom. Representative carbohydrates include the sugars (mono-, di-, tri- and oligosaccharides containing from about 4, 5, 6, 7, 8, or 9 monosaccharide units), and polysaccharides such as starches, glycogen, cellulose and polysaccharide gums. Specific monosaccharides include C5 and above (e.g., C5, C6, C7, or C8) sugars; di- and trisaccharides include sugars having two or three monosaccharide units (e.g., C5, C6, C7, or C8).

In one embodiment, a carbohydrate conjugate for use in the compositions and methods of the invention is a monosaccharide. In one embodiment, the monosaccharide is an N-acetylgalactosamine (GalNAc) or a GalNAc derivative.

In one embodiment, a carbohydrate conjugate for use in the compositions and methods of the invention is selected from the group consisting of:

Formula II

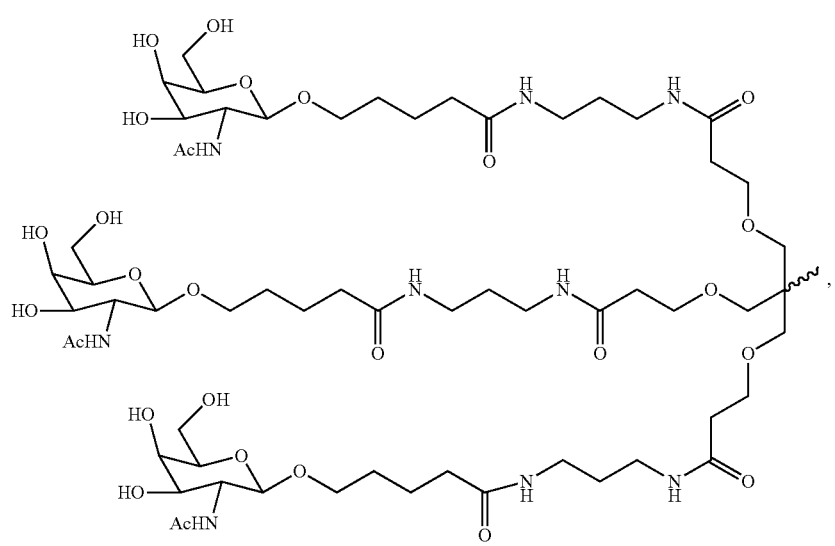

-continued
Formula III
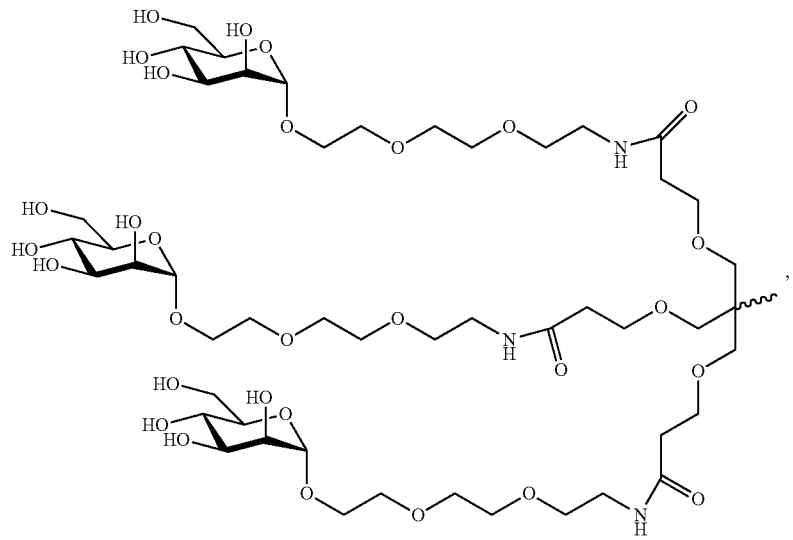
Formula IV
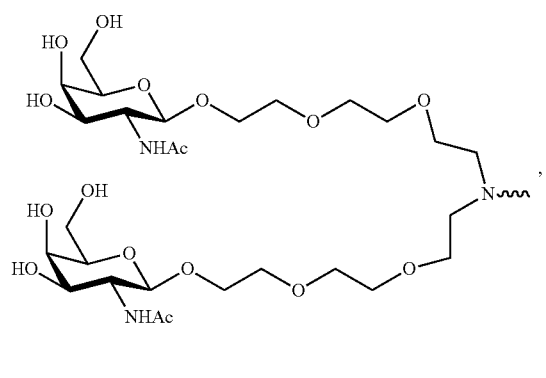
Formula V
Formula VI
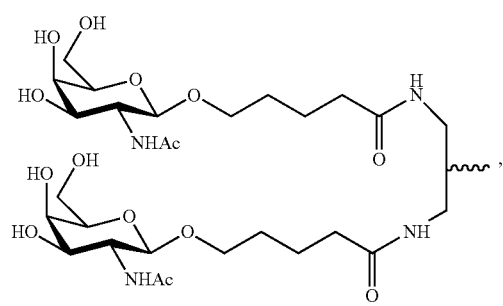
Formula VII
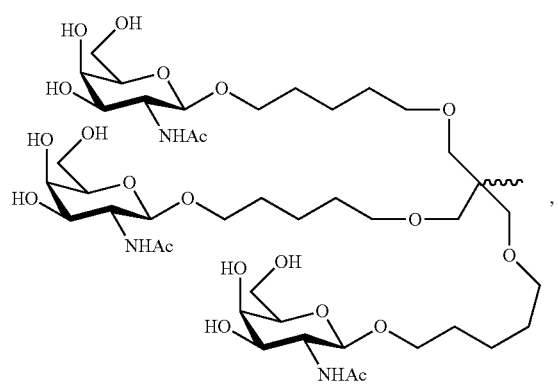
Formula VIII
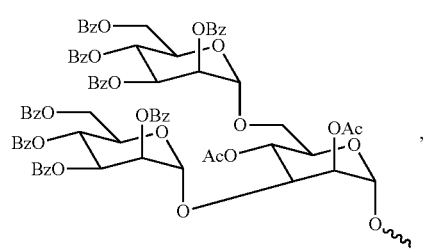

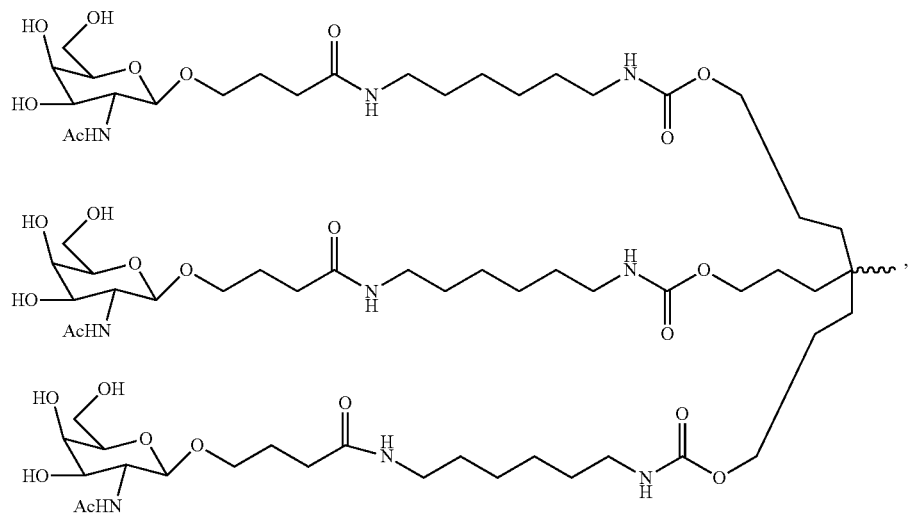
Formula IX
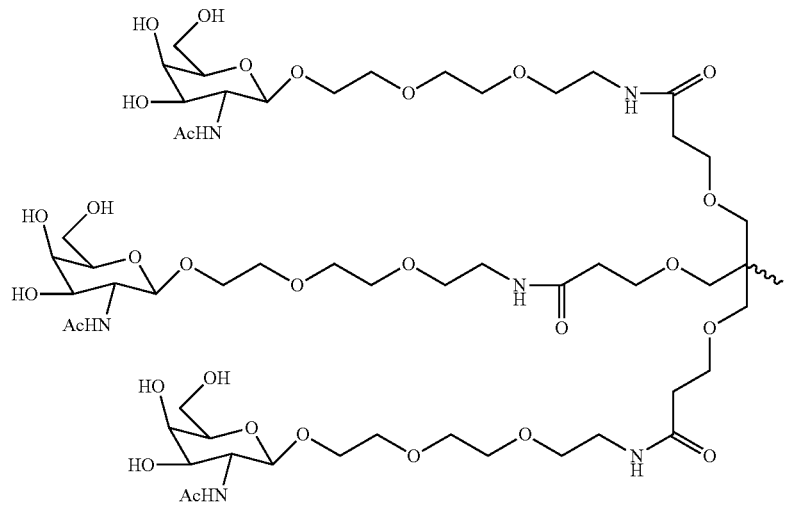
Formula X
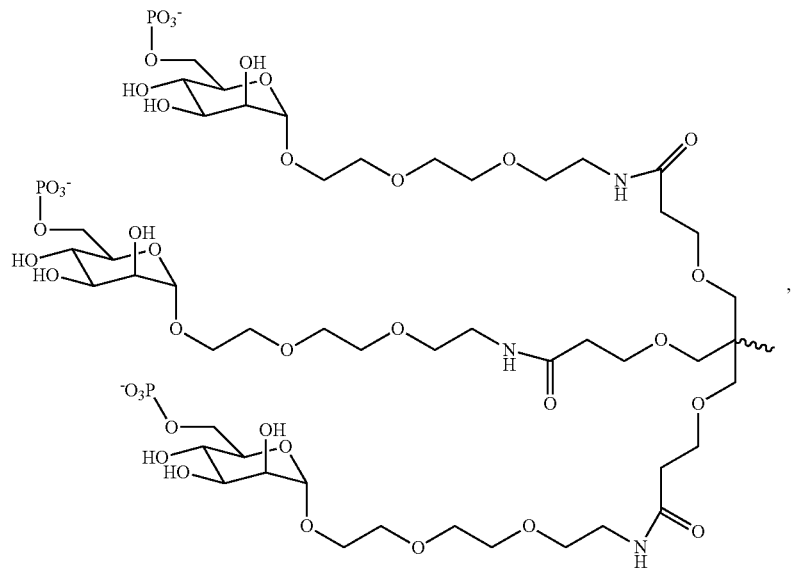
Formula XI

Formula XII
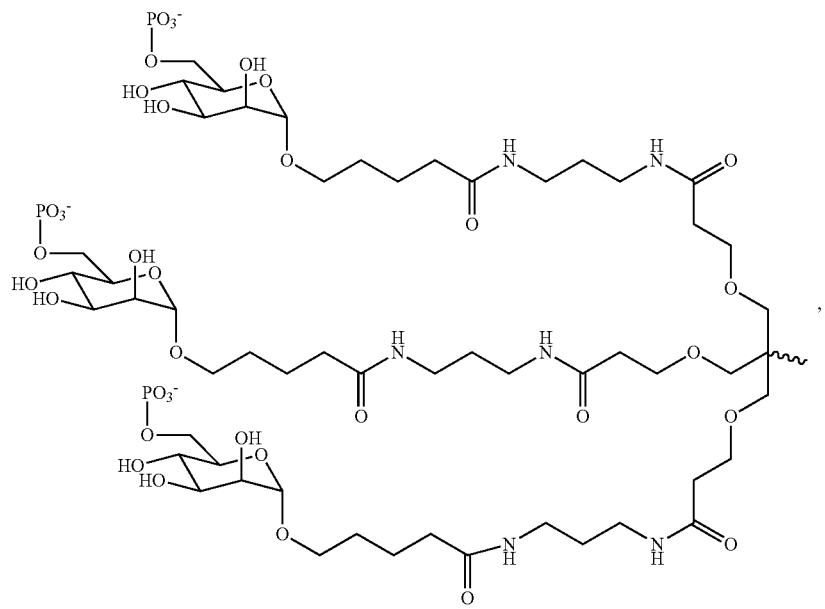
Formula XIII
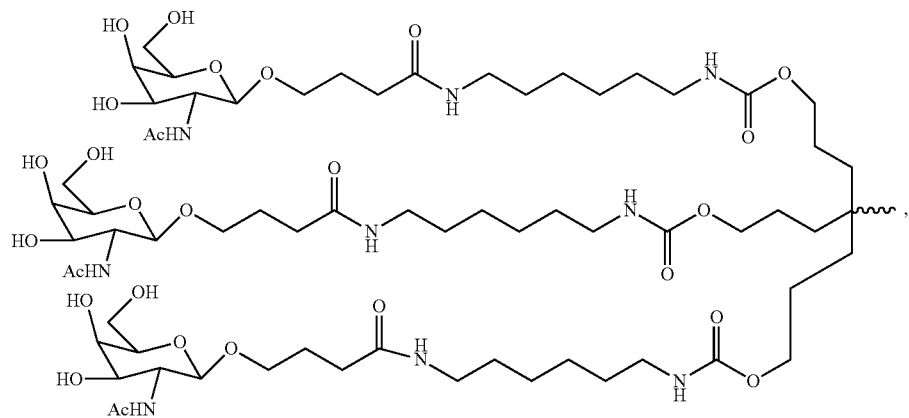
Formula XIV
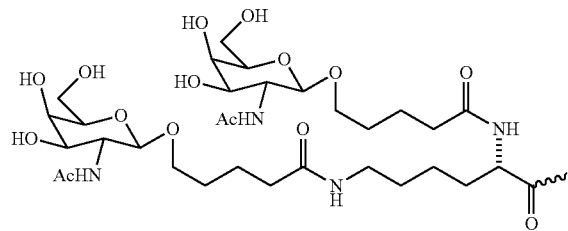
Formula XV
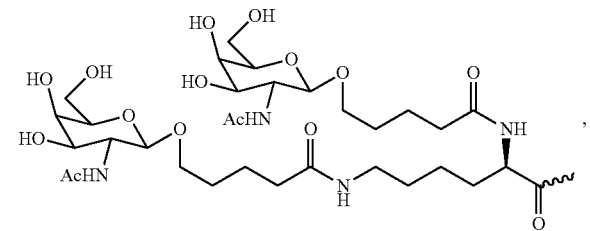
Formula XVI
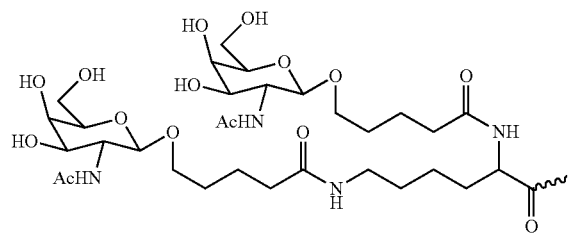
Formula XVII
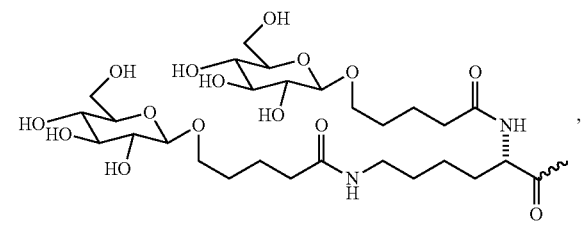

Formula XVIII
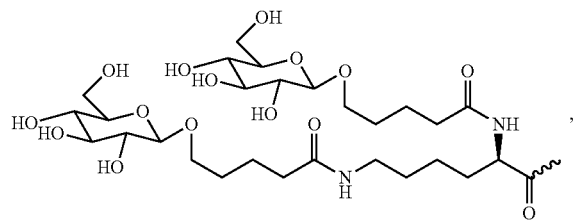
Formula XIX
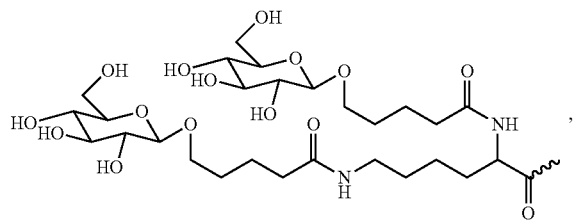
Formula XX
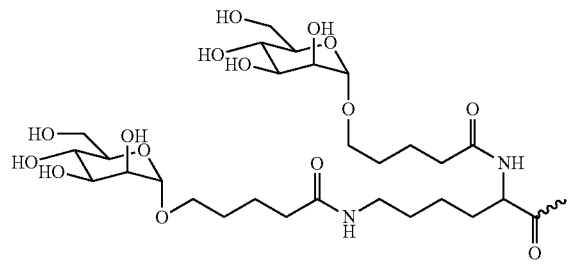
Formula XXI
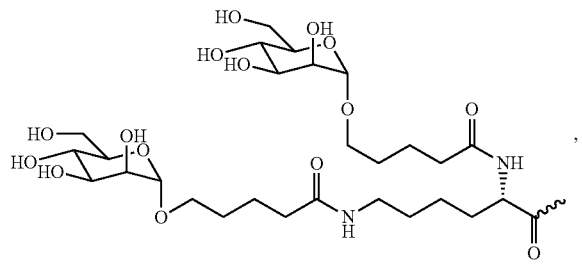
Formula XXII
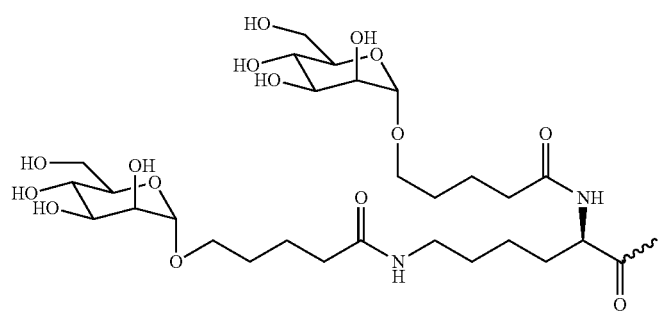
In one embodiment, the GalNAc or a GalNAc derivative is
Formula II
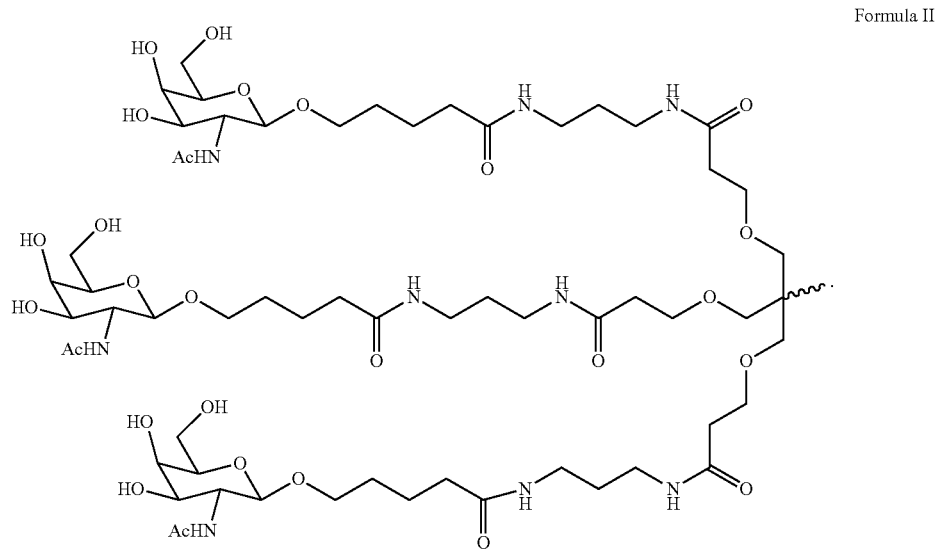 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

Another representative carbohydrate conjugate for use in the embodiments described herein includes, but is not limited to, (Formula XXIII)

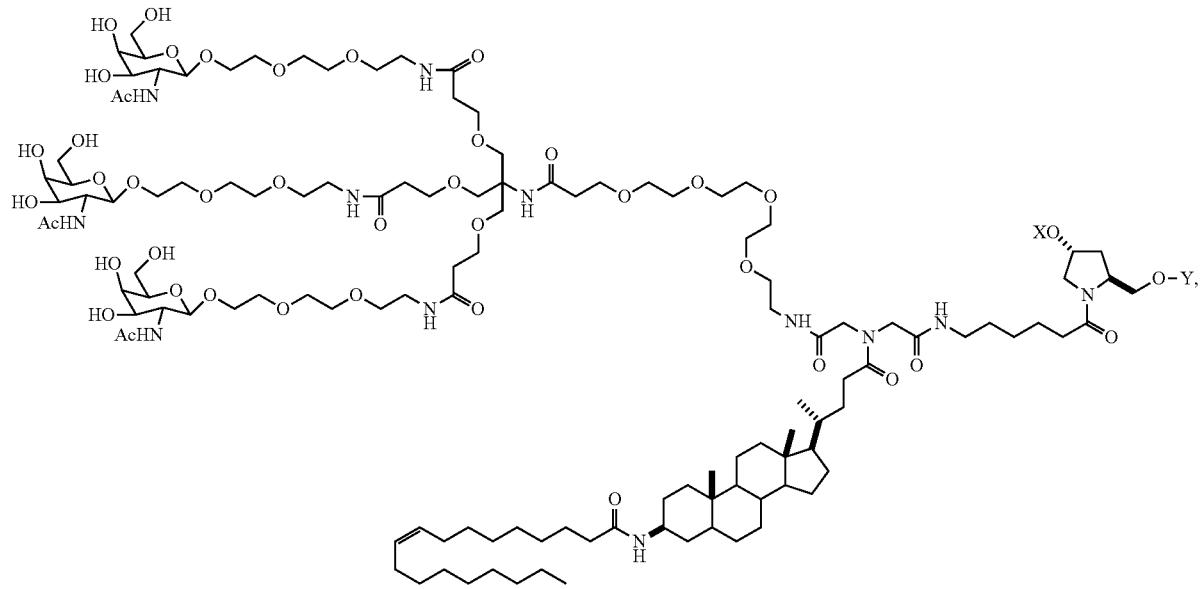

when one of X or Y is an oligonucleotide, the other is a hydrogen.

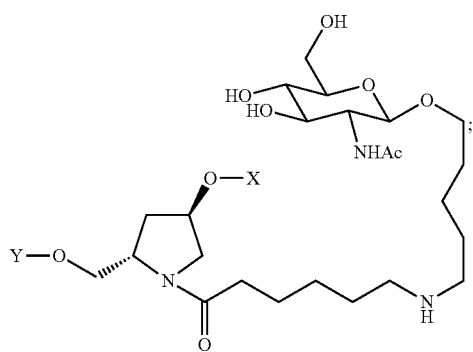

when one of X or Y is an oligonucleotide, the other is a hydrogen; or both X and Y are oligonucleotides

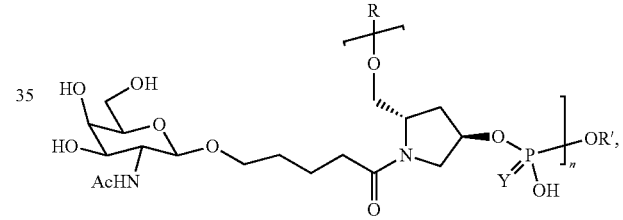

wherein Y=O or S. n is 1-6, R is hydrogen or nucleic acid, R' is nucleic acid.

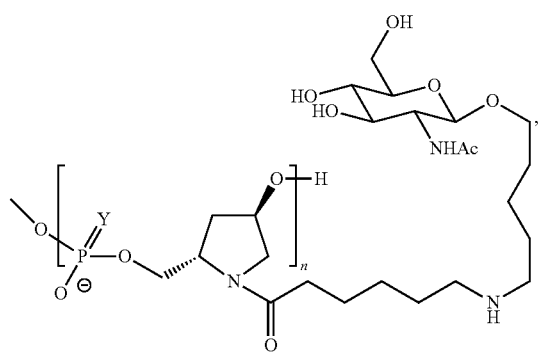

wherein Y is O or S and n is 1-6.

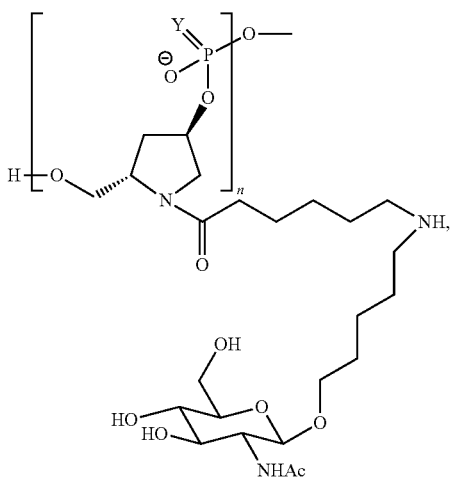

wherein Y is O or S and n is 1-6.

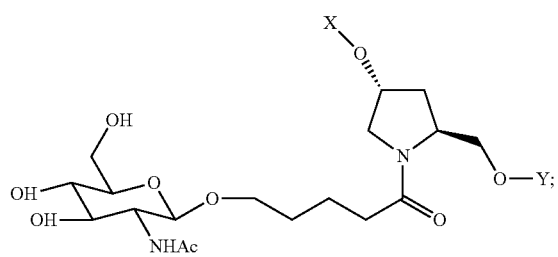

when one of X or Y is an oligonucleotide, the other is a hydrogen; or both X and Y are oligonucleotides

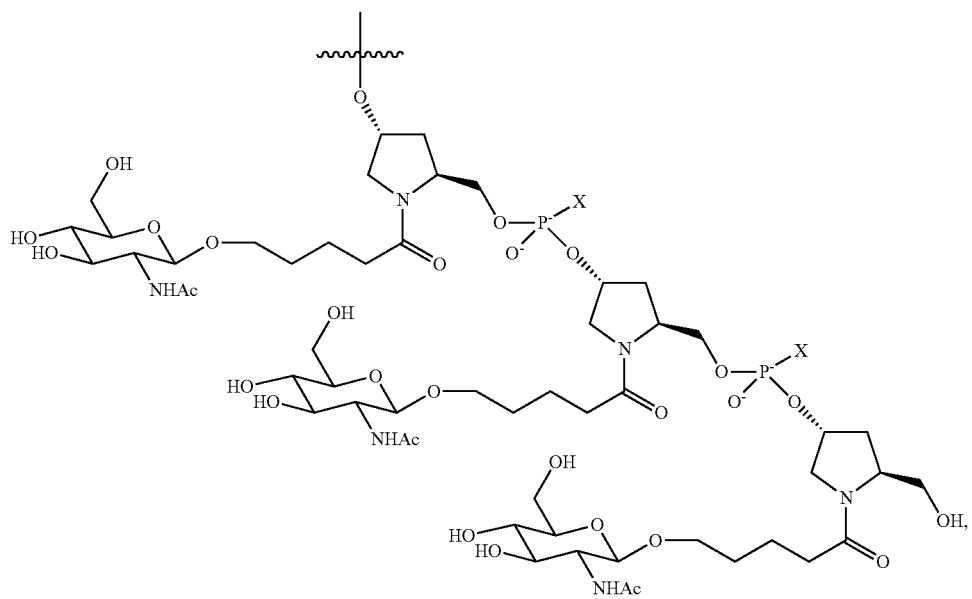

wherein X is O or S.

In certain embodiments of the invention, the GalNAc or GalNAc derivative is attached to an polynucleotide agent of the invention via a monovalent linker. In some embodiments, the GalNAc or GalNAc derivative is attached to an iRNA agent of the invention via a bivalent linker. In yet other embodiments of the invention, the GalNAc or GalNAc derivative is attached to an iRNA agent of the invention via a trivalent linker.

In one embodiment, the double stranded RNAi agents of the invention comprise one GalNAc or GalNAc derivative attached to the polynucleotide agent. In another embodiment, the polynucleotide agents of the invention comprise a plurality (e.g., 2, 3, 4, 5, or 6) GalNAc or GalNAc derivatives, each independently attached to a plurality of nucleotides of the polynucleotide agent through a plurality of monovalent linkers.

In some embodiments, the carbohydrate conjugate further comprises one or more additional ligands as described above, such as, but not limited to, a PK modulator and/or a cell permeation peptide.

Additional carbohydrate conjugates (and linkers) suitable for use in the present invention include those described in PCT Publication Nos. WO 2014/179620 and WO 2014/179627, the entire contents of each of which are incorporated herein by reference.

D. Linkers

In some embodiments, the conjugate or ligand described herein can be attached to an antisense polynucleotide agent with various linkers that can be cleavable or non-cleavable.

The term "linker" or "linking group" means an organic moiety that connects two parts of a compound, e.g., covalently attaches two parts of a compound. Linkers typically comprise a direct bond or an atom such as oxygen or sulfur, a unit such as NR8, C(O), C(O)NH, SO, $SO_2$, $SO_2NH$ or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), $SO_2$, N(R8), C(O), substituted or unsubstituted aryl, substituted or unsubstituted heteroaryl, substituted or unsubstituted heterocyclic; where R8 is hydrogen, acyl, aliphatic or substituted aliphatic. In one embodiment, the linker is between about 1-24 atoms, 2-24, 3-24, 4-24, 5-24, 6-24, 6-18, 7-18, 8-18 atoms, 7-17, 8-17, 6-16, 7-16, or 8-16 atoms.

A cleavable linking group is one which is sufficiently stable outside the cell, but which upon entry into a target cell is cleaved to release the two parts the linker is holding together. In a preferred embodiment, the cleavable linking group is cleaved at least about 10 times, 20, times, 30 times, 40 times, 50 times, 60 times, 70 times, 80 times, 90 times or more, or at least about 100 times faster in a target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing a cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, a liver-targeting ligand can be linked to a cationic lipid through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus, one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It can be useful to make initial evaluations in cell-free or culture conditions and to confirm by further evaluations in whole animals. In preferred embodiments, useful candidate compounds are cleaved at least about 2, 4, 10, 20, 30, 40, 50, 60, 70, 80, 90, or about 100 times faster in the cell (or under in vitro conditions selected to mimic intracellular conditions) as compared to blood or serum (or under in vitro conditions selected to mimic extracellular conditions).

i. Redox Cleavable Linking Groups

In one embodiment, a cleavable linking group is a redox cleavable linking group that is cleaved upon reduction or oxidation. An example of reductively cleavable linking group is a disulphide linking group (—S—S—). To determine if a candidate cleavable linking group is a suitable "reductively cleavable linking group," or for example is suitable for use with a particular antisense polynucleotide agent moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In one, candidate compounds are cleaved by at most about 10% in the blood. In other embodiments, useful candidate compounds are degraded at least about 2, 4, 10, 20, 30, 40, 50, 60, 70, 80, 90, or about 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

ii. Phosphate-Based Cleavable Linking Groups

In another embodiment, a cleavable linker comprises a phosphate-based cleavable linking group. A phosphate-based cleavable linking group is cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O, —S—P(S)(H)—O—, —S—P(O)(H)—S—, —O—P(S)(H)—S—. A preferred embodiment is —O—P(O)(OH)—O—. These candidates can be evaluated using methods analogous to those described above.

iii. Acid Cleavable Linking Groups

In another embodiment, a cleavable linker comprises an acid cleavable linking group. An acid cleavable linking group is a linking group that is cleaved under acidic conditions. In preferred embodiments acid cleavable linking groups are cleaved in an acidic environment with a pH of about 6.5 or lower (e.g., about 6.0, 5.75, 5.5, 5.25, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C=NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

iv. Ester-Based Linking Groups

In another embodiment, a cleavable linker comprises an ester-based cleavable linking group. An ester-based cleavable linking group is cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

v. Peptide-Based Cleaving Groups

In yet another embodiment, a cleavable linker comprises a peptide-based cleavable linking group. A peptide-based cleavable linking group is cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCHRAC(O)NHCHRBC(O)—, where RA and RB are the R groups of the two adjacent amino acids. These candidates can be evaluated using methods analogous to those described above.

In one embodiment, an antisense polynucleotide agent of the invention is conjugated to a carbohydrate through a linker. Non-limiting examples of antisense polynucleotide agent carbohydrate conjugates with linkers of the compositions and methods of the invention include, but are not limited to, (Formula XXIV)
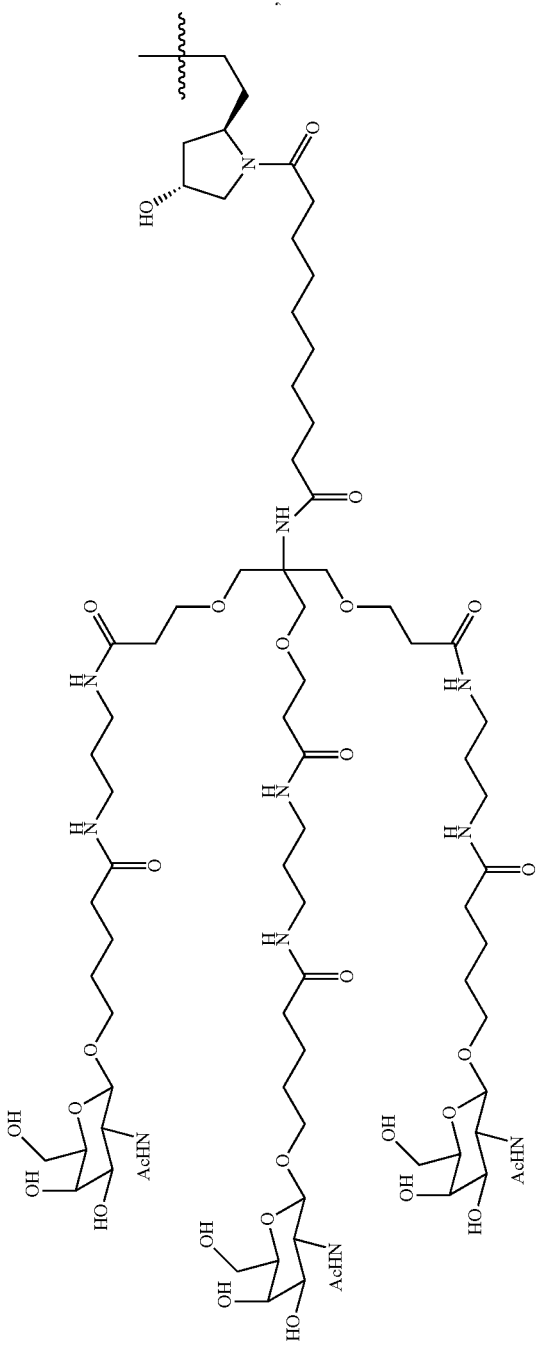
(Formula XXV)
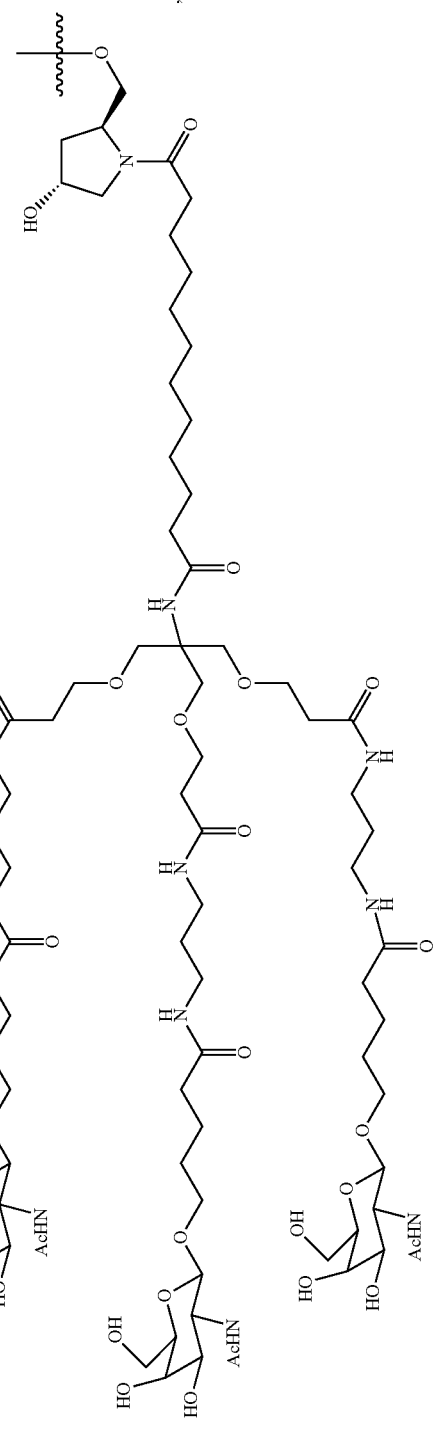

-continued
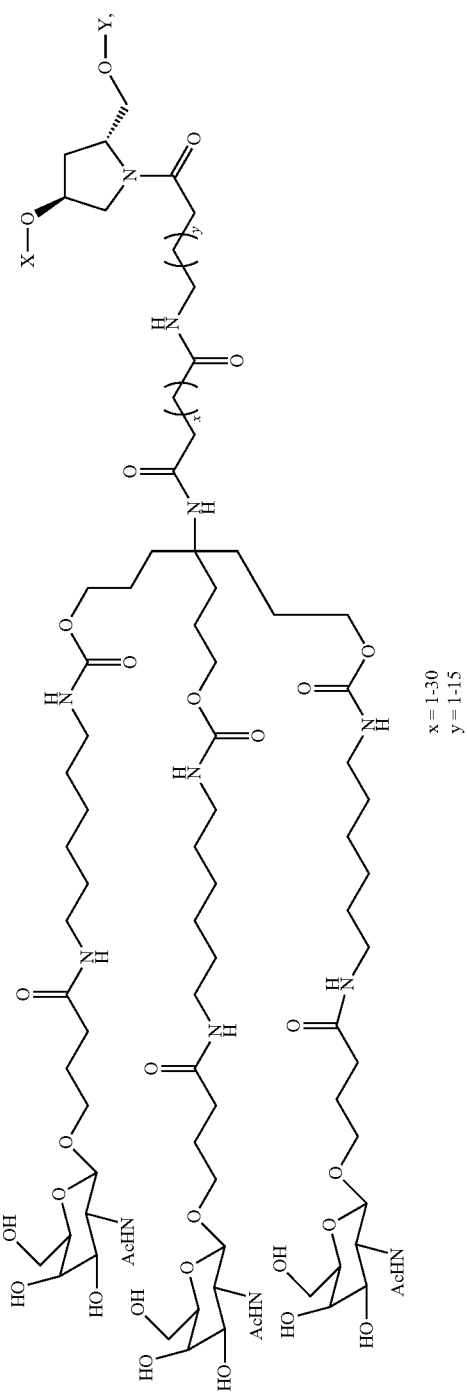
(Formula XXVI)
x = 1-30
y = 1-15
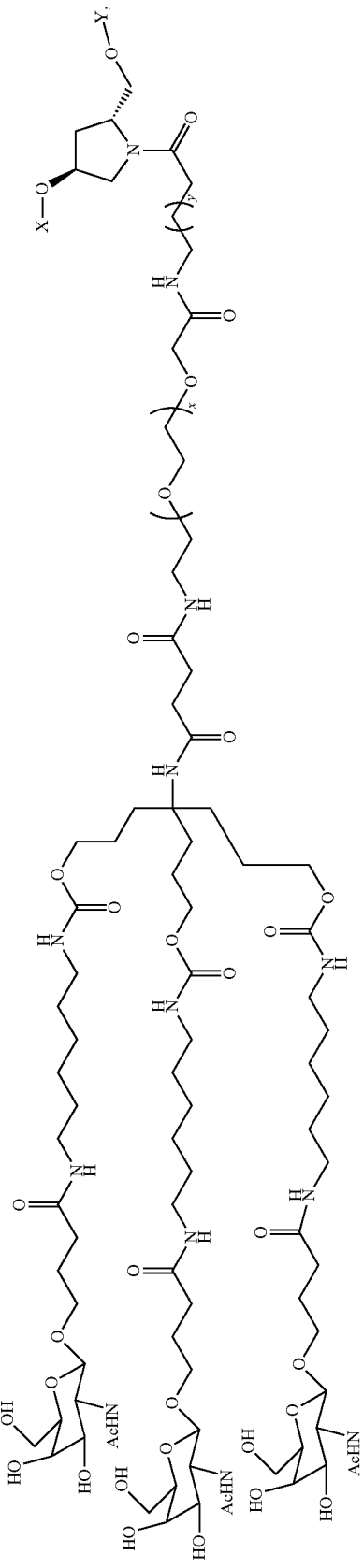
(Formula XXVII)
x = 1-30
y = 1-15

-continued
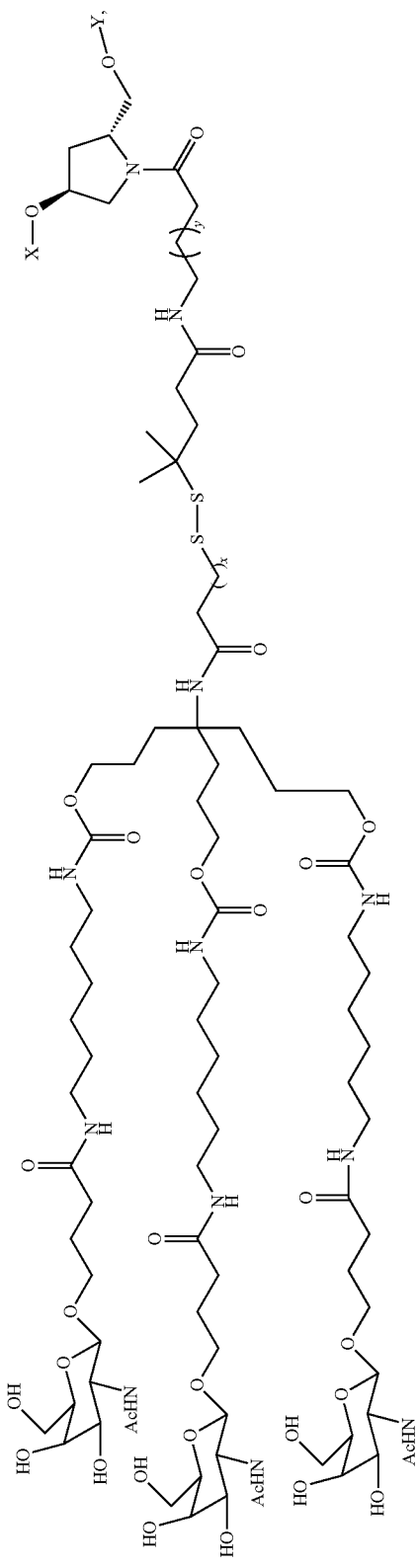
(Formula XXVIII)
x = 0-30
y = 1-15
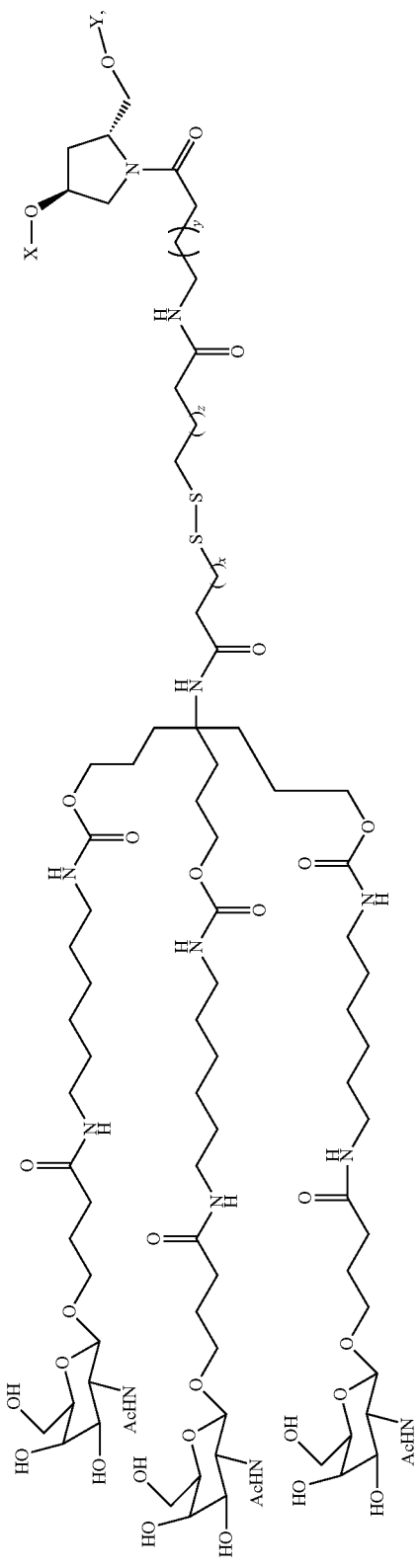
(Formula XXIX)
x = 0-30
y = 1-15
z = 1-20

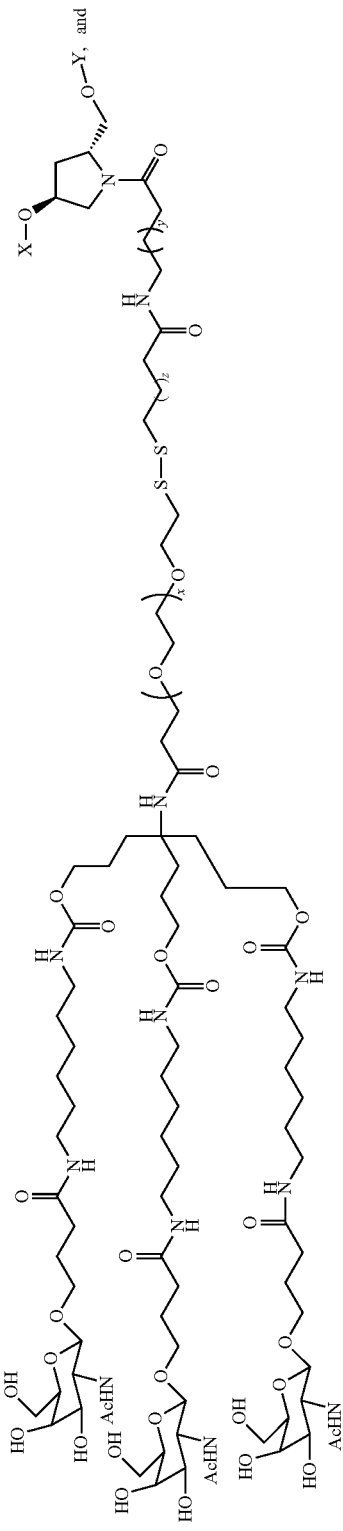
x = 1-30
y = 1-15
z = 1-20
(Formula XXXX)
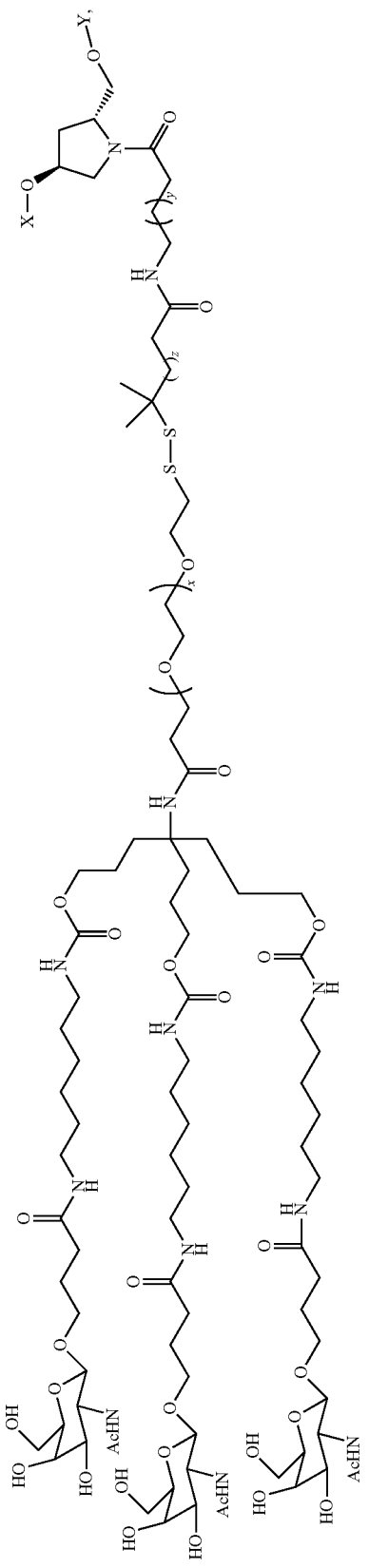
x = 1-30
y = 1-15
z = 1-20
(Formula XXXI)

when one of X or Y is an oligonucleotide, the other is a hydrogen.

In certain embodiments of the compositions and methods of the invention, a ligand is one or more "GalNAc" (N-acetylgalactosamine) derivatives attached through a bivalent or trivalent branched linker.

In one embodiment, a antisense polynucleotide agent of the invention is conjugated to a bivalent or trivalent branched linker selected from the group of structures shown in any of formula (XXXII)-(XXXV):

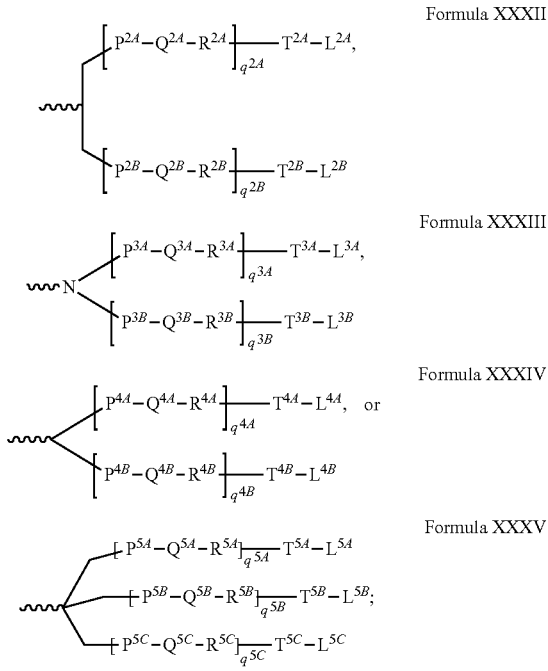

Formula XXXII

Formula XXXIII

Formula XXXIV

Formula XXXV wherein:

q2A, q2B, q3A, q3B, q4A, q4B, q5A, q5B and q5C represent independently for each occurrence 0-20 and wherein the repeating unit can be the same or different;

$P^{2A}$, $P^{2B}$, $P^{3A}$, $P^{3B}$, $P^{4A}$, $P^{4B}$, $P^{5A}$, $P^{5B}$, $P^{5C}$, $T^{2A}$, $T^{2B}$, $T^{3A}$, $T^{3B}$, $T^{4A}$, $T^{4B}$, $T^{4A}$, $T^{5B}$, $T^{5C}$ are each independently for each occurrence absent, CO, NH, O, S, OC(O), NHC(O), CH$_2$, CH$_2$NH or CH$_2$O;

$Q^{2A}$, $Q^{2B}$, $Q^{3A}$, $Q^{3B}$, $Q^{4A}$, $Q^{4B}$, $Q^{5A}$, $Q^{5B}$, $Q^{5C}$ are independently for each occurrence absent, alkylene, substituted alkylene wherein one or more methylenes can be interrupted or terminated by one or more of O, S, S(O), SO$_2$, N(R$^N$), C(R')=C(R"), CC or C(O);

$R^{2A}$, $R^{2B}$, $R^{3A}$, $R^{3B}$, $R^{4A}$, $R^{4B}$, $R^{5A}$, $R^{5B}$, $R^{5C}$ are each independently for each occurrence absent, NH, O, S, CH$_2$, C(O)O, C(O)NH, NHCH(R$^a$)C(O), —C(O)—CH(R$^a$)—NH—, CO, CH=N—O,

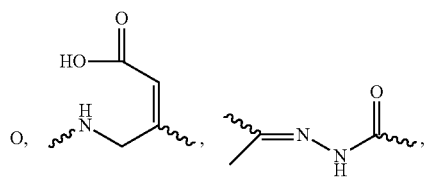

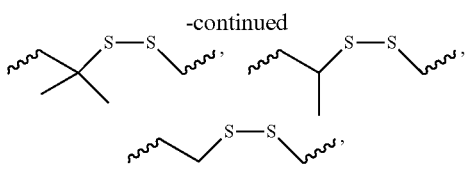

or heterocyclyl;

$L^{2A}$, $L^{2B}$, $L^{3A}$, $L^{3B}$, $L^{4A}$, $L^{4B}$, $L^{5A}$, $L^{5B}$ and $L^{5C}$ represent the ligand; i.e. each independently for each occurrence a monosaccharide (such as GalNAc), disaccharide, trisaccharide, tetrasaccharide, oligosaccharide, or polysaccharide; and R$^a$ is H or amino acid side chain. Trivalent conjugating GalNAc derivatives are particularly useful for use with antisense polynucleotide agents for inhibiting the expression of a target gene, such as those of formula (XXXVI):

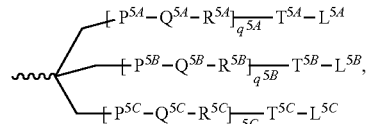

Formula XXXVI wherein $L^{5A}$, $L^{5B}$ and $L^{5C}$ represent a monosaccharide, such as GalNAc derivative.

Examples of suitable bivalent and trivalent branched linker groups conjugating GalNAc derivatives include, but are not limited to, the structures recited above as formulas II, VII, XI, X, and XIII.

Representative U.S. patents that teach the preparation of RNA conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941; 6,294,664; 6,320,017; 6,576,752; 6,783,931; 6,900,297; 7,037,646; 8,106,022, the entire contents of each of which are hereby incorporated herein by reference.

It is not necessary for all positions in a given compound to be uniformly modified, and in fact more than one of the aforementioned modifications can be incorporated in a single compound or even at a single nucleoside within an antisense polynucleotide agent. The present invention also includes antisense polynucleotide agents that are chimeric compounds.

"Chimeric" antisense polynucleotide agents or "chimeras," in the context of this invention, are antisense polynucleotide agent compounds, which contain two or more chemically distinct regions, each made up of at least one monomer unit, i.e., a nucleotide in the case of an antisense polynucleotide agent. These antisense polynucleotide agents typically contain at least one region wherein the RNA is modified so as to confer upon the antisense polynucleotide agent increased resistance to nuclease degradation, increased cellular uptake, and/or increased binding affinity for the target nucleic acid. An additional region of the antisense polynucleotide agent can serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense polynucleotide agent inhibition of gene expression. Consequently, comparable results can often be obtained with shorter antisense polynucleotide agents when chimeric antisense polynucleotide agents are used, compared to phosphorothioate deoxy antisense polynucleotide agents hybridizing to the same target region. Cleavage of the RNA target can be routinely detected by gel electrophoresis and, if necessary, associated nucleic acid hybridization techniques known in the art.

In certain instances, the nucleotide of an antisense polynucleotide agent can be modified by a non-ligand group. A number of non-ligand molecules have been conjugated to antisense polynucleotide agents in order to enhance the activity, cellular distribution or cellular uptake of the antisense polynucleotide agent, and procedures for performing such conjugations are available in the scientific literature. Such non-ligand moieties have included lipid moieties, such as cholesterol (Kubo, T. et al., *Biochem. Biophys. Res. Comm.*, 2007, 365(1):54-61; Letsinger et al., *Proc. Natl. Acad. Sci. USA*, 1989, 86:6553), cholic acid (Manoharan et al., *Bioorg. Med. Chem. Lett.*, 1994, 4:1053), a thioether, e.g., hexyl-S-tritylthiol (Manoharan et al., *Ann. N.Y. Acad. Sci.*, 1992, 660:306; Manoharan et al., *Bioorg. Med. Chem. Let.*, 1993, 3:2765), a thiocholesterol (Oberhauser et al., *Nucl. Acids Res.*, 1992, 20:533), an aliphatic chain, e.g., dodecandiol or undecyl residues (Saison-Behmoaras et al., *EMBO J.*, 1991, 10:111; Kabanov et al., *FEBS Lett.*, 1990, 259:327; Svinarchuk et al., *Biochimie*, 1993, 75:49), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36:3651; Shea et al., *Nucl. Acids Res.*, 1990, 18:3777), a polyamine or a polyethylene glycol chain (Manoharan et al., *Nucleosides & Nucleotides*, 1995, 14:969), or adamantane acetic acid (Manoharan et al., *Tetrahedron Lett.*, 1995, 36:3651), a palmityl moiety (Mishra et al., *Biochim. Biophys. Acta*, 1995, 1264:229), or an octadecylamine or hexylaminocarbonyl-oxycholesterol moiety (Crooke et al., *J. Pharmacol. Exp. Ther.*, 1996, 277:923). Representative United States patents that teach the preparation of such RNA conjugates have been listed above. Typical conjugation protocols involve the synthesis of an RNAs bearing an aminolinker at one or more positions of the sequence. The amino group is then reacted with the molecule being conjugated using appropriate coupling or activating reagents. The conjugation reaction can be performed either with the RNA still bound to the solid support or following cleavage of the RNA, in solution phase. Purification of the RNA conjugate by HPLC typically affords the pure conjugate.

V. Delivery of an Antisense Polynucleotide Agent of the Invention

The delivery of an antisense polynucleotide agent of the invention to a cell e.g., a cell within a subject, such as a human subject (e.g., a subject in need thereof, such as a subject having a PNPLA3-associated disease) can be achieved in a number of different ways. For example, delivery may be performed by contacting a cell with an antisense polynucleotide agent of the invention either in vitro or in vivo. In vivo delivery may also be performed directly by administering a composition comprising an antisense polynucleotide agent to a subject.

In general, any method of delivering a nucleic acid molecule (in vitro or in vivo) can be adapted for use with an antisense polynucleotide agent of the invention (see e.g., Akhtar S. and Julian R L. (1992) *Trends Cell. Biol.* 2(5): 139-144 and WO94/02595, which are incorporated herein by reference in their entireties). For in vivo delivery, factors to consider in order to deliver an antisense polynucleotide agent include, for example, biological stability of the delivered molecule, prevention of non-specific effects, and accumulation of the delivered molecule in the target tissue. The non-specific effects of an antisense polynucleotide agent can be minimized by local administration, for example, by direct injection or implantation into a tissue or topically administering the preparation. Local administration to a treatment site maximizes local concentration of the agent, limits the exposure of the agent to systemic tissues that can otherwise be harmed by the agent or that can degrade the agent, and permits a lower total dose of the antisense polynucleotide agent to be administered. Several studies have shown successful knockdown of gene products when an antisense polynucleotide agent is administered locally. For example, intraocular delivery of a VEGF antisense polynucleotide agent by intravitreal injection in cynomolgus monkeys (Tolentino, M J., et al (2004) *Retina* 24:132-138) and subretinal injections in mice (Reich, S J., et al (2003) *Mol. Vis.* 9:210-216) were both shown to prevent neovascularization in an experimental model of age-related macular degeneration. In addition, direct intratumoral injection of a antisense polynucleotide agent in mice reduces tumor volume (Pille, J., et al (2005) *Mol. Ther.* 11:267-274) and can prolong survival of tumor-bearing mice (Kim, W J., et al (2006) *Mol. Ther.* 14:343-350; Li, S., et al (2007) *Mol. Ther.* 15:515-523). RNA interference has also shown success with local delivery to the CNS by direct injection (Dorn, G., et al. (2004) *Nucleic Acids* 32:e49; Tan, P H., et al (2005) *Gene Ther.* 12:59-66; Makimura, H., et al (2002) *BMC Neurosci.* 3:18; Shishkina, G T., et al (2004) *Neuroscience* 129:521-528; Thakker, E R., et al (2004) *Proc. Natl. Acad. Sci. U.S.A.* 101:17270-17275; Akaneya, Y., et al (2005) *J. Neurophysiol.* 93:594-602) and to the lungs by intranasal administration (Howard, K A., et al (2006) *Mol. Ther.* 14:476-484; Zhang, X., et al (2004) *J. Biol. Chem.* 279:10677-10684; Bitko, V., et al (2005) *Nat. Med.* 11:50-55). For administering an antisense polynucleotide agent systemically for the treatment of a disease, the agent can be modified or alternatively delivered using a drug delivery system; both methods act to prevent the rapid degradation of the antisense polynucleotide agent by endo- and exo-nucleases in vivo. Modification of the agent or the pharmaceutical carrier can also permit targeting of the antisense polynucleotide agent composition to the target tissue and avoid undesirable off-target effects. Antisense polynucleotide agent can be modified by chemical conjugation to lipophilic groups such as cholesterol to enhance cellular uptake and prevent degradation. In an alternative embodiment, the antisense polynucleotide agent can be delivered using drug delivery systems such as a nanoparticle, a dendrimer, a polymer, liposomes, or a cationic delivery system. Positively charged cationic delivery systems facilitate binding of an antisense polynucleotide agent molecule (negatively charged) and also enhance interactions at the negatively charged cell membrane to permit efficient uptake of an antisense polynucleotide agent by the cell. Cationic lipids, dendrimers, or polymers can either be bound to an antisense polynucleotide agent, or induced to form a vesicle or micelle (see e.g., Kim S H., et al (2008) *Journal of Controlled Release* 129(2):107-116) that encases an antisense polynucleotide agent. The formation of vesicles or micelles further prevents degradation of the antisense polynucleotide agent when administered systemically. Methods for making and administering cationic-antisense polynucleotide agent complexes are well within the abilities of one skilled in the art (see e.g., Sorensen, D R., et al (2003) *J. Mol. Biol* 327:761-766; Verma, U N, et al (2003) *Clin. Cancer Res.* 9:1291-1300; Arnold, A S et al (2007) *J. Hypertens.* 25:197-205, which are incorporated herein by reference in their entirety). Some non-limiting examples of drug delivery systems useful for systemic delivery of antisense polynucleotide agents include DOTAP (Sorensen, D R., et al (2003), supra; Verma, U N., et al (2003), supra), Oligofectamine, "solid nucleic acid lipid particles" (Zimmermann, T S., et al (2006) *Nature* 441:111-114), cardiolipin (Chien, P Y., et al (2005) *Cancer Gene Ther.* 12:321-328; Pal, A., et al (2005) *Int J. Oncol.* 26:1087-1091), polyethyleneimine (Bonnet M E., et al (2008) *Pharm. Res. August 16* Epub ahead of print; Aigner, A. (2006) *J. Biomed. Biotechnol.* 71659), Arg-Gly-Asp (RGD) peptides (Liu, S. (2006) *Mol. Pharm.* 3:472-487), and polyamidoamines (Tomalia, D A., et al (2007) *Biochem. Soc. Trans.* 35:61-67; Yoo, H., et al (1999) *Pharm. Res.* 16:1799-1804). In some embodiments, an antisense polynucleotide agent forms a complex with cyclodextrin for systemic administration. Methods for administration and pharmaceutical compositions of antisense polynucleotide agents and cyclodextrins can be found in U.S. Pat. No. 7,427,605, which is herein incorporated by reference in its entirety.

VI. Pharmaceutical Compositions of the Invention

The present invention also includes pharmaceutical compositions and formulations which include the antisense polynucleotide agents of the invention. In one embodiment, provided herein are pharmaceutical compositions containing an antisense polynucleotide agent, as described herein, and a pharmaceutically acceptable carrier.

The phrase "pharmaceutically acceptable" is employed herein to refer to those compounds, materials, compositions, and/or dosage forms which are, within the scope of sound medical judgment, suitable for use in contact with the tissues of human subjects and animal subjects without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the subject being treated. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) lubricating agents, such as magnesium state, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum components, such as serum albumin, HDL and LDL; and (22) other non-toxic compatible substances employed in pharmaceutical formulations.

The pharmaceutical compositions containing the antisense polynucleotide agents are useful for treating a disease or disorder associated with the expression or activity of a PNPLA3 gene, e.g. a PNPLA3-associated disease. Such pharmaceutical compositions are formulated based on the mode of delivery. One example is compositions that are formulated for systemic administration via parenteral delivery, e.g., by subcutaneous (SC) or intravenous (IV) delivery. Another example is compositions that are formulated for direct delivery into the brain parenchyma, e.g., by infusion into the brain, such as by continuous pump infusion. The pharmaceutical compositions of the invention may be administered in dosages sufficient to inhibit expression of a PNPLA3 gene. In general, a suitable dose of an antisense polynucleotide agent of the invention will be in the range of about 0.001 to about 200.0 milligrams per kilogram body weight of the recipient per day, generally in the range of about 1 to 50 mg per kilogram body weight per day. For example, the antisense polynucleotide agent can be administered at about 0.01 mg/kg, about 0.05 mg/kg, about 0.5 mg/kg, about 1 mg/kg, about 1.5 mg/kg, about 2 mg/kg, about 3 mg/kg, about 10 mg/kg, about 20 mg/kg, about 30 mg/kg, about 40 mg/kg, or about 50 mg/kg per single dose.

For example, the antisense polynucleotide agent may be administered at a dose of about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 11, 12, 13, 14, 15, 16, 17, 18, 19, 20, 21, 2, 23, 24, 25, 26, 27, 28, 29, 30, 31, 32, 33, 34, 35, 36, 37, 38, 39, 40, 41, 42, 43, 44, 45, 46, 47, 48, 49, or about 50 mg/kg. Values and ranges intermediate to the recited values are also intended to be part of this invention.

In another embodiment, the antisense polynucleotide agent is administered at a dose of about 0.1 to about 50 mg/kg, about 0.25 to about 50 mg/kg, about 0.5 to about 50 mg/kg, about 0.75 to about 50 mg/kg, about 1 to about 50 mg/mg, about 1.5 to about 50 mg/kb, about 2 to about 50 mg/kg, about 2.5 to about 50 mg/kg, about 3 to about 50 mg/kg, about 3.5 to about 50 mg/kg, about 4 to about 50 mg/kg, about 4.5 to about 50 mg/kg, about 5 to about 50 mg/kg, about 7.5 to about 50 mg/kg, about 10 to about 50 mg/kg, about 15 to about 50 mg/kg, about 20 to about 50 mg/kg, about 20 to about 50 mg/kg, about 25 to about 50 mg/kg, about 25 to about 50 mg/kg, about 30 to about 50 mg/kg, about 35 to about 50 mg/kg, about 40 to about 50 mg/kg, about 45 to about 50 mg/kg, about 0.1 to about 45 mg/kg, about 0.25 to about 45 mg/kg, about 0.5 to about 45 mg/kg, about 0.75 to about 45 mg/kg, about 1 to about 45 mg/mg, about 1.5 to about 45 mg/kb, about 2 to about 45 mg/kg, about 2.5 to about 45 mg/kg, about 3 to about 45 mg/kg, about 3.5 to about 45 mg/kg, about 4 to about 45 mg/kg, about 4.5 to about 45 mg/kg, about 5 to about 45 mg/kg, about 7.5 to about 45 mg/kg, about 10 to about 45 mg/kg, about 15 to about 45 mg/kg, about 20 to about 45 mg/kg, about 20 to about 45 mg/kg, about 25 to about 45 mg/kg, about 25 to about 45 mg/kg, about 30 to about 45 mg/kg, about 35 to about 45 mg/kg, about 40 to about 45 mg/kg, about 0.1 to about 40 mg/kg, about 0.25 to about 40 mg/kg, about 0.5 to about 40 mg/kg, about 0.75 to about 40 mg/kg, about 1 to about 40 mg/mg, about 1.5 to about 40 mg/kb, about 2 to about 40 mg/kg, about 2.5 to about 40 mg/kg, about 3 to about 40 mg/kg, about 3.5 to about 40 mg/kg, about 4 to about 40 mg/kg, about 4.5 to about 40 mg/kg, about 5 to about 40 mg/kg, about 7.5 to about 40 mg/kg, about 10 to about 40 mg/kg, about 15 to about 40 mg/kg, about 20 to about 40 mg/kg, about 20 to about 40 mg/kg, about 25 to about 40 mg/kg, about 25 to about 40 mg/kg, about 30 to about 40 mg/kg, about 35 to about 40 mg/kg, about 0.1 to about 30 mg/kg, about 0.25 to about 30 mg/kg, about 0.5 to about 30 mg/kg, about 0.75 to about 30 mg/kg, about 1 to about 30 mg/mg, about 1.5 to about 30 mg/kb, about 2 to about 30 mg/kg, about 2.5 to about 30 mg/kg, about 3 to about 30 mg/kg, about 3.5 to about 30 mg/kg, about 4 to about 30 mg/kg, about 4.5 to about 30 mg/kg, about 5 to about 30 mg/kg, about 7.5 to about 30 mg/kg, about 10 to about 30 mg/kg, about 15 to about 30 mg/kg, about 20 to about 30 mg/kg, about 20 to about 30 mg/kg, about 25 to about 30 mg/kg, about 0.1 to about 20 mg/kg, about 0.25 to about 20 mg/kg, about 0.5 to about 20 mg/kg, about 0.75 to about 20 mg/kg, about 1 to about 20 mg/mg, about 1.5 to about 20 mg/kb, about 2 to about 20 mg/kg, about 2.5 to about 20 mg/kg, about 3 to about 20 mg/kg, about 3.5 to about 20 mg/kg, about 4 to about 20 mg/kg, about 4.5 to about 20 mg/kg, about 5 to about 20 mg/kg, about 7.5 to about 20 mg/kg, about 10 to about 20 mg/kg, or about 15 to about 20 mg/kg. Values and ranges intermediate to the recited values are also intended to be part of this invention.

For example, the antisense polynucleotide agent may be administered at a dose of about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 11, 12, 13, 14, 15, 16, 17, 18, 19, 20, 21, 2, 23, 24, 25, 26, 27, 28, 29, 30, 31, 32, 33, 34, 35, 36, 37, 38, 39, 40, 41, 42, 43, 44, 45, 46, 47, 48, 49, or about 50 mg/kg. Values and ranges intermediate to the recited values are also intended to be part of this invention.

In another embodiment, the antisense polynucleotide agent is administered at a dose of about 0.5 to about 50 mg/kg, about 0.75 to about 50 mg/kg, about 1 to about 50 mg/mg, about 1.5 to about 50 mg/kgb, about 2 to about 50 mg/kg, about 2.5 to about 50 mg/kg, about 3 to about 50 mg/kg, about 3.5 to about 50 mg/kg, about 4 to about 50 mg/kg, about 4.5 to about 50 mg/kg, about 5 to about 50 mg/kg, about 7.5 to about 50 mg/kg, about 10 to about 50 mg/kg, about 15 to about 50 mg/kg, about 20 to about 50 mg/kg, about 20 to about 50 mg/kg, about 25 to about 50 mg/kg, about 25 to about 50 mg/kg, about 30 to about 50 mg/kg, about 35 to about 50 mg/kg, about 40 to about 50 mg/kg, about 45 to about 50 mg/kg, about 0.5 to about 45 mg/kg, about 0.75 to about 45 mg/kg, about 1 to about 45 mg/mg, about 1.5 to about 45 mg/kb, about 2 to about 45 mg/kg, about 2.5 to about 45 mg/kg, about 3 to about 45 mg/kg, about 3.5 to about 45 mg/kg, about 4 to about 45 mg/kg, about 4.5 to about 45 mg/kg, about 5 to about 45 mg/kg, about 7.5 to about 45 mg/kg, about 10 to about 45 mg/kg, about 15 to about 45 mg/kg, about 20 to about 45 mg/kg, about 20 to about 45 mg/kg, about 25 to about 45 mg/kg, about 25 to about 45 mg/kg, about 30 to about 45 mg/kg, about 35 to about 45 mg/kg, about 40 to about 45 mg/kg, about 0.5 to about 40 mg/kg, about 0.75 to about 40 mg/kg, about 1 to about 40 mg/mg, about 1.5 to about 40 mg/kb, about 2 to about 40 mg/kg, about 2.5 to about 40 mg/kg, about 3 to about 40 mg/kg, about 3.5 to about 40 mg/kg, about 4 to about 40 mg/kg, about 4.5 to about 40 mg/kg, about 5 to about 40 mg/kg, about 7.5 to about 40 mg/kg, about 10 to about 40 mg/kg, about 15 to about 40 mg/kg, about 20 to about 40 mg/kg, about 20 to about 40 mg/kg, about 25 to about 40 mg/kg, about 25 to about 40 mg/kg, about 30 to about 40 mg/kg, about 35 to about 40 mg/kg, about 0.5 to about 30 mg/kg, about 0.75 to about 30 mg/kg, about 1 to about 30 mg/mg, about 1.5 to about 30 mg/kb, about 2 to about 30 mg/kg, about 2.5 to about 30 mg/kg, about 3 to about 30 mg/kg, about 3.5 to about 30 mg/kg, about 4 to about 30 mg/kg, about 4.5 to about 30 mg/kg, about 5 to about 30 mg/kg, about 7.5 to about 30 mg/kg, about 10 to about 30 mg/kg, about 15 to about 30 mg/kg, about 20 to about 30 mg/kg, about 20 to about 30 mg/kg, about 25 to about 30 mg/kg, about 0.5 to about 20 mg/kg, about 0.75 to about 20 mg/kg, about 1 to about 20 mg/mg, about 1.5 to about 20 mg/kb, about 2 to about 20 mg/kg, about 2.5 to about 20 mg/kg, about 3 to about 20 mg/kg, about 3.5 to about 20 mg/kg, about 4 to about 20 mg/kg, about 4.5 to about 20 mg/kg, about 5 to about 20 mg/kg, about 7.5 to about 20 mg/kg, about 10 to about 20 mg/kg, or about 15 to about 20 mg/kg. In one embodiment, the antisense polynucleotide agent is administered at a dose of about 10 mg/kg to about 30 mg/kg. Values and ranges intermediate to the recited values are also intended to be part of this invention.

For example, subjects can be administered, e.g., subcutaneously or intravenously, a single therapeutic amount of antisense polynucleotide agent, such as about 0.1, 0.125, 0.15, 0.175, 0.2, 0.225, 0.25, 0.275, 0.3, 0.325, 0.35, 0.375, 0.4, 0.425, 0.45, 0.475, 0.5, 0.525, 0.55, 0.575, 0.6, 0.625, 0.65, 0.675, 0.7, 0.725, 0.75, 0.775, 0.8, 0.825, 0.85, 0.875, 0.9, 0.925, 0.95, 0.975, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 31, 32, 33, 34, 34, 35, 36, 37, 38, 39, 40, 41, 42, 43, 44, 45, 46, 47, 48, 49, or about 50 mg/kg. Values and ranges intermediate to the recited values are also intended to be part of this invention.

In some embodiments, subjects are administered, e.g., subcutaneously or intravenously, multiple doses of a therapeutic amount of antisense polynucleotide agent, such as a dose about 0.1, 0.125, 0.15, 0.175, 0.2, 0.225, 0.25, 0.275, 0.3, 0.325, 0.35, 0.375, 0.4, 0.425, 0.45, 0.475, 0.5, 0.525, 0.55, 0.575, 0.6, 0.625, 0.65, 0.675, 0.7, 0.725, 0.75, 0.775, 0.8, 0.825, 0.85, 0.875, 0.9, 0.925, 0.95, 0.975, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 31, 32, 33, 34, 34, 35, 36, 37, 38, 39, 40, 41, 42, 43, 44, 45, 46, 47, 48, 49, or about 50 mg/kg. A multi-dose regimen may include administration of a therapeutic amount of antisense polynucleotide agent daily, such as for two days, three days, four days, five days, six days, seven days, or longer.

In other embodiments, subjects are administered, e.g., subcutaneously or intravenously, a repeat dose of a therapeutic amount of antisense polynucleotide agent, such as a dose about 0.1, 0.125, 0.15, 0.175, 0.2, 0.225, 0.25, 0.275, 0.3, 0.325, 0.35, 0.375, 0.4, 0.425, 0.45, 0.475, 0.5, 0.525, 0.55, 0.575, 0.6, 0.625, 0.65, 0.675, 0.7, 0.725, 0.75, 0.775, 0.8, 0.825, 0.85, 0.875, 0.9, 0.925, 0.95, 0.975, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 31, 32, 33, 34, 34, 35, 36, 37, 38, 39, 40, 41, 42, 43, 44, 45, 46, 47, 48, 49, or about 50 mg/kg. A repeat-dose regimen may include administration of a therapeutic amount of antisense polynucleotide agent on a regular basis, such as every other day, every third day, every fourth day, twice a week, once a week, every other week, or once a month.

The pharmaceutical composition can be administered by intravenous infusion over a period of time, such as over a 5, 6, 7, 8, 9, 10, 11, 12, 13, 14, 15, 16, 17, 18, 19, 20, and 21, 22, 23, 24, or about a 25 minute period. The administration may be repeated, for example, on a regular basis, such as weekly, biweekly (i.e., every two weeks) for one month, two months, three months, four months or longer. After an initial treatment regimen, the treatments can be administered on a less frequent basis. For example, after administration weekly or biweekly for three months, administration can be repeated once per month, for six months or a year or longer.

The pharmaceutical composition can be administered once daily, or the pharmaceutical composition can be administered as two, three, or more sub-doses at appropriate intervals throughout the day or even using continuous infusion or delivery through a controlled release formulation. In that case, the antisense polynucleotide agent contained in each sub-dose must be correspondingly smaller in order to achieve the total daily dosage. The dosage unit can also be compounded for delivery over several days, e.g., using a conventional sustained release formulation which provides sustained release of the antisense polynucleotide agent over a several day period. Sustained release formulations are well known in the art and are particularly useful for delivery of agents at a particular site, such as could be used with the agents of the present invention. In this embodiment, the dosage unit contains a corresponding multiple of the daily dose.

In other embodiments, a single dose of the pharmaceutical compositions can be long lasting, such that subsequent doses are administered at not more than 3, 4, or 5 day intervals, or at not more than 1, 2, 3, or 4 week intervals. In some embodiments of the invention, a single dose of the pharmaceutical compositions of the invention is administered once per week. In other embodiments of the invention, a single dose of the pharmaceutical compositions of the invention is administered bi-monthly.

The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual antisense polynucleotide agents encompassed by the invention can be made using conventional methodologies or on the basis of in vivo testing using an appropriate animal model, as described elsewhere herein.

Advances in mouse genetics have generated a number of mouse models for the study of various human diseases, such as a disorder that would benefit from reduction in the expression of PNPLA3. Such models can be used for in vivo testing of an antisense polynucleotide agent, as well as for determining a therapeutically effective dose. Suitable dietary and genetic mouse models are reviewed in Kanuri and Bergheim (*Int. J. Mol. Sci.* (2013) 14:11963-11980). Non-alcoholic steatohepatitis (NASH) mouse models (ob/ob mice) that are fed a high fat diet can be used in the present invention. Mouse models with overexpression of mutant PNPLA3 may also be suitable to be used in the present invention.

The pharmaceutical compositions of the present invention can be administered in a number of ways depending upon whether local or systemic treatment is desired and upon the area to be treated. Administration can be topical (e.g., by a transdermal patch), pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; subdermal, e.g., via an implanted device; or intracranial, e.g., by intraparenchymal, intrathecal or intraventricular, administration.

The antisense polynucleotide agent can be delivered in a manner to target a particular tissue, such as the liver (e.g., the hepatocytes of the liver).

Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like can be necessary or desirable. Coated condoms, gloves and the like can also be useful. Suitable topical formulations include those in which the antisense polynucleotide agents featured in the invention are in admixture with a topical delivery agent such as lipids, liposomes, fatty acids, fatty acid esters, steroids, chelating agents and surfactants. Suitable lipids and liposomes include neutral (e.g., dioleoylphosphatidyl DOPE ethanolamine, dimyristoylphosphatidyl choline DMPC, distearolyphosphatidyl choline) negative (e.g., dimyristoylphosphatidyl glycerol DMPG) and cationic (e.g., dioleoyltetramethylaminopropyl DOTAP and dioleoylphosphatidyl ethanolamine DOTMA). Antisense polynucleotide agents featured in the invention can be encapsulated within liposomes or can form complexes thereto, in particular to cationic liposomes. Alternatively, antisense polynucleotide agents can be complexed to lipids, in particular to cationic lipids. Suitable fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-20}$ alkyl ester (e.g., isopropylmyristate IPM), monoglyceride, diglyceride or pharmaceutically acceptable salt thereof). Topical formulations are described in detail in U.S. Pat. No. 6,747,014, which is incorporated herein by reference.

A. Antisense Polynucleotide Agent Formulations Comprising Membranous Molecular Assemblies An antisense polynucleotide agent for use in the compositions and methods of the invention can be formulated for delivery in a membranous molecular assembly, e.g., a liposome or a micelle. As used herein, the term "liposome" refers to a vesicle composed of amphiphilic lipids arranged in at least one bilayer, e.g., one bilayer or a plurality of bilayers. Liposomes include unilamellar and multilamellar vesicles that have a membrane formed from a lipophilic material and an aqueous interior. The aqueous portion contains the antisense polynucleotide agent composition. The lipophilic material isolates the aqueous interior from an aqueous exterior, which typically does not include the antisense polynucleotide agent composition, although in some examples, it may. Liposomes are useful for the transfer and delivery of active ingredients to the site of action. Because the liposomal membrane is structurally similar to biological membranes, when liposomes are applied to a tissue, the liposomal bilayer fuses with bilayer of the cellular membranes. As the merging of the liposome and cell progresses, the internal aqueous contents that include the antisense polynucleotide agent are delivered into the cell where the antisense polynucleotide agent can specifically bind to a target RNA and can mediate antisense inhibition. In some cases the liposomes are also specifically targeted, e.g., to direct the antisense polynucleotide agent to particular cell types.

A liposome containing an antisense polynucleotide agent can be prepared by a variety of methods. In one example, the lipid component of a liposome is dissolved in a detergent so that micelles are formed with the lipid component. For example, the lipid component can be an amphipathic cationic lipid or lipid conjugate. The detergent can have a high critical micelle concentration and may be nonionic. Exemplary detergents include cholate, CHAPS, octylglucoside, deoxycholate, and lauroyl sarcosine. The antisense polynucleotide agent preparation is then added to the micelles that include the lipid component. The cationic groups on the lipid interact with the antisense polynucleotide agent and condense around the antisense polynucleotide agent to form a liposome. After condensation, the detergent is removed, e.g., by dialysis, to yield a liposomal preparation of antisense polynucleotide agent.

If necessary a carrier compound that assists in condensation can be added during the condensation reaction, e.g., by controlled addition. For example, the carrier compound can be a polymer other than a nucleic acid (e.g., spermine or spermidine). pH can also be adjusted to favor condensation.

Methods for producing stable polynucleotide delivery vehicles, which incorporate a polynucleotide/cationic lipid complex as structural components of the delivery vehicle, are further described in, e.g., WO 96/37194, the entire contents of which are incorporated herein by reference. Liposome formation can also include one or more aspects of exemplary methods described in Felgner, P. L. et al., *Proc. Natl. Acad. Sci., USA* 8:7413-7417, 1987; U.S. Pat. Nos. 4,897,355; 5,171,678; Bangham, et al. *M. Mol. Biol.* 23:238, 1965; Olson, et al. *Biochim. Biophys. Acta* 557:9, 1979; Szoka, et al. *Proc. Natl. Acad. Sci.* 75: 4194, 1978; Mayhew, et al. *Biochim. Biophys. Acta* 775:169, 1984; Kim, et al. *Biochim. Biophys. Acta* 728:339, 1983; and Fukunaga, et al. *Endocrinol.* 115:757, 1984. Commonly used techniques for preparing lipid aggregates of appropriate size for use as delivery vehicles include sonication and freeze-thaw plus extrusion (see, e.g., Mayer, et al. *Biochim. Biophys. Acta* 858:161, 1986). Microfluidization can be used when consistently small (50 to 200 nm) and relatively uniform aggregates are desired (Mayhew, et al. *Biochim. Biophys. Acta* 775:169, 1984). These methods are readily adapted to packaging antisense polynucleotide agent preparations into liposomes.

Liposomes fall into two broad classes. Cationic liposomes are positively charged liposomes which interact with the negatively charged nucleic acid molecules to form a stable complex. The positively charged nucleic acid/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.*, 1987, 147, 980-985).

Liposomes which are pH-sensitive or negatively-charged, entrap nucleic acids rather than complex with it. Since both the nucleic acid and the lipid are similarly charged, repulsion rather than complex formation occurs. Nevertheless, some nucleic acid is entrapped within the aqueous interior of these liposomes. pH-sensitive liposomes have been used to deliver nucleic acids encoding the thymidine kinase gene to cell monolayers in culture. Expression of the exogenous gene was detected in the target cells (Zhou et al., *Journal of Controlled Release*, 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Examples of other methods to introduce liposomes into cells in vitro and in vivo include U.S. Pat. Nos. 5,283,185; 5,171,678; WO 94/00569; WO 93/24640; WO 91/16024; Felgner, *J. Biol. Chem.* 269:2550, 1994; Nabel, *Proc. Natl. Acad. Sci.* 90:11307, 1993; Nabel, *Human Gene Ther.* 3:649, 1992; Gershon, *Biochem.* 32:7143, 1993; and Strauss *EMBO J.* 11:417, 1992.

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin Results indicated that such non-ionic liposomal systems were effective in facilitating the deposition of cyclosporine A into different layers of the skin (Hu et al. *S.T.P. Pharma. Sci.*, 1994, 4(6) 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., FEBS Letters, 1987, 223, 42; Wu et al., Cancer Research, 1993, 53, 3765).

Various liposomes comprising one or more glycolipids are known in the art. Papahadjopoulos et al. (Ann. N.Y. Acad. Sci., 1987, 507, 64) reported the ability of monosialoganglioside $G_{M1}$, galactocerebroside sulfate and phosphatidylinositol to improve blood half-lives of liposomes. These findings were expounded upon by Gabizon et al. (Proc. Natl. Acad. Sci. U.S.A., 1988, 85, 6949). U.S. Pat. No. 4,837,028 and WO 88/04924, both to Allen et al., disclose liposomes comprising (1) sphingomyelin and (2) the ganglioside $G_{mi}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al).

In one embodiment, cationic liposomes are used. Cationic liposomes possess the advantage of being able to fuse to the cell membrane. Non-cationic liposomes, although not able to fuse as efficiently with the plasma membrane, are taken up by macrophages in vivo and can be used to deliver antisense polynucleotide agents to macrophages.

Further advantages of liposomes include: liposomes obtained from natural phospholipids are biocompatible and biodegradable; liposomes can incorporate a wide range of water and lipid soluble drugs; liposomes can protect encapsulated antisense polynucleotide agents in their internal compartments from metabolism and degradation (Rosoff, in "Pharmaceutical Dosage Forms," Lieberman, Rieger and Banker (Eds.), 1988, volume 1, p. 245). Important considerations in the preparation of liposome formulations are the lipid surface charge, vesicle size and the aqueous volume of the liposomes.

A positively charged synthetic cationic lipid, N-[1-(2,3-dioleyloxy)propyl]-N,N,N-trimethylammonium chloride (DOTMA) can be used to form small liposomes that interact spontaneously with nucleic acid to form lipid-nucleic acid complexes which are capable of fusing with the negatively charged lipids of the cell membranes of tissue culture cells, resulting in delivery of Antisense polynucleotide agent (see, e.g., Felgner, P. L. et al., Proc. Natl. Acad. Sci., USA 8:7413-7417, 1987 and U.S. Pat. No. 4,897,355 for a description of DOTMA and its use with DNA).

A DOTMA analogue, 1,2-bis(oleoyloxy)-3-(trimethylammonia)propane (DOTAP) can be used in combination with a phospholipid to form DNA-complexing vesicles. Lipofectin™ Bethesda Research Laboratories, Gaithersburg, Md.) is an effective agent for the delivery of highly anionic nucleic acids into living tissue culture cells that comprise positively charged DOTMA liposomes which interact spontaneously with negatively charged polynucleotides to form complexes. When enough positively charged liposomes are used, the net charge on the resulting complexes is also positive. Positively charged complexes prepared in this way spontaneously attach to negatively charged cell surfaces, fuse with the plasma membrane, and efficiently deliver functional nucleic acids into, for example, tissue culture cells. Another commercially available cationic lipid, 1,2-bis(oleoyloxy)-3,3-(trimethylammonia)propane ("DOTAP") (Boehringer Mannheim, Indianapolis, Ind.) differs from DOTMA in that the oleoyl moieties are linked by ester, rather than ether linkages.

Other reported cationic lipid compounds include those that have been conjugated to a variety of moieties including, for example, carboxyspermine which has been conjugated to one of two types of lipids and includes compounds such as 5-carboxyspermylglycine dioctaoleoylamide ("DOGS") (Transfectam™, Promega, Madison, Wis.) and dipalmitoyl-phosphatidylethanolamine 5-carboxyspermyl-amide ("DPPES") (see, e.g., U.S. Pat. No. 5,171,678).

Another cationic lipid conjugate includes derivatization of the lipid with cholesterol ("DC-Chol") which has been formulated into liposomes in combination with DOPE (See, Gao, X. and Huang, L., Biochim. Biophys. Res. Commun. 179:280, 1991). Lipopolylysine, made by conjugating polylysine to DOPE, has been reported to be effective for transfection in the presence of serum (Zhou, X. et al., Biochim. Biophys. Acta 1065:8, 1991). For certain cell lines, these liposomes containing conjugated cationic lipids, are said to exhibit lower toxicity and provide more efficient transfection than the DOTMA-containing compositions. Other commercially available cationic lipid products include DMRIE and DMRIE-HP (Vical, La Jolla, Calif.) and Lipofectamine (DOSPA) (Life Technology, Inc., Gaithersburg, Md.). Other cationic lipids suitable for the delivery of oligonucleotides are described in WO 98/39359 and WO 96/37194.

Liposomal formulations are particularly suited for topical administration; liposomes present several advantages over other formulations. Such advantages include reduced side effects related to high systemic absorption of the administered drug, increased accumulation of the administered drug at the desired target, and the ability to administer an antisense polynucleotide agent into the skin. In some implementations, liposomes are used for delivering antisense polynucleotide agents to epidermal cells and also to enhance the penetration of antisense polynucleotide agents into dermal tissues, e.g., into skin. For example, the liposomes can be applied topically. Topical delivery of drugs formulated as liposomes to the skin has been documented (see, e.g., Weiner et al., Journal of Drug Targeting, 1992, vol. 2, 405-410 and du Plessis et al., Antiviral Research, 18, 1992, 259-265; Mannino, R. J. and Fould-Fogerite, S., Biotechniques 6:682-690, 1988; Itani, T. et al. Gene 56:267-276. 1987; Nicolau, C. et al. Meth. Enz. 149:157-176, 1987; Straubinger, R. M. and Papahadjopoulos, D. Meth. Enz. 101:512-527, 1983; Wang, C. Y. and Huang, L., Proc. Natl. Acad. Sci. USA 84:7851-7855, 1987).

Non-ionic liposomal systems have also been examined to determine their utility in the delivery of drugs to the skin, in particular systems comprising non-ionic surfactant and cholesterol. Non-ionic liposomal formulations comprising Novasome I (glyceryl dilaurate/cholesterol/polyoxyethylene-10-stearyl ether) and Novasome II (glyceryl distearate/cholesterol/polyoxyethylene-10-stearyl ether) were used to deliver a drug into the dermis of mouse skin Such formulations with antisense polynucleotide agents are useful for treating a dermatological disorder.

Liposomes that include antisense polynucleotide agent can be made highly deformable. Such deformability can enable the liposomes to penetrate through pore that are smaller than the average radius of the liposome. For example, transfersomes are a type of deformable liposomes. Transferosomes can be made by adding surface edge activators, usually surfactants, to a standard liposomal composition. Transfersomes that include antisense polynucleotide agents can be delivered, for example, subcutaneously by infection in order to deliver antisense polynucleotide agents to keratinocytes in the skin. In order to cross intact mammalian skin, lipid vesicles must pass through a series of fine pores, each with a diameter less than 50 nm, under the influence of a suitable transdermal gradient. In addition, due to the lipid properties, these transferosomes can be self-optimizing (adaptive to the shape of pores, e.g., in the skin), self-repairing, and can frequently reach their targets without fragmenting, and often self-loading.

Other formulations amenable to the present invention are described in U.S. provisional application Ser. No. 61/018,616, filed Jan. 2, 2008; 61/018,611, filed Jan. 2, 2008; 61/039,748, filed Mar. 26, 2008; 61/047,087, filed Apr. 22, 2008 and 61/051,528, filed May 8, 2008. PCT application no PCT/US2007/080331, filed Oct. 3, 2007 also describes formulations that are amenable to the present invention.

Transfersomes are yet another type of liposomes, and are highly deformable lipid aggregates which are attractive candidates for drug delivery vehicles. Transfersomes can be described as lipid droplets which are so highly deformable that they are easily able to penetrate through pores which are smaller than the droplet. Transfersomes are adaptable to the environment in which they are used, e.g., they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in "Pharmaceutical Dosage Forms", Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric Amphoteric surfactants include acrylic acid derivatives, substituted alkylamides, N-alkylbetaines and phosphatides.

The use of surfactants in drug products, formulations and in emulsions has been reviewed (Rieger, in "Pharmaceutical Dosage Forms", Marcel Dekker, Inc., New York, N.Y., 1988, p. 285).

The antisense polynucleotide agent for use in the compositions and methods of the invention can also be provided as micellar formulations. "Micelles" are defined herein as a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic.

A mixed micellar formulation suitable for delivery through transdermal membranes may be prepared by mixing an aqueous solution of the antisense polynucleotide agent composition, an alkali metal $C_8$ to $C_{22}$ alkyl sulphate, and a micelle forming compounds. Exemplary micelle forming compounds include lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerin, polyglycerin, lysine, polylysine, triolein, polyoxyethylene ethers and analogues thereof, polidocanol alkyl ethers and analogues thereof, chenodeoxycholate, deoxycholate, and mixtures thereof. The micelle forming compounds may be added at the same time or after addition of the alkali metal alkyl sulphate. Mixed micelles will form with substantially any kind of mixing of the ingredients but vigorous mixing in order to provide smaller size micelles.

In one method a first micellar composition is prepared which contains the antisense polynucleotide agent composition and at least the alkali metal alkyl sulphate. The first micellar composition is then mixed with at least three micelle forming compounds to form a mixed micellar composition. In another method, the micellar composition is prepared by mixing the antisense polynucleotide agent composition, the alkali metal alkyl sulphate and at least one of the micelle forming compounds, followed by addition of the remaining micelle forming compounds, with vigorous mixing.

Phenol and/or m-cresol may be added to the mixed micellar composition to stabilize the formulation and protect against bacterial growth. Alternatively, phenol and/or m-cresol may be added with the micelle forming ingredients. An isotonic agent such as glycerin may also be added after formation of the mixed micellar composition.

For delivery of the micellar formulation as a spray, the formulation can be put into an aerosol dispenser and the dispenser is charged with a propellant. The propellant, which is under pressure, is in liquid form in the dispenser. The ratios of the ingredients are adjusted so that the aqueous and propellant phases become one, i.e., there is one phase. If there are two phases, it is necessary to shake the dispenser prior to dispensing a portion of the contents, e.g., through a metered valve. The dispensed dose of pharmaceutical agent is propelled from the metered valve in a fine spray.

Propellants may include hydrogen-containing chlorofluorocarbons, hydrogen-containing fluorocarbons, dimethyl ether and diethyl ether. In certain embodiments, HFA 134a (1,1,1,2 tetrafluoroethane) may be used.

The specific concentrations of the essential ingredients can be determined by relatively straightforward experimentation. For absorption through the oral cavities, it is often desirable to increase, e.g., at least double or triple, the dosage for through injection or administration through the gastrointestinal tract.

B. Lipid Particles

Antisense polynucleotide agents of in the invention may be fully encapsulated in a lipid formulation, e.g., a LNP, or other nucleic acid-lipid particle.

As used herein, the term "LNP" refers to a stable nucleic acid-lipid particle comprising a lipid layer encapsulating a pharmaceutically active molecule. LNPs typically contain a cationic lipid, a non-cationic lipid, and a lipid that prevents aggregation of the particle (e.g., a PEG-lipid conjugate). LNPs are extremely useful for systemic applications, as they exhibit extended circulation lifetimes following intravenous (i.v.) injection and accumulate at distal sites (e.g., sites physically separated from the administration site). LNPs include "pSPLP," which include an encapsulated condensing agent-nucleic acid complex as set forth in PCT Publication No. WO 00/03683. The particles of the present invention typically have a mean diameter of about 50 nm to about 150 nm, more typically about 60 nm to about 130 nm, more typically about 70 nm to about 110 nm, most typically about 70 nm to about 90 nm, and are substantially nontoxic. In addition, the nucleic acids when present in the nucleic acid-lipid particles of the present invention are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; 6,815,432; 6,858,225; 8,158,601; and 8,058,069; U.S. Publication No. 2010/0324120 and PCT Publication No. WO 96/40964.

In one embodiment, the lipid to drug ratio (mass/mass ratio) (e.g., lipid to antisense polynucleotide agent ratio) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1. Ranges intermediate to the above recited ranges are also contemplated to be part of the invention.

The cationic lipid can be, for example, N,N-dioleyl-N,N-dimethylammonium chloride (DODAC), N,N-distearyl-N,N-dimethylammonium bromide (DDAB), N-(I-(2,3-dioleoyloxy)propyl)-N,N,N-trimethylammonium chloride (DOTAP), N-(I-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino) acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 1,2-Dilinolenyloxy-N,N-dimethylaminopropane (DLinDMA), 2,2-Dilinoleyl-4-dimethylaminomethyl-[1,3]-dioxolane (DLin-K-DMA) or analogs thereof, (3aR,5s,6aS)-N,N-dimethyl-2,2-di((9Z,12Z)-octadeca-9,12-dienyl)tetrahydro-3aH-cyclopenta[d][1,3]dioxol-5-amine (ALN100), (6Z,9Z,28Z,31Z)-heptatriaconta-6,9,28,31-tetraen-19-yl 4-(dimethylamino)butanoate (MC3), 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (Tech G1), or a mixture thereof. The cationic lipid can comprise from about 20 mol % to about 50 mol % or about 40 mol % of the total lipid present in the particle.

In another embodiment, the compound 2,2-Dilinoleyl-4-dimethylaminoethyl-[1,3]-dioxolane can be used to prepare lipid-santisense polynucleotide agent nanoparticles. Synthesis of 2,2-Dilinoleyl-4-dimethylaminoethyl-[1,3]-dioxolane is described in U.S. provisional patent application No. 61/107,998 filed on Oct. 23, 2008, which is herein incorporated by reference.

In one embodiment, the lipid-antisense polynucleotide agent particle includes 40% 2, 2-Dilinoleyl-4-dimethylaminoethyl-[1,3]-dioxolane: 10% DSPC: 40% Cholesterol: 10% PEG-C-DOMG (mole percent) with a particle size of 63.0±20 nm and a 0.027 antisense polynucleotide agent/Lipid Ratio.

The ionizable/non-cationic lipid can be an anionic lipid or a neutral lipid including, but not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. The non-cationic lipid can be from about 5 mol % to about 90 mol %, about 10 mol %, or about 58 mol % if cholesterol is included, of the total lipid present in the particle.

The conjugated lipid that inhibits aggregation of particles can be, for example, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate can be, for example, a PEG-dilauryloxypropyl ($Ci_2$), a PEG-dimyristyloxypropyl ($Ci_4$), a PEG-dipalmityloxypropyl ($Ci_6$), or a PEG-distearyloxypropyl ($C]_8$). The conjugated lipid that prevents aggregation of particles can be from 0 mol % to about 20 mol % or about 2 mol % of the total lipid present in the particle.

In some embodiments, the nucleic acid-lipid particle further includes cholesterol at, e.g., about 10 mol % to about 60 mol % or about 48 mol % of the total lipid present in the particle.

In one embodiment, the lipidoid ND98.4HCl (MW 1487) (see U.S. patent application Ser. No. 12/056,230, filed Mar. 26, 2008, which is incorporated herein by reference), Cholesterol (Sigma-Aldrich), and PEG-Ceramide C16 (Avanti Polar Lipids) can be used to prepare lipid-antisense polynucleotide agent nanoparticles (i.e., LNP01 particles). Stock solutions of each in ethanol can be prepared as follows: ND98, 133 mg/ml; Cholesterol, 25 mg/ml, PEG-Ceramide C16, 100 mg/ml. The ND98, Cholesterol, and PEG-Ceramide C16 stock solutions can then be combined in a, e.g., 42:48:10 molar ratio. The combined lipid solution can be mixed with aqueous antisense polynucleotide agent (e.g., in sodium acetate pH 5) such that the final ethanol concentration is about 35-45% and the final sodium acetate concentration is about 100-300 mM. Lipid-antisense polynucleotide agent nanoparticles typically form spontaneously upon mixing. Depending on the desired particle size distribution, the resultant nanoparticle mixture can be extruded through a polycarbonate membrane (e.g., 100 nm cut-off) using, for example, a thermobarrel extruder, such as Lipex Extruder (Northern Lipids, Inc). In some cases, the extrusion step can be omitted. Ethanol removal and simultaneous buffer exchange can be accomplished by, for example, dialysis or tangential flow filtration. Buffer can be exchanged with, for example, phosphate buffered saline (PBS) at about pH 7, e.g., about pH 6.9, about pH 7.0, about pH 7.1, about pH 7.2, about pH 7.3, or about pH 7.4.

Formula 1

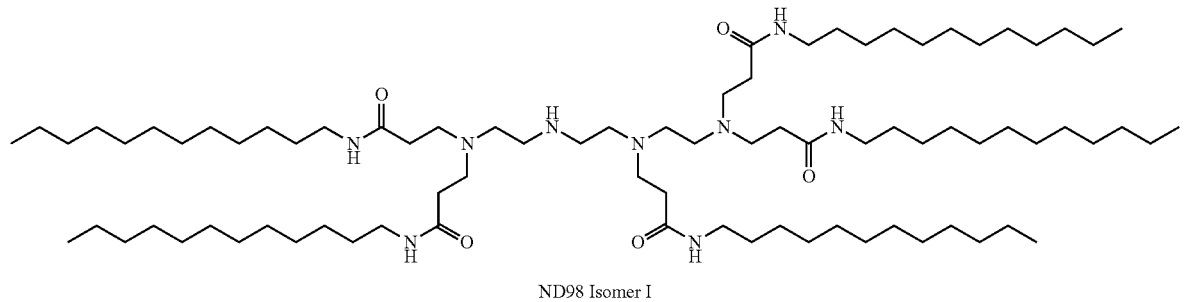

ND98 Isomer I

LNP01 formulations are described, e.g., in International Application Publication No. WO 2008/042973, which is hereby incorporated by reference.

Additional exemplary lipid-antisense polynucleotide agent formulations are described in Table 1.

TABLE 1

|  | Ionizable/Cationic Lipid | cationic lipid/non-cationic lipid/cholesterol/PEG-lipid conjugate Lipid:santisense polynucleotide agent ratio |
|---|---|---|
| SNALP-1 | 1,2-Dilinolenyloxy-N,N-dimethylaminopropane (DLinDMA) | DLinDMA/DPPC/Cholesterol/PEG-cDMA (57.1/7.1/34.4/1.4) lipid:santisense polynucleotide agent ~7:1 |
| 2-XTC | 2,2-Dilinoleyl-4-dimethylaminoethyl-[1,3]-dioxolane (XTC) | XTC/DPPC/Cholesterol/PEG-cDMA 57.1/7.1/34.4/1.4 lipid:santisense polynucleotide agent ~7:1 |
| LNP05 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:santisense polynucleotide agent ~6:1 |
| LNP06 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:santisense polynucleotide agent ~11:1 |
| LNP07 | 2,2-Dilinoleyl-4-dimethylaminoethyl-[1,3]-dioxolane (XTC) | XTC/DSPC/Cholesterol/PEG-DMG 60/7.5/31/1.5, lipid:santisense polynucleotide agent ~6:1 |
| LNP08 | 2,2-Dilinoleyl-4-dimethylaminoethyl-[1,3]-dioxolane (XTC) | XTC/DSPC/Cholesterol/PEG-DMG 60/7.5/31/1.5, lipid:santisense polynucleotide agent ~11:1 |
| LNP09 | 2,2-Dilinoleyl-4-dimethylaminoethyl-[1,3]-dioxolane (XTC) | XTC/DSPC/Cholesterol/PEG-DMG 50/10/38.5/1.5 Lipid:santisense polynucleotide agent 10:1 |
| LNP10 | (3aR,5s,6aS)-N,N-dimethyl-2,2-di((9Z,12Z)-octadeca-9,12-dienyl)tetrahydro-3aH-cyclopenta[d][1,3]dioxol-5-amine (ALN100) | ALN100/DSPC/Cholesterol/PEG-DMG 50/10/38.5/1.5 Lipid:santisense polynucleotide agent 10:1 |
| LNP11 | (6Z,9Z,28Z,31Z)-heptatriaconta-6,9,28,31-tetraen-19-yl 4-(dimethylamino)butanoate (MC3) | MC-3/DSPC/Cholesterol/PEG-DMG 50/10/38.5/1.5 Lipid:santisense polynucleotide agent 10:1 |

TABLE 1-continued

| | Ionizable/Cationic Lipid | cationic lipid/non-cationic lipid/cholesterol/PEG-lipid conjugate Lipid:santisense polynucleotide agent ratio |
|---|---|---|
| LNP12 | 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (Tech G1) | Tech G1/DSPC/Cholesterol/PEG-DMG 50/10/38.5/1.5 Lipid:santisense polynucleotide agent 10:1 |
| LNP13 | XTC | XTC/DSPC/Chol/PEG-DMG 50/10/38.5/1.5 Lipid:santisense polynucleotide agent: 33:1 |
| LNP14 | MC3 | MC3/DSPC/Chol/PEG-DMG 40/15/40/5 Lipid:santisense polynucleotide agent: 11:1 |
| LNP15 | MC3 | MC3/DSPC/Chol/PEG-DSG/GalNAc-PEG-DSG 50/10/35/4.5/0.5 Lipid:santisense polynucleotide agent: 11:1 |
| LNP16 | MC3 | MC3/DSPC/Chol/PEG-DMG 50/10/38.5/1.5 Lipid:santisense polynucleotide agent: 7:1 |
| LNP17 | MC3 | MC3/DSPC/Chol/PEG-DSG 50/10/38.5/1.5 Lipid:santisense polynucleotide agent: 10:1 |
| LNP18 | MC3 | MC3/DSPC/Chol/PEG-DMG 50/10/38.5/1.5 Lipid:santisense polynucleotide agent: 12:1 |
| LNP19 | MC3 | MC3/DSPC/Chol/PEG-DMG 50/10/35/5 Lipid:santisense polynucleotide agent: 8:1 |
| LNP20 | MC3 | MC3/DSPC/Chol/PEG-DPG 50/10/38.5/1.5 Lipid:santisense polynucleotide agent: 10:1 |
| LNP21 | C12-200 | C12-200/DSPC/Chol/PEG-DSG 50/10/38.5/1.5 Lipid:santisense polynucleotide agent: 7:1 |
| LNP22 | XTC | XTC/DSPC/Chol/PEG-DSG 50/10/38.5/1.5 Lipid:santisense polynucleotide agent: 10:1 |

DSPC: distearoylphosphatidylcholine
DPPC: dipalmitoylphosphatidylcholine
PEG-DMG: PEG-didimyristoyl glycerol (C14-PEG, or PEG-C14) (PEG with avg mol wt of 2000)
PEG-DSG: PEG-distyryl glycerol (C18-PEG, or PEG-C18) (PEG with avg mol wt of 2000)
PEG-cDMA: PEG-carbamoyl-1,2-dimyristyloxypropylamine (PEG with avg mol wt of 2000)
SNALP (1,2-Dilinolenyloxy-N,N-dimethylaminopropane (DLinDMA)) comprising formulations are described in International Publication No. WO2009/127060, filed Apr. 15, 2009 which is hereby incorporated by reference.
XTC comprising formulations are described in PCT Publication No. WO 2010/088537, the entire contents of which are hereby incorporated herein by reference.
MC3 comprising formulations are described, e.g., in U.S. Publication No. 2010/0324120, filed Jun. 10, 2010, the entire contents of which are hereby incorporated by reference.
ALNY-100 comprising formulations are described in PCT Publication No. WO 2010/054406, the entire contents of which are hereby incorporated herein by reference.
C12-200 comprising formulations are described in PCT Publication No. WO 2010/129709, the entire contents of which are hereby incorporated herein by reference.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders can be desirable. In some embodiments, oral formulations are those in which the antisense polynucleotide agents featured in the invention are administered in conjunction with one or more penetration enhancer surfactants and chelators. Suitable surfactants include fatty acids and/or esters or salts thereof, bile acids and/or salts thereof. Suitable bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydrofusidate and sodium glycodihydrofusidate. Suitable fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g., sodium). In some embodiments, combinations of penetration enhancers are used, for example, fatty acids/salts in combination with bile acids/salts. One exemplary combination is the sodium salt of lauric acid, capric acid and UDCA. Further penetration enhancers include polyoxyethylene-9-lauryl ether, polyoxyethylene-20-cetyl ether. Antisense polynucleotide agents featured in the invention can be delivered orally, in granular form including sprayed dried particles, or complexed to form micro or nanoparticles. Antisense polynucleotide agent complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Suitable complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g., p-amino), poly(methylcyanoacrylate), poly(ethylcyanoacrylate), poly(butylcyanoacrylate), poly(isobutylcyanoacrylate), poly(isohexylcyanoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for antisense polynucleotide agents and their preparation are described in detail in U.S. Pat. No. 6,887,906, US Publn. No. 20030027780, and U.S. Pat. No. 6,747,014, each of which is incorporated herein by reference.

Compositions and formulations for parenteral, intraparenchymal (into the brain), intrathecal, intraventricular or intrahepatic administration can include sterile aqueous solutions which can also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions can be generated from a variety of components that include, but are not limited to, preformed liquids, self-emulsifying solids and self-emulsifying semisolids. Particularly preferred are formulations that target the liver, e.g., when treating hepatic disorders, e.g., hepatic carcinoma.

The pharmaceutical formulations of the present invention, which can conveniently be presented in unit dosage form, can be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention can be formulated into any of many possible dosage forms such as, but not limited to, tablets, capsules, gel capsules, liquid syrups, soft gels, suppositories, and enemas. The compositions of the present invention can also be formulated as suspensions in aqueous, non-aqueous or mixed media. Aqueous suspensions can further contain substances which increase the viscosity of the suspension including, for example, sodium carboxymethylcellulose, sorbitol and/or dextran. The suspension can also contain stabilizers.

C. Additional Formulations
i. Emulsions

The compositions of the present invention can be prepared and formulated as emulsions. Emulsions are typically heterogeneous systems of one liquid dispersed in another in the form of droplets usually exceeding 0.1 μm in diameter (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions can be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions can contain additional components in addition to the dispersed phases, and the active drug which can be present as a solution in either the aqueous phase, oily phase or itself as a separate phase. Pharmaceutical excipients such as emulsifiers, stabilizers, dyes, and antioxidants can also be present in emulsions as needed. Pharmaceutical emulsions can also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion can be a semisolid or a solid, as is the case of emulsion-style ointment bases and creams. Other means of stabilizing emulsions entail the use of emulsifiers that can be incorporated into either phase of the emulsion. Emulsifiers can broadly be classified into four categories: synthetic surfactants, naturally occurring emulsifiers, absorption bases, and finely dispersed solids (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants can be classified into different classes based on the nature of the hydrophilic group: nonionic, anionic, cationic and amphoteric (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y. Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that can readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used can be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

ii. Microemulsions

In one embodiment of the present invention, the compositions of antisense polynucleotide agents are formulated as microemulsions. A microemulsion can be defined as a system of water, oil and amphiphile which is a single optically isotropic and thermodynamically stable liquid solution (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions can, however, be prepared without the use of cosurfactants and alcohol-free self-emulsifying microemulsion systems are known in the art. The aqueous phase can typically be, but is not limited to, water, an aqueous solution of the drug, glycerol, PEG300, PEG400, polyglycerols, propylene glycols, and derivatives of ethylene glycol. The oil phase can include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (see e.g., U.S. Pat. Nos. 6,191,105; 7,063,860; 7,070,802; 7,157,099; Constantinides et al., *Pharmaceutical Research,* 1994, 11, 1385-1390; Ritschel, *Meth. Find. Exp. Clin. Pharmacol.,* 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (see e.g., U.S. Pat. Nos. 6,191,105; 7,063,860; 7,070,802; 7,157,099; Constantinides et al., *Pharmaceutical Research,* 1994, 11, 1385; Ho et al., *J. Pharm. Sci.,* 1996, 85, 138-143). Often microemulsions can form spontaneously when their components are brought together at ambient temperature. This can be particularly advantageous when formulating thermolabile drugs, peptides or antisense polynucleotide agents. Microemulsions have also been effective in the transdermal delivery of active components in both cosmetic and pharmaceutical applications. It is expected that the microemulsion compositions and formulations of the present invention will facilitate the increased systemic absorption of antisense polynucleotide agents from the gastrointestinal tract, as well as improve the local cellular uptake of antisense polynucleotide agents and nucleic acids.

Microemulsions of the present invention can also contain additional components and additives such as sorbitan monostearate (Grill 3), Labrasol, and penetration enhancers to improve the properties of the formulation and to enhance the absorption of the antisense polynucleotide agents of the present invention. Penetration enhancers used in the microemulsions of the present invention can be classified as belonging to one of five broad categories—surfactants, fatty acids, bile salts, chelating agents, and non-chelating non-surfactants (Lee et al., *Critical Reviews in Therapeutic Drug Carrier Systems,* 1991, p. 92). Each of these classes has been discussed above.

iii. Microparticles

An antisense polynucleotide agent of the invention may be incorporated into a particle, e.g., a microparticle. Microparticles can be produced by spray-drying, but may also be produced by other methods including lyophilization, evaporation, fluid bed drying, vacuum drying, or a combination of these techniques.

iv. Penetration Enhancers

In one embodiment, the present invention employs various penetration enhancers to effect the efficient delivery of nucleic acids, particularly antisense polynucleotide agents, to the skin of animals. Most drugs are present in solution in both ionized and nonionized forms. However, usually only lipid soluble or lipophilic drugs readily cross cell membranes. It has been discovered that even non-lipophilic drugs can cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers can be classified as belonging to one of five broad categories, i.e., surfactants, fatty acids, bile salts, chelating agents, and non-chelating non-surfactants (see e.g., Malmsten, M. Surfactants and polymers in drug delivery, Informa Health Care, New York, N.Y., 2002; Lee et al., Critical Reviews in Therapeutic Drug Carrier Systems, 1991, p. 92). Each of the above mentioned classes of penetration enhancers are described below in greater detail.

Surfactants (or "surface-active agents") are chemical entities which, when dissolved in an aqueous solution, reduce the surface tension of the solution or the interfacial tension between the aqueous solution and another liquid, with the result that absorption of antisense polynucleotide agents through the mucosa is enhanced. In addition to bile salts and fatty acids, these penetration enhancers include, for example, sodium lauryl sulfate, polyoxyethylene-9-lauryl ether and polyoxyethylene-20-cetyl ether) (see e.g., Malmsten, M. Surfactants and polymers in drug delivery, Informa Health Care, New York, N.Y., 2002; Lee et al., Critical Reviews in Therapeutic Drug Carrier Systems, 1991, p. 92); and perfluorochemical emulsions, such as FC-43. Takahashi et al., *J. Pharm. Pharmacol.,* 1988, 40, 252).

Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-20}$ alkyl esters thereof (e.g., methyl, isopropyl and t-butyl), and mono- and di-glycerides thereof (i.e., oleate, laurate, caprate, myristate, palmitate, stearate, linoleate, etc.) (see e.g., Touitou, E., et al. Enhancement in Drug Delivery, CRC Press, Danvers, Mass., 2006; Lee et al., Critical Reviews in Therapeutic Drug Carrier Systems, 1991, p. 92; Muranishi, Critical Reviews in Therapeutic Drug Carrier Systems, 1990, 7, 1-33; El Hariri et al., *J. Pharm. Pharmacol.,* 1992, 44, 651-654).

The physiological role of bile includes the facilitation of dispersion and absorption of lipids and fat-soluble vitamins (see e.g., Malmsten, M. Surfactants and polymers in drug delivery, Informa Health Care, New York, N.Y., 2002; Brunton, Chapter 38 in: Goodman & Gilman's The Pharmacological Basis of Therapeutics, 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. Suitable bile salts include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (see e.g., Malmsten, M. Surfactants and polymers in drug delivery, Informa Health Care, New York, N.Y., 2002; Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1-33; Yamamoto et al., *J. Pharm. Exp. Ther.*, 1992, 263, 25; Yamashita et al., *J. Pharm. Sci.*, 1990, 79, 579-583).

Chelating agents, as used in connection with the present invention, can be defined as compounds that remove metallic ions from solution by forming complexes therewith, with the result that absorption of antisense polynucleotide agents through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.*, 1993, 618, 315-339). Suitable chelating agents include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(see e.g., Katdare, A. et al., Excipient development for pharmaceutical, biotechnology, and drug delivery, CRC Press, Danvers, Mass., 2006; Lee et al., Critical Reviews in Therapeutic Drug Carrier Systems, 1991, page 92; Muranishi, Critical Reviews in Therapeutic Drug Carrier Systems, 1990, 7, 1-33; Buur et al., *J. Control Rel.*, 1990, 14, 43-51).

As used herein, non-chelating non-surfactant penetration enhancing compounds can be defined as compounds that demonstrate insignificant activity as chelating agents or as surfactants but that nonetheless enhance absorption of antisense polynucleotide agents through the alimentary mucosa (see e.g., Muranishi, Critical Reviews in Therapeutic Drug Carrier Systems, 1990, 7, 1-33). This class of penetration enhancers includes, for example, unsaturated cyclic ureas, 1-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., *J. Pharm. Pharmacol.*, 1987, 39, 621-626).

Agents that enhance uptake of antisense polynucleotide agents at the cellular level can also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of antisense polynucleotide agents. Examples of commercially available transfection reagents include, for example Lipofectamine™ (Invitrogen; Carlsbad, Calif.), Lipofectamine 2000™ (Invitrogen; Carlsbad, Calif.), 293Fectin™ (Invitrogen; Carlsbad, Calif.), Cellfectin™ (Invitrogen; Carlsbad, Calif.), DMRIE-C™ (Invitrogen; Carlsbad, Calif.), FreeStyle™ MAX (Invitrogen; Carlsbad, Calif.), Lipofectamine™ 2000 CD (Invitrogen; Carlsbad, Calif.), Lipofectamine™ (Invitrogen; Carlsbad, Calif.), RNAiMAX (Invitrogen; Carlsbad, Calif.), Oligofectamine™ (Invitrogen; Carlsbad, Calif.), Optifect™ (Invitrogen; Carlsbad, Calif.), X-tremeGENE Q2 Transfection Reagent (Roche; Grenzacherstrasse, Switzerland), DOTAP Liposomal Transfection Reagent (Grenzacherstrasse, Switzerland), DOSPER Liposomal Transfection Reagent (Grenzacherstrasse, Switzerland), or Fugene (Grenzacherstrasse, Switzerland), Transfectam® Reagent (Promega; Madison, Wis.), TransFast™ Transfection Reagent (Promega; Madison, Wis.), Tfx™-20 Reagent (Promega; Madison, Wis.), Tfx™-50 Reagent (Promega; Madison, Wis.), DreamFect™ (OZ Biosciences; Marseille, France), EcoTransfect (OZ Biosciences; Marseille, France), TransPass$^a$ D1 Transfection Reagent (New England Biolabs; Ipswich, Mass., USA), LyoVec™/LipoGen™ (Invitrogen; San Diego, Calif., USA), PerFectin Transfection Reagent (Genlantis; San Diego, Calif., USA), NeuroPORTER Transfection Reagent (Genlantis; San Diego, Calif., USA), GenePORTER Transfection reagent (Genlantis; San Diego, Calif., USA), GenePORTER 2 Transfection reagent (Genlantis; San Diego, Calif., USA), Cytofectin Transfection Reagent (Genlantis; San Diego, Calif., USA), BaculoPORTER Transfection Reagent (Genlantis; San Diego, Calif., USA), TroganPORTER™ transfection Reagent (Genlantis; San Diego, Calif., USA), RiboFect (Bioline; Taunton, Mass., USA), PlasFect (Bioline; Taunton, Mass., USA), UniFECTOR (B-Bridge International; Mountain View, Calif., USA), SureFECTOR (B-Bridge International; Mountain View, Calif., USA), or HiFect™ (B-Bridge International, Mountain View, Calif., USA), among others.

Other agents can be utilized to enhance the penetration of the administered nucleic acids, including glycols such as ethylene glycol and propylene glycol, pyrrols such as 2-pyrrol, azones, and terpenes such as limonene and menthone.

v. Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioated antisense polynucleotide agent in hepatic tissue can be reduced when it is coadministered with polyinosinic acid, dextran sulfate, polycytidic acid or 4-acetamido-4'isothiocyano-stilbene-2,2'-disulfonic acid (Miyao et al., Antisense polynucleotide agent Res. Dev., 1995, 5, 115-121; Takakura et al., Antisense polynucleotide agent & Nucl. Acid Drug Dev., 1996, 6, 177-183.

vi. Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient can be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc).

Pharmaceutically acceptable organic or inorganic excipients suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids can include sterile and non-sterile aqueous solutions, non-aqueous solutions in common solvents such as alcohols, or solutions of the nucleic acids in liquid or solid oil bases. The solutions can also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

vii. Other Components

The compositions of the present invention can additionally contain other adjunct components conventionally found in pharmaceutical compositions, at their art-established usage levels. Thus, for example, the compositions can contain additional, compatible, pharmaceutically-active materials such as, for example, antipruritics, astringents, local anesthetics or anti-inflammatory agents, or can contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions can contain substances which increase the viscosity of the suspension including, for example, sodium carboxymethylcellulose, sorbitol and/or dextran. The suspension can also contain stabilizers.

In some embodiments, pharmaceutical compositions featured in the invention include (a) one or more antisense polynucleotide agents and (b) one or more agents which function by a non-antisense inhibition mechanism and which are useful in treating a hemolytic disorder. Examples of such agents include, but are not lmited to an anti-inflammatory agent, anti-steatosis agent, anti-viral, and/or anti-fibrosis agent. In addition, other substances commonly used to protect the liver, such as silymarin, can also be used in conjunction with the antisense polynucleotide agents described herein. Other agents useful for treating liver diseases include telbivudine, entecavir, and protease inhibitors such as telaprevir and other disclosed, for example, in Tung et al., U.S. Application Publication Nos. 2005/0148548, 2004/0167116, and 2003/0144217; and in Hale et al., U.S. Application Publication No. 2004/0127488.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit high therapeutic indices are preferred.

The data obtained from cell culture assays and animal studies can be used in formulating a range of dosage for use in humans. The dosage of compositions featured herein in the invention lies generally within a range of circulating concentrations that include the $ED_{50}$ with little or no toxicity. The dosage can vary within this range depending upon the dosage form employed and the route of administration utilized. For any compound used in the methods featured in the invention, the therapeutically effective dose can be estimated initially from cell culture assays. A dose can be formulated in animal models to achieve a circulating plasma concentration range of the compound or, when appropriate, of the polypeptide product of a target sequence (e.g., achieving a decreased concentration of the polypeptide) that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

In addition to their administration, as discussed above, the antisense polynucleotide agents featured in the invention can be administered in combination with other known agents effective in treatment of pathological processes mediated by PNPLA3 expression. In any event, the administering physician can adjust the amount and timing of antisense polynucleotide agent administration on the basis of results observed using standard measures of efficacy known in the art or described herein.

VII. Methods for Inhibiting PNPLA3 Expression

The present invention provides methods of inhibiting expression of a PNPLA3 gene in a cell. The methods include contacting a cell with an antisense polynucleotide agent of the invention in an amount effective to inhibit expression of the PNPLA3 gene in the cell, thereby inhibiting expression of the PNPLA3 gene in the cell.

Contacting of a cell with an antisense polynucleotide agent may be done in vitro or in vivo. Contacting a cell in vivo with the antisense polynucleotide agent includes contacting a cell or group of cells within a subject, e.g., a human subject, with the antisense polynucleotide agent. Combinations of in vitro and in vivo methods of contacting are also possible. Contacting may be direct or indirect, as discussed above. Furthermore, contacting a cell may be accomplished via a targeting ligand, including any ligand described herein or known in the art. In preferred embodiments, the targeting ligand is a carbohydrate moiety, e.g., a $GalNAc_3$ ligand, or any other ligand that directs the antisense polynucleotide agent to a site of interest, e.g., the liver or pancreas of a subject.

The term "inhibiting," as used herein, is used interchangeably with "reducing," "silencing," "downregulating" and other similar terms, and includes any level of inhibition.

"Inhibiting expression of a PNPLA3 gene" includes any level of inhibition of a PNPLA3 gene, e.g., at least partial suppression of the expression of a PNPLA3 gene. The expression of the PNPLA3 gene may be assessed based on the level, or the change in the level, of any variable associated with PNPLA3 gene expression, e.g., PNPLA3 mRNA level, PNPLA3 protein level. This level may be assessed in an individual cell or in a group of cells, including, for example, a sample derived from a subject.

Inhibition may be assessed by a decrease in an absolute or relative level of one or more variables that are associated with PNPLA3 expression compared with a control level. The control level may be any type of control level that is utilized in the art, e.g., a pre-dose baseline level, or a level determined from a similar subject, cell, or sample that is untreated or treated with a control (such as, e.g., buffer only control or inactive agent control).

In some embodiments of the methods of the invention, expression of a PNPLA3 gene is inhibited by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%. Preferably expression is inhibited by at least about 20%.

Inhibition of the expression of a PNPLA3 gene may be manifested by a reduction of the amount of mRNA expressed by a first cell or group of cells (such cells may be present, for example, in a sample derived from a subject) in which a PNPLA3 gene is transcribed and which has or have been treated (e.g., by contacting the cell or cells with an antisense polynucleotide agent of the invention, or by administering an antisense polynucleotide agent of the invention to a subject in which the cells are or were present) such that the expression of a PNPLA3 gene is inhibited, as compared to a second cell or group of cells substantially identical to the first cell or group of cells but which has not or have not been so treated (control cell(s)). In preferred embodiments, the inhibition is assessed by expressing the level of mRNA in treated cells as a percentage of the level of mRNA in control cells, using the following formula:

$$\frac{(mRNA \text{ in control cells}) - (mRNA \text{ in treated cells})}{(mRNA \text{ in control cells})} \cdot 100\%$$

Alternatively, inhibition of the expression of a PNPLA3 gene may be assessed in terms of a reduction of a parameter that is functionally linked to PNPLA3 gene expression, e.g., PNPLA3 protein expression or Hedgehog pathway protein activities. PNPLA3 gene silencing may be determined in any cell expressing PNPLA3, either constitutively or by genomic engineering, and by any assay known in the art.

Inhibition of the expression of a PNPLA3 protein may be manifested by a reduction in the level of the PNPLA3 protein that is expressed by a cell or group of cells (e.g., the level of protein expressed in a sample derived from a subject). As explained above, for the assessment of mRNA suppression, the inhibition of protein expression levels in a treated cell or group of cells may similarly be expressed as a percentage of the level of protein in a control cell or group of cells.

A control cell or group of cells that may be used to assess the inhibition of the expression of a PNPLA3 gene includes a cell or group of cells that has not yet been contacted with an RNAi agent of the invention. For example, the control cell or group of cells may be derived from an individual subject (e.g., a human or animal subject) prior to treatment of the subject with an RNAi agent.

The level of PNPLA3 mRNA that is expressed by a cell or group of cells, or the level of circulating PNPLA3 mRNA, may be determined using any method known in the art for assessing mRNA expression. In one embodiment, the level of expression of PNPLA3 in a sample is determined by detecting a transcribed polynucleotide, or portion thereof, e.g., mRNA of the PNPLA3 gene. RNA may be extracted from cells using RNA extraction techniques including, for example, using acid phenol/guanidine isothiocyanate extraction (RNAzol B; Biogenesis), RNeasy RNA preparation kits (Qiagen) or PAXgene (PreAnalytix, Switzerland). Typical assay formats utilizing ribonucleic acid hybridization include nuclear run-on assays, RT-PCR, RNase protection assays (Melton et al., *Nuc. Acids Res.* 12:7035), Northern blotting, in situ hybridization, and microarray analysis. Circulating PNPLA3 mRNA may be detected using methods the described in PCT/US2012/043584, the entire contents of which are hereby incorporated herein by reference.

In one embodiment, the level of expression of PNPLA3 is determined using a nucleic acid probe. The term "probe", as used herein, refers to any molecule that is capable of selectively binding to a specific PNPLA3. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules.

Isolated mRNA can be used in hybridization or amplification assays that include, but are not limited to, Southern or northern analyses, polymerase chain reaction (PCR) analyses and probe arrays. One method for the determination of mRNA levels involves contacting the isolated mRNA with a nucleic acid molecule (probe) that can hybridize to PNPLA3 mRNA. In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in an Affymetrix® gene chip array. A skilled artisan can readily adapt known mRNA detection methods for use in determining the level of PNPLA3 mRNA.

An alternative method for determining the level of expression of PNPLA3 in a sample involves the process of nucleic acid amplification and/or reverse transcriptase (to prepare cDNA) of for example mRNA in the sample, e.g., by RT-PCR (the experimental embodiment set forth in Mullis, 1987, U.S. Pat. No. 4,683,202), ligase chain reaction (Barany (1991) *Proc. Natl. Acad. Sci. USA* 88:189-193), self sustained sequence replication (Guatelli et al. (1990) *Proc. Natl. Acad. Sci. USA* 87:1874-1878), transcriptional amplification system (Kwoh et al. (1989) *Proc. Natl. Acad. Sci. USA* 86:1173-1177), Q-Beta Replicase (Lizardi et al. (1988) *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, the level of expression of PNPLA3 is determined by quantitative fluorogenic RT-PCR (i.e., the TaqMan™ System).

The expression levels of PNPLA3 mRNA may be monitored using a membrane blot (such as used in hybridization analysis such as northern, Southern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The determination of PNPLA3 expression level may also comprise using nucleic acid probes in solution.

In preferred embodiments, the level of mRNA expression is assessed using branched DNA (bDNA) assays or real time PCR (qPCR).

The level of PNPLA3 protein expression may be determined using any method known in the art for the measurement of protein levels. Such methods include, for example, electrophoresis, capillary electrophoresis, high performance liquid chromatography (HPLC), thin layer chromatography (TLC), hyperdiffusion chromatography, fluid or gel precipitin reactions, absorption spectroscopy, a colorimetric assays, spectrophotometric assays, flow cytometry, immunodiffusion (single or double), immunoelectrophoresis, western blotting, radioimmunoassay (RIA), enzyme-linked immunosorbent assays (ELISAs), immunofluorescent assays, electrochemiluminescence assays, and the like.

The term "sample" as used herein refers to a collection of similar fluids, cells, or tissues isolated from a subject, as well as fluids, cells, or tissues present within a subject. Examples of biological fluids include blood, serum and serosal fluids, plasma, lymph, urine, cerebrospinal fluid, saliva, ocular fluids, and the like. Tissue samples may include samples from tissues, organs or localized regions. For example, samples may be derived from particular organs, parts of organs, or fluids or cells within those organs. In certain embodiments, samples may be derived from the liver (e.g., whole liver or certain segments of liver or certain types of cells in the liver, such as, e.g., hepatocytes). In preferred embodiments, a "sample derived from a subject" refers to urine drawn from the subject. In further embodiments, a "sample derived from a subject" refers to liver tissue derived from the subject.

In some embodiments of the methods of the invention, the antisense polynucleotide agent is administered to a subject such that the antisense polynucleotide agent is delivered to a specific site within the subject. The inhibition of expression of PNPLA3 may be assessed using measurements of the level or change in the level of PNPLA3 mRNA or PNPLA3 protein in a sample derived from fluid or tissue from the specific site within the subject. In preferred embodiments, the site is the liver. The site may also be a subsection or subgroup of cells from any one of the aforementioned sites. The site may also include cells that express a particular type of receptor.

The phrase "contacting a cell with an antisense polynucleotide agent," as used herein, includes contacting a cell by any possible means. Contacting a cell with an antisense polynucleotide agent includes contacting a cell in vitro with the antisense polynucleotide agent or contacting a cell in vivo with the antisense polynucleotide agent. The contacting may be done directly or indirectly. Thus, for example, the antisense polynucleotide agent may be put into physical contact with the cell by the individual performing the method, or alternatively, the antisense polynucleotide agent may be put into a situation that will permit or cause it to subsequently come into contact with the cell.

Contacting a cell in vitro may be done, for example, by incubating the cell with the antisense polynucleotide agent. Contacting a cell in vivo may be done, for example, by injecting the antisense polynucleotide agent into or near the tissue where the cell is located, or by injecting the antisense polynucleotide agent into another area, e.g., the bloodstream or the subcutaneous space, such that the agent will subsequently reach the tissue where the cell to be contacted is located. For example, the antisense polynucleotide agent may contain and/or be coupled to a ligand, e.g., GalNAc3, that directs the antisense polynucleotide agent to a site of interest, e.g., the liver. Combinations of in vitro and in vivo methods of contacting are also possible. For example, a cell may also be contacted in vitro with an antisense polynucleotide agent and subsequently transplanted into a subject.

In one embodiment, contacting a cell with an antisense polynucleotide agent includes "introducing" or "delivering the antisense polynucleotide agent into the cell" by facilitating or effecting uptake or absorption into the cell. Absorption or uptake of an antisense polynucleotide agent can occur through unaided diffusive or active cellular processes, or by auxiliary agents or devices. Introducing an antisense polynucleotide agent into a cell may be in vitro and/or in vivo. For example, for in vivo introduction, antisense polynucleotide agent can be injected into a tissue site or administered systemically. In vivo delivery can also be done by a beta-glucan delivery system, such as those described in U.S. Pat. Nos. 5,032,401 and 5,607,677, and U.S. Publication No. 2005/0281781, the entire contents of which are hereby incorporated herein by reference. In vitro introduction into a cell includes methods known in the art such as electroporation and lipofection. Further approaches are described herein below and/or are known in the art.

VIII. Methods for Treating or Preventing PNPLA3-Associated Disorders

The present invention provides therapeutic and prophylactic methods which include administering to a subject with a PNPLA3-associated disease, disorder, and/or condition, or prone to developing, a PNPLA3-associated disease, disorder, and/or condition, an antisense polynucleotide agent or a pharmaceutical composition comprising an antisense polynucleotide agent of the invention. Non-limiting examples of PNPLA3-associated diseases include, for example, fatty liver (steatosis), nonalcoholic steatohepatitis (NASH), cirrhosis of the liver, accumulation of fat in the liver, inflammation of the liver, hepatocellular necrosis, liver fibrosis, obesity, or nonalcoholic fatty liver disease (NAFLD). In one embodiment, the PNPLA3-associated disease is NAFLD. In another embodiment, the PNPLA3-associated disease is NASH. In another embodiment, the PNPLA3-associated disease is fatty liver (steatosis). In another embodiment, the PNPLA3-associated disease is insulin resistance. In another embodiment, the PNPLA3-associated disease is not insulin resistance.

The methods of the invention are useful for treating a subject having a PNPLA3-associated disease, e.g., a subject that would benefit from reduction in PNPLA3 gene expression and/or PNPLA3 protein production. In one aspect, the present invention provides methods of reducing the level of Patatin-Like Phospholipase Domain Containing 3 (PNPLA3) gene expression in a subject having nonalcoholic fatty liver disease (NAFLD). In another aspect, the present invention provides methods of reducing the level of PNPLA3 protein in a subject with NAFLD. The present invention also provides methods of reducing the level of activity of the hedgehog pathway in a subject with NAFLD.

In another aspect, the present invention provides methods of treating a subject having an NAFLD. In one aspect, the present invention provides methods of treating a subject having an PNPLA3-associated disease, e.g., fatty liver (steatosis), nonalcoholic steatohepatitis (NASH), cirrhosis of the liver, accumulation of fat in the liver, inflammation of the liver, hepatocellular necrosis, liver fibrosis, obesity, or non-alcoholic fatty liver disease (NAFLD). The treatment methods (and uses) of the invention include administering to the subject, e.g., a human, a therapeutically effective amount of an antisense polynucleotide agent or a pharmaceutical composition comprising an antisense polynucleotide agent of the invention.

In one aspect, the invention provides methods of preventing at least one symptom in a subject having NAFLD, e.g., the presence of elevated hedgehog signaling pathways, fatigue, weakness, weight loss, loss of apetite, nausea, abdominal pain, spider-like blood vessels, yellowing of the skin and eyes (jaundice), itching, fluid build up and swelling of the legs (edema), abdomen swelling (ascites), and mental confusion. The methods include administering to the subject a therapeutically effective amount of the antisense polynucleotide agent or a pharmaceutical composition comprising an antisense polynucleotide agent of the invention, thereby preventing at least one symptom in the subject having a disorder that would benefit from reduction in PNPLA3 gene expression.

In another aspect, the present invention provides uses of a therapeutically effective amount of an iRNA agent of the invention for treating a subject, e.g., a subject that would benefit from a reduction and/or inhibition of PNPLA3 gene expression.

In a further aspect, the present invention provides uses of an antisense polynucleotide agent or a pharmaceutical composition comprising an antisense polynucleotide agent of the invention in the manufacture of a medicament for treating a subject, e.g., a subject that would benefit from a reduction and/or inhibition of PNPLA3 gene expression and/or PNPLA3 protein production, such as a subject having a disorder that would benefit from reduction in PNPLA3 gene expression, e.g., a PNPLA3-associated disease.

In another aspect, the invention provides uses of an antisense polynucleotide agent or a pharmaceutical composition comprising an antisense polynucleotide agent of the invention for preventing at least one symptom in a subject suffering from a disorder that would benefit from a reduction and/or inhibition of PNPLA3 gene expression and/or PNPLA3 protein production.

In a further aspect, the present invention provides uses of an antisense polynucleotide agent or a pharmaceutical composition comprising an antisense polynucleotide agent of the invention in the manufacture of a medicament for preventing at least one symptom in a subject suffering from a disorder that would benefit from a reduction and/or inhibition of PNPLA3 gene expression and/or SREBP cleavage-activating protein (SCAP) protein production, such as a PNPLA3-associated disease.

"Therapeutically effective amount," as used herein, is intended to include the amount of an agent that, when administered to a patient for treating a subject havinga PNPLA3-associated disease, is sufficient to effect treatment of the disease (e.g., by diminishing, ameliorating or maintaining the existing disease or one or more symptoms of disease). The "therapeutically effective amount" may vary depending on the agent, how the agent is administered, the disease and its severity and the history, age, weight, family history, genetic makeup, stage of pathological processes mediated by PNPLA3 gene expression, the types of preceding or concomitant treatments, if any, and other individual characteristics of the patient to be treated.

"Prophylactically effective amount," as used herein, is intended to include the amount of an agent that, when administered to a subject who does not yet experience or display symptoms of a PNPLA3-associated disease, but who may be predisposed, is sufficient to prevent or ameliorate the disease or one or more symptoms of the disease. Ameliorating the disease includes slowing the course of the disease or reducing the severity of later-developing disease. The "prophylactically effective amount" may vary depending on the agent, how the agent is administered, the degree of risk of disease, and the history, age, weight, family history, genetic makeup, the types of preceding or concomitant treatments, if any, and other individual characteristics of the patient to be treated.

A "therapeutically-effective amount" or "prophylacticaly effective amount" also includes an amount of an agent that produces some desired local or systemic effect at a reasonable benefit/risk ratio applicable to any treatment. Agents employed in the methods of the present invention may be administered in a sufficient amount to produce a reasonable benefit/risk ratio applicable to such treatment.

In one embodiment, an antisense polynucleotide agent targeting PNPLA3 is administered to a subject having an PNPLA3-associated disease such that PNPLA3 levels, e.g., in a cell, tissue, blood, urine or other tissue or fluid of the subject are reduced by at least about 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 62%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least about 99% or more and, subsequently, an additional therapeutic (as described below) is administered to the subject.

The methods and uses of the invention include administering a composition described herein such that expression of the target PNPLA3 gene is decreased, such as for about 1, 2, 3, 4, 5, 6, 7, 8, 12, 16, 18, 24, 28, 32, 36, 40, 44, 48, 52, 56, 60, 64, 68, 72, 76, or about 80 hours. In certain embodiments, expression of the target PNPLA3 gene is decreased for an extended duration, e.g., at least about two, three, four, five, six, seven days or more, e.g., about one week, two weeks, three weeks, or about four weeks or longer.

Administration of the antisense polynucleotide agent according to the methods and uses of the invention may result in a reduction of the severity, signs, symptoms, and/or markers of such diseases or disorders in a patient with a PNPLA3-associated disease. By "reduction" in this context is meant a statistically significant decrease in such level. The reduction can be, for example, at least about 5%, 10%, 15%, 20%, 25%, 30%, 35%, 40%, 45%, 50%, 55%, 60%, 65%, 70%, 75%, 80%, 85%, 90%, 95%, or about 100%.

Efficacy of treatment or prevention of disease can be assessed, for example by measuring disease progression, disease remission, symptom severity, reduction in pain, quality of life, dose of a medication required to sustain a treatment effect, level of a disease marker or any other measurable parameter appropriate for a given disease being treated or targeted for prevention. It is well within the ability of one skilled in the art to monitor efficacy of treatment or prevention by measuring any one of such parameters, or any combination of parameters. For example, efficacy of treatment of a PNPLA3-associated disorder may be assessed, for example, by periodic monitoring of NAFLD symptoms, liver fat levels, or expression of downstream genes in the subject being treated. Comparisons of the later measurements with the initial measurements provide a physician an indication of whether the treatment is effective. It is well within the ability of one skilled in the art to monitor efficacy of treatment or prevention by measuring such a parameter, or any combination of parameters. In connection with the administration of an antisense polynucleotide agent targeting PNPLA3 or pharmaceutical composition thereof, "effective against" a PNPLA3-associated disease indicates that administration in a clinically appropriate manner results in a beneficial effect for at least a statistically significant fraction of patients, such as improvement of symptoms, a cure, a reduction in disease, extension of life, improvement in quality of life, or other effect generally recognized as positive by medical doctors familiar with treating a PNPLA3-associated disease and the related causes.

A treatment or preventive effect is evident when there is a statistically significant improvement in one or more parameters of disease status, or by a failure to worsen or to develop symptoms where they would otherwise be anticipated. As an example, a favorable change of at least 10% in a measurable parameter of disease, and preferably at least 20%, 30%, 40%, 50% or more can be indicative of effective treatment. Efficacy for a given antisense polynucleotide agent drug or formulation of that drug can also be judged using an experimental animal model for the given disease as known in the art. When using an experimental animal model, efficacy of treatment is evidenced when a statistically significant reduction in a marker or symptom is observed.

Any positive change resulting in e.g., lessening of severity of disease measured using the appropriate scale, represents adequate treatment using an antisense polynucleotide agent or antisense polynucleotide agent formulation as described herein.

Subjects can be administered a therapeutic amount of antisense polynucleotide agent, such as about 0.01 mg/kg, 0.02 mg/kg, 0.03 mg/kg, 0.04 mg/kg, 0.05 mg/kg, 0.1 mg/kg, 0.15 mg/kg, 0.2 mg/kg, 0.25 mg/kg, 0.3 mg/kg, 0.35 mg/kg, 0.4 mg/kg, 0.45 mg/kg, 0.5 mg/kg, 0.55 mg/kg, 0.6 mg/kg, 0.65 mg/kg, 0.7 mg/kg, 0.75 mg/kg, 0.8 mg/kg, 0.85 mg/kg, 0.9 mg/kg, 0.95 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3.0 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, 4.0 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, 5.0 mg/kg, 5.1 mg/kg, 5.2 mg/kg, 5.3 mg/kg, 5.4 mg/kg, 5.5 mg/kg, 5.6 mg/kg, 5.7 mg/kg, 5.8 mg/kg, 5.9 mg/kg, 6.0 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7.0 mg/kg, 7.1 mg/kg, 7.2 mg/kg, 7.3 mg/kg, 7.4 mg/kg, 7.5 mg/kg, 7.6 mg/kg, 7.7 mg/kg, 7.8 mg/kg, 7.9 mg/kg, 8.0 mg/kg, 8.1 mg/kg, 8.2 mg/kg, 8.3 mg/kg, 8.4 mg/kg, 8.5 mg/kg, 8.6 mg/kg, 8.7 mg/kg, 8.8 mg/kg, 8.9 mg/kg, 9.0 mg/kg, 9.1 mg/kg, 9.2 mg/kg, 9.3 mg/kg, 9.4 mg/kg, 9.5 mg/kg, 9.6 mg/kg, 9.7 mg/kg, 9.8 mg/kg, 9.9 mg/kg, 9.0 mg/kg, 10 mg/kg, 15 mg/kg, 20 mg/kg, 25 mg/kg, 30 mg/kg, 35 mg/kg, 40 mg/kg, 45 mg/kg, or about 50 mg/kg. Values and ranges intermediate to the recited values are also intended to be part of this invention.

In certain embodiments, for example, when a composition of the invention comprises an antisense polynucleotide agent as described herein and a lipid, subjects can be administered a therapeutic amount of antisense polynucleotide agent, such as about 0.01 mg/kg to about 5 mg/kg, about 0.01 mg/kg to about 10 mg/kg, about 0.05 mg/kg to about 5 mg/kg, about 0.05 mg/kg to about 10 mg/kg, about 0.1 mg/kg to about 5 mg/kg, about 0.1 mg/kg to about 10 mg/kg, about 0.2 mg/kg to about 5 mg/kg, about 0.2 mg/kg to about 10 mg/kg, about 0.3 mg/kg to about 5 mg/kg, about 0.3 mg/kg to about 10 mg/kg, about 0.4 mg/kg to about 5 mg/kg, about 0.4 mg/kg to about 10 mg/kg, about 0.5 mg/kg to about 5 mg/kg, about 0.5 mg/kg to about 10 mg/kg, about 1 mg/kg to about 5 mg/kg, about 1 mg/kg to about 10 mg/kg, about 1.5 mg/kg to about 5 mg/kg, about 1.5 mg/kg to about 10 mg/kg, about 2 mg/kg to about 2.5 mg/kg, about 2 mg/kg to about 10 mg/kg, about 3 mg/kg to about 5 mg/kg, about 3 mg/kg to about 10 mg/kg, about 3.5 mg/kg to about 5 mg/kg, about 4 mg/kg to about 5 mg/kg, about 4.5 mg/kg to about 5 mg/kg, about 4 mg/kg to about 10 mg/kg, about 4.5 mg/kg to about 10 mg/kg, about 5 mg/kg to about 10 mg/kg, about 5.5 mg/kg to about 10 mg/kg, about 6 mg/kg to about 10 mg/kg, about 6.5 mg/kg to about 10 mg/kg, about 7 mg/kg to about 10 mg/kg, about 7.5 mg/kg to about 10 mg/kg, about 8 mg/kg to about 10 mg/kg, about 8.5 mg/kg to about 10 mg/kg, about 9 mg/kg to about 10 mg/kg, or about 9.5 mg/kg to about 10 mg/kg. Values and ranges intermediate to the recited values are also intended to be part of this invention.

For example, the antisense polynucleotide agent may be administered at a dose of about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or about 10 mg/kg. Values and ranges intermediate to the recited values are also intended to be part of this invention.

In other embodiments, subjects can be administered a therapeutic amount of antisense polynucleotide agent, such as a dose of about 0.1 to about 50 mg/kg, about 0.25 to about 50 mg/kg, about 0.5 to about 50 mg/kg, about 0.75 to about 50 mg/kg, about 1 to about 50 mg/mg, about 1.5 to about 50 mg/kb, about 2 to about 50 mg/kg, about 2.5 to about 50 mg/kg, about 3 to about 50 mg/kg, about 3.5 to about 50 mg/kg, about 4 to about 50 mg/kg, about 4.5 to about 50 mg/kg, about 5 to about 50 mg/kg, about 7.5 to about 50 mg/kg, about 10 to about 50 mg/kg, about 15 to about 50 mg/kg, about 20 to about 50 mg/kg, about 20 to about 50 mg/kg, about 25 to about 50 mg/kg, about 25 to about 50 mg/kg, about 30 to about 50 mg/kg, about 35 to about 50 mg/kg, about 40 to about 50 mg/kg, about 45 to about 50 mg/kg, about 0.1 to about 45 mg/kg, about 0.25 to about 45 mg/kg, about 0.5 to about 45 mg/kg, about 0.75 to about 45 mg/kg, about 1 to about 45 mg/mg, about 1.5 to about 45 mg/kb, about 2 to about 45 mg/kg, about 2.5 to about 45 mg/kg, about 3 to about 45 mg/kg, about 3.5 to about 45 mg/kg, about 4 to about 45 mg/kg, about 4.5 to about 45 mg/kg, about 5 to about 45 mg/kg, about 7.5 to about 45 mg/kg, about 10 to about 45 mg/kg, about 15 to about 45 mg/kg, about 20 to about 45 mg/kg, about 20 to about 45 mg/kg, about 25 to about 45 mg/kg, about 25 to about 45 mg/kg, about 30 to about 45 mg/kg, about 35 to about 45 mg/kg, about 40 to about 45 mg/kg, about 0.1 to about 40 mg/kg, about 0.25 to about 40 mg/kg, about 0.5 to about 40 mg/kg, about 0.75 to about 40 mg/kg, about 1 to about 40 mg/mg, about 1.5 to about 40 mg/kb, about 2 to about 40 mg/kg, about 2.5 to about 40 mg/kg, about 3 to about 40 mg/kg, about 3.5 to about 40 mg/kg, about 4 to about 40 mg/kg, about 4.5 to about 40 mg/kg, about 5 to about 40 mg/kg, about 7.5 to about 40 mg/kg, about 10 to about 40 mg/kg, about 15 to about 40 mg/kg, about 20 to about 40 mg/kg, about 20 to about 40 mg/kg, about 25 to about 40 mg/kg, about 25 to about 40 mg/kg, about 30 to about 40 mg/kg, about 35 to about 40 mg/kg, about 0.1 to about 30 mg/kg, about 0.25 to about 30 mg/kg, about 0.5 to about 30 mg/kg, about 0.75 to about 30 mg/kg, about 1 to about 30 mg/mg, about 1.5 to about 30 mg/kb, about 2 to about 30 mg/kg, about 2.5 to about 30 mg/kg, about 3 to about 30 mg/kg, about 3.5 to about 30 mg/kg, about 4 to about 30 mg/kg, about 4.5 to about 30 mg/kg, about 5 to about 30 mg/kg, about 7.5 to about 30 mg/kg, about 10 to about 30 mg/kg, about 15 to about 30 mg/kg, about 20 to about 30 mg/kg, about 20 to about 30 mg/kg, about 25 to about 30 mg/kg, about 0.1 to about 20 mg/kg, about 0.25 to about 20 mg/kg, about 0.5 to about 20 mg/kg, about 0.75 to about 20 mg/kg, about 1 to about 20 mg/mg, about 1.5 to about 20 mg/kb, about 2 to about 20 mg/kg, about 2.5 to about 20 mg/kg, about 3 to about 20 mg/kg, about 3.5 to about 20 mg/kg, about 4 to about 20 mg/kg, about 4.5 to about 20 mg/kg, about 5 to about 20 mg/kg, about 7.5 to about 20 mg/kg, about 10 to about 20 mg/kg, or about 15 to about 20 mg/kg. In one embodiment, when a composition of the invention comprises a antisense polynucleotide agent as described herein and an N-acetylgalactosamine, subjects can be administered a therapeutic amount of about 10 to about 30 mg/kg of antisense polynucleotide agent. Values and ranges intermediate to the recited values are also intended to be part of this invention.

For example, subjects can be administered a therapeutic amount of antisense polynucleotide agent, such as about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 31, 32, 33, 34, 34, 35, 36, 37, 38, 39, 40, 41, 42, 43, 44, 45, 46, 47, 48, 49, or about 50 mg/kg. Values and ranges intermediate to the recited values are also intended to be part of this invention.

The antisense polynucleotide agent can be administered by intravenous infusion over a period of time, such as over a 5, 6, 7, 8, 9, 10, 11, 12, 13, 14, 15, 16, 17, 18, 19, 20, 21, 22, 23, 24, or about a 25 minute period. The administration may be repeated, for example, on a regular basis, such as weekly, biweekly (i.e., every two weeks) for one month, two months, three months, four months or longer. After an initial treatment regimen, the treatments can be administered on a less frequent basis. For example, after administration weekly or biweekly for three months, administration can be repeated once per month, for six months or a year or longer.

Administration of the antisense polynucleotide agent can reduce PNPLA3 levels, e.g., in a cell, tissue, blood, urine or other compartment of the patient by at least about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least about 99% or more.

Before administration of a full dose of the antisense polynucleotide agent, patients can be administered a smaller dose, such as a 5% infusion, and monitored for adverse effects, such as an allergic reaction. In another example, the patient can be monitored for unwanted immunostimulatory effects, such as increased cytokine (e.g., TNF-alpha or INF-alpha) levels.

Owing to the inhibitory effects on PNPLA3 expression, a composition according to the invention or a pharmaceutical composition prepared therefrom can enhance the quality of life.

An antisense polynucleotide agent of the invention may be administered in "naked" form, or as a "free antisense polynucleotide agent." A naked antisense polynucleotide agent is administered in the absence of a pharmaceutical composition. The naked antisense polynucleotide agent may be in a suitable buffer solution. The buffer solution may comprise acetate, citrate, prolamine, carbonate, or phosphate, or any combination thereof. In one embodiment, the buffer solution is phosphate buffered saline (PBS). The pH and osmolarity of the buffer solution containing the antisense polynucleotide agent can be adjusted such that it is suitable for administering to a subject.

Alternatively, an antisense polynucleotide agent of the invention may be administered as a pharmaceutical composition, such as an antisense polynucleotide agent liposomal formulation.

Subjects that would benefit from a reduction and/or inhibition of PNPLA3 gene expression are those having nonalcoholic fatty liver disease (NAFLD) and/or an PNPLA3-associated disease or disorder as described herein.

Treatment of a subject that would benefit from a reduction and/or inhibition of PNPLA3 gene expression includes therapeutic and prophylactic treatment.

The invention further provides methods and uses of an antisense polynucleotide agent or a pharmaceutical composition thereof (including methods and uses of an antisense polynucleotide agent or a pharmaceutical composition comprising an antisense polynucleotide agent and an for treatment of the PNPLA3-associated diseases) for treating a subject that would benefit from reduction and/or inhibition of PNPLA3 expression, e.g., a subject having a PNPLA3-associated disease, in combination with other pharmaceuticals and/or other therapeutic methods, e.g., with known pharmaceuticals and/or known therapeutic methods, such as, for example, those which are currently employed for treating these disorders. For example, in certain embodiments, an antisense polynucleotide agent targeting PNPLA3 is administered in combination with, e.g., an agent useful in treating a PNPLA3-associated disease as described elsewhere herein.

The antisense polynucleotide agent (and/or agent(s) for treatment of the PNPLA3-associated disease) and an additional therapeutic agent and/or treatment may be administered at the same time and/or in the same combination, e.g., parenterally, or the additional therapeutic agent can be administered as part of a separate composition or at separate times and/or by another method known in the art or described herein.

The present invention also provides methods of using an antisense polynucleotide agent of the invention and/or a composition containing an antisense polynucleotide agent of the invention to reduce and/or inhibit PNPLA3 expression in a cell. In other aspects, the present invention provides an antisense polynucleotide agent of the invention and/or a composition comprising an antisense polynucleotide agent of the invention for use in reducing and/or inhibiting PNPLA3 expression in a cell. In yet other aspects, use of an antisense polynucleotide agent of the invention and/or a composition comprising an antisense polynucleotide agent of the invention for the manufacture of a medicament for reducing and/or inhibiting PNPLA3 expression in a cell are provided.

The methods and uses include contacting the cell with an antisense polynucleotide agent, e.g., a antisense polynucleotide agent, of the invention and maintaining the cell for a time sufficient to obtain antisense inhibition of a PNPLA3 gene, thereby inhibiting expression of the PNPLA3 gene in the cell.

Reduction in gene expression can be assessed by any methods known in the art. For example, a reduction in the expression of PNPLA3 may be determined by determining the mRNA expression level of PNPLA3 using methods routine to one of ordinary skill in the art, e.g., northern blotting, qRT-PCR, by determining the protein level of PNPLA3 using methods routine to one of ordinary skill in the art, such as western blotting, immunological techniques, flow cytometry methods, ELISA, and/or by determining a biological activity of PNPLA3.

In the methods and uses of the invention the cell may be contacted in vitro or in vivo, i.e., the cell may be within a subject. In embodiments of the invention in which the cell is within a subject, the methods may include further contacting the cell with an agent for treatment of the PNPLA3-associated disease.

A cell suitable for treatment using the methods of the invention may be any cell that expresses a PNPLA3 gene. A cell suitable for use in the methods and uses of the invention may be a mammalian cell, e.g., a primate cell (such as a human cell or a non-human primate cell, e.g., a monkey cell or a chimpanzee cell), a non-primate cell (such as a cow cell, a pig cell, a camel cell, a llama cell, a horse cell, a goat cell, a rabbit cell, a sheep cell, a hamster, a guinea pig cell, a cat cell, a dog cell, a rat cell, a mouse cell, a lion cell, a tiger cell, a bear cell, or a buffalo cell), a bird cell (e.g., a duck cell or a goose cell), or a whale cell. In one embodiment, the cell is a human cell, e.g., a human liver cell.

PNPLA3 expression may be inhibited in the cell by at least about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or about 100%.

The in vivo methods and uses of the invention may include administering to a subject a composition containing an antisense polynucleotide agent, where the antisense polynucleotide agent includes a nucleotide sequence that is complementary to at least a part of an RNA transcript of the PNPLA3 gene of the mammal to be treated. When the organism to be treated is a mammal such as a human, the composition can be administered by any means known in the art including, but not limited to subcutaneous, intravenous, oral, intraperitoneal, or parenteral routes, including intracranial (e.g., intraventricular, intraparenchymal and intrathecal), intramuscular, transdermal, airway (aerosol), nasal, rectal, and topical (including buccal and sublingual) administration. In certain embodiments, the compositions are administered by subcutaneous or intravenous infusion or injection.

In some embodiments, the administration is via a depot injection. A depot injection may release the antisense polynucleotide agent in a consistent way over a prolonged time period. Thus, a depot injection may reduce the frequency of dosing needed to obtain a desired effect, e.g., a desired inhibition of PNPLA3, or a therapeutic or prophylactic effect. A depot injection may also provide more consistent serum concentrations. Depot injections may include subcutaneous injections or intramuscular injections. In preferred embodiments, the depot injection is a subcutaneous injection.

In some embodiments, the administration is via a pump. The pump may be an external pump or a surgically implanted pump. In certain embodiments, the pump is a subcutaneously implanted osmotic pump. In other embodiments, the pump is an infusion pump. An infusion pump may be used for intravenous, subcutaneous, arterial, or epidural infusions. In preferred embodiments, the infusion pump is a subcutaneous infusion pump. In other embodiments, the pump is a surgically implanted pump that delivers the antisense polynucleotide agent to the liver.

The mode of administration may be chosen based upon whether local or systemic treatment is desired and based upon the area to be treated. The route and site of administration may be chosen to enhance targeting.

In one aspect, the present invention also provides methods for inhibiting the expression of an PNPLA3 gene in a mammal, e.g., a human. The present invention also provides a composition comprising an antisense polynucleotide agen that targets a PNPLA3 gene in a cell of a mammal for use in inhibiting expression of the PNPLA3 gene in the mammal. In another aspect, the present invention provides use of an antisense polynucleotide agent that targets an PNPLA3 gene in a cell of a mammal in the manufacture of a medicament for inhibiting expression of the PNPLA3 gene in the mammal.

The methods and uses include administering to the mammal, e.g., a human, a composition comprising an antisense polynucleotide agent that targets a PNPLA3 gene in a cell of the mammal and maintaining the mammal for a time sufficient to obtain antisense inhibition of the mRNA transcript of the PNPLA3 gene, thereby inhibiting expression of the PNPLA3 gene in the mammal. In some embodiment, the methods further comprise administering an agent for treatment of the PNPLA3-associated disease to the subject.

Reduction in gene expression can be assessed by any methods known it the art and by methods, e.g. qRT-PCR, described herein. Reduction in protein production can be assessed by any methods known it the art and by methods, e.g., ELISA or western blotting, described herein. In one embodiment, a puncture liver biopsy sample serves as the tissue material for monitoring the reduction in PNPLA3 gene and/or protein expression. In another embodiment, a blood sample serves as the tissue material for monitoring the reduction in PNPLA3 gene and/or protein expression. Suitable assays are further described in the Examples section below.

Unless otherwise defined, all technical and scientific terms used herein have the same meaning as commonly understood by one of ordinary skill in the art to which this invention belongs. Although methods and materials similar or equivalent to those described herein can be used in the practice or testing of the antisense polynucleotide agents and methods featured in the invention, suitable methods and materials are described below. All publications, patent applications, patents, and other references mentioned herein are incorporated by reference in their entirety. In addition, the materials, methods, and examples are illustrative only and not intended to be limiting.

EXAMPLES

Example 1. Design and Synthesis of Antisense Polynucleotides

Source of Reagents

Where the source of a reagent is not specifically given herein, such reagent can be obtained from any supplier of reagents for molecular biology at a quality/purity standard for application in molecular biology.

Transcripts

Design of Antisense Polynucleotide Agents

A set of antisense oligos (ASOs) targeting the human PNPLA3, "patatin-like phospholipase domain containing 3", (human: NCBI refseqID NM_025225; NCBI GeneID: 80339) were designed using custom R and Python scripts. The rationale and method for the set of ASO designs is as follows: the predicted efficacy for every potential 19mer ASO from position 1 through the end of the mRNA was determined with a linear model derived the direct measure of mRNA knockdown from more than 20,000 distinct siRNA designs targeting a large number of vertebrate genes. Starting from position 1 a set of ASOs was created by systematically picking an ASO design whose 5' base began every 11 bases along the entire length of the mRNA. Predicted efficacy was used to allow for the substitution of a neighboring, predicted-to-be-more-potent ASO design where the neighboring ASO was 1 base either toward the 5' or 3' end of the mRNA. Low complexity ASO designs were removed by filtering with a Shannon entropy index greater than 1.35.

The antisense polynucleotides targeting PNPLA3 were synthesized using standard synthesis methods well known in the art.

A detailed list of the unmodified antisense polynucleotide molecules targeting PNPLA3 is shown in Table 3 and a detailed list of the modified antisense polynucleotide molecules targeting PNPLA3 is shown in Table 4.

Example 2. In Vitro Screening

Human hepatoma cells (HuH7 cells) were transfected with 500 nM of each single stranded antisense oligonucleotide (ASO). To do so, Lipofectamine 2000 (Invitrogen) was incubated with each ASO according to the manufacturer's protocol and then added to $2 \times 10^4$ cells in each well of a 96 well plate. Plates were incubated for 24 hours prior to harvesting for analysis.

For measurement of PNPLA3 mRNA, cells were harvested 24 hours after transfection and lysed at 53° C. following procedures recommended by the manufacturer of the Quantigene II Kit for PNPLA3 and Quantigene I Explore Kit for (Panomics, Fremont, Calif., USA,) bDNA. Afterwards, 50 µl of the lysates were incubated with probesets specific to human PNPLA3 and 10 µl of the lysates for human GAPDH and processed according to the manufacturer's protocol for QuantiGene. Chemoluminescence was measured in a Victor2-Light (Perkin Elmer, Wiesbaden, Germany) as RLUs (relative light units) and values obtained with the human PNPLA3 probeset were normalized to the respective human GAPDH values for each well and then related to the mean of an unrelated control gene. Table 5 shows the results of single dose transfection screen in cells transfected with the indicated antisense polynucleotide.

TABLE 2

Abbreviations of nucleotide monomers used in nucleic acid sequence representation. It will be understood that these monomers, when present in an oligonucleotide, are mutually linked by 5'-3'-phosphodiester bonds.

| Abbreviation | Nucleotide(s) |
| --- | --- |
| A | Adenosine-3'-phosphate |
| Af | 2'-fluoroadenosine-3'-phosphate |
| Afs | 2'-fluoroadenosine-3'-phosphorothioate |
| As | adenosine-3'-phosphorothioate |
| a | 2'-O-methyladenosine-3'-phosphate |
| as | 2'-O-methyladenosine-3'-phosphorothioate |
| C | cytidine-3'-phosphate |
| dA | 2'-deoxyadenosine-3'-phosphate |
| dAs | 2'-deoxyadenosine-3'-phosphorothioate |
| Cf | 2'-fluorocytidine-3'-phosphate |
| Cfs | 2'-fluorocytidine-3'-phosphorothioate |
| Cs | cytidine-3'-phosphorothioate |
| c | 2'-O-methylcytidine-3'-phosphate |
| cs | 2'-O-methylcytidine-3'-phosphorothioate |
| dC | 2'-deoxycytidine-3'-phosphate |
| dCs | 2'-deoxycytidine-3'-phosphorothioate |
| G | guanosine-3'-phosphate |
| Gf | 2'-fluoroguanosine-3'-phosphate |
| Gfs | 2'-fluoroguanosine-3'-phosphorothioate |
| Gs | guanosine-3'-phosphorothioate |
| g | 2'-O-methylguanosine-3'-phosphate |
| gs | 2'-O-methylguanosine-3'-phosphorothioate |
| dG | 2'-deoxyguanosine-3'-phosphate |
| dGs | 2'-deoxyguanosine-3'-phosphorothioate |
| T | 5'-methyluridine-3'-phosphate |
| Tf | 2'-fluoro-5-methyluridine-3'-phosphate |
| Tfs | 2'-fluoro-5-methyluridine-3'-phosphorothioate |
| Ts | 5-methyluridine-3'-phosphorothioate |
| t | 2'-O-methyl-5-methyluridine-3'-phosphate |
| ts | 2'-O-methyl-5-methyluridine-3'-phosphorothioate |
| dT | 2'-deoxythymidine-3'-phosphate |
| dTs | 2'-deoxythymidine-3'-phosphorothioate |
| U | Uridine-3'-phosphate |
| Uf | 2'-fluorouridine-3'-phosphate |
| Ufs | 2'-fluorouridine-3'-phosphorothioate |
| Us | uridine-3'-phosphorothioate |
| u | 2'-O-methyluridine-3'-phosphate |
| us | 2'-O-methyluridine-3'-phosphorothioate |
| dU | 2'-deoxyuridine-3'-phosphate |
| dUs | 2'-deoxyuridine-3'-phosphorothioate |
| s | phosphorothioate linkage |
| N | any nucleotide (G, A, C, T or U) |
| L96 | N-[tris(GalNAc-alkyl)-amidodecanoyl)]-4-hydroxyprolinol Hyp-(GalNAc-alkyl)3 |
| (dt) | deoxy-thymine |
| (5MdC) | 5'-methyl-deoxycytidine-3'-phosphate |
| (5MdC)s | 5'-methyl-deoxycytidine-3'-phosphorothioate |

TABLE 3

Unmodified Antisense Polynucleotides Agents Targeting PNPLA3.

| Oligo Name | Sequence (5' to 3') | SEQ ID NO | Position in NM_025225.2 |
|---|---|---|---|
| A-137806.1 | CGACGUCAGCCCCGCCCCC | 17 | 10 |
| A-137807.1 | GGCAUUCCCAGCGCGACGUC | 18 | 23 |
| A-137808.1 | GUCUCGGCCAGGGCAUUCCC | 19 | 34 |
| A-137809.1 | UGCCUCAGUGUCUCGGCCAG | 20 | 43 |
| A-137810.1 | CGCUCUCUACCCUGCCUCAG | 21 | 55 |
| A-137811.1 | GCGCCCGCAAGCGCUCUCUA | 22 | 66 |
| A-137812.1 | CAGCUCCGCCCGGCGCCCGC | 23 | 78 |
| A-137813.1 | UGAUCCGCAGCAGCUCCGCC | 24 | 88 |
| A-137814.1 | GCUCGGGUCCUGAUCCGCAG | 25 | 98 |
| A-137815.1 | AUCGGGAAUCGGCUCGGGUC | 26 | 109 |
| A-137816.1 | UCUGGGUCGGGAUCGGGAAU | 27 | 120 |
| A-137817.1 | CGCGGGUUAGGAUCUGGGUC | 28 | 132 |
| A-137818.1 | GGGGCGGGGCGCGGGUUAG | 29 | 142 |
| A-137819.1 | GGCGGCGGCGGCGGGGCGGG | 30 | 154 |
| A-137820.1 | UGCGUCGUACAUGGCGGCGG | 31 | 166 |
| A-137821.1 | AGCCGCGCUCUGCGUCGUAC | 32 | 176 |
| A-137822.1 | AGGACAAGCUCCAGCCGCGC | 33 | 188 |
| A-137823.1 | AGCCCGCGAAGGACAAGCUC | 34 | 197 |
| A-137824.1 | CAGGAAGCCGCAGCCCGCGA | 35 | 208 |
| A-137825.1 | CGUGGUAGAAGCCCAGGAAG | 36 | 221 |
| A-137826.1 | UCGCCCCGACGUGGUAGAAG | 37 | 230 |
| A-137827.1 | CAGGCAGCGGGUCGCCCCGA | 38 | 241 |
| A-137828.1 | GGGCGUGCUCGCUCAGGCAG | 39 | 254 |
| A-137829.1 | AGGAGGUGCGGGGCGUGCUC | 40 | 264 |
| A-137830.1 | CGCGCGUCGCGGAGGAGGUG | 41 | 276 |
| A-137831.1 | AACAACAUGCGCGCGUCGCG | 42 | 285 |
| A-137832.1 | GCCGAAGCGCCGAACAACAU | 43 | 297 |
| A-137833.1 | UGCAACGCCCCGGCCGAAGC | 44 | 309 |
| A-137834.1 | GCCGACGCAGUGCAACGCCC | 45 | 319 |
| A-137835.1 | CGGAGAGGACGCCGACGCAG | 46 | 329 |
| A-137836.1 | UCCAGCGGGAUACCGGAGAG | 47 | 342 |
| A-137837.1 | AGAGUCUGCUCCAGCGGGAU | 48 | 351 |
| A-137838.1 | AGAGGACCUGCAGAGUCUGC | 49 | 362 |
| A-137839.1 | CGCACAAGAUCUGAGAGGAC | 50 | 375 |
| A-137840.1 | CCUGGCCUUCCGCACAAGAU | 51 | 385 |
| A-137841.1 | UGUUCCGACUCCUGGCCUUC | 52 | 395 |
| A-137842.1 | GGAAGAUGCCAAUGUUCCGA | 53 | 407 |
| A-137843.1 | AAGGAUGGAUGGAAGAUGCC | 54 | 417 |

TABLE 3 -continued

Unmodified Antisense Polynucleotides Agents Targeting PNPLA3.

| Oligo Name | Sequence (5' to 3') | SEQ ID NO | Position in NM_025225.2 |
|---|---|---|---|
| A-137844.1 | UGCUUAAGUUGAAGGAUGGA | 55 | 428 |
| A-137845.1 | GUCGGAGGAACUUGCUUAAG | 56 | 440 |
| A-137846.1 | GCAGAGACCCUGUCGGAGGA | 57 | 451 |
| A-137847.1 | CGGGAGGCAUUUGCAGAGAC | 58 | 463 |
| A-137848.1 | GGACAUUGGCCGGGAGGCAU | 59 | 473 |
| A-137849.1 | AGAUGAGCUGGUGGACAUUG | 60 | 485 |
| A-137850.1 | AUUUUGCCGGAGAUGAGCUG | 61 | 495 |
| A-137851.1 | AGAGAUGCCUAUUUUGCCGG | 62 | 505 |
| A-137852.1 | ACACUCUGGUAAGAGAGAUG | 63 | 518 |
| A-137853.1 | CCCCAUCAGACACUCUGGUA | 64 | 527 |
| A-137854.1 | ACCAGAACGUUUUCCCCAUC | 65 | 540 |
| A-137855.1 | AAGUCAGACACCAGAACGUU | 66 | 549 |
| A-137856.1 | CUUUGGACCGAAAGUCAGAC | 67 | 560 |
| A-137857.1 | CCACGACUUCGUCUUUGGAC | 68 | 572 |
| A-137858.1 | ACCAAGGCAUCCACGACUUC | 69 | 582 |
| A-137859.1 | AAGCAGGAACAUACCAAGGC | 70 | 594 |
| A-137860.1 | AGAAGGGGAUGAAGCAGGAA | 71 | 605 |
| A-137861.1 | AGGCCACUGUAGAAGGGGAU | 72 | 615 |
| A-137862.1 | AAGGAGGGAUAAGGCCACUG | 73 | 626 |
| A-137863.1 | CGCCUCUGAAGGAAGGAGGG | 74 | 638 |
| A-137864.1 | ACAUAUCGCACGCCUCUGAA | 75 | 648 |
| A-137865.1 | ACUCCUCCAUCCACAUAUCG | 76 | 660 |
| A-137866.1 | ACGUUGUCACUCACUCCUCC | 77 | 672 |
| A-137867.1 | AAUGAAGGGUACGUUGUCAC | 78 | 682 |
| A-137868.1 | GUUUUGGCAUCAAUGAAGGG | 79 | 693 |
| A-137869.1 | GGUGAUGGUUGUUUUGGCAU | 80 | 703 |
| A-137870.1 | AGAAGGGGACACGGUGAUG | 81 | 716 |
| A-137871.1 | ACUCCCCAUAGAAGGGGAC | 82 | 725 |
| A-137872.1 | GCAGAUGUCGUACUCCCCAU | 83 | 736 |
| A-137873.1 | ACUUGACUUUAGGGCAGAUG | 84 | 749 |
| A-137874.1 | AAAGUUCGUGGACUUGACUU | 85 | 760 |
| A-137875.1 | CCACAUGAAGAAAGUUCGUG | 86 | 770 |
| A-137876.1 | UUGGUGAUGUCCACAUGAAG | 87 | 780 |
| A-137877.1 | CGUAGACUGAGCUUGGUGAU | 88 | 792 |
| A-137878.1 | CUGUGCAGAGGCGUAGACUG | 89 | 803 |
| A-137879.1 | GUAGAGGUUCCCUGUGCAGA | 90 | 814 |
| A-137880.1 | UCGAGAGAAGGUAGAGGUUC | 91 | 824 |
| A-137881.1 | GGGACAAAAGCUCUCGAGAG | 92 | 837 |

TABLE 3 -continued

Unmodified Antisense Polynucleotides Agents Targeting PNPLA3.

| Oligo Name | Sequence (5' to 3') | SEQ ID NO | Position in NM_025225.2 |
|---|---|---|---|
| A-137882.1 | UGAGAUCCGGGGGACAAAA | 93 | 848 |
| A-137883.1 | CCAGCACCUUGAGAUCCGGG | 94 | 857 |
| A-137884.1 | AGGCAUAUCUCUCCCAGCAC | 95 | 870 |
| A-137885.1 | UAUCCUCGAAGGCAUAUCUC | 96 | 879 |
| A-137886.1 | GAAUGCAUCCAAAUAUCCUC | 97 | 892 |
| A-137887.1 | UCCAAGAACCUGAAUGCAUC | 98 | 903 |
| A-137888.1 | UGCCCUUCUCUUCCAAGAAC | 99 | 914 |
| A-137889.1 | UGUUGCAGAUGCCCUUCUCU | 100 | 923 |
| A-137890.1 | CUGGCUGGGGCCUGUUGCAG | 101 | 935 |
| A-137891.1 | AUGACUUCAGGCCUGGCUGG | 102 | 947 |
| A-137892.1 | CCCUUCUGAGGAUGACUUCA | 103 | 958 |
| A-137893.1 | CAGGAUCCAUCCCUUCUGAG | 104 | 968 |
| A-137894.1 | AUGGCGACCUCAGGAUCCAU | 105 | 978 |
| A-137895.1 | UGCCCAGCUGGGCAUGGCGA | 106 | 991 |
| A-137896.1 | ACUCAUGUUUGCCCAGCUGG | 107 | 1000 |
| A-137897.1 | GGAAGAAUCCAGACUCAUGU | 108 | 1012 |
| A-137898.1 | AGCCGACUCCGGGGAAGAAU | 109 | 1024 |
| A-137899.1 | ACAGCCAAGGCAGCCGACUC | 110 | 1035 |
| A-137900.1 | CCUCCAGCCUCACAGCCAAG | 111 | 1046 |
| A-137901.1 | GCUCAUCUCCCUCCAGCCUC | 112 | 1055 |
| A-137902.1 | AGGUGGUCUAGCAGCUCAUC | 113 | 1068 |
| A-137903.1 | CUGAGACGCAGGUGGUCUAG | 114 | 1077 |
| A-137904.1 | AGGGCAGGAUGCUGAGACGC | 115 | 1088 |
| A-137905.1 | GCUCUCAUCCCAGGGCAGGA | 116 | 1099 |
| A-137906.1 | GUGUCCAGGAUGCUCUCAUC | 117 | 1110 |
| A-137907.1 | CUGGGCGAGAGGGUGUCCAG | 118 | 1122 |
| A-137908.1 | CUGUAGCGAGCCUGGGCGAG | 119 | 1133 |
| A-137909.1 | UCACUCAGUGCUGUAGCGAG | 120 | 1143 |
| A-137910.1 | CUUUCAUUUCUUCACUCAGU | 121 | 1154 |
| A-137911.1 | AUCCACCUUUGUCUUUCAUU | 122 | 1166 |
| A-137912.1 | UUGCUCAUGUAUCCACCUUU | 123 | 1176 |
| A-137913.1 | AGUUGCAAAUCUUGCUCAUG | 124 | 1187 |
| A-137914.1 | AAUGGGUAGCAAGUUGCAAA | 125 | 1198 |
| A-137915.1 | AGACAUUAUCCUAAUGGGUA | 126 | 1210 |
| A-137916.1 | AGCAUUACAUAAGACAUUAU | 127 | 1221 |
| A-137917.1 | AGGGUACAGGGCAGCAUUAC | 128 | 1233 |
| A-137918.1 | AUUCCACAGGCAGGGUACAG | 129 | 1244 |
| A-137919.1 | CGCAAUGGCAGAUUCCACAG | 130 | 1255 |

TABLE 3 -continued

Unmodified Antisense Polynucleotides Agents Targeting PNPLA3.

| Oligo Name | Sequence (5' to 3') | SEQ ID NO | Position in NM_025225.2 |
|---|---|---|---|
| A-137920.1 | CUGGACAAUCGCAAUGGCAG | 131 | 1264 |
| A-137921.1 | GUCACCAGUCUCUGGACAAU | 132 | 1275 |
| A-137922.1 | AUCUGGAAGCCAUGUCACCA | 133 | 1288 |
| A-137923.1 | UCGUCGGGCAUAUCUGGAAG | 134 | 1299 |
| A-137924.1 | CACAGGACAUCGUCGGGCAU | 135 | 1308 |
| A-137925.1 | ACCCACUGCAACCACAGGAC | 136 | 1320 |
| A-137926.1 | ACCUGUGAGGUCACCCACUG | 137 | 1332 |
| A-137927.1 | CUCGAGUGAACACCUGUGAG | 138 | 1343 |
| A-137928.1 | ACAUCAGCACUCGAGUGAAC | 139 | 1352 |
| A-137929.1 | GCGGGGAGCAGACACAUCAG | 140 | 1365 |
| A-137930.1 | GACCUGGAGGCGGGGAGCAG | 141 | 1374 |
| A-137931.1 | ACUGGCAUUUGGGACCUGGA | 142 | 1386 |
| A-137932.1 | UUGGCUGCUCACUGGCAUUU | 143 | 1396 |
| A-137933.1 | AUGGGGAGGCCUGUUGGCUG | 144 | 1409 |
| A-137934.1 | UCAGGUGUGCAUGGGGAGGC | 145 | 1419 |
| A-137935.1 | GGCCAGUCCUGCUCAGGUGU | 146 | 1431 |
| A-137936.1 | GAGUCCAGCAGGGCCAGUCC | 147 | 1442 |
| A-137937.1 | GGGAGCAGGGAGUCCAGCAG | 148 | 1451 |
| A-137938.1 | ACAGCCCUUGGGGGAGCAGG | 149 | 1462 |
| A-137939.1 | GUCUCUGCUGGACAGCCCUU | 150 | 1473 |
| A-137940.1 | GCCUCUGCUUUGGUCUCUGC | 151 | 1485 |
| A-137941.1 | CCGCGGGGUGGCCUCUGCUU | 152 | 1495 |
| A-137942.1 | ACCUGAGGAUGGACCGCGGG | 153 | 1508 |
| A-137943.1 | GUUCAGGCUGGACCUGAGGA | 154 | 1519 |
| A-137944.1 | CCAAGAAGAAGUUCAGGCUG | 155 | 1529 |
| A-137945.1 | GUACUUUAUUGCCCAAGAAG | 156 | 1541 |
| A-137946.1 | AGCACCAGCAGGUACUUUAU | 157 | 1552 |
| A-137947.1 | GAGAGCCCUCAGCACCAGC | 158 | 1563 |
| A-137948.1 | GGAAAGGUGGAGAGCCCCUC | 159 | 1572 |
| A-137949.1 | AGUGAAAACUGGGAAAGGU | 160 | 1584 |
| A-137950.1 | ACUCUUCUCUAGUGAAAAAC | 161 | 1594 |
| A-137951.1 | AAGUGACUCACAGACUCUUC | 162 | 1607 |
| A-137952.1 | CUCGCCUCCUCAAGUGACUC | 163 | 1618 |
| A-137953.1 | UCUGCUAGACUCGCCUCCUC | 164 | 1627 |
| A-137954.1 | ACCUCUGAAAGAAUCUGCUA | 165 | 1640 |
| A-137955.1 | AAACUUUAGCACCUCUGAAA | 166 | 1650 |
| A-137956.1 | ACAAAGAUGGGAAACUUUAG | 167 | 1661 |
| A-137957.1 | GGAGGUAGCUGCACAAAGAU | 168 | 1673 |

TABLE 3 -continued

Unmodified Antisense Polynucleotides Agents Targeting PNPLA3.

| Oligo Name | Sequence (5' to 3') | SEQ ID NO | Position in NM_025225.2 |
|---|---|---|---|
| A-137958.1 | CAGCAAUGCGGAGGUAGCUG | 169 | 1682 |
| A-137959.1 | AGGGGUCACUACACAGCAAU | 170 | 1695 |
| A-137960.1 | ACGUCACAGGCAGGGGUCAC | 171 | 1706 |
| A-137961.1 | UGGGAUCCUCCACGUCACAG | 172 | 1717 |
| A-137962.1 | GCUCAGAGGCUGGGAUCCUC | 173 | 1727 |
| A-137963.1 | AAACCAACUCAGCUCAGAGG | 174 | 1738 |
| A-137964.1 | UAGCUUUUCAUAAAACCAAC | 175 | 1750 |
| A-137965.1 | AGGUUGCUUCCUAGCUUUUC | 176 | 1761 |
| A-137966.1 | ACAGGCGAAAGGUUGCUUCC | 177 | 1770 |
| A-137967.1 | UGGACCGCUGCACAGGCGAA | 178 | 1781 |
| A-137968.1 | AGAGUUAAGUGCUGGACCGC | 179 | 1793 |
| A-137969.1 | GCUGAUGUAUUAGAGUUAAG | 180 | 1804 |
| A-137970.1 | AUUAACGCAUGCUGAUGUAU | 181 | 1814 |
| A-137971.1 | CCAACCAGCUGAAUUAACGC | 182 | 1826 |
| A-137972.1 | GGUGUCAUUUCCCAACCAGC | 183 | 1837 |
| A-137973.1 | UGGGCUUCCUGGUGUCAUUU | 184 | 1847 |
| A-137974.1 | GACCCUCUGCACUGGGCUUC | 185 | 1859 |
| A-137975.1 | AGUCAGUAAGGGACCCUCUG | 186 | 1870 |
| A-137976.1 | GCCACGAAACAGUCAGUAAG | 187 | 1880 |
| A-137977.1 | CCAUUAAUAGGGCCACGAAA | 188 | 1891 |
| A-137978.1 | GGAACAGUCUGACCAUUAAU | 189 | 1903 |
| A-137979.1 | ACCUCAUGCUGGAACAGUCU | 190 | 1913 |
| A-137980.1 | UGUCAUUCUAAGAACCUCAU | 191 | 1926 |
| A-137981.1 | CCAAACACCUGUCAUUCUAA | 192 | 1935 |
| A-137982.1 | GCCCCCACCCAUCCAAACAC | 193 | 1947 |
| A-137983.1 | CCCCAUCACAAGGCCCCCAC | 194 | 1959 |
| A-137984.1 | CAGCCUACCCCCCAUCACAA | 195 | 1968 |
| A-137985.1 | UCACACAUGGGCCAGCCUAC | 196 | 1980 |
| A-137986.1 | CACCCCACAAGAUCACACAU | 197 | 1992 |
| A-137987.1 | UCUUCCCUCCACCCCACAAG | 198 | 2001 |
| A-137988.1 | UCAUGCUAUUCUCUUCCCUC | 199 | 2012 |
| A-137989.1 | GGGAAGUGGGAUCAUGCUAU | 200 | 2023 |
| A-137990.1 | UCCCACAGCAUGGGGAAGUG | 201 | 2035 |
| A-137991.1 | ACUGCACCCCUUCCCACAGC | 202 | 2046 |
| A-137992.1 | UCUUGGGGACGAACUGCACC | 203 | 2058 |
| A-137993.1 | GCAGUGUCGUUCUUGGGGAC | 204 | 2068 |
| A-137994.1 | ACCACCUGACAGGCAGUGUC | 205 | 2080 |
| A-137995.1 | AUCUUUGCAGACCACCUGAC | 206 | 2090 |

TABLE 3 -continued

Unmodified Antisense Polynucleotides Agents Targeting PNPLA3.

| Oligo Name | Sequence (5' to 3') | SEQ ID NO | Position in NM_025225.2 |
|---|---|---|---|
| A-137996.1 | CAAGGUUAUCAUCUUUGCAG | 207 | 2100 |
| A-137997.1 | GUUUUUAGUAGUCAAGGUUA | 208 | 2112 |
| A-137998.1 | CGCCAUGGAGACGUUUUUAG | 209 | 2124 |
| A-137999.1 | CUUGUUACCCCCGCCAUGGA | 210 | 2135 |
| A-138000.1 | AGAUUAUCAUCUUGUUACCC | 211 | 2145 |
| A-138001.1 | AAAAUUAAGUAGAUUAUCAU | 212 | 2155 |
| A-138002.1 | AAAGGUGUUCUAAAAUUAAG | 213 | 2166 |
| A-138003.1 | AGUUAGGUGAAAAAGGUGUU | 214 | 2177 |
| A-138004.1 | AAACAUUAUUUUAGUUAGGU | 215 | 2189 |
| A-138005.1 | AAAACUCUUUAAACAUUAUU | 216 | 2199 |
| A-138006.1 | ACAUUUUUAUACAAAACUCU | 217 | 2211 |
| A-138007.1 | AACGCUUCCUUACAUUUUUA | 218 | 2222 |
| A-138008.1 | AACAGGUAACAACGCUUCCU | 219 | 2232 |
| A-138009.1 | AUACAAAAUUCAACAGGUAA | 220 | 2243 |
| A-138010.1 | ACUGAUUCACAUAAUACAAA | 221 | 2256 |
| A-138011.1 | ACUAACAUCUCACUGAUUCA | 222 | 2267 |
| A-138012.1 | AGGCUUAUUCUACUAACAUC | 223 | 2278 |
| A-138013.1 | UUUUUUUUUUAAGGCUUAUU | 224 | 2289 |
| A-138014.1 | AACCGAUUUUUUUUUUUUUA | 225 | 2298 |
| A-138015.1 | CCACUGCACCCAACCGAUUU | 226 | 2309 |
| A-138016.1 | ACAGCCGUGUGCCACUGCAC | 227 | 2320 |
| A-138017.1 | AAGUGCUGGGAUUACAGCCG | 228 | 2333 |
| A-138018.1 | UUGGCCUCCCAAAGUGCUGG | 229 | 2344 |
| A-138019.1 | AUCUGCCAACCUUGGCCUCC | 230 | 2355 |
| A-138020.1 | ACCUCAGGUGAUCUGCCAAC | 231 | 2365 |
| A-138021.1 | CUUGAACUCCUGACCUCAGG | 232 | 2377 |
| A-138022.1 | CCAGACGGUCUUGAACUCC | 233 | 2387 |
| A-138023.1 | UGCUAUGUUGGCCAGACUGG | 234 | 2398 |
| A-138024.1 | GACAGGGUUUUGCUAUGUUG | 235 | 2408 |
| A-138025.1 | AUUUUUAGUAGAGACAGGGU | 236 | 2420 |
| A-138026.1 | AUAAUUUUUGUAUUUUUAGU | 237 | 2431 |
| A-138027.1 | ACCAUGCCCAGAUAAUUUUU | 238 | 2442 |
| A-138028.1 | AGGCAUGCACCACCAUGCCC | 239 | 2453 |
| A-138029.1 | AGCUGGGAUUACAGGCAUGC | 240 | 2465 |
| A-138030.1 | CUUCCGAAUAGCUGGGAUUA | 241 | 2474 |
| A-138031.1 | CCUGCCUCAGCCUUCCGAAU | 242 | 2485 |
| A-138032.1 | UCAAGUGAUUCUCCUGCCUC | 243 | 2497 |
| A-138033.1 | CCUCCUGGGUUCAAGUGAUU | 244 | 2507 |

TABLE 3-continued

Unmodified Antisense Polynucleotides Agents Targeting PNPLA3.

| Oligo Name | Sequence (5' to 3') | SEQ ID NO | Position in NM_025225.2 |
|---|---|---|---|
| A-138034.1 | CCGCAACCUCCGCCUCCUGG | 245 | 2519 |
| A-138035.1 | AAUCUCAGCUCACCGCAACC | 246 | 2531 |
| A-138036.1 | UGAAAUGGUGCAAUCUCAGC | 247 | 2542 |
| A-138037.1 | AGGCUGGAAUGAAAUGGUGC | 248 | 2551 |
| A-138038.1 | ACUCAUGUUGCCCAGGCUGG | 249 | 2564 |
| A-138039.1 | UCAGACUUUCACUCAUGUUG | 250 | 2574 |
| A-138040.1 | UUUUUUUUUGAGUCAGACUU | 251 | 2586 |
| A-138041.1 | UUUUAAAUUUUUUUUUUUUG | 252 | 2596 |
| A-138042.1 | GAUUAUUUGUUUUUUAAAU | 253 | 2608 |
| A-138043.1 | CUGCACACUAGAUUAUUUG | 254 | 2618 |
| A-138044.1 | AGGUGAAUGCCCUGCACACU | 255 | 2629 |
| A-138045.1 | UGGGGGGCUGAGGUGAAUGC | 256 | 2639 |
| A-138046.1 | CUUGGCUCCUGCCUGGGGGG | 257 | 2652 |
| A-138047.1 | CCUGCUGUGCUUGGCUCCUG | 258 | 2661 |
| A-138048.1 | AGGCGGAAGCUCCUGCUGUG | 259 | 2672 |
| A-138049.1 | CAGUGGAGAGGAGGCGGAAG | 260 | 2683 |
| A-138050.1 | AGUUGUGUGCUCCAGUGGAG | 261 | 2695 |
| A-138051.1 | AGCCAGGUUCAAGUUGUGUG | 262 | 2706 |
| A-138052.1 | GCAGAAAAUAAGCCAGGUUC | 263 | 2716 |
| A-138053.1 | GGGGCUGGUCCCUGCAGAAA | 264 | 2729 |
| A-138054.1 | ACUGACCAUGUGGGGCUGGU | 265 | 2740 |
| A-138055.1 | GGAGAAACUCACUGACCAUG | 266 | 2750 |
| A-138056.1 | CGCCACACAUGGGGAGAAAC | 267 | 2762 |
| A-138057.1 | ACUCUCUCAUCGCCACACAU | 268 | 2772 |
| A-138058.1 | CUUUAUUUCUACACUCUCUC | 269 | 2784 |

TABLE 4

Modified Antisense Polynucleotides Agents Targeting PNPLA3.

| Oligo Name Sequence 5'-3' | SEQ ID NO |
|---|---|
| A-137806.1csgsascsgsdTs(5MdC)sdAsdGs(5MdC)s(5MdC)s(5MdC)s(5MdC)sdGs(5MdC)scscscscsc | 270 |
| A-137807.1gsgscsasusdTs(5MdC)s(5MdC)s(5MdC)sdAsdGs(5MdC)sdGs(5MdC)sdGsascsgsusc | 271 |
| A-137808.1gsuscsuscsdGsdGs(5MdC)s(5MdC)sdAsdGsdGsdGs(5MdC)sdAsususcscsc | 272 |
| A-137809.1usgscscsus(5MdC)sdAsdGsdTsdGsdTs(5MdC)sdTs(5MdC)sdGsgscscsasg | 273 |
| A-137810.1csgscsuscsdTs(5MdC)sdTsdAs(5MdC)s(5MdC)s(5MdC)sdTsdGs(5MdC)scsuscsasg | 274 |
| A-137811.1gscsgscscs(5MdC)sdGs(5MdC)sdAsdAsdGs(5MdC)sdGs(5MdC)sdTscsuscsusa | 275 |
| A-137812.1csasgscsus(5MdC)s(5MdC)sdGs(5MdC)s(5MdC)s(5MdC)sdGsdGs(5MdC)sdGscscscsgsc | 276 |
| A-137813.1usgsasuscs(5MdC)sdGs(5MdC)sdAsdGs(5MdC)sdAsdGs(5MdC)sdTscscsgscsc | 277 |

TABLE 4 -continued

Modified Antisense Polynucleotides Agents Targeting PNPLA3.

| Oligo Name Sequence 5'-3' | SEQ ID NO |
|---|---|
| A-137814.1gscsuscsgsdGsdGsdTs(5MdC)s(5MdC)sdTsdGsdAsdTs(5MdC)scsgscsasg | 278 |
| A-137815.1asuscsgsgsdGsdAsdAsdTs(5MdC)sdGsdGs(5MdC)sdTs(5MdC)sgsgsgsusc | 279 |
| A-137816.1uscsusgsgsdGsdTs(5MdC)sdGsdGsdGsdAsdTs(5MdC)sdGsgsgsasasu | 280 |
| A-137817.1csgscsgsgsdGsdTsdTsdAsdGsdGsdAsdTs(5MdC)sdTsgsgsgsusc | 281 |
| A-137818.1gsgsgsgscsdGsdGsdGsdGsdGs(5MdC)sdGs(5MdC)sdGsdGsgsususasg | 282 |
| A-137819.1gsgscsgsgs(5MdC)sdGsdGs(5MdC)sdGsdGs(5MdC)sdGsdGsdGsgscsgsgsg | 283 |
| A-137820.1usgscsgsus(5MdC)sdGsdTsdAs(5MdC)sdAsdTsdGsdGs(5MdC)sgsgscsgsg | 284 |
| A-137821.1asgscscsgs(5MdC)sdGs(5MdC)sdTs(5MdC)sdTsdGs(5MdC)sdGsdTscsgsusasc | 285 |
| A-137822.1asgsgsascsdAsdAsdGs(5MdC)sdTs(5MdC)s(5MdC)sdAsdGs(5MdC)scsgscsgsc | 286 |
| A-137823.1asgscscscsdGs(5MdC)sdGsdAsdAsdGsdGsdAs(5MdC)sdAsasgscsusc | 287 |
| A-137824.1csasgsgsasdAsdGs(5MdC)s(5MdC)sdGs(5MdC)sdAsdGs(5MdC)s(5MdC)scsgscsgsa | 288 |
| A-137825.1csgsusgsgsdTsdAsdGsdAsdAsdGs(5MdC)s(5MdC)s(5MdC)sdAsgsgsasasg | 289 |
| A-137826.1uscsgscscs(5MdC)s(5MdC)sdGsdAs(5MdC)sdGsdTsdGsdGsdTsasgsasasg | 290 |
| A-137827.1csasgsgscsdAsdGs(5MdC)sdGsdGsdGsdTs(5MdC)sdGs(5MdC)scscscsgsa | 291 |
| A-137828.1gsgsgscsgsdTsdGs(5MdC)sdTs(5MdC)sdGs(5MdC)sdTs(5MdC)sdAsgsgscsasg | 292 |
| A-137829.1asgsgsasgsdGsdTsdGs(5MdC)sdGsdGsdGsdGs(5MdC)sdGsusgscsusc | 293 |
| A-137830.1csgscsgscsdGsdTs(5MdC)sdGs(5MdC)sdGsdGsdAsdGsdGsasgsgsusg | 294 |
| A-137831.1asascsasas(5MdC)sdAsdTsdGs(5MdC)sdGs(5MdC)sdGs(5MdC)sdGsuscsgscsg | 295 |
| A-137832.1gscscsgsasdAsdGs(5MdC)sdGs(5MdC)s(5MdC)sdGsdAsdAs(5MdC)sasascsasu | 296 |
| A-137833.1usgscsasas(5MdC)sdGs(5MdC)s(5MdC)s(5MdC)s(5MdC)sdGsdGs(5MdC)s(5MdC)sgsasasgsc | 297 |
| A-137834.1gscscsgsas(5MdC)sdGs(5MdC)sdAsdGsdTsdGs(5MdC)sdAsdAscsgscscsc | 298 |
| A-137835.1csgsgsasgsdAsdGsdGsdAs(5MdC)sdGs(5MdC)s(5MdC)sdGsdAscsgscsasg | 299 |
| A-137836.1uscscsasgs(5MdC)sdGsdGsdGsdAsdTsdAs(5MdC)s(5MdC)sdGsasgsasg | 300 |
| A-137837.1asgsasgsus(5MdC)sdTsdGs(5MdC)sdTs(5MdC)s(5MdC)sdAsdGs(5MdC)sgsgsgsasu | 301 |
| A-137838.1asgsasgsgsdAs(5MdC)s(5MdC)sdTsdGs(5MdC)sdAsdGsdAsdGsuscsusgsc | 302 |
| A-137839.1csgscsascsdAsdAsdGsdAsdTs(5MdC)sdTsdGsdAsdGsasgsgsasc | 303 |
| A-137840.1cscsusgsgs(5MdC)s(5MdC)sdTsdTs(5MdC)s(5MdC)sdGs(5MdC)sdAs(5MdC)sasasgsasu | 304 |
| A-137841.1usgsususcs(5MdC)sdGsdAs(5MdC)sdTs(5MdC)s(5MdC)sdTsdGsdGscscsususc | 305 |
| A-137842.1gsgsasasgsdAsdTsdGs(5MdC)s(5MdC)sdAsdAsdTsdGsdTsuscscsgsa | 306 |
| A-137843.1asasgsgsasdTsdGsdGsdAsdTsdGsdGsdAsdAsdGsasusgscsc | 307 |
| A-137844.1usgscsususdAsdAsdGsdT TABLE 4-continued Modified Antisense Polynucleotides Agents Targeting PNPLA3.

| Oligo Name Sequence 5'-3' | SEQ ID NO |
|---|---|
| A-137851.1 asgsasgsasdTsdGs(5MdC)s(5MdC)sdTsdAsdTsdTsdTsgscscsgsg | 315 |
| A-137852.1 ascsascsus(5MdC)sdTsdGsdGsdTsdAsdAsdGsdAsdGsasgsasusg | 316 |
| A-137853.1 cscscscsasdTs(5MdC)sdAsdGsdAs(5MdC)sdAs(5MdC)sdTs(5MdC)susgsgsusa | 317 |
| A-137854.1 ascscsasgsdAsdAs(5MdC)sdGsdTsdTsdTsdTs(5MdC)s(5MdC)scscsasusc | 318 |
| A-137855.1 asasgsuscsdAsdGsdAs(5MdC)sdAs(5MdC)s(5MdC)sdAsdGsdAsascsgsusu | 319 |
| A-137856.1 csusususgsdGsdAs(5MdC)s(5MdC)sdGsdAsdAsdAsdGsdTscsasgsasc | 320 |
| A-137857.1 cscsascsgsdAs(5MdC)sdTsdTs(5MdC)sdGsdTs(5MdC)sdTsdTsusgsgsasc | 321 |
| A-137858.1 ascscsasasdGsdGs(5MdC)sdAsdTs(5MdC)s(5MdC)sdAs(5MdC)sdGsascsususc | 322 |
| A-137859.1 asasgscsasdGsdGsdAsdAs(5MdC)sdAsdTsdAs(5MdC)s(5MdC)sasasgsgsc | 323 |
| A-137860.1 asgsasasgsdGsdGsdGsdAsdTsdGsdAsdAsdGs(5MdC)sasgsgsasa | 324 |
| A-137861.1 asgsgscscsdAs(5MdC)sdTsdGsdTsdAsdGsdAsdAsdGsgsgsgsasu | 325 |
| A-137862.1 asasgsgsasdGsdGsdGsdAsdTsdAsdAsdGsdGs(5MdC)scsascsusg | 326 |
| A-137863.1 csgscscsus(5MdC)sdTsdGsdAsdGsdGsdGsdAsdAsdGsgsasgsgsg | 327 |
| A-137864.1 ascsasusasdTs(5MdC)sdGs(5MdC)sdAs(5MdC)sdGs(5MdC)s(5MdC)sdTscsusgsasa | 328 |
| A-137865.1 ascsuscscsdTs(5MdC)s(5MdC)sdAsdTs(5MdC)s(5MdC)sdAs(5MdC)sdAsusasuscsg | 329 |
| A-137866.1 ascsgsusussdGsdTs(5MdC)sdAs(5MdC)sdTs(5MdC)sdAs(5MdC)sdTscscsuscsc | 330 |
| A-137867.1 asasusgsasdAsdGsdGsdGsdTsdAs(5MdC)sdGsdTsdTsgsuscsasc | 331 |
| A-137868.1 gsusususdGsdGs(5MdC)sdAsdTs(5MdC)sdAsdAsdTsdGsasasgsgsg | 332 |
| A-137869.1 gssgsusgsasdTsdGsdGsdTsdTsdGsdTsdTsdTsgsgscsasu | 333 |
| A-137870.1 asgsasasgsdGsdGsdGsdGsdAs(5MdC)sdAs(5MdC)sdGsdGsusgsasusg | 334 |
| A-137871.1 ascsuscscs(5MdC)s(5MdC)sdAsdTsdAsdGsdAsdAsdGsdGsgsgsgsasc | 335 |
| A-137872.1 gscsasgsasdTsdGsdTs(5MdC)sdGsdAs(5MdC)sdTs(5MdC)scscscsasu | 336 |
| A-137873.1 ascsusussdAs(5MdC)sdTsdTsdTsdAsdGsdGsdGs(5MdC)sasgsasusg | 337 |
| A-137874.1 asasasgsusdTs(5MdC)sdGsdTsdGsdGsdAs(5MdC)sdTsdTsgsascsusu | 338 |
| A-137875.1 cscsascsasdTsdGsdAsdAsdGsdAsdAsdAsdGsdTsuscsgsusg | 339 |
| A-137876.1 ususgsgsusdGsdAsdTsdGsdTs(5MdC)s(5MdC)sdAs(5MdC)sdAsusgsasasg | 340 |
| A-137877.1 csgsusasgsdAs(5MdC)sdTsdGsdAsdGs(5MdC)sdTsdTsdGsgsusgsasu | 341 |
| A-137878.1 csusgsusgs(5MdC)sdAsdGsdAsdGsdGs(5MdC)sdGsdTsdAsgsascsusg | 342 |
| A-137879.1 gsusasgsasdGsdGsdTsdTs(5MdC)s(5MdC)s(5MdC)sdTsdGsdTsgscsasgsa | 343 |
| A-137880.1 uscsgsasgsdAsdGsdAsdAsdGsdGsdTsdAsdGsdAsgsgsususc | 344 |
| A-137881.1 gsgsgsasascsdAsdAsdAsdAsdGs(5MdC)sdTs(5MdC)sdTs(5MdC)sgsasgsasg | 345 |
| A-137882.1 usgsasgsasdTs(5MdC)s(5MdC)sdGsdGsdGsdGsdGsdGsdAscsasasasa | 346 |
| A-137883.1 cscsasgscsdAs(5MdC)s(5MdC)sdTsdTsdGsdAsdGsdAsdTscscscsgsg | 347 |
| A-137884.1 asgsgscsasdTsdAsdTs(5MdC)sdTs(5MdC)sdTs(5MdC)s(5MdC)s(5MdC)sasgscsasc | 348 |
| A-137885.1 ususasuscscsdTs(5MdC)sdGsdAsdAsdGsdGs(5MdC)sdAsdTsasuscsusc | 349 |
| A-137886.1 gsasasusgsgs(5MdC)sdAsdTs(5MdC)s(5MdC)sdAsdAsdAsdTsdAsuscscsusc | 350 |
| A-137887.1 uscscsasasdGsdAsdAs(5MdC)s(5MdC)sdTsdGsdAsdAsdTsgscsasusc | 351 |
| A-137888.1 usgscscscscsdTsdTs(5MdC)sdTs(5MdC)sdTsdTs(5MdC)s(5MdC)sdAsasgsasasc | 352 |

TABLE 4 -continued

| Modified Antisense Polynucleotides Agents Targeting PNPLA3. | |
|---|---|
| Oligo NameSequence 5'-3' | SEQ ID NO |
| A-137889.1usgsususgs(5MdC)sdAsdGsdAsdTsdGs(5MdC)s(5MdC)s(5MdC)sdTsuscsuscsu | 353 |
| A-137890.1csusgsgscsdTsdGsdGsdGsdGs(5MdC)s(5MdC)sdTsdGsdTsusgscsasg | 354 |
| A-137891.1asusgsascsdTsdTs(5MdC)sdAsdGsdGs(5MdC)s(5MdC)sdTsdGsgscsusgsg | 355 |
| A-137892.1cscscsusus(5MdC)sdTsdGsdAsdGsdGsdAsdTsdGsdAscsususcsa | 356 |
| A-137893.1csasgsgsasdTs(5MdC)s(5MdC)sdAsdTs(5MdC)s(5MdC)s(5MdC)sdTsdTscsusgsasg | 357 |
| A-137894.1asusgsgscsdGsdAs(5MdC)s(5MdC)sdTs(5MdC)sdAsdGsdGsdAsuscscsasu | 358 |
| A-137895.1usgscscsdAsdGs(5MdC)sdTsdGsdGsdGs(5MdC)sdAsdTsgsgscsgsa | 359 |
| A-137896.1ascsuscsasdTsdGsdTsdTsdTsdGs(5MdC)s(5MdC)s(5MdC)sdAsgscsusgsg | 360 |
| A-137897.1gsgsasasgsdAsdAsdTs(5MdC)s(5MdC)sdAsdGsdAs(5MdC)sdTscsasusgsu | 361 |
| A-137898.1asgscscsgsdAs(5MdC)sdTs(5MdC)s(5MdC)sdGsdGsdGsdGsdAsasgsasasu | 362 |
| A-137899.1ascsasgscs(5MdC)sdAsdAsdGsdGs(5MdC)sdAsdGs(5MdC)s(5MdC)sgsascsusc | 363 |
| A-137900.1cscsuscscsdAsdGs(5MdC)s(5MdC)sdTs(5MdC)sdAs(5MdC)sdAsdGscscsasasg | 364 |
| A-137901.1gscsuscsasdTs(5MdC)sdTs(5MdC)s(5MdC)s(5MdC)sdTs(5MdC)s(5MdC)sdAsgscscsusc | 365 |
| A-137902.1asgsgsusgsdGsdTs(5MdC)sdTsdAsdGs(5MdC)sdAsdGs(5MdC)suscsasusc | 366 |
| A-137903.1csusgsasgsdAs(5MdC)sdGs(5MdC)sdAsdGsdGsdTsdGsdGsuscsusasg | 367 |
| A-137904.1asgsgsgscsdAsdGsdGsdAsdTsdGs(5MdC)sdTsdGsdAsgsascsgsc | 368 |
| A-137905.1gscsuscsus(5MdC)sdAsdTs(5MdC)s(5MdC)sdAsdGsdGsdGscsasgsgsa | 369 |
| A-137906.1gsusgsuscs(5MdC)sdAsdGsdGsdAsdTsdGs(5MdC)sdTs(5MdC)suscsasusc | 370 |
| A-137907.1csusgsgsgs(5MdC)sdGsdAsdGsdAsdGsdGsdGsdTsdGsuscscsasg | 371 |
| A-137908.1csusgsusasdGs(5MdC)sdGsdAsdGs(5MdC)s(5MdC)sdTsdGsdGsgscsgsasg | 372 |
| A-137909.1uscsascsus(5MdC)sdAsdGsdTsdGs(5MdC)sdTsdGsdTsdAsgscsgsasg | 373 |
| A-137910.1csususcsdAsdTsdTsdTs(5MdC)sdTsdTs(5MdC)sdAs(5MdC)suscsasgsu | 374 |
| A-137911.1asuscscsas(5MdC)s(5MdC)sdTsdTsdTsdGsdTs(5MdC)sdTsdTsuscsasusu | 375 |
| A-137912.1usgscsus(5MdC)sdAsdTsdGsdTsdAsdTs(5MdC)s(5MdC)sdAscscsususu | 376 |
| A-137913.1asgsususgs(5MdC)sdAsdAsdAsdTs(5MdC)sdTsdTsdGs(5MdC)suscsasusg | 377 |
| A-137914.1asasusgsgsdGsdTsdAsdGs(5MdC)sdAsdAsdGsdTsdTsgscsasasa | 378 |
| A-137915.1asgsascsasdTsdTsdAsdTs(5MdC)s(5MdC)sdTsdAsdAsdTsgsgsgsusa | 379 |
| A-137916.1asgscsasusdTsdAs(5MdC)sdAsdTsdAsdAsdGsdAs(5MdC)sasususasu | 380 |
| A-137917.1asgsgsgsusdAs(5MdC)sdAsdGsdGsdGs(5MdC)sdAsdGs(5MdC)sasususasc | 381 |
| A-137918.1asususcscsdAs(5MdC)sdAsdGsdGs(5MdC)sdAsdGsdGsdGsusascsasg | 382 |
| A-137919.1csgscsasasdTsdGsdGs(5MdC)sdAsdGsdAsdTsdTs(5MdC)scsascsasg | 383 |
| A-137920.1csusgsgsas(5MdC)sdAsdAsdTs(5MdC)sdGs(5MdC)sdAsdAsdTsgsgscsasg | 384 |
| A-137921.1gsuscsascs(5MdC)sdAsdGsdTs(5MdC)sdTs(5MdC)sdTsdGsdGsascsasasu | 385 |
| A-137922.1asuscsusgsdGsdAsdAsdGs(5MdC)s(5MdC)sdAsdTsdGsdTscsascscsa | 386 |
| A-137923.1uscsgsuscsdGsdGsdGs(5MdC)sdAsdTsdAsdTs(5MdC)sdTsgsgsasasg | 387 |
| A-137924.1csascsasgsdGsdAs(5MdC)sdAsdTs(5MdC)sdGsdTs(5MdC)sdGsgsgscsasu | 388 |
| A-137925.1ascscscsas(5MdC)sdTsdGs(5MdC)sdAsdAs(5MdC)s(5MdC)sdAs(5MdC)sasgsgsasc | 389 |
| A-137926.1ascscsusgsdTsdGsdAsdGsdGsdTs(5MdC)sdAs(5MdC)s(5MdC)scsascsusg | 390 |

TABLE 4 -continued

| Modified Antisense Polynucleotides Agents Targeting PNPLA3. | |
|---|---|
| Oligo NameSequence 5'-3' | SEQ ID NO |
| A-137927.1csuscsgsasdGsdTsdGsdAsdAs(5MdC)sdAs(5MdC)s(5MdC)sdTsgsusgsasg | 391 |
| A-137928.1ascsasuscsdAsdGs(5MdC)sdAs(5MdC)sdTs(5MdC)sdGsdAsdGsusgsasasc | 392 |
| A-137929.1gscsgsgsgsdGsdAsdGs(5MdC)sdAsdGsdAs(5MdC)sdAs(5MdC)sasuscsasg | 393 |
| A-137930.1gsascscsusdGsdGsdAsdGsdGs(5MdC)sdGsdGsdGsdGsasgscsasg | 394 |
| A-137931.1ascsusgsgs(5MdC)sdAsdTsdTsdTsdGsdGsdGsdAs(5MdC)scsusgsgsa | 395 |
| A-137932.1ususgsgscsdTsdGs(5MdC)sdTs(5MdC)sdAs(5MdC)sdTsdGsdGscsasususu | 396 |
| A-137933.1asusgsgsgsdGsdAsdGsdGs(5MdC)s(5MdC)sdTsdGsdTsdTsgsgscsusg | 397 |
| A-137934.1uscsasgsgsdTsdGsdTsdGs(5MdC)sdAsdTsdGsdGsdGsgsasgsgsc | 398 |
| A-137935.1gsgscscsasdGsdTs(5MdC)s(5MdC)sdTsdGs(5MdC)sdTs(5MdC)sdAsgsgsusgsu | 399 |
| A-137936.1gsasgsuscs(5MdC)sdAsdGs(5MdC)sdAsdGsdGsdGs(5MdC)s(5MdC)sasgsuscsc | 400 |
| A-137937.1gsgsgsasgs(5MdC)sdAsdGsdGsdGsdAsdGsdTs(5MdC)s(5MdC)sasgscsasg | 401 |
| A-137938.1ascsasgscs(5MdC)s(5MdC)sdTsdTsdGsdGsdGsdGsdGsdAsgscsasgsg | 402 |
| A-137939.1gsuscsuscsdTsdGs(5MdC)sdTsdGsdGsdAs(5MdC)sdAsdGscscscsusu | 403 |
| A-137940.1gscscsuscsdTsdGs(5MdC)sdTsdTsdTsdGsdGsdTs(5MdC)suscsusgsc | 404 |
| A-137941.1cscsgscsgsdGsdGsdGsdTsdGsdGs(5MdC)s(5MdC)sdTs(5MdC)susgscsusu | 405 |
| A-137942.1ascscsusgsdAsdGsdGsdAsdTsdGsdGsdAs(5MdC)s(5MdC)sgscsgsgsg | 406 |
| A-137943.1gsususcsasdGsdGs(5MdC)sdTsdGsdGsdAs(5MdC)s(5MdC)sdTsgsasgsgsa | 407 |
| A-137944.1cscsasasgsdAsdAsdGsdAsdAsdGsdTsdTs(5MdC)sdAsgsgscsusg | 408 |
| A-137945.1gsusascsusdTsdTsdAsdTsdTsdGs(5MdC)s(5MdC)s(5MdC)sdAsasgsasasg | 409 |
| A-137946.1asgscsascs(5MdC)sdAsdGs(5MdC)sdAsdGsdGsdTsdAs(5MdC)susususasu | 410 |
| A-137947.1gsasgsasgs(5MdC)s(5MdC)s(5MdC)s(5MdC)sdTs(5MdC)sdAsdGs(5MdC)sdAscscsasgsc | 411 |
| A-137948.1gsgsasasasdGsdGsdTsdGsdGsdAsdGsdAsdGs(5MdC)scscscsusc | 412 |
| A-137949.1asgsusgsasdAsdAsdAsdAs(5MdC)sdTsdGsdGsdGsdAsasasgsgsu | 413 |
| A-137950.1ascsuscsusdTs(5MdC)sdTs(5MdC)sdTsdAsdGsdTsdGsdAsasasasasc | 414 |
| A-137951.1asasgsusgsdAs(5MdC)sdTs(5MdC)sdAs(5MdC)sdAsdGsdAs(5MdC)suscsususc | 415 |
| A-137952.1csuscsgscs(5MdC)sdTs(5MdC)s(5MdC)sdTs(5MdC)sdAsdAsdGsdTsgsascsusc | 416 |
| A-137953.1uscsusgscsdTsdAsdGsdAs(5MdC)sdTs(5MdC)sdGs(5MdC)s(5MdC)suscscsusc | 417 |
| A-137954.1ascscsuscsdTsdGsdAsdAsdAsdGsdAsdAsdTs(5MdC)susgscsusa | 418 |
| A-137955.1asasascsusdTsdTsdAsdGs(5MdC)sdAs(5MdC)s(5MdC)sdTs(5MdC)susgsasasa | 419 |
| A-137956.1ascsasasasdGsdAsdTsdGsdGsdGsdAsdAsdAs(5MdC)susususasg | 420 |
| A-137957.1gsgsasgsgsdTsdAsdGs(5MdC)sdTsdGs(5MdC)sdAs(5MdC)sdAsasasgsasu | 421 |
| A-137958.1csasgscsasdAsdTsdGs(5MdC)sdGsdGsdAsdGsdGsdTsasgscsusg | 422 |
| A-137959.1asgsgsgsgsdTs(5MdC)sdAs(5MdC)sdTsdAs(5MdC)sdAs(5MdC)sdAsgscsasasu | 423 |
| A-137960.1ascsgsuscsdAs(5MdC)sdAsdGsdGs(5MdC)sdAsdGsdGsdGsgsuscsasc | 424 |
| A-137961.1usgsgsgsasdTs(5MdC)s(5MdC)sdTs(5MdC)s(5MdC)sdAs(5MdC)sdGsdTscsascsasg | 425 |
| A-137962.1gscsuscsasdGsdAsdGsdGs(5MdC)sdTsdGsdGsdGsdAsuscscsusc | 426 |
| A-137963.1asasascscsdAsdAs(5MdC)sdTs(5MdC)sdAsdGs(5MdC)sdTs(5MdC)sasgsasgsg | 427 |
| A-137964.1usasgscsusdTsdTsdTs(5MdC)sdAsdTsdAsdAsdAsdAscscsasasc | 428 |

TABLE 4-continued

Modified Antisense Polynucleotides Agents Targeting PNPLA3.

| Oligo Name Sequence 5'-3' | SEQ ID NO |
|---|---|
| A-137965.1 asgsgsusudGs(5MdC)sdTsdTs(5MdC)s(5MdC)sdTsdAsdGs(5MdC)sususususc | 429 |
| A-137966.1 ascsasgsgs(5MdC)sdGsdAsdAsdAsdGsdGsdTsdTsdGscsususcsc | 430 |
| A-137967.1 usgsgsascs(5MdC)sdGs(5MdC)sdTsdGs(5MdC)sdAs(5MdC)sdAsdGsgscsgsasa | 431 |
| A-137968.1 asgsasgsusdTsdAsdAsdGsdTsdGs(5MdC)sdTsdGsdGsascscsgsc | 432 |
| A-137969.1 gscsusgsasdTsdGsdTsdAsdTsdTsdAsdGsdAsdGsususasasg | 433 |
| A-137970.1 asususasas(5MdC)sdGs(5MdC)sdAsdTsdGs(5MdC)sdTsdGsdAsusgsusasu | 434 |
| A-137971.1 cscsasascs(5MdC)sdAsdGs(5MdC)sdTsdGsdAsdAsdTsdTsasascsgsc | 435 |
| A-137972.1 gsgsusgsus(5MdC)sdAsdTsdTsdTs(5MdC)s(5MdC)s(5MdC)sdAsdAscscsasgsc | 436 |
| A-137973.1 usgsgsgscsdTsdTs(5MdC)s(5MdC)sdTsdGsdGsdTsdGsdTscsasususu | 437 |
| A-137974.1 gsascscscsdTs(5MdC)sdTsdGs(5MdC)sdAs(5MdC)sdTsdGsdGsgscsususc | 438 |
| A-137975.1 asgsuscsasdGsdTsdAsdAsdGsdGsdGsdAs(5MdC)s(5MdC)scsuscsusg | 439 |
| A-137976.1 gscscsascsdGsdAsdAsdAs(5MdC)sdAsdGsdTs(5MdC)sdAsgsusasasg | 440 |
| A-137977.1 cscsasususdAsdAsdTsdAsdGsdGsdGs(5MdC)s(5MdC)sdAscsgsasasa | 441 |
| A-137978.1 gsgsasascsdAsdGsdTs(5MdC)sdTsdGsdAs(5MdC)s(5MdC)sdAsusususasu | 442 |
| A-137979.1 ascscsuscsdAsdTsdGs(5MdC)sdTsdGsdGsdAsdAs(5MdC)sasgsuscsu | 443 |
| A-137980.1 usgsuscsasdTsdTs(5MdC)sdTsdAsdAsdGsdAsdAs(5MdC)scsuscsasu | 444 |
| A-137981.1 cscsasasas(5MdC)sdAs(5MdC)s(5MdC)sdTsdGsdTs(5MdC)sdAsdTsuscsusasa | 445 |
| A-137982.1 gscscscscs(5MdC)sdAs(5MdC)s(5MdC)s(5MdC)sdAsdTs(5MdC)s(5MdC)sdAsasascsasc | 446 |
| A-137983.1 cscscscsasdTs(5MdC)sdAs(5MdC)sdAsdAsdGsdGs(5MdC)s(5MdC)scscscsasc | 447 |
| A-137984.1 csasgscscsdTsdAs(5MdC)s(5MdC)s(5MdC)s(5MdC)s(5MdC)s(5MdC)sdAsdTscsascsasa | 448 |
| A-137985.1 uscsascsascsas(5MdC)sdAsdTsdGsdGsdGs(5MdC)s(5MdC)sdAsdGscscsusasc | 449 |
| A-137986.1 csascscscs(5MdC)sdAs(5MdC)sdAsdAsdGsdAsdTs(5MdC)sdAscsascsasu | 450 |
| A-137987.1 uscsusususcs(5MdC)s(5MdC)sdTs(5MdC)s(5MdC)sdAs(5MdC)s(5MdC)s(5MdC)s(5MdC)sascsasasg | 451 |
| A-137988.1 uscsasusgs(5MdC)sdTsdAsdTsdTs(5MdC)sdTs(5MdC)sdTsdTscscscsusc | 452 |
| A-137989.1 gsgsgsasasdGsdTsdGsdGsdGsdAsdTs(5MdC)sdAsdTsgscsusasu | 453 |
| A-137990.1 uscscscsas(5MdC)sdAsdGs(5MdC)sdAsdTsdGsdGsdGsdGsasasgsusg | 454 |
| A-137991.1 ascsusgscsdAs(5MdC)s(5MdC)s(5MdC)s(5MdC)s(5MdC)sdTsdTs(5MdC)s(5MdC)s(5MdC)sascsasgsc | 455 |
| A-137992.1 uscsususgsdGsdGsdGsdAs(5MdC)sdGsdAsdAs(5MdC)sdTsgscsascsc | 456 |
| A-137993.1 gscsasgsusdGsdTs(5MdC)sdGsdTsdTs(5MdC)sdTsdTsdGsgsgsasc | 457 |
| A-137994.1 ascscsascs(5MdC)sdTsdGsdAs(5MdC)sdAsdGsdGs(5MdC)sdAsgsusgsusc | 458 |
| A-137995.1 asuscsususdTsdGs(5MdC)sdAsdGsdAs(5MdC)sdAs(5MdC)scsusgsasc | 459 |
| A-137996.1 csasasgsgsdTsdTsdAsdTs(5MdC)sdAsdTs(5MdC)sdTsdTsusgscsasg | 460 |
| A-137997.1 gsusususdTsdAsdGsdTsdAsdGsdTs(5MdC)sdAsdAsgsgsusus | 461 |
| A-137998.1 csgscscsasdTsdGsdGsdAsdGsdAs(5

TABLE 4 -continued

Modified Antisense Polynucleotides Agents Targeting PNPLA3.

| Oligo Name Sequence 5'-3' | SEQ ID NO |
|---|---|
| A-138001.1 asasasasusdTsdAsdAsdGsdTsdAsdGsdAsdTsdTsasuscsasu | 465 |
| A-138002.1 asasasgsgsdTsdGsdTsdTs(5MdC)sdTsdAsdAsdAsdAsusususasasg | 466 |
| A-138003.1 asgsusususasdGsdGsdTsdGsdAsdAsdAsdAsdGsgsusgsusu | 467 |
| A-138004.1 asasascsasdTsdTsdAsdTsdTsdTsdTsdAsdGsdTsusasgsgsu | 468 |
| A-138005.1 asasasascsdTs(5MdC)sdTsdTsdTsdAsdAsdAs(5MdC)sdAsususasusu | 469 |
| A-138006.1 ascsasususdTsdTsdTsdAsdTsdAs(5MdC)sdAsdAsdAsascsuscsu | 470 |
| A-138007.1 asascsgscsdTsdTs(5MdC)s(5MdC)sdTsdTsdAs(5MdC)sdAsdTsususususa | 471 |
| A-138008.1 asascsasgsdGsdTsdAsdAs(5MdC)sdAsdAs(5MdC)sdGs(5MdC)sususcscsu | 472 |
| A-138009.1 asususascsasdAsdAsdAsdTsdTs(5MdC)sdAsdAs(5MdC)sdAsgsgsusasa | 473 |
| A-138010.1 ascsusgsasdTsdTs(5MdC)sdAs(5MdC)sdAsdTsdAsdAsdTsascsasasa | 474 |
| A-138011.1 ascsusasas(5MdC)sdAsdTs(5MdC)sdTs(5MdC)sdAs(5MdC)sdTsdGsasususcsa | 475 |
| A-138012.1 asgsgscsusdTsdAsdTsdTs(5MdC)sdTsdAs(5MdC)sdTsdAsascsasusc | 476 |
| A-138013.1 usussusususdTsdTsdTsdTsdTsdAsdAsdGsdGs(5MdC)sususasusu | 477 |
| A-138014.1 asascscsgsdAsdTsdTsdTsdTsdTsdTsdTsdTsususususa | 478 |
| A-138015.1 cscsascsusdGs(5MdC)sdAs(5MdC)s(5MdC)s(5MdC)sdAsdAs(5MdC)s(5MdC)sgsasususu | 479 |
| A-138016.1 ascsasgscs(5MdC)sdGsdTsdGsdTsdGs(5MdC)s(5MdC)sdAs(5MdC)susgscsasc | 480 |
| A-138017.1 asasgsusgs(5MdC)sdTsdGsdGsdGsdAsdTsdTsdAs(5MdC)sasgscscsg | 481 |
| A-138018.1 ususgsgscs(5MdC)sdTs(5MdC)s(5MdC)s(5MdC)sdAsdAsdAsdGsdTsgscsusgsg | 482 |
| A-138019.1 asuscsusgs(5MdC)s(5MdC)sdAsdAs(5MdC)s(5MdC)sdTsdTsdGsdGscscsuscsc | 483 |
| A-138020.1 ascscsuscsdAsdGsdGsdTsdGsdAsdTs(5MdC)sdTsdGscscsasasc | 484 |
| A-138021.1 csususgsasdAs(5MdC)sdTs(5MdC)s(5MdC)sdTsdGsdAs(5MdC)s(5MdC)suscsasgsg | 485 |
| A-138022.1 cscsasgsas(5MdC)sdTsdGsdGsdTs(5MdC)sdTsdTsdGsdAsascsuscsc | 486 |
| A-138023.1 usgscsusasdTsdGsdTsdTsdGsdGs(5MdC)s(5MdC)sdAsdGsascsusgsg | 487 |
| A-138024.1 gsascsasgsdGsdGsdGsdTsdTsdTsdTsdGs(5MdC)sdTsdAsusgsususg | 488 |
| A-138025.1 asususususdTsdAsdGsdTsdAsdGsdAsdGsdAs(5MdC)sasgsgsgsu | 489 |
| A-138026.1 asusasasasusdTsdTsdTsdGsdTsdAsdTsdTsdTsususasgsu | 490 |
| A-138027.1 ascscsasusdGs(5MdC)s(5MdC)s(5MdC)sdAsdGsdAsdTsdAsdAsusususu | 491 |
| A-138028.1 asgsgscsasdTsdGs(5MdC)sdAs(5MdC)s(5MdC)sdAs(5MdC)s(5MdC)sdAsusgscscsc | 492 |
| A-138029.1 asgscsusgsdGsdGsdAsdTsdTsdAs(5MdC)sdAsdGsdGscsasusgsc | 493 |
| A-138030.1 csususcscsdGsdAsdAsdTsdAsdGs(5MdC)sdTsdGsdGsgsasususa | 494 |
| A-138031.1 cscsusgscs(5MdC)sdTs(5MdC)sdAsdGs(5MdC)s(5MdC)sdTsdTs(5MdC)scsgsasasu | 495 |
| A-138032.1 uscsasasgsdTsdGsdAsdTs(5MdC)sdTs(5MdC)s(5MdC)sdTsgscscsusc | 496 |
| A-138033.1 cscsuscscsdTsdGsdGsdGsdTsdTs(5MdC)sdAsdAsdGsusgsasusu | 497 |
| A-138034.1 cscsgscsasdAs(5MdC)s(5MdC)sdTs(5MdC)sdGs(5MdC)s(5MdC)sdTscscsusgsg | 498 |
| A-138035.1 asasasuscsus(5MdC)sdAsdGs(5MdC)sdTs(5MdC)sdAs(5MdC)s(5MdC)sdGscsasasscsc | 499 |
| A-138036.1 usgsasasasdTsdGsdGsdTsdGs(5MdC)sdAsdAsdTs(5MdC)suscsasgsc | 500 |
| A-138037.1 asgsgscsusdGsdGsdAsdAsdTsdGsdAsdAsdAsdTsgsgsusgsc | 501 |
| A-138038.1 ascsuscsasdTsdGsdTsdTsdGs(5MdC)s(5MdC)s(5MdC)sdAsdGsgscsusgsg | 502 |

TABLE 4 -continued

Modified Antisense Polynucleotides Agents Targeting PNPLA3.

| Oligo Name | Sequence 5'-3' | SEQ ID NO |
|---|---|---|
| A-138039.1 | uscsasgsas(5MdC)sdTsdTsdTs(5MdC)sdAs(5MdC)sdTs(5MdC)sdAsusgsususg | 503 |
| A-138040.1 | usususususdTsdTsdTsdGsdAsdGsdTs(5MdC)sdAsgsascsusu | 504 |
| A-138041.1 | ususususasdAsdAsdTsdTsdTsdTsdTsdTsdTsususususg | 505 |
| A-138042.1 | gsasususasdTsdTsdTsdGsdTsdTsdTsdTsusasasasu | 506 |
| A-138043.1 | csusgscsas(5MdC)sdAs(5MdC)sdTsdAsdGsdAsdTsdTsdAsususususg | 507 |
| A-138044.1 | asgsgsusgsdAsdAsdTsdGs(5MdC)s(5MdC)s(5MdC)sdTsdGs(5MdC)sascsascsu | 508 |
| A-138045.1 | usgsgsgsgsdGsdGs(5MdC)sdTsdGsdAsdGsdGsdTsdGsasasusgsc | 509 |
| A-138046.1 | csususgsgs(5MdC)sdTs(5MdC)s(5MdC)sdTsdGs(5MdC)s(5MdC)sdTsdGsgsgsgsgsg | 510 |
| A-138047.1 | cscsusgscsdTsdGsdTsdGs(5MdC)sdTsdTsdGsdGs(5MdC)suscscsusg | 511 |
| A-138048.1 | asgsgscsgsdGsdAsdAsdGs(5MdC)sdTs(5MdC)s(5MdC)sdTsdGscsusgsusg | 512 |
| A-138049.1 | csasgsusgsdGsdAsdGsdAsdGsdGsdAsdGsdGs(5MdC)sgsgsasasg | 513 |
| A-138050.1 | asgsususgsdTsdGsdTsdGs(5MdC)sdTs(5MdC)s(5MdC)sdAsdGsusgsgsasg | 514 |
| A-138051.1 | asgscscsasdGsdGsdTsdTs(5MdC)sdAsdAsdGsdTsdTsgsusgsusg | 515 |
| A-138052.1 | gscsasgsasdAsdAsdAsdTsdAsdAsdGs(5MdC)s(5MdC)sdAsgsgsususc | 516 |
| A-138053.1 | gsgsgsgscsdTsdGsdGsdTs(5MdC)s(5MdC)s(5MdC)sdTsdGs(5MdC)sasgsasasa | 517 |
| A-138054.1 | ascsusgsas(5MdC)s(5MdC)sdAsdTsdGsdTsdGsdGsdGsdGscsusgsgsu | 518 |
| A-138055.1 | gsgsasgsasdAsdAs(5MdC)sdTs(5MdC)sdAs(5MdC)sdTsdGsdAscscsasusg | 519 |
| A-138056.1 | csgscscsas(5MdC)sdAs(5MdC)sdAsdTsdGsdGsdGsdGsdAsgsasasasc | 520 |
| A-138057.1 | ascsuscsus(5MdC)sdTs(5MdC)sdAsdTs(5MdC)sdGs(5MdC)s(5MdC)sdAscsascsasu | 521 |
| A-138058.1 | cususususasdTsdTsdTs(5MdC)sdTsdAs(5MdC)sdAs(5MdC)sdTscsuscsusc | 522 |

TABLE 5

PNPLA3 Single Dose Screen in HuH7 Cells.

| Oligo Name | Avg. 500 nM | SD |
|---|---|---|
| A-133284.1 | 51.5 | 11.4 |
| A-133285.1 | 54.9 | 9.0 |
| A-133286.1 | 49.7 | 11.0 |
| A-133287.1 | 36.3 | 4.7 |
| A-133288.1 | 31.5 | 5.0 |
| A-133289.1 | 27.4 | 2.5 |
| A-133290.1 | 57.2 | 16.1 |
| A-133291.1 | 56.5 | 8.5 |
| A-133292.1 | 32.6 | 2.2 |
| A-133293.1 | 42.1 | 4.1 |
| A-133294.1 | 57.1 | 32.5 |
| A-133295.1 | 40.2 | 12.6 |
| A-133296.1 | 58.6 | 28.7 |
| A-133297.1 | 54.2 | 19.7 |
| A-133298.1 | 35.2 | 10.8 |
| A-133299.1 | 42.2 | 8.4 |
| A-133300.1 | 24.9 | 4.2 |
| A-133301.1 | 47.7 | 5.7 |
| A-133302.1 | 70.2 | 10.7 |
| A-133303.1 | 45.0 | 3.9 |
| A-133304.1 | 33.9 | 8.3 |
| A-133305.1 | 25.2 | 8.5 |
| A-133306.1 | 36.1 | 10.9 |
| A-133307.1 | 84.0 | 24.6 |
| A-133308.1 | 49.4 | 8.0 |
| A-133309.1 | 56.4 | 3.6 |
| A-133310.1 | 49.1 | 6.6 |
| A-133311.1 | 51.4 | 3.4 |
| A-133312.1 | 31.3 | 3.5 |
| A-133313.1 | 52.5 | 4.1 |
| A-133314.1 | 71.1 | 8.8 |
| A-133315.1 | 70.0 | 22.7 |
| A-133316.1 | 78.5 | 35.3 |
| A-133317.1 | 59.1 | 21.4 |
| A-133318.1 | 46.2 | 12.9 |
| A-133319.1 | 50.0 | 9.3 |
| A-133320.1 | 45.1 | 9.1 |
| A-133321.1 | 45.3 | 3.6 |
| A-133322.1 | 38.0 | 4.1 |
| A-133323.1 | 40.7 | 5.5 |
| A-133324.1 | 31.8 | 8.4 |
| A-133325.1 | 37.1 | 8.7 |
| A-133326.1 | 40.9 | 5.6 |
| A-133327.1 | 38.4 | 4.4 |
| A-133328.1 | 21.3 | 3.5 |
| A-133329.1 | 34.7 | 4.4 |
| A-133330.1 | 53.5 | 10.4 |
| A-133331.1 | 65.0 | 10.9 |
| A-133332.1 | 62.3 | 6.9 |
| A-133333.1 | 58.8 | 5.7 |
| A-133334.1 | 76.6 | 9.2 |
| A-133335.1 | 70.0 | 5.1 |

TABLE 5-continued

PNPLA3 Single Dose Screen in HuH7 Cells.

| Oligo Name | Avg. 500 nM | SD |
|---|---|---|
| A-133336.1 | 63.7 | 4.3 |
| A-133337.1 | 71.7 | 3.7 |
| A-133338.1 | 77.7 | 18.3 |
| A-133339.1 | 42.0 | 5.2 |
| A-133340.1 | 48.0 | 11.6 |
| A-133341.1 | 33.7 | 6.3 |
| A-133342.1 | 36.8 | 10.4 |
| A-133343.1 | 53.0 | 11.8 |
| A-133344.1 | 71.7 | 9.1 |
| A-133345.1 | 71.9 | 22.0 |
| A-133346.1 | 45.5 | 6.4 |
| A-133347.1 | 57.7 | 10.5 |
| A-133348.1 | 37.2 | 6.6 |
| A-133349.1 | 57.8 | 10.3 |
| A-133350.1 | 83.7 | 17.1 |
| A-133351.1 | 52.1 | 6.4 |
| A-133352.1 | 34.1 | 4.0 |
| A-133353.1 | 46.3 | 3.1 |
| A-133354.1 | 52.0 | 2.2 |
| A-133355.1 | 36.4 | 3.9 |
| A-133356.1 | 41.0 | 7.0 |
| A-133357.1 | 44.9 | 5.0 |
| A-133358.1 | 69.8 | 3.8 |
| A-133359.1 | 53.0 | 3.9 |
| A-133360.1 | 35.0 | 2.3 |
| A-133361.1 | 34.2 | 2.4 |
| A-133362.1 | 69.5 | 4.5 |
| A-133363.1 | 49.3 | 4.0 |
| A-133364.1 | 20.0 | 3.6 |
| A-133365.1 | 36.4 | 4.8 |
| A-133366.1 | 27.3 | 2.2 |
| A-133367.1 | 35.8 | 6.7 |
| A-133368.1 | 26.1 | 3.9 |
| A-133369.1 | 24.1 | 5.6 |
| A-133370.1 | 46.7 | 6.2 |
| A-133371.1 | 22.9 | 4.2 |
| A-133372.1 | 20.9 | 4.7 |
| A-133373.1 | 39.4 | 4.2 |
| A-133374.1 | 85.2 | 8.4 |
| A-133375.1 | 49.3 | 3.8 |
| A-133376.1 | 83.1 | 9.1 |
| A-133377.1 | 38.6 | 5.0 |
| A-133378.1 | 32.4 | 6.1 |
| A-133379.1 | 48.3 | 15.0 |
| A-133380.1 | 44.5 | 14.6 |
| A-133381.1 | 41.8 | 14.5 |
| A-133382.1 | 62.5 | 23.6 |
| A-133383.1 | 62.8 | 19.5 |
| A-133384.1 | 36.0 | 6.8 |
| A-133385.1 | 34.3 | 5.6 |
| A-133386.1 | 44.9 | 11.8 |
| A-133387.1 | 60.1 | 11.0 |
| A-133388.1 | 71.6 | 14.4 |
| A-133389.1 | 67.0 | 13.3 |
| A-133390.1 | 38.7 | 8.9 |
| A-133391.1 | 20.2 | 4.6 |
| A-133392.1 | 18.0 | 3.3 |
| A-133393.1 | 15.6 | 2.3 |
| A-133394.1 | 98.3 | 10.1 |
| A-133395.1 | 39.0 | 3.2 |
| A-133396.1 | 23.4 | 7.0 |
| A-133397.1 | 80.4 | 7.9 |
| A-133398.1 | 64.8 | 9.7 |
| A-133399.1 | 86.8 | 17.9 |
| A-133400.1 | 63.1 | 6.9 |
| A-133401.1 | 24.0 | 5.6 |
| A-133402.1 | 15.8 | 1.0 |
| A-133403.1 | 53.5 | 6.7 |
| A-133404.1 | 50.3 | 7.4 |
| A-133405.1 | 47.0 | 6.8 |
| A-133406.1 | 72.1 | 11.9 |
| A-133407.1 | 57.1 | 13.2 |
| A-133408.1 | 60.2 | 11.7 |
| A-133409.1 | 42.2 | 9.4 |
| A-133410.1 | 79.8 | 15.8 |
| A-133411.1 | 77.7 | 15.1 |
| A-133412.1 | 28.6 | 5.5 |
| A-133413.1 | 96.3 | 8.5 |
| A-133414.1 | 65.0 | 7.8 |
| A-133415.1 | 28.3 | 2.7 |
| A-133416.1 | 62.7 | 12.2 |
| A-133417.1 | 71.1 | 6.6 |
| A-133418.1 | 74.8 | 14.2 |
| A-133419.1 | 49.4 | 6.9 |
| A-133420.1 | 82.6 | 19.7 |
| A-133421.1 | 38.0 | 7.2 |
| A-133422.1 | 78.3 | 13.6 |
| A-133423.1 | 47.7 | 8.4 |
| A-133424.1 | 41.9 | 9.8 |
| A-133425.1 | 14.0 | 4.0 |
| A-133426.1 | 25.3 | 6.3 |
| A-133427.1 | 41.8 | 7.3 |
| A-133428.1 | 42.6 | 6.7 |
| A-133429.1 | 62.0 | 3.1 |
| A-133430.1 | 44.3 | 4.0 |
| A-133431.1 | 78.5 | 5.9 |
| A-133432.1 | 62.7 | 9.5 |
| A-133433.1 | 51.0 | 9.8 |
| A-133434.1 | 35.3 | 2.8 |
| A-133435.1 | 59.0 | 1.9 |
| A-133436.1 | 88.7 | 11.0 |
| A-133437.1 | 81.0 | 11.4 |
| A-133438.1 | 55.3 | 3.7 |
| A-133439.1 | 37.6 | 6.4 |

I claim:

1. A single stranded polynucleotide agent for inhibiting expression of a Patatin-Like Phospholipase Domain Containing 3 (PNPLA3) gene, wherein the agent comprises at least 8 contiguous nucleotides differing by no more than 3 nucleotides from the nucleotide sequence of 5'-ACCCA-CUGCAACCACAGGAC-3' (SEQ ID NO:136), wherein the agent is about 10 to about 24 nucleotides in length, and wherein at least one of the nucleotides is a modified nucleotide.

2. The agent of claim 1, wherein substantially all of the nucleotides of the antisense polynucleotide agent are modified nucleotides; or wherein all of the nucleotides of the antisense polynucleotide agent are modified nucleotides.

3. The agent of claim 1, which is 18 to 24 nucleotides in length; 21-24 nucleotides in length; 20 nucleotides in length; or 14 nucleotides in length.

4. The agent of claim 1, wherein the modified nucleotide comprises a modified sugar moiety selected from the group consisting of: a 2'-O-methoxyethyl modified sugar moiety, a 2'-O-alkyl modified sugar moiety, and a bicyclic sugar moiety.

5. The agent of claim 1, wherein the modified nucleotide is a 5-methylcytosine.

6. The agent of claim 1, wherein the modified nucleotide comprises a modified internucleoside linkage.

7. The agent of claim 1, comprising a plurality of 2'-deoxynucleotides flanked on each side by at least one nucleotide having a modified sugar moiety.

8. The agent of claim 7, wherein the agent is a gapmer comprising a gap segment comprised of linked 2'-deoxynucleotides positioned between a 5' and a 3' wing segment.

9. A single stranded polynucleotide agent for inhibiting expression of a Patatin-Like Phospholipase Domain Containing 3 (PNPLA3) gene, comprising at least 8 contiguous nucleotides differing by no more than 3 nucleotides from the nucleotide sequence of 5'-ACCCACUGCAACCACAG-GAC-3' (SEQ ID NO:136), wherein the agent comprises a gap segment consisting of linked deoxynucleotides;
a 5'-wing segment consisting of linked nucleotides;
a 3'-wing segment consisting of linked nucleotides;
wherein the gap segment is positioned between the 5'-wing segment and the 3'-wing segment and wherein each nucleotide of each wing segment comprises a modified sugar moiety.

10. The agent of claim 9, wherein the gap segment is 5 to 14 2'-deoxynucleotides in length and each of the wing segments is 1 to 6 nucleotides in length.

11. The agent of claim 1 or 9, wherein the agent further comprises a ligand conjugated at the 3'-terminus.

12. The agent of claim 11, wherein the ligand is an N-acetylgalactosamine (GalNAc) derivative.

13. A pharmaceutical composition for inhibiting expression of a Patatin-Like Phospholipase Domain Containing 3 (PNPLA3) gene, comprising the agent of claim 1.

14. A pharmaceutical composition comprising the agent of claim 1 or 9, and a lipid formulation.

15. The agent of claim 9, which is 18 to 24 nucleotides in length; 21-24 nucleotides in length; 20 nucleotides in length; or 14 nucleotides in length.

16. The agent of claim 9, wherein the modified sugar moiety is selected from the group consisting of a 2'-O-methoxyethyl modified sugar moiety, a 2'-methoxy modified sugar moiety, a 2'-O-alkyl modified sugar moiety, and a bicyclic sugar moiety.

17. The agent of claim 9, further comprising a modified internucleoside linkage.

18. The agent of claim 10, wherein the 5'-wing segment is 4 to 6 nucleotides in length, the 3'-wing segment is 4 to 6 nucleotides in length, and the gap segment is 9 to 13 nucleotides in length.

19. The agent of claim 1 or 9, comprising 5'-ascscscsas (5MdC)sdTsdGs(5MdC)sdAsdAs(5MdC)s(5MdC)sdAs (5MdC)sasgsgsasc-3' (SEQ ID NO:389),
wherein a, c, g, and u are 2'-O-methyl (2'-OMe) A, C, G, and U; Af, Cf, Gf, and Uf are 2'-fluoro A, C, G, and U;

dA, dC, dG, and dT are 2'-deoxy (d) A, C, G, and T; (5MdC) is 5'-methyl-deoxycytidine; and s is a phosphorothioate linkage.

20. A pharmaceutical composition for inhibiting expression of a Patatin-Like Phospholipase Domain Containing 3 (PNPLA3) gene, comprising the agent of claim 9.

21. The pharmaceutical composition of claim 13 or 20, wherein agent is present in an unbuffered solution or a buffer solution.

22. A method of inhibiting expression of a Patatin-Like Phospholipase Domain Containing 3 (PNPLA3) gene in a cell, the method comprising:
   (a) contacting the cell with the agent of claim 1 or 9 or a pharmaceutical composition of claim 13 or 20; and
   (b) maintaining the cell produced in step (a) for a time sufficient to obtain antisense inhibition of a PNPLA3 gene, thereby inhibiting expression of the PNPLA3 gene in the cell.

23. The method of claim 22, wherein the cell is within a subject.

24. The method of claim 23, wherein the subject is a human.

* * * * *